(12) United States Patent
Dragovich et al.

(10) Patent No.: US 10,632,196 B2
(45) Date of Patent: Apr. 28, 2020

(54) PYRROLOBENZODIAZEPINE ANTIBODY DRUG CONJUGATES AND METHODS OF USE

(71) Applicant: Genentech, Inc., South San Francisco, CA (US)

(72) Inventors: Peter Dragovich, San Diego, CA (US); Thomas Pillow, San Francisco, CA (US); Jack Sadowsky, Dublin, CA (US); Mark X. Sliwkowski, San Carlos, CA (US); BinQing Wei, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 156 days.

(21) Appl. No.: 15/899,612

(22) Filed: Feb. 20, 2018

(65) Prior Publication Data
US 2018/0185486 A1  Jul. 5, 2018

Related U.S. Application Data

(62) Division of application No. 15/281,830, filed on Sep. 30, 2016, now Pat. No. 10,058,613.

(60) Provisional application No. 62/236,429, filed on Oct. 2, 2015.

(51) Int. Cl.
| | |
|---|---|
| *A61K 39/395* | (2006.01) |
| *A61K 45/06* | (2006.01) |
| *C07K 16/28* | (2006.01) |
| *C07D 519/00* | (2006.01) |
| *C07K 16/32* | (2006.01) |
| *A61K 47/68* | (2017.01) |
| *A61K 31/5517* | (2006.01) |

(52) U.S. Cl.
CPC .......... *A61K 45/06* (2013.01); *A61K 31/5517* (2013.01); *A61K 47/6803* (2017.08); *A61K 47/6851* (2017.08); *A61K 47/6855* (2017.08); *A61K 47/6889* (2017.08); *C07D 519/00* (2013.01); *C07K 16/2803* (2013.01); *C07K 16/32* (2013.01); *C07K 2317/40* (2013.01); *C07K 2317/522* (2013.01); *C07K 2317/567* (2013.01)

(58) Field of Classification Search
CPC ..................................................... A61K 45/06
See application file for complete search history.

(56) References Cited

U.S. PATENT DOCUMENTS

| | | | |
|---|---|---|---|
| 4,427,588 A | 1/1984 | Kaneko et al. |
| 6,660,856 B2 | 12/2003 | Wang |
| 6,949,245 B1 | 9/2005 | Sliwkowski |
| 6,984,494 B2 | 1/2006 | Ralph |
| 7,041,292 B1 | 5/2006 | Sliwkowski |
| 7,049,311 B1 | 5/2006 | Thurston et al. |
| 7,129,254 B2 | 10/2006 | Berger et al. |
| 7,265,105 B2 | 9/2007 | Thurston et al. |
| 7,449,184 B2 | 11/2008 | Allison et al. |
| 7,498,298 B2 | 3/2009 | Doronina et al. |
| 7,521,541 B2 | 4/2009 | Eigenbrot et al. |
| 7,855,275 B2 | 12/2010 | Eigenbrot et al. |
| 7,993,834 B2 | 8/2011 | Mass |
| 8,034,808 B2 | 10/2011 | Delavault et al. |
| 8,309,300 B2 | 11/2012 | Junutula et al. |
| 8,372,396 B2 | 2/2013 | Andya et al. |
| 8,481,042 B2 | 7/2013 | Commercon et al. |
| 8,487,092 B2 | 7/2013 | Howard et al. |
| 8,592,576 B2 | 11/2013 | Howard et al. |
| 8,691,232 B2 | 4/2014 | Derynck et al. |
| 8,765,740 B2 | 7/2014 | Li et al. |
| 8,802,667 B2 | 8/2014 | Li et al. |
| 8,809,320 B2 | 8/2014 | Li et al. |
| 9,000,130 B2 | 4/2015 | Bhakta et al. |
| 9,518,118 B2 | 12/2016 | Chen et al. |
| 2002/0141993 A1 | 10/2002 | Ashkenazi et al. |
| 2005/0208043 A1 | 9/2005 | Adams et al. |
| 2005/0244417 A1 | 11/2005 | Ashkenazi et al. |
| 2007/0092940 A1 | 4/2007 | Eigenbrot et al. |
| 2008/0112957 A1 | 5/2008 | Fendly et al. |
| 2009/0175865 A1 | 7/2009 | Eigenbrot et al. |
| 2010/0003766 A1 | 1/2010 | Eigenbrot et al. |
| 2010/0111856 A1 | 5/2010 | Gill et al. |
| 2011/0033460 A1 | 2/2011 | Fendly et al. |
| 2011/0137017 A1 | 6/2011 | Eigenbrot et al. |
| 2011/0256157 A1 | 10/2011 | Howard et al. |
| 2011/0301334 A1 | 12/2011 | Bhakta et al. |

(Continued)

FOREIGN PATENT DOCUMENTS

| | | |
|---|---|---|
| EP | 1413582 B1 | 3/2006 |
| EP | 2540745 A1 | 1/2013 |

(Continued)

OTHER PUBLICATIONS

Kang, et al., "Synthesis of a novel C2-aryl substituted 1,2-unsaturated pyrrolobenzodiazepine", Chemical Communications 14, 1688-1689 (2003).

(Continued)

*Primary Examiner* — Sheela J. Huff
(74) *Attorney, Agent, or Firm* — Viksnins Harris Padys Malen LLP

(57) ABSTRACT

The invention provides antibody-drug conjugates comprising an antibody conjugated to a pyrrolobenzodiazepine drug moiety via a disulfide linker, pyrrolobenzodiazepine linker-drug intermediates, and methods of using the antibody-drug conjugates.

58 Claims, 19 Drawing Sheets
Specification includes a Sequence Listing.

(56) References Cited

U.S. PATENT DOCUMENTS

| | | | |
|---|---|---|---|
| 2012/0121615 A1 | 5/2012 | Flygare et al. |
| 2013/0028917 A1 | 1/2013 | Howard et al. |
| 2013/0195845 A1 | 8/2013 | Fendly et al. |
| 2013/0266595 A1 | 10/2013 | Flygare et al. |
| 2014/0120118 A1 | 5/2014 | Howard |
| 2014/0288280 A1 | 9/2014 | Bhakta et al. |
| 2015/0017094 A1 | 1/2015 | Gill et al. |
| 2015/0017188 A1 | 1/2015 | Eigenbrot et al. |
| 2015/0111298 A1 | 4/2015 | Lattemann et al. |
| 2015/0209444 A1 | 7/2015 | Chari et al. |
| 2015/0344482 A1 | 12/2015 | Howard |
| 2016/0074527 A1 | 3/2016 | Flygare et al. |
| 2016/0096893 A1 | 4/2016 | Chen et al. |
| 2016/0130358 A1 | 5/2016 | Bhakta et al. |
| 2016/0310611 A1 | 10/2016 | Flygare et al. |
| 2017/0095570 A1 | 4/2017 | Dragovich et al. |

FOREIGN PATENT DOCUMENTS

| | | | |
|---|---|---|---|
| WO | 1998017797 A1 | 4/1998 | |
| WO | 2000012507 A2 | 3/2000 | |
| WO | 2004016801 A2 | 2/2004 | |
| WO | 2004087717 A1 | 10/2004 | |
| WO | 2005023814 A1 | 3/2005 | |
| WO | 2005085251 A1 | 9/2005 | |
| WO | 2006034488 A2 | 3/2006 | |
| WO | 2007085930 A1 | 8/2007 | |
| WO | 2007144709 A2 | 12/2007 | |
| WO | 2010043877 A1 | 4/2010 | |
| WO | 2010091150 A1 | 8/2010 | |
| WO | 2011056983 A1 | 5/2011 | |
| WO | 2011130598 A1 | 10/2011 | |
| WO | 2011130613 A1 | 10/2011 | |
| WO | 2011130616 A1 | 10/2011 | |
| WO | 2011156328 A1 | 12/2011 | |
| WO | 2012014147 A1 | 2/2012 | |
| WO | 2012112708 A1 | 8/2012 | |
| WO | 2013041606 A1 | 3/2013 | |
| WO | 2013053873 A1 | 4/2013 | |
| WO | 2013055987 A1 | 4/2013 | |
| WO | 2013055990 A1 | 4/2013 | |
| WO | 2013055993 A1 | 4/2013 | |
| WO | 2013177481 A1 | 11/2013 | |
| WO | 2014011518 A1 | 1/2014 | |
| WO | 2014057072 A1 | 4/2014 | |
| WO | 2014057113 A1 | 4/2014 | |
| WO | 2014057114 A1 | 4/2014 | |
| WO | 2014057115 A1 | 4/2014 | |
| WO | 2014057117 A1 | 4/2014 | |
| WO | 2014057118 A1 | 4/2014 | |
| WO | 2014057119 A1 | 4/2014 | |
| WO | 2014057120 A1 | 4/2014 | |
| WO | 2014057122 A1 | 4/2014 | |
| WO | 2014096365 A1 | 6/2014 | |
| WO | 2014096368 A1 | 6/2014 | |
| WO | 2014130879 A2 | 8/2014 | |
| WO | 2015023355 A1 | 2/2015 | |
| WO | 2015095124 A1 | 6/2015 | |
| WO | 2015095223 A2 | 6/2015 | |
| WO | 2016040723 A1 | 3/2016 | |
| WO | 2016040856 A2 | 3/2016 | |
| WO | 2016044396 A1 | 3/2016 | |
| WO | 2016044560 A1 | 3/2016 | |
| WO | WO-2017020972 A1 * | 2/2017 | ............ A61P 35/02 |

OTHER PUBLICATIONS

Pillow, et al., "Site-specific trastuzumab maytansinoid antibody-drug conjugates with improved therapeutic activity through linker and antibody engineering", J Med Chem 57(19), 7890-7899 (2014).
Antonow, et al., "Synthesis of a novel C2-aryl pyrrolo[2,1-c][1,4]benzodiazepine-5,11-dione library: effect of C2-aryl substitution on cytotoxicity and non-covalent DNA binding", Bioorg Med Chem 15(8), 3041-3053 (2007).
Antonow, et al., "Synthesis of DNA-Interactive Pyrrolo[2,1-c][1,4]benzodiazepines (PBDs)", Chem Rev 111(4), 2815-2864 (2011).
Arima, et al., "Studies on tomaymycin, a new antibiotic. I. Isolation and properties of tomaymycin", J Antibiot (Tokyo) 25(8), 437-444 (1972).
Baselga, et al., "Recombinant humanized anti-HER2 antibody (Herceptin) enhances the antitumor activity of paclitaxel and doxorubicin against HER2/neu overexpressing human breast cancer xenografts", Cancer Res 58, 2825-2831 (1998).
Bookman, et al., "Evaluation of Monoclonal Humanized Anti-HER2 Antibody, Trastuzumab, in Patients With Recurrent or Refractory Ovarian or Primary Peritoneal Carcinoma With Overexpression of HER2: A Phase II Trial of the Gynecologic Oncology Group", Journal of Clinical Oncology 21(2), 283-290 (2003).
Bose, et al., "New approaches to pyrrolo[2,1-c][1,4]benzodiazepines: synthesis, DNA-binding and cytotoxicity of DC-81", Tetrahedron 48(4), 751-758 (1992).
Fendly, et al., "Characterization of Murine Monoclonal Antibodies Reactive to Either the Human Epidermal Growth Factor Receptor or HER2/neu Gene Product", Cancer Res 50, 1550-1558 (1990).
Gregson, et al., "Design, Synthesis, and Evaluation of a Novel Pyrrolobenzodiazepine DNA-Interactive Agent with Highly Efficient Cross-Linking Ability and Potent Cytotoxicity", J Med Chem 44, 737-748 (2001).
Gregson, et al., "Linker Length Modulates DNA Cross-Linking Reactivity and Cytotoxic Potency of C8/C8' Ether-Linked C2-exo-Unsaturated Pyrrolo[2,1-c][1,4]benzodiazepine (PBD) Dimers", J Med Chem 47(5), 1161-1174 (2004).
Gregson, et al., "Synthesis of a novel C2/C2'-exo unsaturated pyrrolobenzodiazepine cross-liniking agent with remarkable DNA binding affinity and cytotoxicity", Chem Commun, 797-798 (1999).
Grimm, et al., "Reaction Safety: An Improved Procedure for the Preparation of 1,3,4,12a-Tetrahydro-11H[1,4]-oxanio[3,4-c][1,4]benzodiazepine-6,12-dione with Iron in Acetic Acid", Organic Process Research and Development 7(6), 1067-1070 (2003).
Hara, et al., "DC 102, a new glycosidic pyrrolo(1,4)benzodiazepine antibiotic produced by *Streptomyces* sp", J Antibiot (Tokyo) 41(5), 702-704 (1988).
Hochlowski, et al., "Abbeymycin, a new anthramycin-type antibiotic produced by a streptomycete", J Antibiot (Tokyo) 40(2), 145-148 (1987).
Howard, et al., "Synthesis of a novel C2/C2'-aryl-substituted pyrrolo[2,1-c][1,4]benzodiazepine dimer prodrug with improved water solubility and reduced DNA reaction rate", Bioorg Med Chem Lett 19(22), 6463-6466 (2009).
Hurley, et al., "Covalent binding of antitumor antibiotics in the minor groove of DNA. Mechanism of action of CC-1065 and the pyrrolo(1,4)benzodiazepines", ACC Chem Res 19, 230-237 (1986).
Itoh, et al., "Sibanomicin, a new pyrrolo[1,4]benzodiazepine antitumor antibiotic produced by a *Micromonospora* sp", J Antibiot (Tokyo) 41(9), 1281-1284 (1988).
Kamal, et al., "Design, synthesis, and evaluation of mixed imine-amine pyrrolobenzodiazepine dimers with efficient DNA binding affinity and potent cytotoxicity", Bioorg Med Chem 12(20), 5427-5436 (2004).
Kamal, et al., "Design, synthesis, and evaluation of new noncrosslinking pyrrolobenzodiazepine dimers with efficient DNA binding ability and potent antitumor activity", J Med Chem 45(21), 4679-4688 (2002).
Kamal, et al., "Pyrrolo[2,1-c][1,4]benzodiazepine-β-glucuronide prodrugs with a potential for selective therapy of solid tumors by PMT and ADEPT strategies", Bioorganic & Medicinal Chemistry Letters 18(13), 3769-3773 (2008).
Kaneko, et al., "A new and mild method for the reduction of secondary amides to carbinolamine ethers and imines: a conversion of oxotomaymycin to tomaymycin", Tetrahedron Letters 24(47), 5165-5168 (1983).
Kaneko, et al., "Bicyclic and tricyclic analogues of anthramycin", Journal of Medicinal Chemistry 28(3), 388-392 (1985).

(56) References Cited

OTHER PUBLICATIONS

Kohn, "Mechanism of Action of Antimicrobial and Antitumor Agents "Anthramycirr"", New York, Springer-Verlag, 3-11 (1975).
Konishi, et al., "Chicamycin, a new antitumor antibiotic. II. Structure determination of chicamycins A and B", J Antibiol (Tokyo) 37(3), 200-206 (1984).
Kunimoto, et al., "Mazethramycin, a new member of anthramycin group antibiotics", J Antibiotics 33(6), 665-667 (1980).
Langley, et al., "A versatile and efficient synthesis of carbinolamine-containing pyrrolo[1,4]benzodiazepines via the ayclization of N-(2-aminobenzoyl)pyrrolidine-2-carboxaldehyde diethyl thioacetals: total synthesis of prothracarcin", J Org Chem 52(1), 91-97 (1987).
Leber, et al., "A revised structure of sibiromycin", J Am Chem Soc 110, 2992-2993 (1988).
Leimgruber, et al., "Isolation and Characterization of Anthramycin, a New Antitumor Antibiotic", J Am Chem Soc 87(24), 5791-5793 (1965).
Leimgruber, et al., "The structure of anthramycin", J Am Chem Soc 87(24), 5793-5795 (1965).
Martin, et al., "Sequence-selective interaction of the minor-groove interstrand cross-linking agent SJG-136 with naked and cellular DNA: footprinting and enzyme inhibition studies", Biochemistry 44(11), 4135-4147 (2005).
Patent Cooperation Treaty, ISR and Written Opinion for PCT/EP2013/077705 (dated 2013).
Patent Cooperation Treaty, ISR and Written Opinion for PCT/US2013/042566 (dated 2013).
Patent Cooperation Treaty, ISR and Written Opinion for PCT/US2015/049549 (dated 2015).
Patent Cooperation Treaty, ISR and Written Opinion for PCT/US2016/054858 (dated 2016).
Shimizu, et al., "Prothracarcin, a novel antitumor antibiotic", J Antibiotics 8, 972-978 (1982).
Takeuchi, et al., "Neothramycins A and B, new antitumor antibiotics", J Antibiot (Toky) 92(1), 93-96 (1976).
Thurston, et al., "Synthesis of DNA-Interactive Pyrrolo[2,1-c][1,4]benzodiazepines", Chem Rev 94, 433-465 (1994).
Thurston, et al., "The Molecular Recognition of DNA", Chem Brit 26(8), 767-772 (1990).
Tsunakawa, et al., "Porothramycin, a new antibiotic of the anthramycin group: production, isolation, structure and biological activity", J Antibiot (Tokyo) 41(10), 1366-1373 (1988).

* cited by examiner

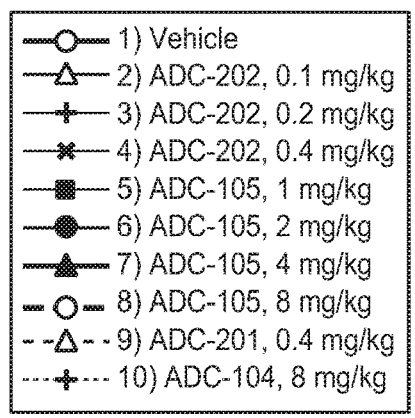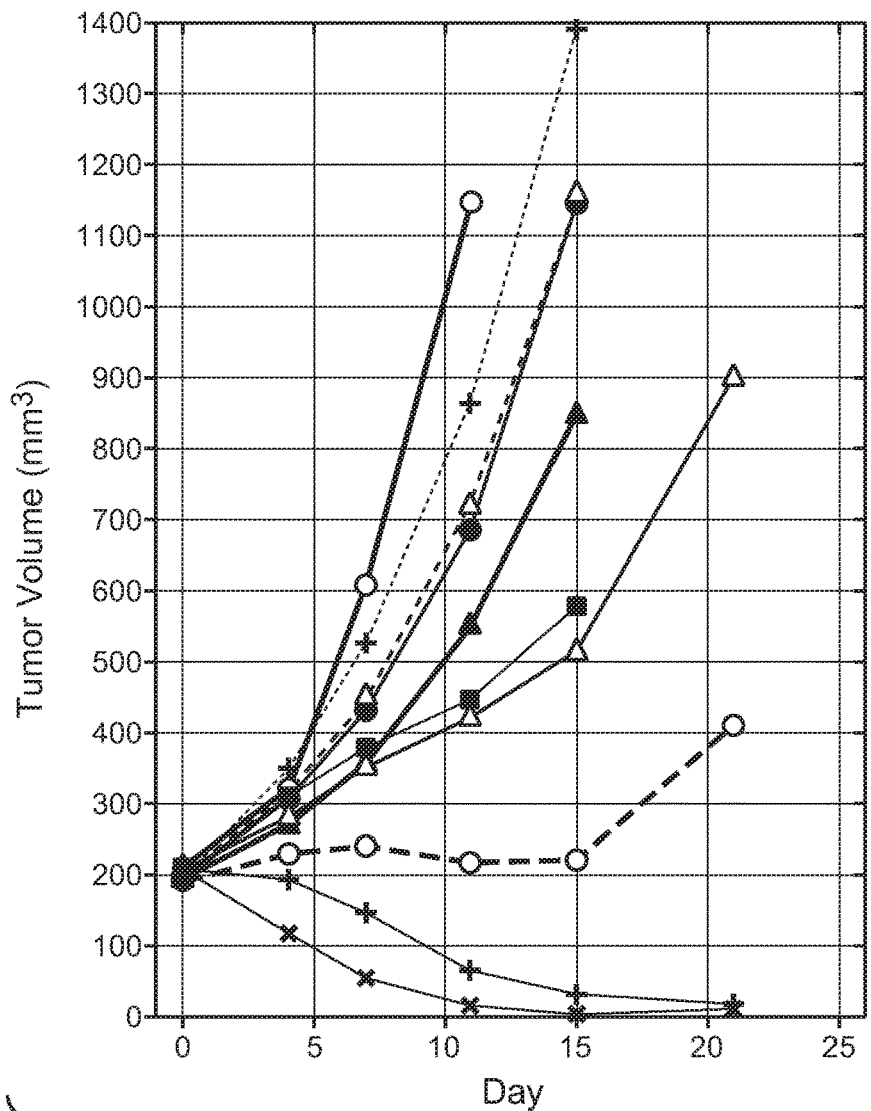
FIG. 3

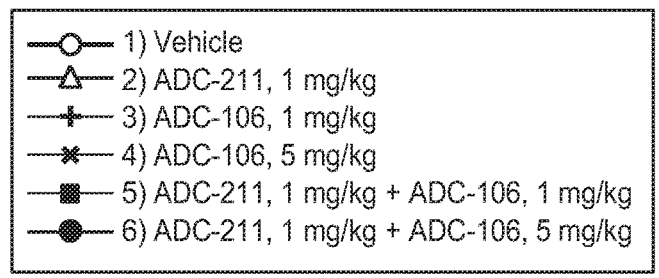
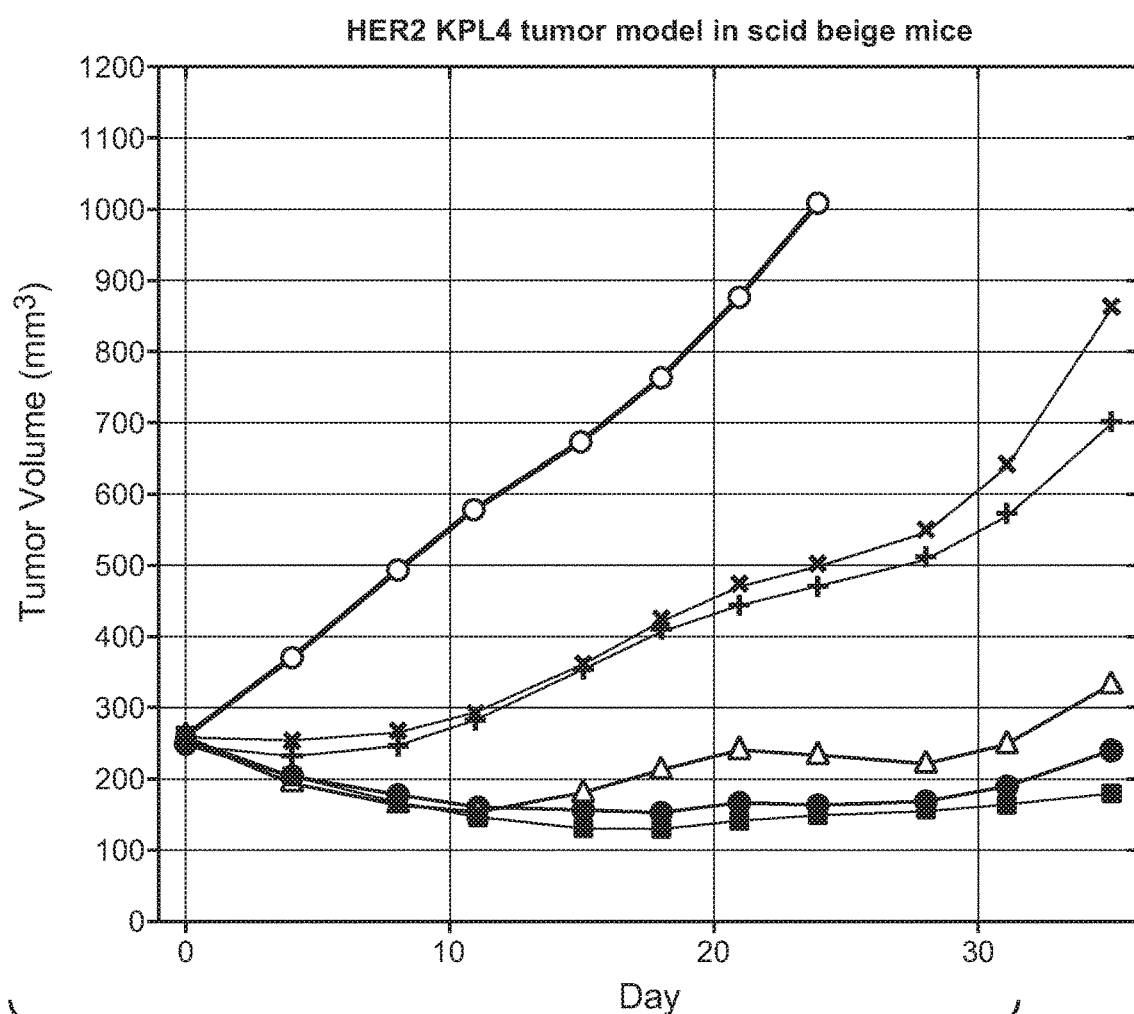
FIG. 5B

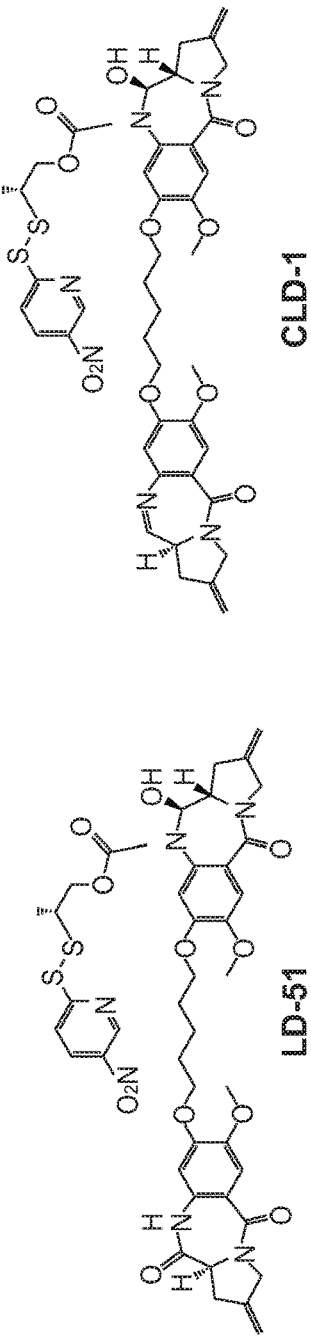

Cynomolgus Monkey Toxicity

| Antigen | Antibody | Regimen | MTD (mg/kg) |
|---|---|---|---|
| Her2 | 7C2 | Q3W x 4 | 8 |
| Her2 | 7C2 | Q3W x 2 | 16 |

| Antigen | Antibody | Regimen | MTD (mg/kg) |
|---|---|---|---|
| NA | gD | Q3W x 2 | 0.5 |

Mouse Efficacy

| Antigen | Antibody | Model | MED (mg/kg) | Exposure Based (TAB AUC) TI[a] | Exposure Based (TAB AUC) TI[b] |
|---|---|---|---|---|---|
| Her2 | 7C2 | Fo5 | 15 | 1.1 | 2.2 |
| Her2 | 7C2 | KPL4 | 8 | 2.1 | 4.1 |
| Her2 | 7C2 | HCC1569X2 | 10 | 1.6 | 3.3 |
| Her2 | 4D5 | HCC1569X2 | 5 | 3.3 | 6.6 |

[a] TI calculated as AUC MTDcyno/AUC MEDmouse based on 8 mg/kg Q3Wx4
[b] TI calculated as AUC MTDcyno/AUC MEDmouse based on 16 mg/kg Q3Wx2

| Antigen | Antibody | Model | Regimen | MED (mg/kg) | Exposure Based (TAB AUC) TI |
|---|---|---|---|---|---|
| Her2 | 7C2 | Fo5 | | 0.5 | 2.8 |
| Her2 | 7C2 | KPL4 | | 1 | 1.4 |
| Her2 | 7C2 | HCC1569X2 | | ND | ND |
| Her2 | 4D5 | HCC1569X2 | | 0.3 | 4.7 |

TI calculated as AUC MTDcyno/AUC MEDmouse

MED = minimum efficacious dose (i.e. 100% TGI at d21 after single dose); MTD = maximum tolerated dose
TDC format; attachment site = LC_K149C; SD (single dose) unless otherwise indicated

FIG. 12

SEQUENCE LISTING

<160> NUMBER OF SEQ ID NOS: 70

<210> SEQ ID NO 1
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 1

Arg Ser Ser Gln Ser Ile Val His Ser Val Gly Asn Thr Phe Leu Glu
1               5                   10                  15

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Lys Val Ser Asn Arg Phe Ser
1               5

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Phe Gln Gly Ser Gln Phe Pro Tyr Thr
1               5

<210> SEQ ID NO 4
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Tyr Glu Phe Ser Arg Ser Trp Met Asn
1               5                   10

<210> SEQ ID NO 5
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Arg Ile Tyr Pro Gly Asp Gly Asp Thr Asn Tyr Ser Gly Lys Phe
1               5                   10                  15

Lys Gly

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

```
Asp Gly Ser Ser Trp Asp Trp Tyr Phe Asp Val
1               5                   10
```

<210> SEQ ID NO 7
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Asn Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys
            100                 105
```

<210> SEQ ID NO 8
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

```
Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

Gly Met Ile Trp Gly Asp Gly Ser Thr Asp Tyr Asn Ser Ala Leu Lys
50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser
        115                 120
```

<210> SEQ ID NO 9
<211> LENGTH: 11
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 9

Ser Ala Ser Gln Gly Ile Ser Asn Tyr Leu Asn
1               5                   10

<210> SEQ ID NO 10
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Tyr Thr Ser Asn Leu His Ser
1               5

<210> SEQ ID NO 11
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gln Gln Tyr Ser Glu Leu Pro Trp Thr
1               5

<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Phe Ser Leu Thr Gly Tyr Ser Val Asn
1               5                   10

<210> SEQ ID NO 13
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Met Ile Trp Gly Asp Gly Ser Thr Asp Tyr Asn Ser Ala Leu Lys Ser
1               5                   10                  15

<210> SEQ ID NO 14
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 14

Asp Tyr Tyr Val Asn Tyr Ala Ser Trp Phe Ala Tyr
1               5                   10

<210> SEQ ID NO 15
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Cys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

```
Gly Met Ile Trp Gly Asp Gly Ser Thr Asp Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450
```

<210> SEQ ID NO 17
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

<210> SEQ ID NO 18
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser
        115

<210> SEQ ID NO 19
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 19

Arg Ala Ser Gln Ser Val Ser Gly Ser Arg Phe Thr Tyr Met His
1               5                   10                  15

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Tyr Ala Ser Ile Leu Glu Ser
1               5

<210> SEQ ID NO 21
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gln His Ser Trp Glu Ile Pro Pro Trp Thr
1               5                   10

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Tyr Trp Met Asn
1               5

<210> SEQ ID NO 23
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Met Ile His Pro Leu Asp Ala Glu Ile Arg Ala Asn Gln Lys Phe Arg
1               5                   10                  15

Asp

<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24
```

Gly Thr Tyr Asp Gly Gly Phe Glu Tyr
1               5

<210> SEQ ID NO 25
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 26
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe

```
                50                  55                  60
Arg Asp Arg Val Thr Ile Thr Val Asp Thr Ser Thr Ser Thr Ala Tyr
 65                  70                  75                  80

Leu Glu Leu Ser Ser Leu Arg Ser Glu Asp Thr Ala Val Tyr Tyr Cys
                     85                  90                  95

Ala Arg Gly Thr Tyr Asp Gly Gly Phe Glu Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 27
<211> LENGTH: 17
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 27

Met Ile His Pro Met Asp Ser Glu Ile Arg Ala Asn Gln Lys Phe Arg
1               5                   10                  15

Asp

<210> SEQ ID NO 28
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Met Ile His Pro Leu Asp Ser Glu Ile Arg Ala Asn Gln Lys Phe Arg
1               5                   10                  15

Asp

<210> SEQ ID NO 29
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gly Thr Tyr Asp Gly Gly Phe Lys Tyr
1               5

<210> SEQ ID NO 30
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
                20                  25                  30

Arg Phe Thr Tyr Met His Trp Tyr Gln Gln Lys Pro Gly Gln Pro Pro
            35                  40                  45

Lys Leu Leu Ile Lys Tyr Ala Ser Ile Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125
```

```
Gln Leu Lys Ser Gly Thr Ala Ser Val Val Cys Leu Leu Asn Asn Phe
        130                 135                 140

Tyr Pro Arg Glu Ala Lys Val Gln Trp Cys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 31
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
            85                  90                  95

Ala Arg Gly Thr Tyr Asp Gly Gly Phe Glu Tyr Trp Gly Gln Gly Thr
        100                 105                 110

Leu Val Thr Val Ser Ser Cys Ser Thr Lys Gly Pro Ser Val Phe Pro
    115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

-continued

```
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 32
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 32

```
Lys Ala Ser Asp Leu Ile His Asn Trp Leu Ala
1               5                   10
```

<210> SEQ ID NO 33
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 33

```
Tyr Gly Ala Thr Ser Leu Glu Thr
1               5
```

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 34

```
Gln Gln Tyr Trp Thr Thr Pro Phe Thr
```

<210> SEQ ID NO 35
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 35

Gly Tyr Ser Ile Thr Asn Asp Tyr Ala Trp Asn
1               5                   10

<210> SEQ ID NO 36
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 36

Gly Tyr Ile Ser Tyr Ser Gly Tyr Thr Thr Tyr Asn Pro Ser Leu Lys
1               5                   10                  15

Ser

<210> SEQ ID NO 37
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 37

Ala Arg Trp Ala Ser Gly Leu Asp Tyr
1               5

<210> SEQ ID NO 38
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
                20                  25                  30

Leu Ala Trp Tyr Gln Gln Lys Pro Gly Lys Ala Pro Lys Leu Leu Ile
            35                  40                  45

Tyr Gly Ala Thr Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys Arg
            100                 105

<210> SEQ ID NO 39
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Glu Val Gln Leu Val Glu Ser Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Ser Tyr Ser Gly Tyr Thr Thr Tyr Asn Pro Ser Leu
    50                  55                  60

Lys Ser Arg Phe Thr Ile Ser Arg Asp Thr Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Trp Ala Ser Gly Leu Asp Tyr Trp Gly Gln Gly Thr Leu Val
            100                 105                 110

Thr Val Ser Ser
        115

<210> SEQ ID NO 40
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gly Tyr Ser Ile Thr Ser Asp Tyr Ala Trp Asn
1               5                   10

<210> SEQ ID NO 41
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gly Tyr Ile Ser Asn Ser Gly Ser Thr Ser Tyr Asn Pro Ser Leu Lys
1               5                   10                  15

Ser

<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 42

Glu Arg Asn Tyr Asp Tyr Asp Asp Tyr Tyr Ala Met Asp Tyr
1               5                   10                  15

<210> SEQ ID NO 43
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Lys Ser Ser Gln Ser Leu Leu Tyr Arg Ser Asn Gln Lys Asn Tyr Leu
1               5                   10                  15
Ala

<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Trp Ala Ser Thr Arg Glu Ser
1               5

<210> SEQ ID NO 45
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gln Gln Tyr Tyr Asn Tyr Pro Arg Thr
1               5

<210> SEQ ID NO 46
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
                20                  25                  30

Tyr Ala Trp Asn Trp Val Arg Gln Ala Pro Gly Lys Gly Leu Glu Trp
            35                  40                  45

Val Gly Tyr Ile Ser Asn Ser Gly Ser Thr Ser Tyr Asn Pro Ser Leu
        50                  55                  60

Lys Ser Arg Phe Thr Ile Ser Arg Asp Thr Ser Lys Asn Thr Leu Tyr

```
                65                  70                  75                  80
Leu Gln Met Asn Ser Leu Arg Ala Glu Asp Thr Ala Val Tyr Tyr Cys
                        85                  90                  95
Ala Arg Glu Arg Asn Tyr Asp Tyr Asp Tyr Tyr Tyr Ala Met Asp
                100                 105                 110
Tyr Trp Gly Gln Gly Thr Leu Val Thr Val Ser Ser
            115                 120
```

<210> SEQ ID NO 47
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

```
Asp Ile Gln Met Thr Gln Ser Pro Ser Ser Leu Ser Ala Ser Val Gly
1               5                   10                  15
Asp Arg Val Thr Ile Thr Cys Lys Ser Ser Gln Ser Leu Leu Tyr Arg
                20                  25                  30
Ser Asn Gln Lys Asn Tyr Leu Ala Trp Tyr Gln Gln Lys Pro Gly Lys
            35                  40                  45
Ala Pro Lys Leu Leu Ile Tyr Trp Ala Ser Thr Arg Glu Ser Gly Val
        50                  55                  60
Pro Ser Arg Phe Ser Gly Ser Gly Ser Gly Thr Asp Phe Thr Leu Thr
65                  70                  75                  80
Ile Ser Ser Leu Gln Pro Glu Asp Phe Ala Thr Tyr Tyr Cys Gln Gln
                85                  90                  95
Tyr Tyr Asn Tyr Pro Arg Thr Phe Gly Gln Gly Thr Lys Val Glu Ile
                100                 105                 110
Lys
```

<210> SEQ ID NO 48
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

```
Gly Phe Ser Phe Ser Asp Phe Ala Met Ser
1               5                   10
```

<210> SEQ ID NO 49
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

```
Ala Thr Ile Gly Arg Val Ala Phe His Thr Tyr Tyr Pro Asp Ser Met
1               5                   10                  15
Lys Gly
```

```
<210> SEQ ID NO 50
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ala Arg His Arg Gly Phe Asp Val Gly His Phe Asp Phe
1               5                   10

<210> SEQ ID NO 51
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Arg Ser Ser Glu Thr Leu Val His Ser Ser Gly Asn Thr Tyr Leu Glu
1               5                   10                  15

<210> SEQ ID NO 52
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Arg Val Ser Asn Arg Phe Ser
1               5

<210> SEQ ID NO 53
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Phe Gln Gly Ser Phe Asn Pro Leu Thr
1               5

<210> SEQ ID NO 54
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45
```

```
Ala Thr Ile Gly Arg Val Ala Phe His Thr Tyr Tyr Pro Asp Ser Met
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg His Arg Gly Phe Asp Val Gly His Phe Asp Phe Trp Gly Gln
            100                 105                 110

Gly Thr Leu Val Thr Val Ser Ser
            115                 120

<210> SEQ ID NO 55
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Asp Ile Gln Met Thr Gln Ser Pro Ser Ser Leu Ser Ala Ser Val Gly
  1               5                  10                  15

Asp Arg Val Thr Ile Thr Cys Arg Ser Ser Glu Thr Leu Val His Ser
             20                  25                  30

Ser Gly Asn Thr Tyr Leu Glu Trp Tyr Gln Gln Lys Pro Gly Lys Ala
         35                  40                  45

Pro Lys Leu Leu Ile Tyr Arg Val Ser Asn Arg Phe Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Phe Gln Gly
             85                  90                  95

Ser Phe Asn Pro Leu Thr Phe Gly Gln Gly Thr Lys Val Glu Ile Lys
            100                 105                 110

Arg

<210> SEQ ID NO 56
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Glu Val Gln Leu Val Glu Ser Gly Gly Gly Leu Val Gln Pro Gly Gly
  1               5                  10                  15

Ser Leu Arg Leu Ser Cys Ala Ala Ser Gly Tyr Thr Phe Ser Ser Tyr
             20                  25                  30

Trp Ile Glu Trp Val Arg Gln Ala Pro Gly Lys Gly Leu Glu Trp Ile
         35                  40                  45

Gly Glu Ile Leu Pro Gly Gly Gly Asp Thr Asn Tyr Asn Glu Ile Phe
 50                  55                  60

Lys Gly Arg Ala Thr Phe Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
```

```
                85                  90                  95
Thr Arg Arg Val Pro Ile Arg Leu Asp Tyr Trp Gly Gln Gly Thr Leu
            100                 105                 110

Val Thr Val Ser Ser
        115

<210> SEQ ID NO 57
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

<210> SEQ ID NO 58
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Tyr Thr Phe Ser Ser Tyr Trp Ile Glu
1               5                   10

<210> SEQ ID NO 59
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gly Glu Ile Leu Pro Gly Gly Gly Asp Thr Asn Tyr Asn Glu Ile Phe
1               5                   10                  15

Lys Gly

<210> SEQ ID NO 60
<211> LENGTH: 10
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 60

Thr Arg Arg Val Pro Ile Arg Leu Asp Tyr
1               5                   10

<210> SEQ ID NO 61
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Lys Ala Ser Gln Ser Val Asp Tyr Glu Gly Asp Ser Phe Leu Asn
1               5                   10                  15

<210> SEQ ID NO 62
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ala Ala Ser Asn Leu Glu Ser
1               5

<210> SEQ ID NO 63
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gln Gln Ser Asn Glu Asp Pro Leu Thr
1               5

<210> SEQ ID NO 64
<211> LENGTH: 1255
<212> TYPE: PRT
<213> ORGANISM: Homo sapiens

<400> SEQUENCE: 64

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95
```

-continued

```
Gln Arg Leu Arg Ile Val Arg Gly Thr Gln Leu Phe Glu Asp Asn Tyr
                100                 105                 110

Ala Leu Ala Val Leu Asp Asn Gly Asp Pro Leu Asn Thr Thr Pro
            115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
                195                 200                 205

Ser Glu Asp Cys Gln Ser Leu Thr Arg Thr Val Cys Ala Gly Gly Cys
        210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
                275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510
```

```
Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
```

```
              930              935              940
Pro Ile Cys Thr Ile Asp Val Tyr Met Ile Met Val Lys Cys Trp Met
945                  950              955                  960

Ile Asp Ser Glu Cys Arg Pro Arg Phe Arg Glu Leu Val Ser Glu Phe
                965              970              975

Ser Arg Met Ala Arg Asp Pro Gln Arg Phe Val Val Ile Gln Asn Glu
            980              985              990

Asp Leu Gly Pro Ala Ser Pro Leu Asp Ser Thr Phe Tyr Arg Ser Leu
        995              1000             1005

Leu Glu Asp Asp Asp Met Gly Asp Leu Val Asp Ala Glu Glu Tyr
    1010            1015             1020

Leu Val Pro Gln Gln Gly Phe Phe Cys Pro Asp Pro Ala Pro Gly
    1025            1030             1035

Ala Gly Gly Met Val His His Arg His Arg Ser Ser Ser Thr Arg
    1040            1045             1050

Ser Gly Gly Gly Asp Leu Thr Leu Gly Leu Glu Pro Ser Glu Glu
    1055            1060             1065

Glu Ala Pro Arg Ser Pro Leu Ala Pro Ser Glu Gly Ala Gly Ser
    1070            1075             1080

Asp Val Phe Asp Gly Asp Leu Gly Met Gly Ala Ala Lys Gly Leu
    1085            1090             1095

Gln Ser Leu Pro Thr His Asp Pro Ser Pro Leu Gln Arg Tyr Ser
    1100            1105             1110

Glu Asp Pro Thr Val Pro Leu Pro Ser Glu Thr Asp Gly Tyr Val
    1115            1120             1125

Ala Pro Leu Thr Cys Ser Pro Gln Pro Glu Tyr Val Asn Gln Pro
    1130            1135             1140

Asp Val Arg Pro Gln Pro Pro Ser Pro Arg Glu Gly Pro Leu Pro
    1145            1150             1155

Ala Ala Arg Pro Ala Gly Ala Thr Leu Glu Arg Pro Lys Thr Leu
    1160            1165             1170

Ser Pro Gly Lys Asn Gly Val Val Lys Asp Val Phe Ala Phe Gly
    1175            1180             1185

Gly Ala Val Glu Asn Pro Glu Tyr Leu Thr Pro Gln Gly Gly Ala
    1190            1195             1200

Ala Pro Gln Pro His Pro Pro Ala Phe Ser Pro Ala Phe Asp
    1205            1210             1215

Asn Leu Tyr Tyr Trp Asp Gln Asp Pro Pro Glu Arg Gly Ala Pro
    1220            1225             1230

Pro Ser Thr Phe Lys Gly Thr Pro Thr Ala Glu Asn Pro Glu Tyr
    1235            1240             1245

Leu Gly Leu Asp Val Pro Val
    1250            1255

<210> SEQ ID NO 65
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
tatagaaatc tata                                                      14
```

<210> SEQ ID NO 66
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 66
tatagatttc tata                                                                 14

<210> SEQ ID NO 67
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 67
tatagaaatg tata                                                                 14

<210> SEQ ID NO 68
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 68
tatacatttc tata                                                                 14

<210> SEQ ID NO 69
<211> LENGTH: 7
<212> TYPE: PRT
<213> ORGANISM: Homo sapiens

<400> SEQUENCE: 69

Met Ala Glu Ala Ile Thr Tyr
1               5

<210> SEQ ID NO 70
<211> LENGTH: 7
<212> TYPE: PRT
<213> ORGANISM: Homo sapiens

<400> SEQUENCE: 70

Thr Ala Phe Arg Phe Pro Asp
1               5

PYRROLOBENZODIAZEPINE ANTIBODY DRUG CONJUGATES AND METHODS OF USE

CROSS REFERENCE TO RELATED APPLICATIONS

This divisional application claims the benefit of priority to U.S. application Ser. No. 15/281,830, filed 30 Sep. 2016, which claims the benefit of priority to U.S. Provisional Application No. 62/236,429, filed 2 Oct. 2015, each of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Sep. 30, 2016, is named P32858_US_1_Sequence_Listing.txt and is 56,525 bytes in size.

FIELD OF THE INVENTION

The invention relates generally to antibodies conjugated to pyrrolobenzodiazepine intermediates to form antibody-drug conjugates with therapeutic or diagnostic applications. The antibodies may be engineered with free cysteine amino acids, reactive for conjugation with the pyrrolobenzodiazepine intermediates. The invention also relates to methods of using the antibody-drug conjugate compounds for treatment of hyperproliferative disorders, such as cancer, or in vitro, in situ, and in vivo diagnosis of such disorders.

BACKGROUND OF THE INVENTION

Antibody drug conjugates (ADC) are targeted chemotherapeutic molecules combining the properties of both antibodies and cytotoxic drugs by targeting potent cytotoxic drugs to antigen-expressing tumor cells, internalization, and release of drug, thereby enhancing their anti-tumor activity (Carter, P. and Senter, P. (2008) The Cancer Jour. 14(3):154-169). Successful ADC development for a given target antigen depends on optimization of antibody selection, linker design and stability, cytotoxic drug potency and mode of drug and linker conjugation to the antibody (Dosio et al (2011) Toxins, 3:848-883; Polakis, P. (2005) Current Opinion in Pharmacology 5:382-387).

Certain pyrrolobenzodiazepine (PBD) compounds have the ability to recognize and bond to specific sequences of DNA; the preferred sequence is PuGPu (Pu=purine, such as adenine A and guanine G). The first PBD antitumor antibiotic, anthramycin, was discovered in 1965 (Leimgruber, et al., J. Am. Chem. Soc., 87:5793-5795 (1965); Leimgruber, et al., J. Am. Chem. Soc., 87, 5791-5793 (1965)). Since then, a number of naturally occurring PBD and analogues have been reported and described (Thurston, et al., Chem. Rev. 1994, 433-465 (1994); Antonow, D. and Thurston, D. E., (2011) Chem. Rev. 111 (4):2815-2864). Family members include abbeymycin (Hochlowski, et al., (1987) J. Antibiotics, 40:145-148), chicamycin (Konishi, et al., (1984) J. Antibiotics, 37:200-206), Thurston, et al., (1990) Chem. Brit., 26:767-772; Bose, et al., (1992) Tetrahedron, 48:751-758), mazethramycin (Kuminoto, et al., J. Antibiotics, 33, 665-667 (1980)), neothramycins A and B (Takeuchi, et al., J. Antibiotics, 29, 93-96 (1976)), porothramycin (Tsunakawa, et al., (1988) J. Antibiotics, 41:1366-1373), prothracarcin (Shimizu, et al, J. Antibiotics, (1982) 29:2492-2503; Langley and Thurston, (1987) J. Org. Chem., 52:91-97), sibanomicin, DC-102 (Hara, et al., (1988) J. Antibiotics, 41:702-704; Itoh, et al., J. Antibiotics, (1988) 41:1281-1284), sibiromycin (Leber, et al., (1988) J. Am. Chem. Soc., 110:2992-2993) and tomamycin (Arima, et al., (1972) J. Antibiotics, 25:437-444).

Pyrrolobenzodiazepines have the general structure:

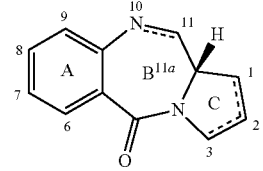

and differ in the number, type and position of substituents, in both the aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position, the electrophilic center responsible for alkylating DNA. All of the known natural products have an (S)-configuration at the chiral C11a position which provides them with a right-handed twist when viewed from the C ring towards the A ring and determines the three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) Acc. Chem. Res., 19:230-237). The ability of PBD to form an adduct in the minor groove, enables them to interfere with DNA processing, hence their use as antitumor agents. Pyrrolobenzodiazepine dimer compounds where two pyrrolobenzodiazepine structures are covalently attached by a linker through the C8 position of the A rings may dialkylate and crosslink double-stranded DNA (WO 2005/085251).

Pyrrolobenzodiazepine compounds can be employed as prodrugs by protecting them at the N10 position with a nitrogen protecting group, such as carbamate, which is removable in vivo (WO 2000/12507; WO 2005/023814). The protecting groups are removable from the N10 position of the PBD moiety to leave an N10-C11 imine bond. A range of protecting groups is described, including groups that can be cleaved by the action of enzymes.

Antibody-drug conjugates where the pyrrolobenzodiazepine (PBD) dimer is linked through the N10 position to an antibody specific for a tumor-associated antigen have in vitro and in vivo efficacy against tumor cells (WO 2011/130598). Antibody-drug conjugates with PBD dimer drug moieties having linker groups for connection to a cell binding agent, such as an antibody, via the bridge ("tether") linking the monomer PBD units of the dimer have been described (WO 2007/085930). Antibody-drug conjugates with PBD dimer drug moieties having amide and amine groups in the B ring at N10-C11 position have been described (WO 2014/096368; WO 2013/177481; WO 2012/112708). Antibody drug conjugates comprising dialkylator pyrrolobenzodiazepine (PBD) dimer drug moieties linked at the N10 of the PBD by a disulfide linkage to antibodies have been described (WO2013/055987; Gregson et al. (2001) J. Med. Chem. 44:1161-1174).

SUMMARY

The invention includes a linker-drug intermediate of Formula I:

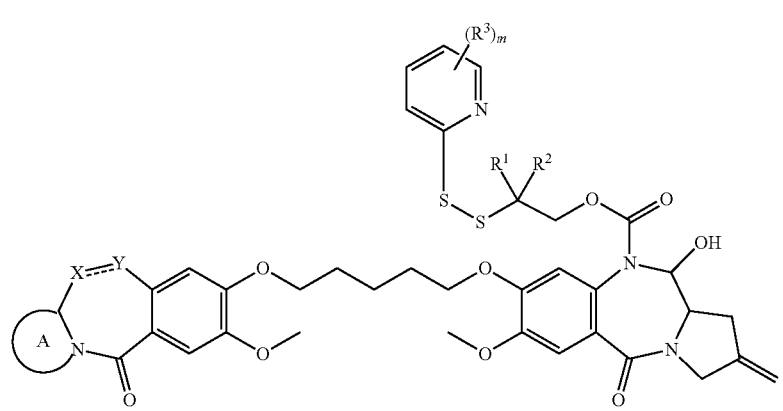

wherein X══Y is selected from CH$_2$—CH$_2$, CH═CH, C(═O)—NH, or CH$_2$—NH;

A is a 5-membered or 6-membered heterocyclic ring, optionally substituted with a group selected from F, C$_1$-C$_6$ alkyl, or ═C(R)$_2$ where R is independently selected from H, F, C$_1$-C$_6$ alkyl, or C$_1$-C$_6$ fluoroalkyl;

R$^1$ and R$^2$ are independently selected from H or C$_1$-C$_6$ alkyl, or R$^1$ and R$^2$ form a 3, 4, 5, or 6-membered cycloalkyl or heterocyclyl group;

R$^3$ is independently selected from NO$_2$, Cl, F, CN, CO$_2$H or Br; and m is 0, 1 or 2.

The invention includes monoalkylator pyrrolobenzodiazepine drug moieties covalently attached to antibodies by a disulfide linker to form antibody-drug conjugate (ADC) compounds with therapeutic or diagnostic applications.

Another aspect of the invention is an antibody-drug conjugate compound of Formula II:

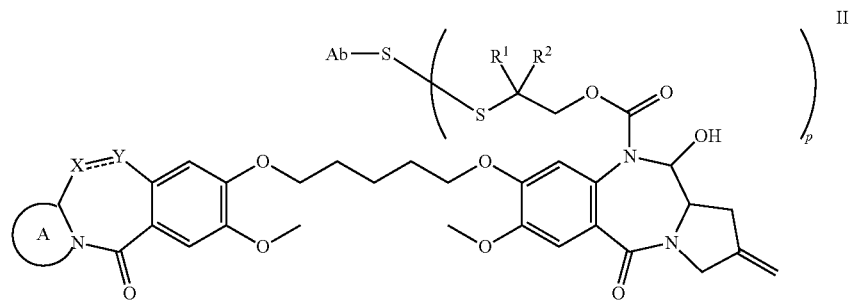

or a pharmaceutically acceptable salt thereof, wherein:

X══Y is selected from CH$_2$—CH$_2$, CH$_2$—C(═O), CH═CH, or CH$_2$—NH;

A is a 5-membered or 6-membered heterocyclic ring, optionally substituted with a group selected from F, C$_1$-C$_6$ alkyl, or ═C(R)$_2$ where R is independently selected from H, F, C$_1$-C$_6$ alkyl, or C$_1$-C$_6$ fluoroalkyl;

R$^1$ and R$^2$ are independently selected from H or C$_1$-C$_6$ alkyl, or R$^1$ and R$^2$ form a 3, 4, 5, or 6-membered cycloalkyl or heterocyclyl group;

p is an integer from 1 to 8; and

Ab is an antibody.

In an exemplary embodiment, the antibody binds to one or more tumor-associated antigens or cell-surface receptors selected from (1)-(53):

(1) BMPR1B (bone morphogenetic protein receptor-type IB);

(2) E16 (LAT1, SLC7A5);

(3) STEAP1 (six transmembrane epithelial antigen of prostate);

(4) MUC16 (0772P, CA125);

(5) MPF (MPF, MSLN, SMR, megakaryocyte potentiating factor, mesothelin);

(6) Napi2b (NAPI-3B, NPTIIb, SLC34A2, solute carrier family 34 (sodium phosphate), member 2, type II sodium-dependent phosphate transporter 3b);

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);

(8) PSCA hlg (2700050C12Rik, C530008O16Rik, RIKEN cDNA 2700050C12, RIKEN cDNA 2700050C12 gene);

(9) ETBR (Endothelin type B receptor);

(10) MSG783 (RNF124, hypothetical protein FLJ20315);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);

(12) TrpM4 (BR22450, FLJ20041, TRPM4, TRPM4B, transient receptor potential cation channel, subfamily M, member 4);

(13) CRIPTO (CR, CR1, CRGF, CRIPTO, TDGF1, teratocarcinoma-derived growth factor);

(14) CD21 (CR2 (Complement receptor 2) or C3DR (C3d/Epstein Barr virus receptor) or Hs 73792);

(15) CD79b (CD79B, CD79β, IGb (immunoglobulin-associated beta), B29);

(16) FcRH2 (IFGP4, IRTA4, SPAP1A (SH2 domain containing phosphatase anchor protein 1a), SPAP1B, SPAP1C);

(17) HER2;

(18) NCA;

(19) MDP;

(20) IL20Rα;

(21) Brevican;

(22) EphB2R;

(23) ASLG659;

(24) PSCA;

(25) GEDA;

(26) BAFF-R (B cell-activating factor receptor, BLyS receptor 3, BR3);

(27) CD22 (B-cell receptor CD22-B isoform);

(28) CD79a (CD79A, CD79α, immunoglobulin-associated alpha);

(29) CXCR5 (Burkitt's lymphoma receptor 1);

(30) HLA-DOB (Beta subunit of MHC class II molecule (Ia antigen));

(31) P2X5 (Purinergic receptor P2X ligand-gated ion channel 5);

(32) CD72 (B-cell differentiation antigen CD72, Lyb-2);

(33) LY64 (Lymphocyte antigen 64 (RP105), type I membrane protein of the leucine rich repeat (LRR) family);

(34) FcRH1 (Fc receptor-like protein 1);

(35) FcRH5 (IRTA2, Immunoglobulin superfamily receptor translocation associated 2);

(36) TENB2 (putative transmembrane proteoglycan);

(37) PMEL17 (silver honmolog; SILV; D12S53E; PMEL17; SI; SIL);

(38) TMEFF1 (transmembrane protein with EGF-like and two follistatin-like domains 1; Tomoregulin-1);

(39) GDNF-Ra1 (GDNF family receptor alpha 1; GFRA1; GDNFR; GDNFRA; RETL1; TRNR1; RET1L; GDNFR-alpha1; GFR-ALPHA-1);

(40) Ly6E (lymphocyte antigen 6 complex, locus E; Ly67, RIG-E, SCA-2, TSA-1);

(41) TMEM46 (shisa homolog 2 (*Xenopus laevis*); SHISA2);

(42) Ly6G6D (lymphocyte antigen 6 complex, locus G6G; Ly6-D, MEGT1);

(43) LGR5 (leucine-rich repeat-containing G protein-coupled receptor 5; GPR49, GPR67);

(44) RET (ret proto-oncogene; MEN2A; HSCR1; MEN2B; MTC1; PTC; CDHF12; Hs.168114; RET51; RET-ELE1);

(45) LY6K (lymphocyte antigen 6 complex, locus K; LY6K; HSJ001348; FLJ35226);

(46) GPR19 (G protein-coupled receptor 19; Mm.4787);

(47) GPR54 (KISS1 receptor; KISS1R; GPR54; HOT7T175; AXOR12);

(48) ASPHD1 (aspartate beta-hydroxylase domain containing 1; LOC253982);

(49) Tyrosinase (TYR; OCAIA; OCA1A; tyrosinase; SHEP3);

(50) TMEM118 (ring finger protein, transmembrane 2; RNFT2; FLJ14627);

(51) GPR172A (G protein-coupled receptor 172A; GPCR41; FLJ11856; D15Ertd747e);

(52) CD33; or

(53) CLL-1.

Another aspect of the invention is a pharmaceutical composition comprising an antibody-drug conjugate compound of Formula II, and a pharmaceutically acceptable diluent, carrier or excipient.

Another aspect of the invention is the use of an antibody-drug conjugate compound of Formula II in the manufacture of a medicament for the treatment of cancer in a mammal.

Another aspect of the invention is a method of treating cancer by administering to a patient a pharmaceutical composition comprising an antibody-drug conjugate compound of Formula II.

Another aspect of the invention is a method of making an antibody-drug conjugate compound of Formula II.

Another aspect of the invention is an article of manufacture comprising a pharmaceutical composition comprising an antibody-drug conjugate compound of Formula II, a container, and a package insert or label indicating that the pharmaceutical composition can be used to treat cancer.

BRIEF DESCRIPTION OF THE DRAWINGS

FIG. 3 shows the efficacy of antibody-drug conjugates in a plot of the in vivo fitted tumor volume change over time in the Bjab-luc xenograft model in CB-17 Fox Chase SCID mice, dosed IV once with the following:
1) Vehicle (Histidine Buffer #8 HisAc 20 mM, Sucrose 240 mM, TW-20 0.02%, pH 5.5), 100 μL (microliter)
2) Thio Hu anti-CD22 10F4v3 LC K149C-(CLD-1), ADC-202, 0.1 mg/kg 3) Thio Hu anti-CD22 10F4v3 LC K149C-(CLD-1), ADC-202, 0.2 mg/kg
4) Thio Hu anti-CD22 10F4v3 LC K149C-(C-LD1), ADC-202, 0.4 mg/kg
5) Thio Hu anti-CD22 10F4v3 LC K149C-(LD-51) monoamide ADC-105, 1 mg/kg
6) Thio Hu anti-CD22 10F4v3 LC K149C-(LD-51) monoamide ADC-105, 2 mg/kg
7) Thio Hu anti-CD22 10F4v3 LC K149C-(LD-51) monoamide ADC-105, 4 mg/kg
8) Thio Hu anti-CD22 10F4v3 LC K149C-(LD-51) monoamide ADC-105, 8 mg/kg
9) Thio Hu anti-Her2 hu7C2 LC K149C-(CLD-1) ADC-201, 0.4 mg/kg
10) Thio Hu anti-Her2 hu7C2 LC K149C-(LD-51) monoamide ADC-104, 8 mg/kg
FIG. 5B shows the efficacy of antibody-drug conjugates in a plot of the in vivo fitted tumor volume change over time in HER2 KPL4 tumor model in scid beige mice, dosed IV once with the following:
1) Vehicle
2) Tmab-DM1, ADC-211, 1 mg/kg
3) Thio-Her2 hu7C2 LC-K149C-(LD-51) monoamide, ADC-106, 1 mg/kg
4) Thio-Her2 hu7C2 LC-K149C-(LD-51) monoamide, ADC-106, 5 mg/kg
5) Tmab-DM1, ADC-211, 1 mg/kg+Thio-Her2 hu7C2 LC-K149C-(LD-51) monoamide, ADC-106, 1 mg/kg
6) Tmab-DM1, ADC-211, 1 mg/kg+Thio-Her2 hu7C2 LC-K149C-(LD-51) monoamide, ADC-106, 5 mg/kg

FIG. 12 shows a comparison of mouse efficacy and cynomolgus monkey toxicology of a HER2 LC K149C LD-51 ADC with a HER2 LC K149C CLD-1 ADC.

DETAILED DESCRIPTION OF EXEMPLARY EMBODIMENTS

Figure 1A:
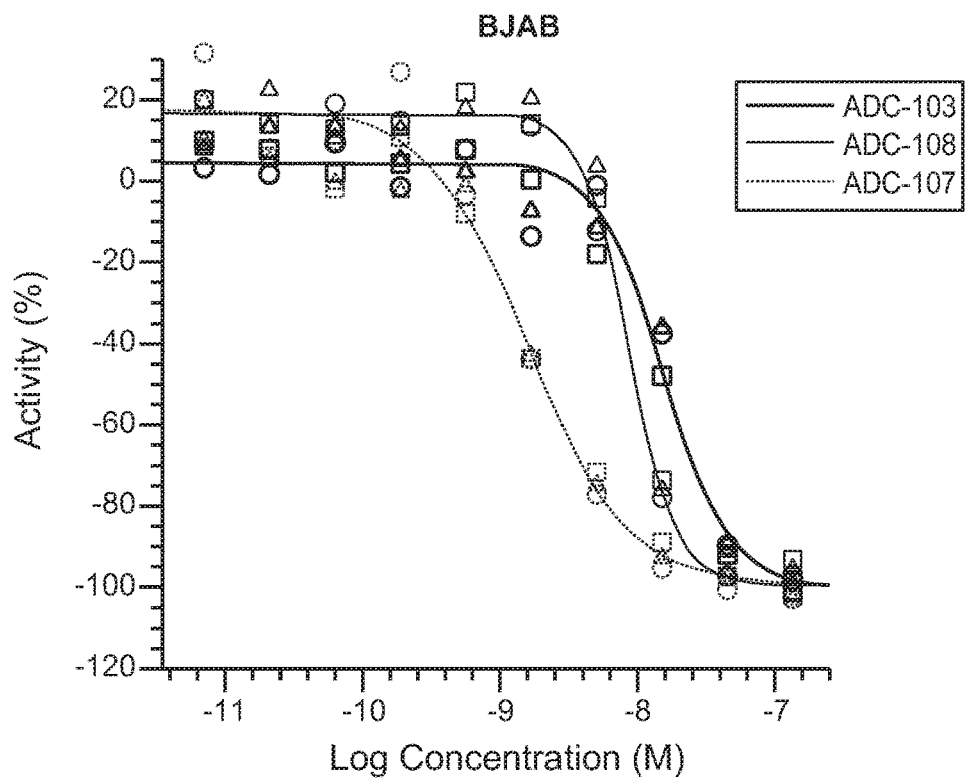
FIG. 1A shows a plot of in vitro cell viability of BJAB cells treated with ADC-107, ADC-103, and non-target control ADC-108.

Reference will now be made in detail to certain embodiments of the invention, examples of which are illustrated in the accompanying structures and formulas. While the invention will be described in conjunction with the illustrated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

Unless defined otherwise, technical and scientific terms used herein have the same meaning as commonly understood by one of ordinary skill in the art to which this invention belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

Definitions

Unless stated otherwise, the following terms and phrases as used herein are intended to have the following meanings:

When trade names are used herein, applicants intend to independently include the trade name product formulation, the generic drug, and the active pharmaceutical ingredient(s) of the trade name product.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

In certain embodiments, an antibody as described herein has dissociation constant (Kd) of $\leq 1$ µM, $\leq 100$ nM, $\leq 10$ nM, $\leq 5$ nm, $\leq 4$ nM, $\leq 3$ nM, $\leq 2$ nM, $\leq 1$ nM, $\leq 0.1$ nM, $\leq 0.01$ nM, or $\leq 0.001$ nM (e.g., $10^{-8}$ M or less, e.g. from $10^{-8}$ M to $10^{-13}$ M, e.g., from $10^{-9}$ M to $10^{-13}$ M).

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The terms "cancer" and "cancerous" refer to or describe the physiological condition in mammals that is typically characterized by unregulated cell growth/proliferation. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "HER2-positive" cancer comprises cancer cells which have higher than normal levels of HER2. Examples of HER2-positive cancer include HER2-positive breast cancer and HER2-positive gastric cancer. Optionally, HER2-positive cancer has an immunohistochemistry (IHC) score of 2+ or 3+ and/or an in situ hybridization (ISH) amplification ratio ≥2.0.

The term "early stage breast cancer (EBC)" or "early breast cancer" is used herein to refer to breast cancer that has not spread beyond the breast or the axillary lymph nodes. This includes ductal carcinoma in situ and stage I, stage IIA, stage IIB, and stage IIIA breast cancers.

Reference to a tumor or cancer as a "Stage 0," "Stage I," "Stage II," "Stage III," or "Stage IV", and various sub-stages within this classification, indicates classification of the tumor or cancer using the Overall Stage Grouping or Roman Numeral Staging methods known in the art. Although the actual stage of the cancer is dependent on the type of cancer, in general, a Stage 0 cancer is an in situ lesion, a Stage I cancer is small localized tumor, a Stage II and III cancer is a local advanced tumor which exhibits involvement of the local lymph nodes, and a Stage IV cancer represents metastatic cancer. The specific stages for each type of tumor are known to the skilled clinician.

The term "metastatic breast cancer" means the state of breast cancer where the cancer cells are transmitted from the original site to one or more sites elsewhere in the body, by the blood vessels or lymphatics, to form one or more secondary tumors in one or more organs besides the breast.

An "advanced" cancer is one which has spread outside the site or organ of origin, either by local invasion or metastasis. Accordingly, the term "advanced" cancer includes both locally advanced and metastatic disease.

A "recurrent" cancer is one which has regrown, either at the initial site or at a distant site, after a response to initial therapy, such as surgery.

A "locally recurrent" cancer is cancer that returns after treatment in the same place as a previously treated cancer.

An "operable" or "resectable" cancer is cancer which is confined to the primary organ and suitable for surgery (resection).

A "non-resectable" or "unresectable" cancer is not able to be removed (resected) by surgery.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result. The effective amount of the drug for treating cancer may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g. as assessed by FOSI).

The term "epitope" refers to the particular site on an antigen molecule to which an antibody binds.

The "epitope 4D5" or "4D5 epitope" or "4D5" is the region in the extracellular domain of HER2 to which the antibody 4D5 (ATCC CRL 10463) and trastuzumab bind. This epitope is close to the transmembrane domain of HER2, and within domain IV of HER2. To screen for antibodies which bind to the 4D5 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 550 to about residue 610, inclusive, of HER2 (SEQ ID NO: 39).

The "epitope 2C4" or "2C4 epitope" is the region in the extracellular domain of HER2 to which the antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of HER2. Epitope 2C4 comprises residues from domain II in the extracellular domain of HER2. The 2C4 antibody and pertuzumab bind to the extracellular domain of HER2 at the junction of domains I, II and III (Franklin et al. *Cancer Cell* 5:317-328 (2004)).

Anti-HER2 murine antibody 7C2 binds to an epitope in domain I of HER2. See, e.g., PCT Publication No. WO 98/17797. This epitope is distinct from the epitope bound by trastuzumab, which binds to domain IV of HER2, and the epitope bound by pertuzumab, which binds to domain II of HER2. By binding domain IV, trastuzumab disrupts ligand-independent HER2-HER3 complexes, thereby inhibiting downstream signaling (e.g. PI3K/AKT). In contrast, pertuzumab binding to domain II prevents ligand-driven HER2 interaction with other HER family members (e.g. HER3, HER1 or HER4), thus also preventing downstream signal transduction. Binding of MAb 7C2 to domain I does not result in interference of trastuzumab or pertuzumab binding to domains IV and II, respectively, thereby offering the potential of combining a MAb 7C2 ADC with trastuzumab, trastuzumab emtansine (T-DM-1), and/or pertuzumab. Murine antibody 7C2, 7C2.B9, is described in PCT Publication No. WO 98/17797. An anti-HER2 7C2 humanized antibody is disclosed in WO2016/040723A1.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest, Fifth Edition, NIH Publication* 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences*

*of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

A "patient" or "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human. In some embodiments, the patient may be a "cancer patient," i.e. one who is suffering or at risk for suffering from one or more symptoms of cancer, in particular gastric or breast cancer.

A "patient population" refers to a group of cancer patients. Such populations can be used to demonstrate statistically significant efficacy and/or safety of a drug.

A "relapsed" patient is one who has signs or symptoms of cancer after remission. Optionally, the patient has relapsed after adjuvant or neoadjuvant therapy.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

"Neoadjuvant therapy" or "preoperative therapy" herein refers to therapy given prior to surgery. The goal of neoadjuvant therapy is to provide immediate systemic treatment, potentially eradicating micrometastases that would otherwise proliferate if the standard sequence of surgery followed by systemic therapy were followed. Neoadjuvant therapy may also help to reduce tumor size thereby allowing complete resection of initially unresectable tumors or preserving portions of the organ and its functions. Furthermore, neoadjuvant therapy permits an in vivo assessment of drug efficacy, which may guide the choice of subsequent treatments.

"Adjuvant therapy" herein refers to therapy given after definitive surgery, where no evidence of residual disease can be detected, so as to reduce the risk of disease recurrence. The goal of adjuvant therapy is to prevent recurrence of the cancer, and therefore to reduce the chance of cancer-related death. Adjuvant therapy herein specifically excludes neoadjuvant therapy.

"Definitive surgery" is used as that term is used within the medical community. Definitive surgery includes, for example, procedures, surgical or otherwise, that result in removal or resection of the tumor, including those that result in the removal or resection of all grossly visible tumor. Definitive surgery includes, for example, complete or curative resection or complete gross resection of the tumor. Definitive surgery includes procedures that occur in one or more stages, and includes, for example, multi-stage surgical procedures where one or more surgical or other procedures are performed prior to resection of the tumor. Definitive surgery includes procedures to remove or resect the tumor including involved organs, parts of organs and tissues, as well as surrounding organs, such as lymph nodes, parts of organs, or tissues. Removal may be incomplete such that tumor cells might remain even though undetected.

"Survival" refers to the patient remaining alive, and includes disease free survival (DFS), progression free survival (PFS) and overall survival (OS). Survival can be estimated by the Kaplan-Meier method, and any differences in survival are computed using the stratified log-rank test.

"Progression-Free Survival" (PFS) is the time from the first day of treatment to documented disease progression (including isolated CNS progression) or death from any cause on study, whichever occurs first.

"Disease free survival (DFS)" refers to the patient remaining alive, without return of the cancer, for a defined period of time such as about 1 year, about 2 years, about 3 years, about 4 years, about 5 years, about 10 years, etc., from initiation of treatment or from initial diagnosis. In one aspect of the invention, DFS is analyzed according to the intent-to-treat principle, i.e., patients are evaluated on the basis of their assigned therapy. The events used in the analysis of DFS can include local, regional and distant recurrence of cancer, occurrence of secondary cancer, and death from any cause in patients without a prior event (e.g, breast cancer recurrence or second primary cancer).

"Overall survival" refers to the patient remaining alive for a defined period of time, such as about 1 year, about 2 years, about 3 years, about 4 years, about 5 years, about 10 years, etc., from initiation of treatment or from initial diagnosis. In the studies underlying the invention the event used for survival analysis was death from any cause.

By "extending survival" is meant increasing DFS and/or OS in a treated patient relative to an untreated patient, or relative to a control treatment protocol. Survival is monitored for at least about six months, or at least about 1 year, or at least about 2 years, or at least about 3 years, or at least about 4 years, or at least about 5 years, or at least about 10 years, etc., following the initiation of treatment or following the initial diagnosis.

By "monotherapy" is meant a therapeutic regimen that includes only a single therapeutic agent for the treatment of the cancer or tumor during the course of the treatment period.

By "maintenance therapy" is meant a therapeutic regimen that is given to reduce the likelihood of disease recurrence or progression. Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "HER2," as used herein, refers to any native, mature HER2 which results from processing of a HER2 precursor protein in a cell. The term includes HER2 from any vertebrate source, including mammals such as primates (e.g. humans and cynomolgus monkeys) and rodents (e.g., mice and rats), unless otherwise indicated. The term also includes naturally occurring variants of HER2, e.g., splice variants or allelic variants. The amino acid sequence of an exemplary human HER2 precursor protein, with signal sequence (with signal sequence, amino acids 1-22) is shown in SEQ ID NO: 64. The amino acid sequence of an exemplary mature human HER2 is amino acids 23-1255 of SEQ ID NO: 64.

The term "HER2-positive cell" refers to a cell that expresses HER2 on its surface.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

A "vial" is a container suitable for holding a liquid or lyophilized preparation. In one embodiment, the vial is a single-use vial, e.g. a 20-cc single-use vial with a stopper.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

By "co-administering" is meant intravenously administering two (or more) drugs during the same administration, rather than sequential infusions of the two or more drugs. Generally, this will involve combining the two (or more) drugs into the same IV bag prior to co-administration thereof.

A drug that is administered "concurrently" with one or more other drugs is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethyl enemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotri ethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies including anti-interferon-alpha, -beta, or -gamma antibodies, anti-tumor necrosis factor (TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists (such as ACTEMRA™ (tocilizumab)); anti-LFA-1 antibodies, including anti-CD 11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990); streptokinase; transforming growth factor-beta (TGF-beta); streptodornase; RNA or DNA from the host; FK506; RS-61443; chlorambucil; deoxyspergualin; rapamycin; T-cell receptor (Cohen et al., U.S. Pat. No. 5,114,721); T-cell receptor fragments (Offner et al., *Science,* 251: 430-432 (1991); WO 90/11294; laneway, *Nature,* 341: 482 (1989); and WO 91/01133); BAFF antagonists such as BAFF antibodies and BR3 antibodies and zTNF4 antagonists (for review, see Mackay and Mackay, *Trends Immunol.,* 23:113-5 (2002) and see also definition below); biologic agents that interfere with T cell helper signals, such as anti-CD40 receptor or anti-CD40 ligand (CD154), including blocking antibodies to CD40-CD40 ligand (e.g., Durie et al., *Science,* 261: 1328-30 (1993); Mohan et al., *J. Immunol.,* 154: 1470-80 (1995)) and CTLA4-Ig (Finck et al., *Science,* 265: 1225-7 (1994)); and T-cell receptor antibodies (EP 340,109) such as T10B9. Some preferred immunosuppressive agents herein include cyclophosphamide, chlorambucil, azathioprine, leflunomide, MMF, or methotrexate.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (lambrolizumab) described herein. In another specific aspect, a PD-1 binding antagonist is CT-011 (pidilizumab) described herein. In another specific aspect, a PD-1 binding antagonist is AMP-224 described herein.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MPDL3280A described herein. In still another specific aspect, an anti-PD-L1 antibody is MEDI4736 described herein.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m2 dose, but rather as an absolute amount of the therapeutic agent.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks, preferably every 3 weeks.

"Infusion" or "infusing" refers to the introduction of a drug-containing solution into the body through a vein for therapeutic purposes. Generally, this is achieved via an intravenous (IV) bag.

An "intravenous bag" or "IV bag" is a bag that can hold a solution which can be administered via the vein of a patient. In one embodiment, the solution is a saline solution (e.g. about 0.9% or about 0.45% NaCl). Optionally, the IV bag is formed from polyolefin or polyvinal chloride.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

A "free cysteine amino acid" refers to a cysteine amino acid residue which has been engineered into a parent antibody, has a thiol functional group (—SH), and is not paired as an intramolecular or intermolecular disulfide bridge.

"Linker", "Linker Unit", or "link" means a chemical moiety comprising a chain of atoms that covalently attaches an antibody to a drug moiety.

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of any length from one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of any length from one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of any length from two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of any length from two to eight carbon atoms ($C_2$-$C_8$) with at least one site of unsaturation, i.e., a carbon-carbon, $sp^2$ double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of any length from two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of any length from two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, 1-methyl-1H-benzo[d]imidazole, [1,2,4]triazolo[1,5-a]pyridine, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of an antibody-drug conjugate (ADC). Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis- (2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The following abbreviations are used herein and have the indicated definitions: BME is beta-mercaptoethanol, Boc is N-(t-butoxycarbonyl), cit is citrulline (2-amino-5-ureido pentanoic acid), DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, DMA is dimethylacetamide, DMAP is 4-dimethylaminopyridine, DME is ethyleneglycol dimethyl ether (or 1,2-dimethoxyethane), DMF is N,N-dimethylformamide, DMSO is dimethylsulfoxide, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN ($CH_3CN$) is acetonitrile, MeOH is methanol, Mtr is 4-anisyldiphenylmethyl (or 4-methoxytrityl), NHS is N-hydroxysuccinimide, PBS is phosphate-buffered saline (pH 7), PEG is polyethylene glycol or a unit of ethylene glycol ($—OCH_2CH_2—$), Ph is phenyl, Pnp is p-nitrophenyl, MC is 6-maleimidocaproyl, phe is L-phenylalanine, PyBrop is bromo tris-pyrrolidino phosphonium hexafluorophosphate, SEC is size-exclusion chromatography, Su is succinimide, TFA is trifluoroacetic acid, TLC is thin layer chromatography, UV is ultraviolet, and val is valine.

Figure 4:
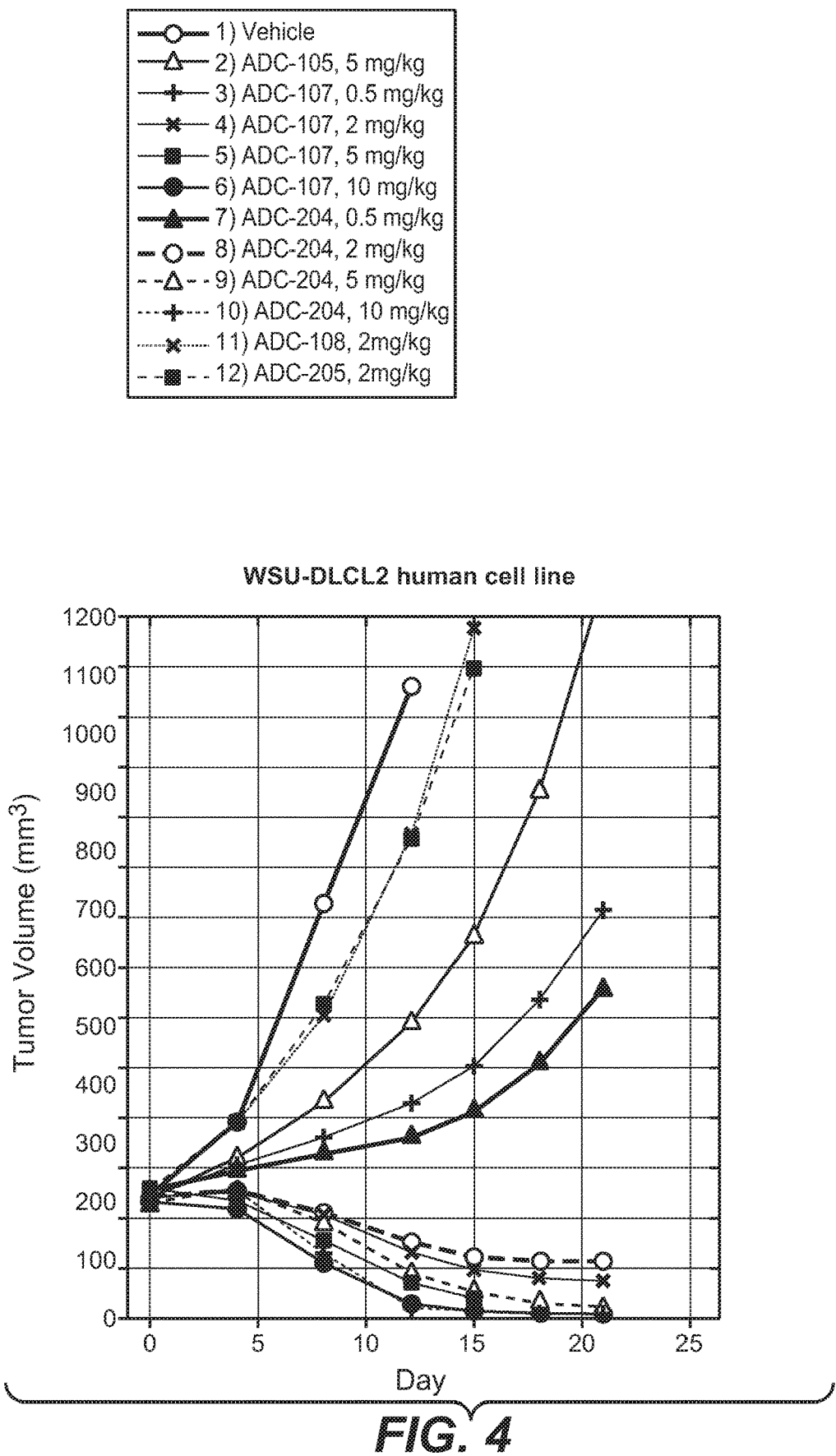
FIG. 4 shows the efficacy of antibody-drug conjugates in a plot of the in vivo fitted tumor volume change over time WSU-DLCL2 human cell line mouse model, dosed IV once with the following:
1) Vehicle (Histidine Buffer #8), 100 μL
2) Thio Hu anti-CD22 10F4v3 LC K149C-(LD-51) monoamide ADC-105, 5 mg/kg
3) Thio Hu anti-CD22 10F4v3 LC K149C-(LD-52) monoamine, ADC-107, 0.5 mg/kg
4) Thio Hu anti-CD22 10F4v3 LC K149C-(LD-52) monoamine, ADC-107, 2 mg/kg
5) Thio Hu anti-CD22 10F4v3 LC K149C-(LD-52) monoamine, ADC-107, 5 mg/kg
6) Thio Hu anti-CD22 10F4v3 LC K149C-(LD-52) monoamine, ADC-107, 10 mg/kg
7) Thio Hu anti-CD22 10F4v3 LC K149C-(CLD-4) monoamine, ADC-204, 0.5 mg/kg
8) Thio Hu anti-CD22 10F4v3 LC K149C-(CLD-4) monoamine, ADC-204, 2 mg/kg
9) Thio Hu anti-CD22 10F4v3 LC K149C-(CLD-4) monoamine, ADC-204, 5 mg/kg
10) Thio Hu anti-CD22 10F4v3 LC K149C-(CLD-4) monoamine, ADC-204, 10 mg/kg
11) Thio Hu anti-Her2 hu7C2 LC K149C-(LD-52) monoamine, ADC-108, 2 mg/kg
12) Thio Hu anti-Her2 hu7C2 LC K149C-(CLD-4) monoamine, ADC-205, 2 mg/kg

Tumor-Associated Antigens:

(1) BMPR1B (bone morphogenetic protein receptor-type IB, Genbank accession no. NM_001203) ten Dijke, P., et al Science 264 (5155):101-104 (1994), Oncogene 14 (11): 1377-1382 (1997)); WO2004063362 (Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377 (Page 349-350); WO200230268 (Claim 27; Page 376); WO200148204 (Example; FIG. 4) NP_001194 bone morphogenetic protein receptor, type IB/pid=NP_001194.1-Cross-references: MIM:603248; NP_001194.1; AY065994

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (Claim 12); WO2003016475 (Claim 1); WP200278524 (Example 2); WP200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150); NP_003477 solute carrier family 7 (cationic amino acid transporter, y+ system), member 5/pid=NP_003477.3—*Homo sapiens* Cross-references: MIM:600182; NP_003477.3; NM 015923; NM 003486_1

Figure 2:
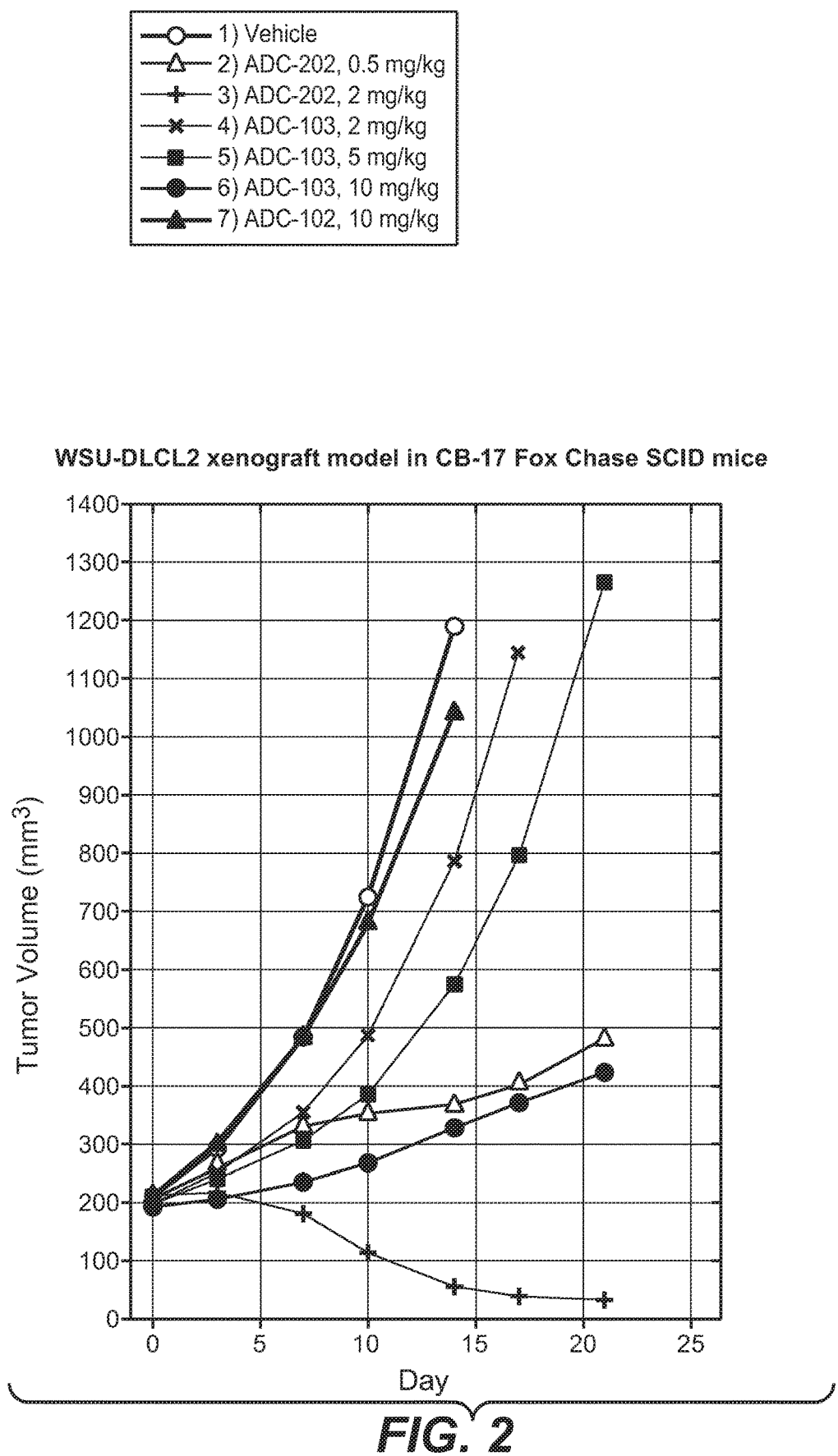
FIG. 2 shows the efficacy of antibody-drug conjugates in a plot of the in vivo fitted tumor volume change over time in the WSU-DLCL2 xenograft model in CB-17 Fox Chase SCID mice, dosed IV once with the following:
1) Vehicle (Histidine Buffer #8), 100 μL
2) Thio Hu anti-CD22 10F4v3 LC K149C-(CLD-1), ADC-202, 0.5 mg/kg
3) Thio Hu anti-CD22 10F4v3 LC K149C-(CLD-1), ADC-202, 2 mg/kg
4) Thio Hu anti-CD22 10F4v3 LC K149C-(LD-51), monoamide, ADC-103, 2 mg/kg
5) Thio Hu anti-CD22 10F4v3 LC K149C-(LD-51), monoamide, ADC-103, 5 mg/kg
6) Thio Hu anti-CD22 10F4v3 LC K149C-(LD-51), monoamide, ADC-103, 10 mg/kg
7) Thio Hu anti-Her2 (hu7C2) LC K149C-(LD-51), monoamide, ADC-102, 10 mg/kg

(3) STEAP1 (six transmembrane epithelial antigen of prostate, Genbank accession no. NM_012449) Cancer Res. 61 (15), 5857-5860 (2001), Hubert, R. S., et al (1999) Proc. Natl. Acad. Sci. U.S.A. 96 (25):14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate Cross-references: MIM:604415; NP_036581.1; NM_012449_1

(4) 0772P (CA125, MUC16, Genbank accession no. AF361486) J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); U.S. Pat. No. 798,959. Cross-references: GI:34501467; AAK74120.3; AF361486_1

(5) MPF (MPF, MSLN, SMR, megakaryocyte potentiating factor, mesothelin, Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57); Cross-references: MIM:601051; NP_005814.2; NM_005823_1

(6) Napi2b (Napi3b, NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22): 19665-19672 (2002), Genomics 62 (2):281-284 (1999), Feild, J. A., et al (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140); Cross-references: MIM:604217; NP_006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878) Nagase T., et al (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11); Accession: Q9P283; EMBL; AB040878; BAA95969.1. Genew; HGNC: 10737;

(8) PSCA hlg (2700050C12Rik, C530008O16Rik, RIKEN cDNA 2700050C12, RIKEN cDNA 2700050C12 gene, Genbank accession no. AY358628); Ross et al (2002) Cancer Res. 62:2546-2553; US2003129192 (Claim 2); US2004044180 (Claim 12); US2004044179 (Claim 11);

US2003096961 (Claim 11); US2003232056 (Example 5); WO2003105758 (Claim 12); US2003206918 (Example 5); EP1347046 (Claim 1); WO2003025148 (Claim 20); Cross-references: GI:37182378; AAQ88991.1; AY358628_1

Figure 6:
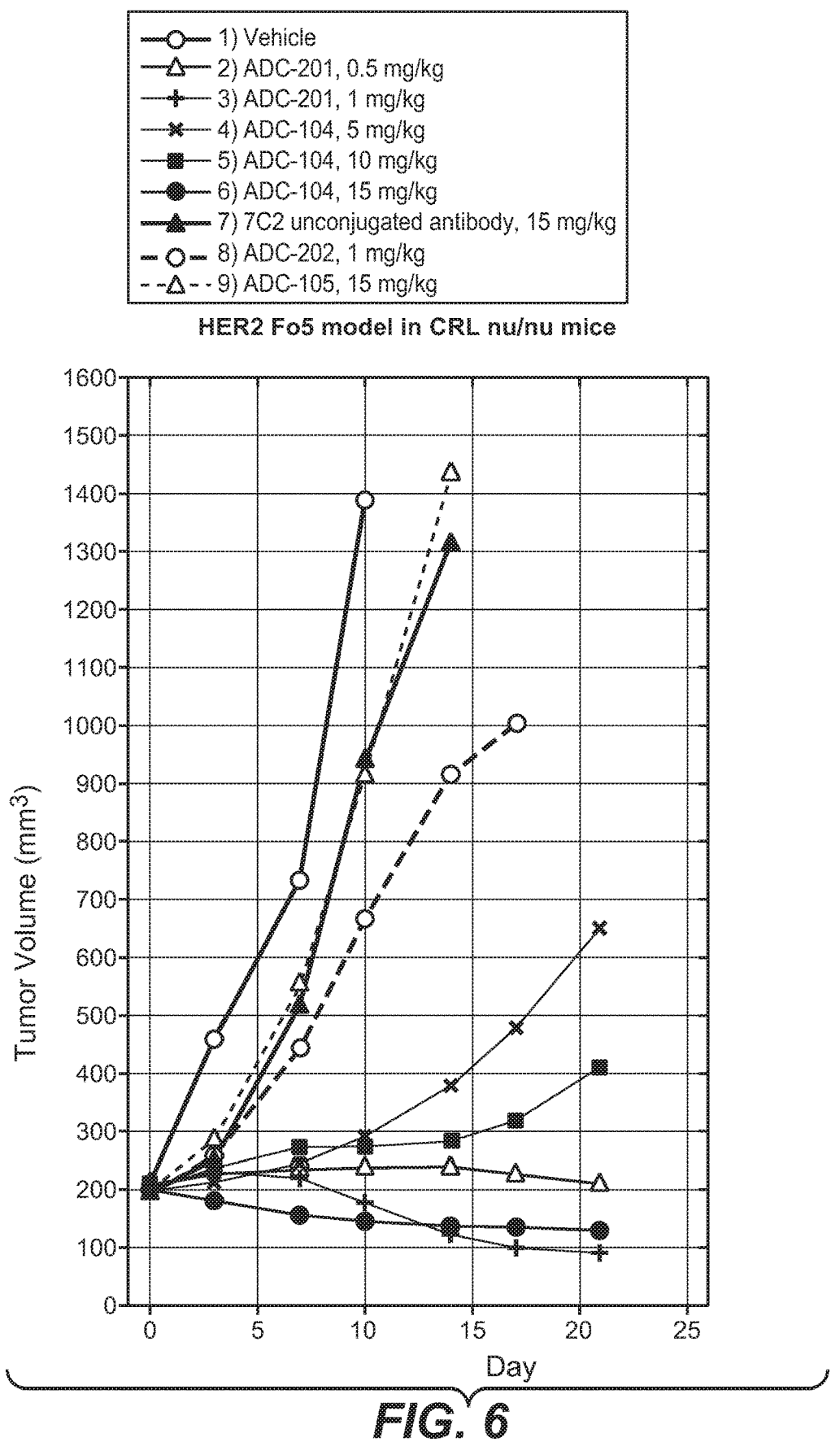
FIG. 6 shows the efficacy of antibody-drug conjugates in a plot of the in vivo fitted tumor volume change over time in HER2 Fo5 model in CRL nu/nu mice, dosed IV once with the following:
1) Vehicle (Histidine Buffer #8), 100 μL
2) Thio-Her2 hu7C2 LC-K149C-(CLD-1), ADC-201, 0.5 mg/kg
3) Thio-Her2 hu7C2 LC-K149C-(CLD-1), ADC-201, 1 mg/kg
4) Thio-Her2 hu7C2 LC-K149C-(LD-51), monoamide, ADC-104, 5 mg/kg
5) Thio-Her2 hu7C2 LC-K149C-(LD-51), monoamide, ADC-104, 10 mg/kg
6) Thio-Her2 hu7C2 LC-K149C-(LD-51), monoamide, ADC-104, 15 mg/kg
7) Thio-Her2 hu7C2 LC-K149C unconjugated antibody 15 mg/kg
8) Thio-CD22 LC-K149C-(CLD-1), ADC-202, 1 mg/kg
9) Thio-CD22 LC-K149C-(LD-51) monoamide ADC-105, 15 mg/kg

(9) ETBR (Endothelin type B receptor, Genbank accession no. AY275463); Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004;

(10) MSG783 (RNF124, hypothetical protein FLJ20315, Genbank accession no. NM_017763); WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6); Cross-references: LocusID:54894; NP_060233.2; NM_017763_1

Figure 10:
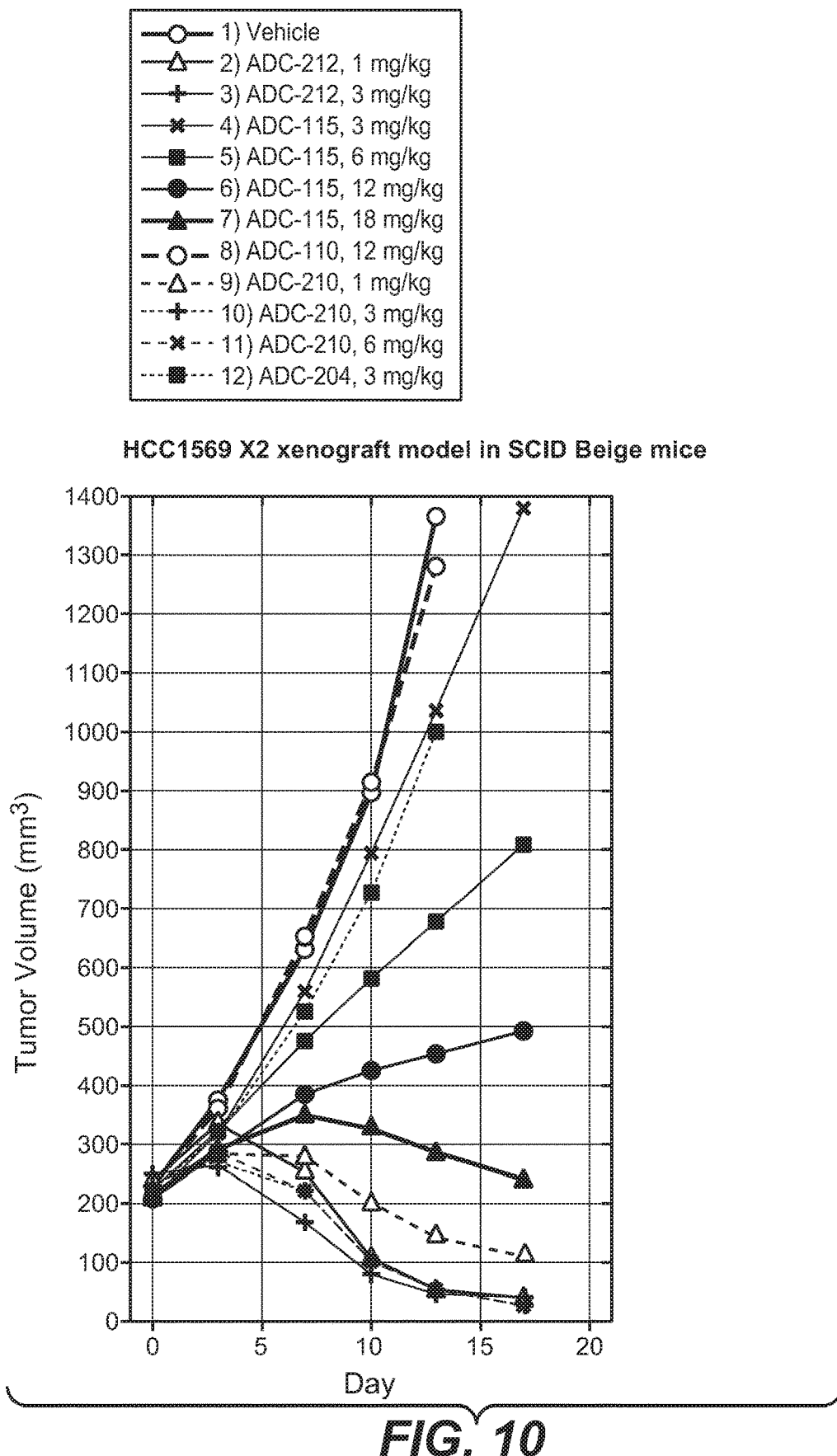
FIG. 10 shows the efficacy of antibody-drug conjugates in a plot of the in vivo fitted tumor volume change over time in HCC1569X2 xenograft model in SCID Beige mice, dosed IV once with the following:
1) Vehicle (Histidine Buffer #8), 100 uL
2) Thio Hu anti-Ly6E LC K149C-(CLD-1), ADC-212, 1 mg/kg
3) Thio Hu anti-Ly6E LC K149C-(CLD-1), ADC-212, 3 mg/kg
4) Thio Hu anti-Ly6E LC K149C-(LD-51) monoamide, ADC-115, 3 mg/kg
5) Thio Hu anti-Ly6E LC K149C-(LD-51) monoamide, ADC-115, 6 mg/kg
6) Thio Hu anti-Ly6E LC K149C-(LD-51) monoamide, ADC-115, 12 mg/kg
7) Thio Hu anti-Ly6E LC K149C-(LD-51) monoamide, ADC-115, 18 mg/kg
8) Thio Hu anti-CD22 10F4v3 LC K149C-(LD-51) monoamide, ADC-110, 12 mg/kg
9) Thio Hu anti-Ly6E LC K149C-(CLD-4), monoamine, ADC-210, 1 mg/kg
10) Thio Hu anti-Ly6E LC K149C-(CLD-4), monoamine, ADC-210, 3 mg/kg
11) Thio Hu anti-Ly6E LC K149C-(CLD-4), monoamine, ADC-210, 6 mg/kg
12) Thio Hu anti-CD22 10F4v3 LC K149C-(CLD-4), monoamine, ADC-204, 3 mg/kg

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WP200226822 (Claim 23; FIG. 2); WO200216429 (Claim 12; FIG. 10); Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636) Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D); Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212) Ciccodicola, A., et al EMBO J. 8 (7):1987-1991 (1989), Am. J. Hum. Genet. 49 (3): 555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2); Cross-references: MIM: 187395; NP_003203.1; NM_003212_1

Figure 9:
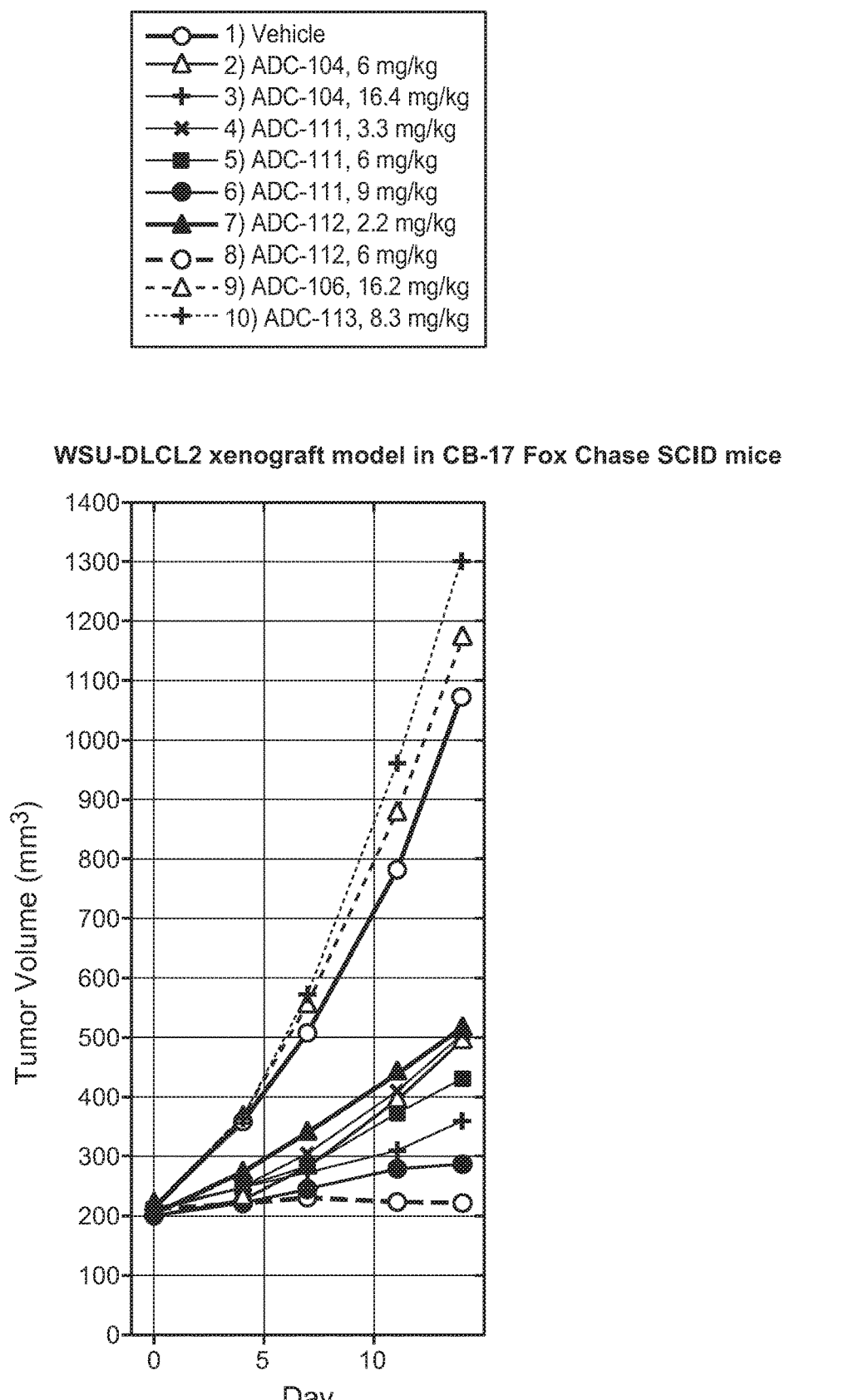
FIG. 9 shows the efficacy of antibody-drug conjugates in a plot of the in vivo fitted tumor volume change over time in WSU-DLCL2 xenograft model in CB-17 Fox Chase SCID mice, dosed IV once with the following:
1) Vehicle (Histidine Buffer #8), 100 uL
2) Thio Hu anti-CD22 LC-K149C-(LD-51), monoamide, ADC-104, 6 mg/kg
3) Thio Hu anti-CD22 LC-K149C-(LD-51), monoamide, ADC-104, 16.4 mg/kg
4) Thio Hu anti-CD22 LC-K149C-HC-L177C-(LD-51), monoamide, ADC-111, 3.3 mg/kg
5) Thio Hu anti-CD22 LC-K149C-HC-L177C-(LD-51), monoamide, ADC-111, 6 mg/kg
6) Thio Hu anti-CD22 LC-K149C-HC-L177C-(LD-51), monoamide, ADC-111, 9 mg/kg
7) Thio Hu anti-CD22 LC-K149C-HC-L177C-HC-Y376C-(LD-51), monoamide, ADC-112, 2.2 mg/kg
8) Thio Hu anti-CD22 LC-K149C-HC-L177C-HC-Y376C-(LD-51), monoamide, ADC-112, 6 mg/kg
9) Thio Hu anti-Her2 hu7C2 LC K149C-(LD-51), monoamide, ADC-106, 16.2 mg/kg
10) Thio Hu anti-Her2 4D5 LC K149C-HC L177C-(LD-51), monoamide, ADC-113, 8.3 mg/kg

(14) CD21 (CR2 (Complement Receptor 2) or C3DR (C3d/Epstein Barr virus receptor) or Hs.73792 Genbank accession no. M26004) Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (Claim 9); WO2004045520 (Example 4); WO9102536 (FIGS. 9.1-9.9); WO2004020595 (Claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674) Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146); Cross-references: MIM:147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130) Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25); Cross-references: MIM:606509; NP_110391.2; NM_030764_1

Figure 1B:
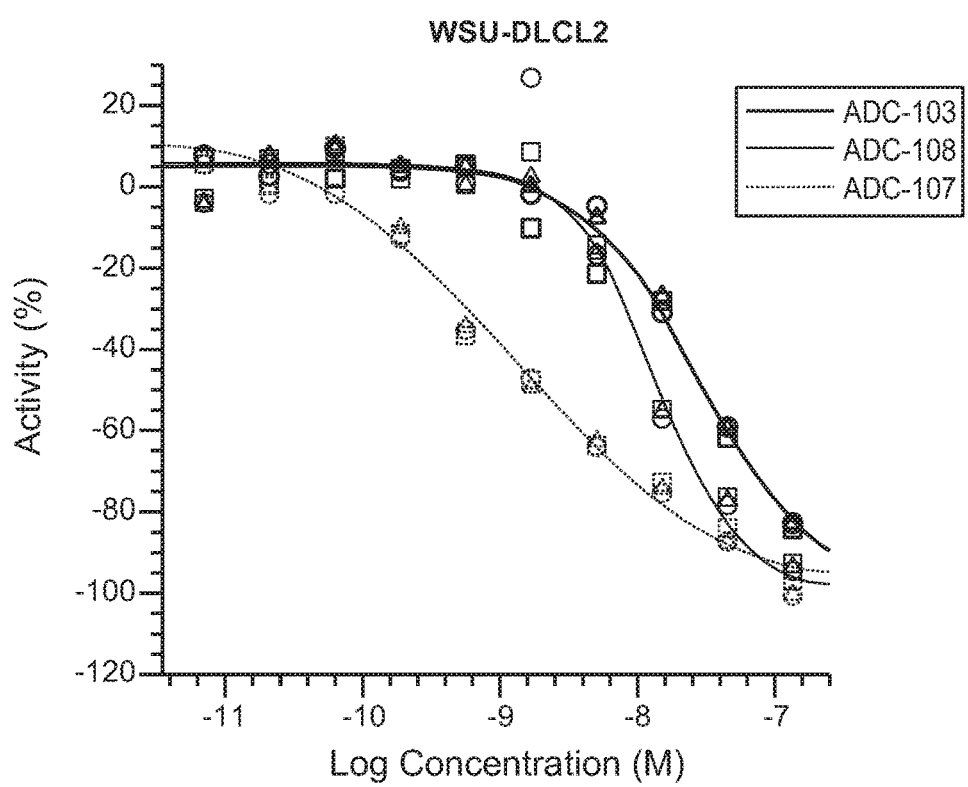
FIG. 1B shows a plot of in vitro cell viability of WSU-DLCL2 cells treated with ADC-107, ADC-103 and non-target control ADC-108.
Figure 7:
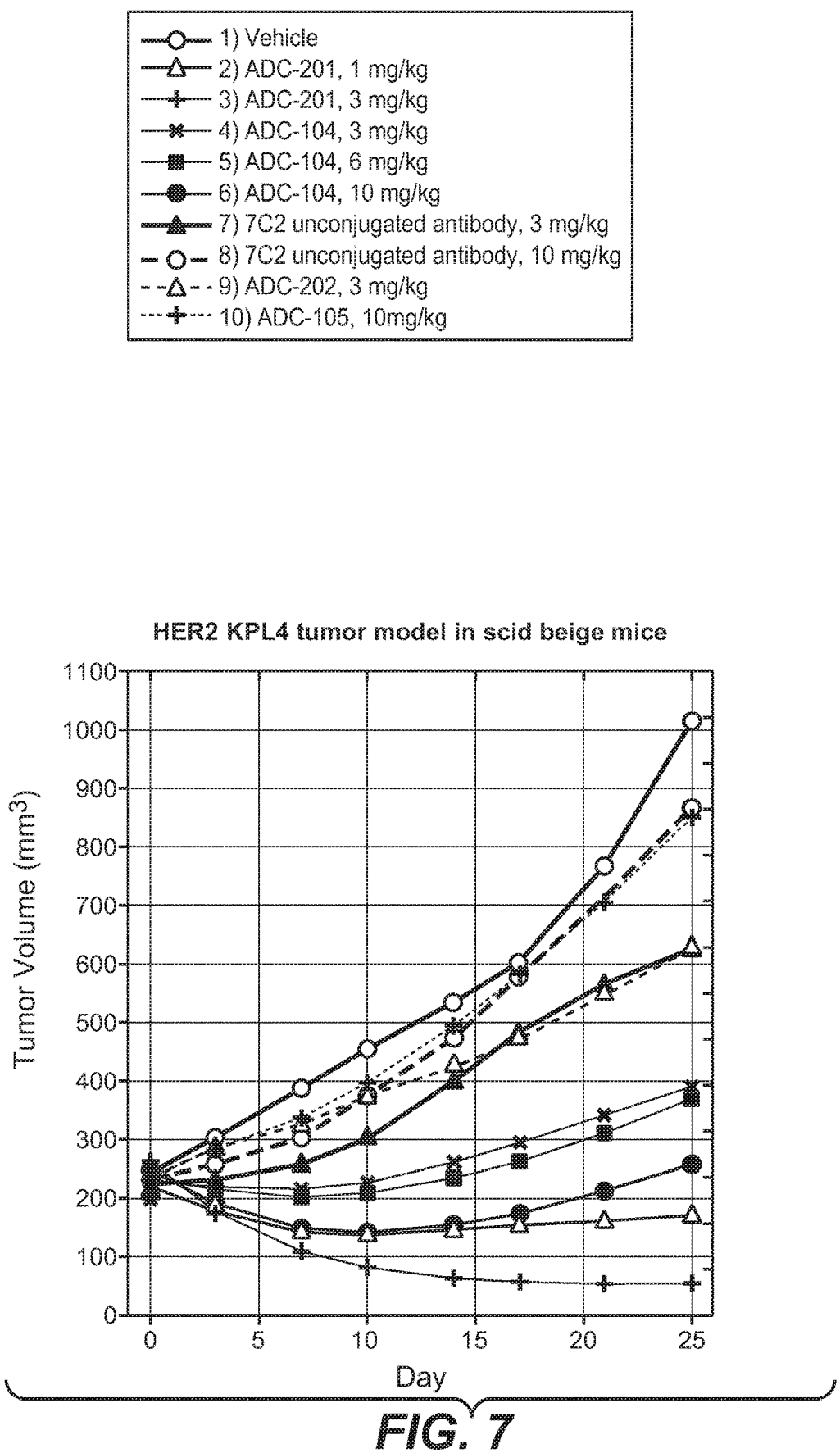
FIG. 7 shows the efficacy of antibody-drug conjugates in a plot of the in vivo fitted tumor volume change over time in HER2 KPL4 tumor model in scid beige mice, dosed IV once with the following:
1) Vehicle
2) Thio-Her2 hu7C2 LC-K149C-(CLD-1), ADC-201, 1 mg/kg
3) Thio-Her2 hu7C2 LC-K149C-(CLD-1), ADC-201, 3 mg/kg
4) Thio-Her2 hu7C2 LC-K149C-(LD-51) monoamide ADC-104, 3 mg/kg
5) Thio-Her2 hu7C2 LC-K149C-(LD-51) monoamide ADC-104, 6 mg/kg
6) Thio-Her2 hu7C2 LC-K149C-(LD-51) monoamide ADC-104, 10 mg/kg
7) Thio-Her2 hu7C2 LC-K149C, unconjugated antibody, 3 mg/kg
8) Thio-Her2 hu7C2 LC-K149C, unconjugated antibody, 10 mg/kg
9) Thio-CD22 LC-K149C-(CLD-1), ADC-202, 3 mg/kg
10) Thio-CD22 LC-K149C-(LD-51) monoamide, ADC-105, 10 mg/kg
Figure 11:
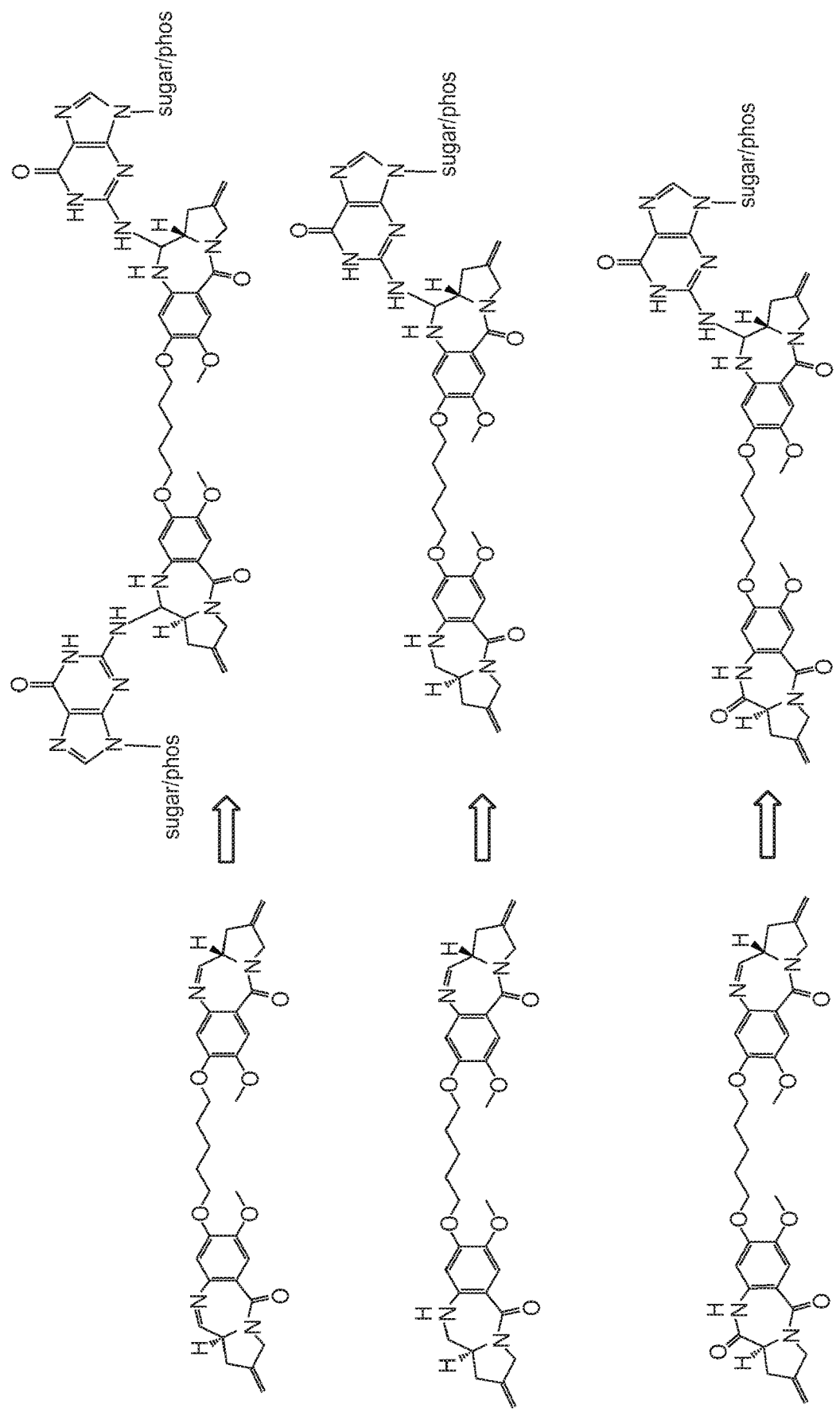
FIG. 11 shows putative interactions of a dialkylator pyrrolobenzodiazepine (PBD) compound and two monoalkylator pyrrolobenzodiazepine compounds with DNA.

(17) HER2 (ErbB2, Genbank accession no. M11730) Coussens L., et al Science (1985) 230(4730): 1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 11); WO2004009622; WO2003081210; WO2003089904 (Claim 9);

WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4); Accession: P04626; EMBL; M11767; AAA35808.1. EMBL; M11761; AAA35808.1.

Figure 8:
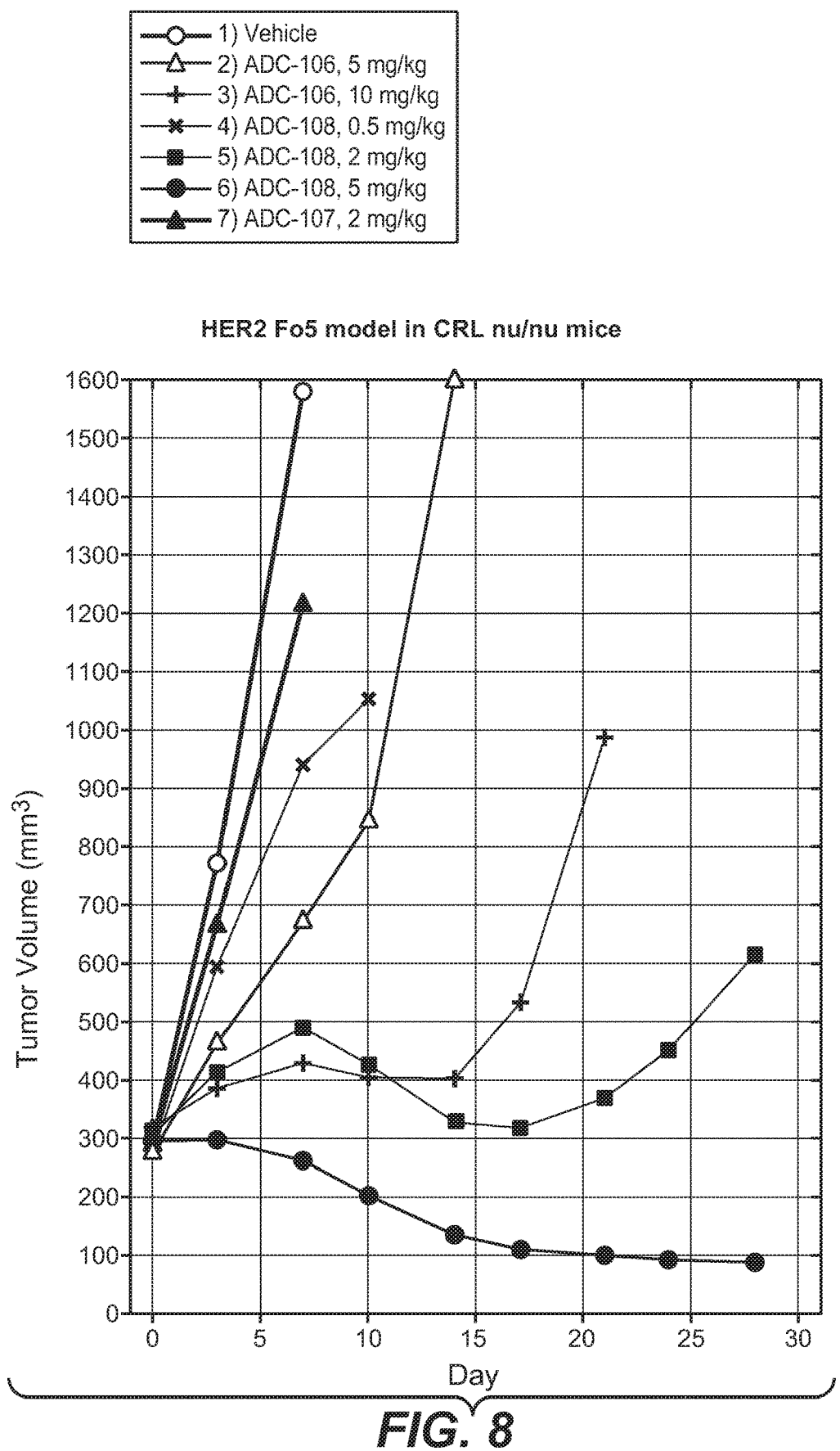
FIG. 8 shows the efficacy of antibody-drug conjugates in a plot of the in vivo fitted tumor volume change over time in HER2 Fo5 model in CRL nu/nu mice, dosed IV once with the following:
1) Vehicle
2) Thio-Her2 hu7C2 LC-K149C-(LD-51), monoamide, ADC-106, 5 mg/kg
3) Thio-Her2 hu7C2 LC-K149C-(LD-51), monoamide, ADC-106, 10 mg/kg
4) Thio-Her2 hu7C2 LC-K149C-(LD-52), monoamine, ADC-108, 0.5 mg/kg
5) Thio-Her2 hu7C2 LC-K149C-(LD-52), monoamine, ADC-108, 2 mg/kg
6) Thio-Her2 hu7C2 LC-K149C-(LD-52), monoamine, ADC-108, 5 mg/kg 7) Ctrl CD22 LC-K149C-(LD-52), monoamine, ADC-107, 2 mg/kg

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2); Accession: P40199; Q14920; EMBL; M29541; AAA59915.1. EMBL; M18728;

(19) MDP (DPEP1, Genbank accession no. BC017023) Proc. Natl. Acad. Sci. U.S.A. 99 (26):16899-16903 (2002)); WO2003016475 (Claim 1); WO200264798 (Claim 33; Page 85-87); JP05003790 (FIG. 6-8); WO9946284 (FIG. 9); Cross-references: MIM:179780; AAH17023.1; BC017023_1

(20) IL20Rα (IL20Ra, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59); Accession: Q9UHF4; Q6UWA9; Q96SH8; EMBL; AF184971; AAF01320.1.

(21) Brevican (BCAN, BEHAB, Genbank accession no. AF229053) Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1);

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41) WO2004065576 (Claim 1); WO2004020583 (Claim 9); WO2003004529 (Page 128-132); WO200053216 (Claim 1; Page 42); Cross-references: MIM:600997; NP_004433.2; NM_004442_1

(23) ASLG659 (B7h, Genbank accession no. AX092328) US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318;

(24) PSCA (Prostate stem cell antigen precursor, Genbank accession no. AJ297436) Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B); Accession: O43653; EMBL; AF043498; AAC39607.1.

(25) GEDA (Genbank accession no. AY260763); AAP14954 lipoma HMGIC fusion-partner-like protein/pid=AAP14954.1—*Homo sapiens* Species: *Homo sapiens* (human) WO2003054152 (Claim 20); WO2003000842 (Claim 1); WO2003023013 (Example 3, Claim 20); US2003194704 (Claim 45); Cross-references: GI:30102449; AAP14954.1; AY260763_1

(26) BAFF-R (B cell-activating factor receptor, BLyS Receptor 3, BR3, Genbank accession No. AF116456); baff receptor/pid=NP_443177.1—*Homo sapiens* Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3); Cross-references: MIM:606269; NP_443177.1; NM_052945_1; AF132600

(27) CD22 (B-cell receptor CD22-B isoform, BL-CAM, Lyb-8, Lyb8, SIGLEC-2, FLJ22814, Genbank accession no. AK026467); Wilson et al (1991) J. Exp. Med. 173: 137-146; WO2003072036 (Claim 1; FIG. 1); Cross-references: MIM:107266; NP_001762.1; NM_001771_1

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession no. NP_001774.10) WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession no. NP_001707.1) WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+T lymphocytes); 273 aa, pI: 6.56 MW: 30820 TM: 1 [P] Gene Chromosome: 6p21.3, Genbank accession no. NP_002111.1) Tonnelle et al (1985) EMBO J. 4(11): 2839-2847; Jonsson et al (1989) Immunogenetics 29(6): 411-413; Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession no. NP_002552.2) Le et al (1997) FEBS Lett. 418 (1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82);

(32) CD72 (B-cell differentiation antigen CD72, Lyb-2) PROTEIN SEQUENCE Full maeaity . . . tafrfpd (1 . . . 359; 359 aa), pI: 8.66, MW: 40225 TM: 1 [P] Gene Chromosome: 9p13.3, Genbank accession no. NP_001773.1) WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosus); 661 aa, pI: 6.20, MW: 74147 TM: 1 [P] Gene Chromosome: 5q12, Genbank accession no. NP_005573.1) US2002193567; WO9707198 (claim 11, pages 39-42); Miura et al (1996) Genomics 38(3):299-304; Miura et al (1998) Blood 92:2815-2822; WO2003083047; WO9744452 (claim 8, pages 57-61); WO200012130 (pages 24-26);

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession no. NP_443170.1) WO2003077836; WO200138490 (claim 6, FIG. 18E-1-18-E-2); Davis et al (2001) Proc. Natl. Acad. Sci USA 98(17):9772-9777; WO2003089624 (claim 8); EP1347046 (claim 1); WO2003089624 (claim 7);

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human: AF343662, AF343663, AF343664, AF343665, AF369794, AF397453, AK090423, AK090475, AL834187, AY358085; Mouse: AK089756, AY158090, AY506558; NP_112571.1 WO2003024392 (claim 2, FIG. 97); Nakayama et al (2000) Biochem. Biophys. Res. Commun. 277(1):124-127; WO2003077836; WO200138490 (claim 3, FIG. 18B-1-18B-2);

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436 WO2004074320 (SEQ ID NO 810); JP2004113151 (SEQ ID NOS 2, 4, 8); WO2003042661 (SEQ ID NO 580); WO2003009814 (SEQ ID NO 411); EP1295944 (pages 69-70); WO200230268 (page 329); WO200190304 (SEQ ID NO 2706); US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2):178-84;

(37) PMEL17 (silver homolog; SILV; D12S53E; PMEL17; SI; SIL); ME20; gp100) BC001414; BT007202; M32295; M77348; NM_006928; McGlinchey, R. P. et al (2009) Proc. Natl. Acad. Sci. U.S.A. 106 (33), 13731-13736; Kummer, M. P. et al (2009) J. Biol. Chem. 284 (4), 2296-2306;

(38) TMEFF1 (transmernbrane protein with EGF-like and two follistatin-like domains 1; Tomoregulin-1); H7365; C9orf2; C9ORF2; U19878; X83961; NM_080655; NM_003692; Harms, P. W. (2003) Genes Dev. 17 (21), 2624-2629; Gery, S. et al (2003) Oncogene 22 (18):2723-2727;

(39) GDNF-Ra1 (GDNF family receptor alpha 1; GFRA1; GDNFR; GDNFRA; RETL1; TRNR1; RET1L; GDNFR-alpha1; GFR-ALPHA-1); U95847; BC014962; NM_145793 NM_005264; Kim, M. H. et al (2009) Mol. Cell. Biol. 29 (8), 2264-2277; Treanor, J. J. et al (1996) Nature 382 (6586):80-83;

(40) Ly6E (lymphocyte antigen 6 complex, locus E; Ly67, RIG-E, SCA-2, TSA-1); NP_002337.1; NM_002346.2; de Nooij-van Dalen, A. G. et al (2003) Int. J. Cancer 103 (6), 768-774; Zammit, D. J. et al (2002) Mol. Cell. Biol. 22 (3):946-952; WO 2013/17705;

(41) TMEM46 (shisa homolog 2 (Xenopus laevis); SHISA2); NP_001007539.1; NM_001007538.1;

Furushima, K. et al (2007) Dev. Biol. 306 (2), 480-492; Clark, H. F. et al (2003) Genome Res. 13 (10):2265-2270;
(42) Ly6G6D (lymphocyte antigen 6 complex, locus G6D; Ly6-D, MEGT1); NP_067079.2; NM_021246.2; Mallya, M. et al (2002) Genomics 80 (1):113-123; Ribas, G. et al (1999) J. Immunol. 163 (1):278-287;
(43) LGR5 (leucine-rich repeat-containing G protein-coupled receptor 5; GPR49, GPR67); NP_003658.1; NM_003667.2; Salanti, G. et al (2009) Am. J. Epidemiol. 170 (5):537-545; Yamamoto, Y. et al (2003) Hepatology 37 (3):528-533;
(44) RET (ret proto-oncogene; MEN2A; HSCR1; MEN2B; MTC1; PTC; CDHF12; Hs.168114; RET51; RET-ELE1); NP_066124.1; NM_020975.4; Tsukamoto, H. et al (2009) Cancer Sci. 100 (10):1895-1901; Narita, N. et al (2009) Oncogene 28 (34):3058-3068;
(45) LY6K (lymphocyte antigen 6 complex, locus K; LY6K; HSJ001348; FLJ35226); NP_059997.3; NM_017527.3; Ishikawa, N. et al (2007) Cancer Res. 67 (24):11601-11611; de Nooij-van Dalen, A. G. et al (2003) Int. J. Cancer 103 (6):768-774;
(46) GPR19 ((ii protein-coupled receptor 19; Mm.4787); NP_006134.1; NM_006143.2; Montpetit, A. and Sinnett, D. (1999) Hum. Genet. 105 (1-2):162-164; O'Dowd, B. F. et al (1996) FEBS Lett. 394 (3):325-329;
(47) GPR54 (KISS1 receptor; KISS1R; GPR54; HOT7T175; AXOR12); NP_115940.2; NM_032551.4; Navenot, J. M. et al (2009) Mol. Pharmacol. 75 (6):1300-1306; Hata, K. et al (2009) Anticancer Res. 29 (2):617-623;
(48) ASPHD1 (aspartate beta-hydroxylase domain containing 1; LOC253982); NP_859069.2; NM_181718.3; Gerhard, D. S. et al (2004) Genome Res. 14 (10B):2121-2127;
(49) Tyrosinase (TYR; OCAIA; OCA1A; tyrosinase; SHEP3); NP_000363.1; NM_000372.4; Bishop, D. T. et al (2009) Nat. Genet. 41 (8):920-925; Nan, H. et al (2009) Int. J. Cancer 125 (4):909-917;
(50) TMEM118 (ring finger protein, transmembrane 2; RNFT2; FLJ14627); NP_001103373.1; NM_001109903.1; Clark, H. F. et al (2003) Genome Res. 13 (10):2265-2270; Scherer, S. E. et al (2006) Nature 440 (7082):346-351
(51) GPR172A (G protein-coupled receptor 172A; GPCR41; FLJ11856; D15Ertd747e); NP_078807.1; NM_024531.3; Ericsson, T. A. et al (2003) Proc. Natl. Acad. Sci. U.S.A. 100 (11):6759-6764; Takeda, S. et al (2002) FEBS Lett. 520 (1-3):97-101.
(52) CD33, a member of the sialic acid binding, immunoglobulin-like lectin family, is a 67-kDa glycosylated transmembrane protein. CD33 is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath et al., (1985) *J. Clin. Invest.* 75:756-56; Andrews et al., (1986) *Blood* 68:1030-5). CD33 contains two tyrosine residues on its cytoplasmic tail, each of which is followed by hydrophobic residues similar to the immunoreceptor tyrosine-based inhibitory motif (ITIM) seen in many inhibitory receptors.
(53) CLL-1 (CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signalling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K (1999) Curr. Opin. Struct. Biol. 9 (5):585-90; van Rhenen A, et al., (2007) Blood 110 (7):2659-66; Chen C H, et al. (2006) Blood 107 (4):1459-67; Marshall A S, et al. (2006) Eur. J. Immunol. 36 (8):2159-69; Bakker A B, et al (2005) Cancer Res. 64 (22):8443-50; Marshall A S, et al (2004) J. Biol. Chem. 279 (15):14792-802). CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.

Anti-CD22 Antibodies

In certain embodiments, the anti-CD22 antibodies of ADC in Tables 3A and 3B comprise three light chain hypervariable regions (HVR-L1, HVR-L2 and HVR-L3) and three heavy chain hypervariable regions (HVR-H1, HVR-H2 and HVR-H3), according to U.S. Pat. No. 8,226,945:

HVR-L1
(SEQ ID NO: 1)
RSSQSIVHSVGNTFLE

HVR-L2
(SEQ ID NO: 2)
KVSNRFS

HVR-L3
(SEQ ID NO: 3)
FQGSQFPYT

HVR-H1
(SEQ ID NO: 4)
GYEFSRSWMN

HVR-H2
(SEQ ID NO: 5)
GRIYPGDGDTNYSGKFKG

HVR-H3
(SEQ ID NO: 6)
DGSSWDWYFDV

Anti-Ly6E Antibodies

In certain embodiments, ADC of Tables 3A and 3B comprise anti-Ly6E antibodies. Lymphocyte antigen 6 complex, locus E (Ly6E), also known as retinoic acid induced gene E (RIG-E) and stem cell antigen 2 (SCA-2). It is a GPI linked, 131 amino acid length, ~8.4 kDa protein of unknown function with no known binding partners. It was initially identified as a transcript expressed in immature thymocyte, thymic medullary epithelial cells in mice (Mao, et al. (1996) *Proc. Natl. Acad. Sci. U.S.A.* 93:5910-5914). In some embodiments, the invention provides an immunoconjugate comprising an anti-Ly6E antibody described in PCT Publication No. WO 2013/177055.

In some embodiments, the invention provides an antibody-drug conjugate comprising an anti-Ly6E antibody comprising at least one, two, three, four, five, or six HVRs selected from (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11.

In one aspect, the invention provides an antibody-drug conjugate comprising an antibody that comprises at least one, at least two, or all three VH HVR sequences selected from (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14. In a further embodiment, the antibody comprises (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14.

In another aspect, the invention provides an antibody-drug conjugate comprising an antibody that comprises at least one, at least two, or all three VL HVR sequences selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In one embodiment, the antibody comprises (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 12, (ii) HVR-H2 comprising the amino acid sequence of SEQ ID NO: 13, and (iii) HVR-H3 comprising an amino acid sequence selected from SEQ ID NO: 14; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 11.

In another aspect, the invention provides an antibody-drug conjugate comprising an antibody that comprises (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11.

In any of the above embodiments, an anti-Ly6E antibody of an antibody-drug conjugate is humanized. In one embodiment, an anti-Ly6E antibody comprises HVRs as in any of the above embodiments, and further comprises a human acceptor framework, e.g. a human immunoglobulin framework or a human consensus framework.

In another aspect, an anti-Ly6E antibody of an antibody-drug conjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 8. In certain embodiments, a VH sequence having at least 90%, 91%, 92%, 93%, 94%, 95%, 96%, 97%, 98%, or 99% identity to the amino acid sequence of SEQ ID NO:8 contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO: 8. In certain embodiments, a total of 1 to 5 amino acids have been substituted, inserted and/or deleted in SEQ ID NO: 8. In certain embodiments, substitutions, insertions, or deletions occur in regions outside the HVRs (i.e., in the FRs). Optionally, the anti-Ly6E antibody comprises the VH sequence of SEQ ID NO: 8, including post-translational modifications of that sequence. In a particular embodiment, the VH comprises one, two or three HVRs selected from: (a) HVR-H1 comprising the amino acid sequence of SEQ ID NO: 12, (b) HVR-H2 comprising the amino acid sequence of SEQ ID NO: 13, and (c) HVR-H3 comprising the amino acid sequence of SEQ ID NO: 14.

In another aspect, an anti-Ly6E antibody of an antibody-drug conjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 7. In certain embodiments, a VL sequence having at least 90%, 91%, 92%, 93%, 94%, 95%, 96%, 97%, 98%, or 99% identity to the amino acid sequence of SEQ ID NO:7 contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO: 7. In certain embodiments, a total of 1 to 5 amino acids have been substituted, inserted and/or deleted in SEQ ID NO: 7. In certain embodiments, the substitutions, insertions, or deletions occur in regions outside the HVRs (i.e., in the FRs). Optionally, the anti-Ly6E antibody comprises the VL sequence of SEQ ID NO: 7, including post-translational modifications of that sequence. In a particular embodiment, the VL comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, an antibody-drug conjugate comprising an anti-Ly6E antibody is provided, wherein the antibody comprises a VH as in any of the embodiments provided above, and a VL as in any of the embodiments provided above.

In one embodiment, an antibody-drug conjugate is provided, wherein the antibody comprises the VH and VL sequences in SEQ ID NO: 8 and SEQ ID NO: 7, respectively, including post-translational modifications of those sequences.

In a further aspect, provided herein are antibody-drug conjugate comprising antibodies that bind to the same epitope as an anti-Ly6E antibody provided herein. For example, in certain embodiments, an immunoconjugate is provided comprising an antibody that binds to the same epitope as an anti-Ly6E antibody comprising a VH sequence of SEQ ID NO: 8 and a VL sequence of SEQ ID NO: 7, respectively.

In a further aspect of the invention, an anti-Ly6E antibody of an antibody-drug conjugate according to any of the above embodiments is a monoclonal antibody, including a human antibody. In one embodiment, an anti-Ly6E antibody of an antibody-drug conjugate is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein. In some embodiments, an immunconjugate (ADC) comprises an anti-Ly6E antibody comprising a heavy chain and a light chain comprising the amino acid sequences of SEQ ID NO: 16 and 15, respectively.

Table of Ly6E Antibody Sequences

| SEQ ID NO | Description | Sequence |
|---|---|---|
| 7 | anti-Ly6E antibody hu9B12 v12 light chain variable region | DIQMTQSPSS LSASVGDRVT ITCSASQGIS NYLNWYQQKP GKTVKLLIYY TSNLHSGVPS RFSGSGSGTD YTLTISSLQP EDFATYYCQQ YSELPWTFGQ GTKVEIK |
| 8 | anti-Ly6E antibody hu9B12 v12 heavy chain variable region | EVQLVESGPA LVKPTQTLTL TCTVSGFSLT GYSVNWIRQPPGKAL EWLGMIWGDG STDYNSALKS RLTISKDTSK NQVVLTMTNM DPVDTATYYC ARDYYFNYAS WFAYWGQGTL VTVSS |
| 9 | anti-Ly6E antibody hu9B12 v12 HVR-L1 | SASQGISNYLN |
| 10 | anti-Ly6E antibody hu9B12 v12 HVR-L2 | YTSNLHS |
| 11 | anti-Ly6E antibody hu9B12 v12 HVR-L3 | QQYSELPWT |
| 12 | anti-Ly6E antibody hu9B12 v12 HVR-H1 | GFSLTGYSVN |
| 13 | anti-Ly6E antibody hu9B12 v12 HVR-H2 | MIWGDGSTDY NSALKS |
| 14 | anti-Ly6E antibody hu9B12 v12 HVR-H3 | DYYVNYASWFAY |
| 15 | anti-Ly6E antibody hu9B12 v12 K149C kappa light chain | DIQMTQSPSS LSASVGDRVT ITCSASQGIS NYLNWYQQKP GKTVKLLIYY TSNLHSGVPS RFSGSGSGTD YTLTISSLQP EDFATYYCQQ YSELPWTFGQ GTKVEIK RTVAAPSVFIF PPSDEQLKSG TASVVCLLNN FYPREAKVQW CVDNALQSGN SQESVTEQDS KDSTYSLSST LTLSKADYEK HKVYACEVTH QGLSSPVTKS FNRGEC |
| 16 | anti-Ly6E antibody hu9B12 v12 IgG1 heavy chain | EVQLVESGPA LVKPTQTLTL TCTVSGFSLT GYSVNWIRQP PGKALEWLGM IWGDGSTDYN SALKSRLTIS KDTSKNQVVL TMTNMDPVDT ATYYCARDYY FNYASWFAW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |

Anti-HER2 Antibodies

In certain embodiments, ADC of Tables 3A and 3B comprise anti-HER2 antibodies. In one embodiment of the invention, an anti-HER2 antibody of an ADC of the invention comprises a humanized anti-HER2 antibody, e.g., huMAb4D5-1, huMAb4D5-2, huMAb4D5-3, huMAb4D5-4, huMAb4D5-5, huMAb4D5-6, huMAb4D5-7 and huMAb4D5-8, as described in Table 3 of U.S. Pat. No. 5,821,337, which is specifically incorporated by reference herein. Those antibodies contain human framework regions with the complementarity-determining regions of a murine antibody (4D5) that binds to HER2. The humanized antibody huMAb4D5-8 is also referred to as trastuzumab, commercially available under the tradename HERCEPTIN®. In another embodiment of the invention, an anti-HER2 antibody of an ADC of the invention comprises a humanized anti-HER2 antibody, e.g., humanized 2C4, as described in U.S. Pat. No. 7,862,817. An exemplary humanized 2C4 antibody is pertuzumab, commercially available under the tradename PERJETA®.

In another embodiment of the invention, an anti-HER2 antibody of an ADC of the invention comprises a humanized 7C2 anti-HER2 antibody. A humanized 7C2 antibody is an anti-HER2 antibody.

In some embodiments, the invention provides an antibody-drug conjugate comprising an anti-HER2 antibody comprising at least one, two, three, four, five, or six HVRs selected from (a) HVR-H1 comprising the amino acid sequence of SEQ ID NO: 22; (b) HVR-H2 comprising the amino acid sequence of SEQ ID NO: 23, 27, or 28; (c) HVR-H3 comprising the amino acid sequence of SEQ ID NO: 24 or 29; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21. In some embodiments, the invention provides an antibody-drug conjugate comprising an anti-HER2 antibody comprising at least one, two, three, four, five, or six HVRs selected from (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In one aspect, the invention provides an antibody-drug conjugate comprising an antibody that comprises at least one, at least two, or all three VH HVR sequences selected from (a) HVR-H1 comprising the amino acid sequence of SEQ ID NO: 22; (b) HVR-H2 comprising the amino acid sequence of SEQ ID NO: 23, 27, or 28; and (c) HVR-H3 comprising the amino acid sequence of SEQ ID NO: 24 or 29. In one aspect, the invention provides an immunoconjugate comprising an antibody that comprises at least one, at least two, or all three VH HVR sequences selected from (a) HVR-H1 comprising the amino acid sequence of SEQ ID NO: 22; (b) HVR-H2 comprising the amino acid sequence of SEQ ID NO: 23,; and (c) HVR-H3 comprising the amino acid sequence of SEQ ID NO: 24. In a further embodiment, the antibody comprises (a) HVR-H1 comprising the amino acid sequence of SEQ ID NO: 22; (b) HVR-H2 comprising the amino acid sequence of SEQ ID NO: 23, 27, or 28; and (c) HVR-H3 comprising the amino acid sequence of SEQ ID NO: 24 or 29. In a further embodiment, the antibody comprises (a) HVR-H1 comprising the amino acid sequence of SEQ ID NO: 22; (b) HVR-H2 comprising the amino acid sequence of SEQ ID NO: 23; and (c) HVR-H3 comprising the amino acid sequence of SEQ ID NO: 24.

In another aspect, the invention provides an antibody-drug conjugate comprising an antibody that comprises at least one, at least two, or all three VL HVR sequences selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21. In one embodiment, the antibody comprises (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21.

In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 22, (ii) HVR-H2 comprising the amino acid sequence of SEQ ID NO: 23, 27, or 28, and (iii) HVR-H3 comprising an amino acid sequence selected from SEQ ID NO: 24 or 29; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 20, and (c) HVR-L3 comprising the amino acid sequence of SEQ ID NO: 21. In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 22, (ii) HVR-H2 comprising the amino acid sequence of SEQ ID NO: 23, and (iii) HVR-H3 comprising an amino acid sequence selected from SEQ ID NO: 24; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 20, and (c) HVR-L3 comprising the amino acid sequence of SEQ ID NO: 21.

In another aspect, the invention provides an antibody-drug conjugate comprising an antibody that comprises (a) HVR-H1 comprising the amino acid sequence of SEQ ID NO: 22; (b) HVR-H2 comprising the amino acid sequence of SEQ ID NO: 23, 27, or 28; (c) HVR-H3 comprising the amino acid sequence of SEQ ID NO: 24 or 29; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21. In another aspect, the invention provides an antibody-drug conjugate comprising an antibody that comprises (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In any of the above embodiments, an anti-HER2 antibody of an antibody-drug conjugate is humanized. In one embodiment, an anti-HER2 antibody of an antibody-drug conjugate comprises HVRs as in any of the above embodiments, and further comprises a human acceptor framework, e.g. a human immunoglobulin framework or a human consensus framework.

In another aspect, an anti-HER2 antibody of an antibody-drug conjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 18. In certain embodiments, a VH sequence having at least 90%, 91%, 92%, 93%, 94%, 95%, 96%, 97%, 98%, or 99% identity to the amino acid sequence of SEQ ID NO: 18 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 18. In certain embodiments, a total of 1 to 5 amino acids have been substituted, inserted and/or deleted in SEQ ID NO: 18. In certain embodiments, substitutions, insertions, or deletions occur in regions outside the HVRs (i.e., in the FRs). Optionally, the anti-HER2 antibody comprises the VH sequence of SEQ ID NO: 18, including post-translational modifications of that sequence. In a particular embodiment, the VH comprises one, two or three HVRs selected from: (a) HVR-H1 comprising the amino acid sequence of SEQ ID NO: 22, (b) HVR-H2 comprising the amino acid sequence of SEQ ID NO: 23, and (c) HVR-H3 comprising the amino acid sequence of SEQ ID NO: 24.

In another aspect, an anti-HER2 antibody of an antibody-drug conjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 17. In certain embodiments, a VL sequence having at least 90%, 91%, 92%, 93%, 94%, 95%, 96%, 97%, 98%, or 99% identity to the amino acid sequence of SEQ ID NO: 17 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 17. In certain embodiments, a total of 1 to 5 amino acids have been substituted, inserted and/or deleted in SEQ ID NO: 17. In certain embodiments, the substitutions, insertions, or deletions occur in regions outside the HVRs (i.e., in the FRs). Optionally, the anti-HER2 antibody comprises the VL sequence of SEQ ID NO: 17, including post-translational modifications of that sequence. In a particular embodiment, the VL comprises one, two or three HVRs selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21.

In another aspect, an antibody-drug conjugate comprising an anti-HER2 antibody is provided, wherein the antibody comprises a VH as in any of the embodiments provided above, and a VL as in any of the embodiments provided above.

In one embodiment, an antibody-drug conjugate comprising an antibody is provided, wherein the antibody comprises the VH and VL sequences in SEQ ID NO: 18 and SEQ ID NO: 17, respectively, including post-translational modifications of those sequences.

In one embodiment, an antibody-drug conjugate comprising an antibody is provided, wherein the antibody comprises the humanized 7C2.v2.2. LA (hu7C2) K149C kappa light chain sequence of SEQ ID NO: 30

In one embodiment, an antibody-drug conjugate comprising an antibody is provided, wherein the antibody comprises the Hu7C2 A118C IgG1 heavy chain sequence of SEQ ID NO: 31

In a further aspect, provided herein are antibody-drug conjugates comprising antibodies that bind to the same epitope as an anti-HER2 antibody provided herein. For example, in certain embodiments, an immunoconjugate is provided, comprising an antibody that binds to the same epitope as an anti-HER2 antibody comprising a VH sequence of SEQ ID NO: 18 and a VL sequence of SEQ ID NO: 17, respectively.

In a further aspect of the invention, an anti-HER2 antibody of an antibody-drug conjugate according to any of the above embodiments is a monoclonal antibody, including a human antibody. In one embodiment, an anti-HER2 antibody of an immunoconjugate is an antibody fragment, e.g., a Fv, Fab, Fab', scFv, diabody, or F(ab')$_2$ fragment. In another embodiment, an immunoconjugate comprises an antibody that is a substantially full length antibody, e.g., an IgG1 antibody, IgG2a antibody or other antibody class or isotype as defined herein.

Table of humanized 7C2 anti-HER2 antibody sequences

| SEQ. ID NO. | Description | Sequence |
|---|---|---|
| 17 | Humanized 7C2.v2.2.LA ("hu7C2") light chain variable region | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IK |
| 18 | Humanized 7C2.v2.2.LA ("hu7C2") heavy chain variable region | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSS |
| 19 | hu7C2 HVR-L1 | RASQSVSGSRFTYMH |
| 20 | hu7C2 HVR-L2 | YASILES |
| 21 | hu7C2 HVR-L3 | QHSWEIPPWT |

Table of humanized 7C2 anti-HER2 antibody sequences

| SEQ. ID NO. | Description | Sequence |
|---|---|---|
| 22 | hu7C2 HVR-H1 | GYWMN |
| 23 | hu7C2 HVR-H2 | MIHPLDAEIRANQKFRD |
| 24 | hu7C2 HVR-H3 | GTYDGGFEY |
| 25 | Humanized 7C2.v2.2.LA (hu7C2) kappa light chain | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 26 | Humanized 7C2.v2.2.LA (hu7C2) IgG1 heavy chain | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 27 | Hu7C2.v2.1.S53M HVR-H2 | MIHPMDSEIRANQKFRD |
| 28 | Hu7C2.v2.1.S53L HVR-H2 | MIHPLDSEIRANQKFRD |
| 29 | Hu7C2.v2.1.E101K HVR-H3 | GTYDGGFKY |
| 30 | Humanized 7C2.v2.2.LA (hu7C2) K149C kappa light chain | DIVMTQSPDS LAVSLGERAT INCRASQSVS GSRFTYMHWY QQKPGQPPKL LIKYASILES GVPDRFSGSG SGTDFTLTIS SLQAEDVAVY YCQHSWEIPP WTFGQGTKVE IKRTVAAPSV FIFPPSDEQL KSGTASVVCL LNNFYPREAK VQWCVDNALQ SGNSQESVTE QDSKDSTYSL SSTLTLSKAD YEKHKVYACE VTHQGLSSPV TKSFNRGEC |
| 31 | Humanized 7C2.v2.2.LA (hu7C2) A118C IgG1 heavy chain | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSSCS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 64 | exemplary human HER2 precursor protein, with | MELAALCRWG LLLALLPPGA ASTQVCTGTD MKLRLPASPE THLDMLRHLY QGCQVVQGNL ELTYLPTNAS LSFLQDIQEV QGYVLIAHNQ VRQVPLQRLR IVRGTQLFED NYALAVLDNG |

-continued

Table of humanized 7C2 anti-HER2 antibody sequences

| SEQ. ID NO. | Description | Sequence |
|---|---|---|
| | signal sequence | DPLNNTTPVT GASPGGLREL QLRSLTEILK GGVLIQRNPQ LCYQDTILWK DIFHKNNQLA LTLIDTNRSR ACHPCSPMCK GSRCWGESSE DCQSLTRTVC AGGCARCKGP LPTDCCHEQC AAGCTGPKHS DCLACLHFNH SGICELHCPA LVTYNTDTFE SMPNPEGRYT FGASCVTACP YNYLSTDVGS CTLVCPLHNQ EVTAEDGTQR CEKCSKPCAR VCYGLGMEHL REVRAVTSAN IQEFAGCKKI FGSLAFLPES FDGDPASNTA PLQPEQLQVF ETLEEITGYL YISAWPDSLP DLSVFQNLQV IRGRILHNGA YSLTLQGLGI SWLGLRSLRE LGSGLALIHH NTHLCFVHTV PWDQLFRNPH QALLHTANRP EDECVGEGLA CHQLCARGHC WGPGPTQCVN CSQFLRGQEC VEECRVLQGL PREYVNARHC LPCHPECQPQ NGSVTCFGPE ADQCVACAHY KDPPFCVARC PSGVKPDLSY MPIWKFPDEE GACQPCPINC THSCVDLDDK GCPAEQRASP LTSIISAVVG ILLVVVLGVV FGILIKRRQQ KIRKYTMRRL LQETELVEPL TPSGAMPNQA QMRILKETEL RKVKVLGSGA FGTVYKGIWI PDGENVKIPV AIKVLRENTS PKANKEILDE AYVMAGVGSP YVSRLLGICL TSTVQLVTQL MPYGCLLDHV RENRGRLGSQ DLLNWCMQIA KGMSYLEDVR LVHRDLAARN VLVKSPNHVK ITDFGLARLL DIDETEYHAD GGKVPIKWMA LESILRRRFT HQSDVWSYGV TVWELMTFGA KPYDGIPARE IPDLLEKGER LPQPPICTID VYMIMVKCWM IDSECRPRFR ELVSEFSRMA RDPQRFVVIQ NEDLGPASPL DSTFYRSLLE DDDMGDLVDA EEYLVPQQGF FCPDDAPGAG GMVHHRHRSS STRSGGGDLT LGLEPSEEEA PRSPLAPSEG AGSDVFDGDL GMGAAKGLQS LPTHDPSPLQ RYSEDPTVPL PSETDGYVAP LTC SPQPEYV NQPDVRPQPP SPREGPLPAA RPAGATLERP KTLSPGKNGV VKDVFAFGGA VENPEYLTPQ GGAAPQPHPP PAFSPAFDNL YYWDQDPPER GAPPSTFKGT PTAENPEYLG LDVPV |

Anti-MUC16 Antibodies

In certain embodiments, ADC of Tables 3A and 3B comprise anti-MUC16 antibodies.

In some embodiments, the invention provides an antibody-drug conjugate comprising an anti-MUC16 antibody comprising at least one, two, three, four, five, or six HVRs selected from (a) HVR-H1 comprising the amino acid sequence of SEQ ID NO: 35; (b) HVR-H2 comprising the amino acid sequence of SEQ ID NO: 36; (c) HVR-H3 comprising the amino acid sequence of SEQ ID NO: 37; (d) HVR-L1 comprising the amino acid sequence of SEQ ID NO: 32; (e) HVR-L2 comprising the amino acid sequence of SEQ ID NO: 33 and (f) HVR-L3 comprising the amino acid sequence of SEQ ID NO: 34.

In one aspect, the invention provides an antibody-drug conjugate comprising an antibody that comprises at least one, at least two, or all three VH HVR sequences selected from (a) HVR-H1 comprising the amino acid sequence of SEQ ID NO: 35; (b) HVR-H2 comprising the amino acid sequence of SEQ ID NO: 36; (c) HVR-H3 comprising the amino acid sequence of SEQ ID NO: 37. In a further embodiment, the antibody comprises (a) HVR-H1 comprising the amino acid sequence of SEQ ID NO: 35; (b) HVR-H2 comprising the amino acid sequence of SEQ ID NO: 36; (c) HVR-H3 comprising the amino acid sequence of SEQ ID NO: 37.

In another aspect, the invention provides an antibody-drug conjugate comprising an antibody that comprises at least one, at least two, or all three VL HVR sequences selected from (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34. In one embodiment, the antibody comprises (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34.

In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 35, (ii) HVR-H2 comprising the amino acid sequence of SEQ ID NO: 36, and (iii) HVR-H3 comprising an amino acid sequence selected from SEQ ID NO: 37; and (b) a VL domain comprising at least one, at least two, or all three VL HVR sequences selected from (i) HVR-L1 comprising the amino acid sequence of SEQ ID NO: 32, (ii) HVR-L2 comprising the amino acid sequence of SEQ ID NO: 33, and (c) HVR-L3 comprising the amino acid sequence of SEQ ID NO: 34.

In another aspect, the invention provides an antibody-drug conjugate comprising an antibody that comprises (a) HVR-H1 comprising the amino acid sequence of SEQ ID NO: 35 (b) HVR-H2 comprising the amino acid sequence of SEQ ID NO: 36; (c) HVR-H3 comprising the amino acid sequence of SEQ ID NO: 37; (d) HVR-L1 comprising the amino acid sequence of SEQ ID NO: 32; (e) HVR-L2 comprising the amino acid sequence of SEQ ID NO: 33; and (f) HVR-L3 comprising the amino acid sequence of SEQ ID NO: 34.

In any of the above embodiments, an anti-MUC16 antibody of an antibody-drug conjugate is humanized. In one embodiment, an anti-MUC16 antibody comprises HVRs as in any of the above embodiments, and further comprises a human acceptor framework, e.g. a human immunoglobulin framework or a human consensus framework.

In another aspect, an anti-MUC16 antibody of an antibody-drug conjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 39. In certain embodiments, a VH sequence having at least 90%, 91%, 92%, 93%, 94%, 95%, 96%, 97%, 98%, or 99% identity to the amino acid sequence of SEQ ID NO: 39 contains substitutions (e.g., conservative substitutions), insertions, or deletions relative to the reference sequence, but an anti-MUC16 antibody comprising that sequence retains the ability to bind to MUC16. In certain embodiments, a total of 1 to 10 amino acids have been substituted, inserted and/or deleted in SEQ ID NO: 39. In certain embodiments, a total of 1 to 5 amino acids have been substituted, inserted and/or deleted in SEQ ID NO: 39. In certain embodiments, substitutions, insertions, or deletions occur in regions outside the HVRs (i.e., in the FRs). Optionally, the anti-MUC16 antibody comprises the VH sequence of SEQ ID NO: 39, including post-translational modifications of that sequence. In a particular embodiment, the VH comprises one, two or three HVRs selected from: (a) HVR-H1 comprising the amino acid sequence of SEQ ID NO: 35, (b) HVR-H2 comprising the amino acid sequence of SEQ ID NO: 36, and (c) HVR-H3 comprising the amino acid sequence of SEQ ID NO: 37.

In another aspect, an anti-MUC16 antibody of an antibody-drug conjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 38. In certain embodiments, a VL sequence having at least 90%, 91%, 92%, 93%, 94%, 95%, 96%, 97%, 98%, or 99% identity to the amino acid sequence of SEQ ID NO:38 contains substitutions (e.g., conservative substitutions), insertions, or deletions relative to the reference sequence, but an anti-MUC16 antibody comprising that sequence retains the ability to bind to MUC16. In certain embodiments, a total of 1 to 10 amino acids have been substituted, inserted and/or deleted in SEQ ID NO: 38. In certain embodiments, a total of 1 to 5 amino acids have been substituted, inserted and/or deleted in SEQ ID NO: 38. In certain embodiments, the substitutions, insertions, or deletions occur in regions outside the HVRs (i.e., in the FRs). Optionally, the anti-MUC16 antibody comprises the VL sequence of SEQ ID NO: 38, including post-translational modifications of that sequence. In a particular embodiment, the VL comprises one, two or three HVRs selected from (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34.

In another aspect, an antibody-drug conjugate comprising an anti-MUC16 antibody is provided, wherein the antibody comprises a VH as in any of the embodiments provided above, and a VL as in any of the embodiments provided above.

In one embodiment, an antibody-drug conjugate is provided, wherein the antibody comprises the VH and VL sequences in SEQ ID NO: 39 and SEQ ID NO: 38, respectively, including post-translational modifications of those sequences.

In a further aspect, provided herein are antibody-drug conjugate comprising antibodies that bind to the same epitope as an anti-MUC16 antibody provided herein. For example, in certain embodiments, an immunoconjugate is provided comprising an antibody that binds to the same epitope as an anti-MUC16 antibody comprising a VH sequence of SEQ ID NO: 39 and a VL sequence of SEQ ID NO: 38, respectively.

In a further aspect of the invention, an anti-MUC16 antibody of an antibody-drug conjugate according to any of the above embodiments is a monoclonal antibody, including a human antibody. In one embodiment, an anti-MUC16 antibody of an antibody-drug conjugate is an antibody fragment, e.g., a Fv, Fab, Fab', scFv, diabody, or F(ab')₂ fragment. In another embodiment, the antibody is a substantially full length antibody, e.g., an IgG1 antibody, IgG2a antibody or other antibody class or isotype as defined herein.

Table of MUC16 Antibody Sequences

| SEQ ID NO: | Description | Sequence |
|---|---|---|
| 32 | Anti-Muc16 antibody HVR-L1 | KASDLIHNWL A |
| 33 | Anti-Muc16 antibody HVR-L2 | YGATSLET |
| 34 | Anti-Muc16 antibody HVR-L3 | QQYWTTPFT |
| 35 | Anti-Muc16 antibody HVR-H1 | GYSITNDYAW N |
| 36 | Anti-Muc16 antibody HVR-H2 | GYISYSGYTT YNPSLKS |
| 37 | Anti-Muc16 antibody HVR-H3 | ARWASGLDY |
| 38 | Anti-Muc16 antibody light chain variable region | DIQMTQSPSS LSASVGDRVT ITCKASDLIH NWLAWYQQKP GKAPKLLIYG ATSLETGVPS RFSGSGSGTD FTLTISSLQP EDFATYYCQQ YWTTPFTFGQ GTKVEIKR |
| 39 | Anti-Muc16 antibody heavy chain variable region | EVQLVESGGG LVQPGGSLRL SCAASGYSIT NDYAWNWVRQ APGKGLEWVG YISYSGYTTY NPSLKSRFTI SRDTSKNTLY LQMNSLRAED TAVYYCARWA SGLDYWGQGT LVTVSS |

Anti-STEAP-1 Antibodies

In certain embodiments, ADC of Tables 3A and 3B comprise anti-STEAP-1 antibodies.

In some embodiments, the invention provides an antibody-drug conjugate comprising an anti-STEAP-1 antibody comprising at least one, two, three, four, five, or six HVRs selected from (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42; (d)

HVR-L1 comprising the amino acid sequence of SEQ ID NO: 43; (e) HVR-L2 comprising the amino acid sequence of SEQ ID NO: 44 and (f) HVR-L3 comprising the amino acid sequence of SEQ ID NO: 45.

In one aspect, the invention provides an antibody-drug conjugate comprising an antibody that comprises at least one, at least two, or all three VH HVR sequences selected from (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42. In a further embodiment, the antibody comprises (a) HVR-H1 comprising the amino acid sequence of SEQ ID NO: 40; (b) HVR-H2 comprising the amino acid sequence of SEQ ID NO: 41; (c) HVR-H3 comprising the amino acid sequence of SEQ ID NO: 42.

In another aspect, the invention provides an antibody-drug conjugate comprising an antibody that comprises at least one, at least two, or all three VL HVR sequences selected from (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45. In one embodiment, the antibody comprises (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45.

In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 40, (ii) HVR-H2 comprising the amino acid sequence of SEQ ID NO: 41, and (iii) HVR-H3 comprising an amino acid sequence selected from SEQ ID NO: 42; and (b) a VL domain comprising at least one, at least two, or all three VL HVR sequences selected from (i) HVR-L1 comprising the amino acid sequence of SEQ ID NO: 43, (ii) HVR-L2 comprising the amino acid sequence of SEQ ID NO: 44, and (c) HVR-L3 comprising the amino acid sequence of SEQ ID NO: 45.

In another aspect, the invention provides an antibody-drug conjugate comprising an antibody that comprises (a) HVR-H1 comprising the amino acid sequence of SEQ ID NO: 40 (b) HVR-H2 comprising the amino acid sequence of SEQ ID NO: 41; (c) HVR-H3 comprising the amino acid sequence of SEQ ID NO: 42; (d) HVR-L1 comprising the amino acid sequence of SEQ ID NO: 43; (e) HVR-L2 comprising the amino acid sequence of SEQ ID NO: 44; and (f) HVR-L3 comprising the amino acid sequence of SEQ ID NO: 45.

In any of the above embodiments, an anti-STEAP-1 antibody of an antibody-drug conjugate is humanized. In one embodiment, an anti-STEAP-1 antibody comprises HVRs as in any of the above embodiments, and further comprises a human acceptor framework, e.g. a human immunoglobulin framework or a human consensus framework.

In another aspect, an anti-STEAP-1 antibody of an antibody-drug conjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 46. In certain embodiments, a VH sequence having at least 90%, 91%, 92%, 93%, 94%, 95%, 96%, 97%, 98%, or 99% identity to the amino acid sequence of SEQ ID NO: 46 contains substitutions (e.g., conservative substitutions), insertions, or deletions relative to the reference sequence, but an anti-STEAP-1 antibody comprising that sequence retains the ability to bind to STEAP-1. In certain embodiments, a total of 1 to 10 amino acids have been substituted, inserted and/or deleted in SEQ ID NO: 46. In certain embodiments, a total of 1 to 5 amino acids have been substituted, inserted and/or deleted in SEQ ID NO: 46. In certain embodiments, substitutions, insertions, or deletions occur in regions outside the HVRs (i.e., in the FRs). Optionally, the anti-STEAP-1 antibody comprises the VH sequence of SEQ ID NO: 46, including post-translational modifications of that sequence. In a particular embodiment, the VH comprises one, two or three HVRs selected from: (a) HVR-H1 comprising the amino acid sequence of SEQ ID NO: 40, (b) HVR-H2 comprising the amino acid sequence of SEQ ID NO: 41, and (c) HVR-H3 comprising the amino acid sequence of SEQ ID NO: 42.

In another aspect, an anti-STEAP-1 antibody of an antibody-drug conjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 47. In certain embodiments, a VL sequence having at least 90%, 91%, 92%, 93%, 94%, 95%, 96%, 97%, 98%, or 99% identity to the amino acid sequence of SEQ ID NO: 47 contains substitutions (e.g., conservative substitutions), insertions, or deletions relative to the reference sequence, but an anti-STEAP-1 antibody comprising that sequence retains the ability to bind to STEAP-1. In certain embodiments, a total of 1 to 10 amino acids have been substituted, inserted and/or deleted in SEQ ID NO: 47 In certain embodiments, a total of 1 to 5 amino acids have been substituted, inserted and/or deleted in SEQ ID NO: 47. In certain embodiments, the substitutions, insertions, or deletions occur in regions outside the HVRs (i.e., in the FRs). Optionally, the anti-STEAP-1 antibody comprises the VL sequence of SEQ ID NO: 47, including post-translational modifications of that sequence. In a particular embodiment, the VL comprises one, two or three HVRs selected from (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45.

In another aspect, an antibody-drug conjugate comprising an anti-STEAP-1 antibody is provided, wherein the antibody comprises a VH as in any of the embodiments provided above, and a VL as in any of the embodiments provided above.

In one embodiment, an antibody-drug conjugate is provided, wherein the antibody comprises the VH and VL sequences in SEQ ID NO: 46 and SEQ ID NO: 47, respectively, including post-translational modifications of those sequences.

In a further aspect, provided herein are antibody-drug conjugate comprising antibodies that bind to the same epitope as an anti-STEAP-1 antibody provided herein. For example, in certain embodiments, an immunoconjugate is provided comprising an antibody that binds to the same epitope as an anti-STEAP-1 antibody comprising a VH sequence of SEQ ID NO: 46 and a VL sequence of SEQ ID NO: 47, respectively.

In a further aspect of the invention, an anti-STEAP-1 antibody of an antibody-drug conjugate according to any of the above embodiments is a monoclonal antibody, including a human antibody. In one embodiment, an anti-STEAP-1 antibody of an antibody-drug conjugate is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

Table of STEAP Antibody Sequences

| SEQ ID NO: | Description | Sequence |
|---|---|---|
| 40 | Anti-STEAP-1 HVR-H1 | GYSITSDYAW N |
| 41 | Anti-STEAP-1 HVR-H2 | GYISNSGSTS YNPSLKS |
| 42 | Anti-STEAP-1 HVR-H3 | ERNYDYDDYY YAMDY |
| 43 | Anti-STEAP-1 HVR-L1 | KSSQSLLYRS NQKNYLA |
| 44 | Anti-STEAP-1 HVR-L2 | WASTRES |
| 45 | Anti-STEAP-1 HVR-L3 | QQYYNYPRT |
| 46 | Anti-STEAP1 heavy chain variable region | EVQLVESGGG LVQPGGSLRL SCAVSGYSIT SDYAWNWVRQ APGKGLEWVG YISNSGSTSY NPSLKSRFTI SRDTSKNTLY LQMNSLRAED TAVYYCARER NYDYDDYYA MDYWGQGTLV TVSS |
| 47 | Anti-STEAP1 light chain variable region | DIQMTQSPSS LSASVGDRVT ITCKSSQSLL YRSNQKNYLA WYQQKPGKAP KLLIYWASTR ESGVPSRFSG SGSGTDFTLT ISSLQPEDFA TYYCQQYYNY PRTFGQGTKV EIK |

Anti-NaPi2b Antibodies

In certain embodiments, ADC of Tables 3A and 3B comprise anti-NaPi2b antibodies.

In some embodiments, the invention provides an antibody-drug conjugate comprising an anti-NaPi2b antibody comprising at least one, two, three, four, five, or six HVRs selected from (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50; (d) HVR-L1 comprising the amino acid sequence of SEQ ID NO: 51; (e) HVR-L2 comprising the amino acid sequence of SEQ ID NO: 52 and (f) HVR-L3 comprising the amino acid sequence of SEQ ID NO: 53.

In one aspect, the invention provides an antibody-drug conjugate comprising an antibody that comprises at least one, at least two, or all three VH HVR sequences selected from (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50. In a further embodiment, the antibody comprises (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50.

In another aspect, the invention provides an antibody-drug conjugate comprising an antibody that comprises at least one, at least two, or all three VL HVR sequences selected from (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53. In one embodiment, the antibody comprises (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53.

In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 48, (ii) HVR-H2 comprising the amino acid sequence of SEQ ID NO: 49, and (iii) HVR-H3 comprising an amino acid sequence selected from SEQ ID NO: 50; and (b) a VL domain comprising at least one, at least two, or all three VL HVR sequences selected from (i) HVR-L1 comprising the amino acid sequence of SEQ ID NO: 51, (ii) HVR-L2 comprising the amino acid sequence of SEQ ID NO: 52, and (c) HVR-L3 comprising the amino acid sequence of SEQ ID NO: 53.

In another aspect, the invention provides an antibody-drug conjugate comprising an antibody that comprises (a) HVR-H1 comprising the amino acid sequence of SEQ ID NO: 48 (b) HVR-H2 comprising the amino acid sequence of SEQ ID NO: 49; (c) HVR-H3 comprising the amino acid sequence of SEQ ID NO: 50; (d) HVR-L1 comprising the amino acid sequence of SEQ ID NO: 51; (e) HVR-L2 comprising the amino acid sequence of SEQ ID NO: 52; and (f) HVR-L3 comprising the amino acid sequence of SEQ ID NO: 53.

In any of the above embodiments, an anti-NaPi2b antibody of an antibody-drug conjugate is humanized. In one embodiment, an anti-NaPi2b antibody comprises HVRs as in any of the above embodiments, and further comprises a human acceptor framework, e.g. a human immunoglobulin framework or a human consensus framework.

In another aspect, an anti-NaPi2b antibody of an antibody-drug conjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 54. In certain embodiments, a VH sequence having at least 90%, 91%, 92%, 93%, 94%, 95%, 96%, 97%, 98%, or 99% identity to the amino acid sequence of SEQ ID NO: 54 contains substitutions (e.g., conservative substitutions), insertions, or deletions relative to the reference sequence, but an anti-NaPi2b antibody comprising that sequence retains the ability to bind to NaPi2b. In certain embodiments, a total of 1 to 10 amino acids have been substituted, inserted and/or deleted in SEQ ID NO: 54. In certain embodiments, a total of 1 to 5 amino acids have been substituted, inserted and/or deleted in SEQ ID NO: 54. In certain embodiments, substitutions, insertions, or deletions occur in regions outside the HVRs (i.e., in the FRs). Optionally, the anti-NaPi2b antibody comprises the VH sequence of SEQ ID NO: 54, including post-translational modifications of that sequence. In a particular embodiment, the VH comprises one, two or three HVRs selected from: (a) HVR-H1 comprising the amino acid sequence of SEQ ID NO: 48, (b) HVR-H2 comprising the amino acid sequence of SEQ ID NO: 49, and (c) HVR-H3 comprising the amino acid sequence of SEQ ID NO: 50.

In another aspect, an anti-NaPi2b antibody of an antibody-drug conjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 55. In certain embodiments, a VL sequence having at least 90%, 91%, 92%, 93%, 94%, 95%, 96%, 97%, 98%, or 99% identity to the amino acid sequence of SEQ ID NO: 55 contains substitutions (e.g., conservative substitutions), insertions, or deletions relative to the reference sequence, but an anti-NaPi2b antibody comprising that sequence retains the ability to bind to anti-NaPi2b. In certain embodiments, a total of 1 to 10 amino acids have been substituted, inserted and/or deleted in SEQ ID NO: 55. In certain embodiments, a total of 1 to 5 amino acids have been substituted, inserted and/or deleted in SEQ ID NO: 55. In certain embodiments, the substitutions, insertions, or deletions occur in regions outside the HVRs (i.e., in the FRs). Optionally, the anti-NaPi2b antibody comprises the VL sequence of SEQ ID NO: 55, including post-translational modifications of that sequence. In a particular embodiment, the VL comprises one, two or three HVRs selected from (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53.

In another aspect, an antibody-drug conjugate comprising an anti-NaPi2b antibody is provided, wherein the antibody comprises a VH as in any of the embodiments provided above, and a VL as in any of the embodiments provided above.

In one embodiment, an antibody-drug conjugate is provided, wherein the antibody comprises the VH and VL sequences in SEQ ID NO: 54 and SEQ ID NO: 55, respectively, including post-translational modifications of those sequences.

In a further aspect, provided herein are antibody-drug conjugate comprising antibodies that bind to the same epitope as an anti-NaPi2b antibody provided herein. For example, in certain embodiments, an immunoconjugate is provided comprising an antibody that binds to the same epitope as an anti-NaPi2b antibody comprising a VH sequence of SEQ ID NO: 54 and a VL sequence of SEQ ID NO: 55, respectively.

In a further aspect of the invention, an anti-NaPi2b antibody of an antibody-drug conjugate according to any of the above embodiments is a monoclonal antibody, including a human antibody. In one embodiment, an anti-NaPi2b antibody of an antibody-drug conjugate is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

Table of NaPi2b Antibody Sequences

| SEQ ID NO: | Description | Sequence |
|---|---|---|
| 48 | Anti-NaPi2b HVR-H1 | GFSFSDFAMS |
| 49 | Anti-NaPi2b HVR-H2 | ATIGRVAFHTYYPDSMKG |
| 50 | Anti-NaPi2b HVR-H3 | ARHRGFDVGHFDF |
| 51 | Anti-NaPi2b HVR-L1 | RSSETLVHSSGNTYLE |
| 52 | Anti-NaPi2b HVR-L2 | RVSNRFS |
| 53 | Anti-NaPi2b HVR-L3 | FQGSFNPLT |
| 54 | Anti-NaPi2b heavy chain variable region | EVQLVESGGGLVQPGGSLRLSCAASGFSFSDFAMSWV RQAPGKGLEWVATIGRVAFHTYYPDSMKGRFTISRDN SKNTLYLQMNSLRAEDTAVYYCARHRGFDVGHFDFW GQGTLVTVSS |
| 55 | Anti-NaPi2b light chain variable region | DIQMTQSPSSLSASVGDRVTITCRSSETLVHSSGNTYLE WYQQKPGKAPKLLIYRVSNRFSGVPSRFSGSGSGTDFT LTISSLQPEDFATYYCFQGSFNPLTFGQGTKVEIKR |

Anti-CD79b Antibodies

In certain embodiments, ADC of Tables 3A and 3B comprise anti-CD79b antibodies.

In some embodiments, the invention provides an antibody-drug conjugate comprising an anti-CD79b antibody comprising at least one, two, three, four, five, or six HVRs selected from (a) HVR-H1 comprising the amino acid sequence of SEQ ID NO: 58; (b) HVR-H2 comprising the amino acid sequence of SEQ ID NO: 59; (c) HVR-H3 comprising the amino acid sequence of SEQ ID NO: 60; (d) HVR-L1 comprising the amino acid sequence of SEQ ID NO: 61; (e) HVR-L2 comprising the amino acid sequence of SEQ ID NO: 62; and (f) HVR-L3 comprising the amino acid sequence of SEQ ID NO: 63.

In one aspect, the invention provides an antibody-drug conjugate comprising an antibody that comprises at least one, at least two, or all three VH HVR sequences selected from (a) HVR-H1 comprising the amino acid sequence of SEQ ID NO: 58; (b) HVR-H2 comprising the amino acid sequence of SEQ ID NO: 59; and (c) HVR-H3 comprising the amino acid sequence of SEQ ID NO: 60. In a further embodiment, the antibody comprises (a) HVR-H1 comprising the amino acid sequence of SEQ ID NO: 58; (b) HVR-H2 comprising the amino acid sequence of SEQ ID NO: 59; and (c) HVR-H3 comprising the amino acid sequence of SEQ ID NO: 60.

In another aspect, the invention provides an antibody-drug conjugate comprising an antibody that comprises at least one, at least two, or all three VL HVR sequences selected from (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63. In one embodiment, the antibody comprises (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63.

In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 58, (ii) HVR-H2 comprising the amino acid sequence of SEQ ID NO: 59, and (iii) HVR-H3 comprising an amino acid sequence selected from SEQ ID NO: 60; and (b) a VL domain comprising at least one, at least two, or all three VL HVR sequences selected from (i) HVR-L1 comprising the amino acid sequence of SEQ ID NO: 61, (ii) HVR-L2 comprising the amino acid sequence of SEQ ID NO: 62, and (c) HVR-L3 comprising the amino acid sequence of SEQ ID NO: 63.

In another aspect, the invention provides an antibody-drug conjugate comprising an antibody that comprises (a) HVR-H1 comprising the amino acid sequence of SEQ ID NO: 58; (b) HVR-H2 comprising the amino acid sequence of SEQ ID NO: 59; (c) HVR-H3 comprising the amino acid sequence of SEQ ID NO: 60; (d) HVR-L1 comprising the amino acid sequence of SEQ ID NO: 61; (e) HVR-L2 comprising the amino acid sequence of SEQ ID NO: 62; and (f) HVR-L3 comprising the amino acid sequence of SEQ ID NO: 63.

In any of the above embodiments, an anti-CD79b antibody of an antibody-drug conjugate is humanized. In one embodiment, an anti-CD79b antibody comprises HVRs as in any of the above embodiments, and further comprises a human acceptor framework, e.g. a human immunoglobulin framework or a human consensus framework.

In another aspect, an anti-CD79b antibody of an antibody-drug conjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 56. In certain embodiments, a VH sequence having at least 90%, 91%, 92%, 93%, 94%, 95%, 96%, 97%, 98%, or 99% identity to the amino acid sequence of SEQ ID NO: 56 contains substitutions (e.g., conservative substitutions), insertions, or deletions relative to the reference sequence, but an anti-CD79b antibody comprising that sequence retains the ability to bind to CD79b. In certain embodiments, a total of 1 to 10 amino acids have been substituted, inserted and/or deleted in SEQ ID NO: 56. In certain embodiments, a total of 1 to 5 amino acids have been substituted, inserted and/or deleted in SEQ ID NO: 56. In certain embodiments, substitutions, insertions, or deletions occur in regions outside the HVRs (i.e., in the FRs). Optionally, the anti-CD79b antibody comprises the VH sequence of SEQ ID NO: 8, including post-translational modifications of that sequence. In a particular embodiment, the VH comprises one, two or three HVRs selected from: (a) HVR-H1 comprising the amino acid sequence of SEQ ID NO: 58, (b) HVR-H2 comprising the amino acid sequence of SEQ ID NO: 59, and (c) HVR-H3 comprising the amino acid sequence of SEQ ID NO: 60.

In another aspect, an anti-CD79b antibody of an antibody-drug conjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 57. In certain embodiments, a VL sequence having at least 90%, 91%, 92%, 93%, 94%, 95%, 96%, 97%, 98%, or 99% identity to the amino acid sequence of SEQ ID NO: 57 contains substitutions (e.g., conservative substitutions), insertions, or deletions relative to the reference sequence, but an anti-Ly6E antibody comprising that sequence retains the ability to bind to CD79b. In certain embodiments, a total of 1 to 10 amino acids have been substituted, inserted and/or deleted in SEQ ID NO: 57. In certain embodiments, a total of 1 to 5 amino acids have been substituted, inserted and/or deleted in SEQ ID NO: 57. In certain embodiments, the substitutions, insertions, or deletions occur in regions outside the HVRs (i.e., in the FRs). Optionally, the anti-CD79b antibody comprises the VL sequence of SEQ ID NO: 57, including post-translational modifications of that sequence. In a particular embodiment, the VL comprises one, two or three HVRs selected from (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63.

In another aspect, an antibody-drug conjugate comprising an anti-CD79b antibody is provided, wherein the antibody comprises a VH as in any of the embodiments provided above, and a VL as in any of the embodiments provided above.

In one embodiment, an antibody-drug conjugate is provided, wherein the antibody comprises the VH and VL sequences in SEQ ID NO: 56 and SEQ ID NO: 57, respectively, including post-translational modifications of those sequences.

In a further aspect, provided herein are antibody-drug conjugate comprising antibodies that bind to the same epitope as an anti-CD79b antibody provided herein. For example, in certain embodiments, an immunoconjugate is provided comprising an antibody that binds to the same epitope as an anti-CD79b antibody comprising a VH sequence of SEQ ID NO: 56 and a VL sequence of SEQ ID NO: 57, respectively.

In a further aspect of the invention, an anti-CD79b antibody of an antibody-drug conjugate according to any of the above embodiments is a monoclonal antibody, including a human antibody. In one embodiment, an anti-CD79b antibody of an antibody-drug conjugate is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

Table of CD79b Antibody Sequences

| SEQ ID NO: | Description | Sequence |
|---|---|---|
| 56 | anti-CD79b huMA79bv28 heavy chain variable region | EVQLVESGGG LVQPGGSLRL SCAASGYTFS SYWIEWVRQA PGKGLEWIGE ILPGGGDTNY NEIFKGRATF SADTSKNTAY LQMNSLRAED TAVYYCTRRV PIRLDYWGQG TLVTVSS |
| 57 | anti-CD79b huMA79bv28 light chain variable region | DIQLTQSPSS LSASVGDRVT ITCKASQSVD YEGDSFLNWY QQKPGKAPKL LIYAASNLES GVPSRFSGSG SGTDFTLTIS SLQPEDFATY YCQQSNEDPL TFGQGTKVEI KR |
| 58 | anti-CD79b huMA79bv28 HVR H1 | GYTFSSYWIE |
| 59 | anti-CD79b huMA79bv28 HVR H2 | GEILPGGGDTNYNEIFKG |
| 60 | anti-CD79b huMA79bv28 HVR H3 | TRRVPIRLDY |
| 61 | anti-CD79b huMA79bv28 HVR L1 | KASQSVDYEGDSFLN |
| 62 | anti-CD79b huMA79bv28 HVR L2 | AASNLES |
| 63 | anti-CD79b huMA79bv28 HVR L3 | QQSNEDPLT |

Antibody Affinity

In certain embodiments, an antibody provided herein has a dissociation constant (Kd) of ≤1 µM, ≤100 nM, ≤50 nM, ≤10 nM, ≤5 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthiin, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA*, 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, bispecific antibodies may bind to two different epitopes of the same target. Bispecific antibodies may also be used to localize cytotoxic agents to cells which express the target. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see, e.g., US 2011/0287009, US2007/0178552, WO 96/027011, WO 98/050431, Zhu et al., 1997, Protein Science 6:781-788, and WO2012/106587). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

The term "hole mutation" as used herein refers to a mutation that introduces a cavity (hole) into a polypeptide at an interface in which the polypeptide interacts with another polypeptide. In some embodiments, the other polypeptide has a knob mutation.

A brief nonlimiting discussion is provided below.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US2011/0287009. A mutation to introduce a "protuberance" may be referred to as a "knob mutation."

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T) and valine (V). In some embodiments, an import residue is serine, alanine or threonine. In some embodiments, the original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG1 constant region is T366W (EU numbering). In some embodiments, a hole mutation in an IgG1 constant region comprises one or more mutations selected from T366S, L368A and Y407V (EU numbering). In some embodiments, a hole mutation in an IgG1 constant region comprises T366S, L368A and Y407V (EU numbering).

In some embodiments, a knob mutation in an IgG4 constant region is T366W (EU numbering). In some embodiments, a hole mutation in an IgG4 constant region comprises one or more mutations selected from T366S, L368A, and Y407V (EU numbering). In some embodiments, a hole mutation in an IgG4 constant region comprises T366S, L368A, and Y407V (EU numbering).

Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to the target as well as another, different antigen (see, US 2008/0069820, for example).

Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |

TABLE 1-continued

| Original Residue | Exemplary Substitutions | Preferred Substitutions |
|---|---|---|
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

In some embodiments, one or more amino acid modifications may be introduced into the Fc portion of the antibody provided herein in order to increase IgG binding to the neonatal Fc receptor. In certain embodiments, the antibody comprises the following three mutations according to EU numbering: M252Y, S254T, and T256E (the "YTE mutation") (U.S. Pat. No. 8,697,650; see also Dall'Acqua et al., Journal of Biological Chemistry 281(33):23514-23524 (2006). In certain embodiments, the YTE mutation does not affect the ability of the antibody to bind to its cognate antigen. In certain embodiments, the YTE mutation increases the antibody's serum half-life compared to the native (i.e., non-YTE mutant) antibody. In some embodiments, the YTE mutation increases the serum half-life of the antibody by 3-fold compared to the native (i.e., non-YTE mutant) antibody. In some embodiments, the YTE mutation increases the serum half-life of the antibody by 2-fold compared to the native (i.e., non-YTE mutant) antibody. In some embodiments, the YTE mutation increases the serum half-life of the antibody by 4-fold compared to the native (i.e., non-YTE mutant) antibody. In some embodiments, the YTE mutation increases the serum half-life of the antibody by at least 5-fold compared to the native (i.e., non-YTE mutant) antibody. In some embodiments, the YTE mutation increases the serum half-life of the antibody by at least 10-fold compared to the native (i.e., non-YTE mutant) antibody. See, e.g., U.S. Pat. No. 8,697,650; see also Dall'Acqua et al., Journal of Biological Chemistry 281(33): 23514-23524 (2006).

In certain embodiments, the YTE mutant provides a means to modulate antibody-dependent cell-mediated cytotoxicity (ADCC) activity of the antibody. In certain embodiments, the YTEO mutant provides a means to modulate ADCC activity of a humanized IgG antibody directed against a human antigen. See, e.g., U.S. Pat. No. 8,697,650; see also Dall'Acqua et al., Journal of Biological Chemistry 281(33):23514-23524 (2006).

In certain embodiments, the YTE mutant allows the simultaneous modulation of serum half-life, tissue distribution, and antibody activity (e.g., the ADCC activity of an IgG antibody). See, e.g., U.S. Pat. No. 8,697,650; see also Dall'Acqua et al., Journal of Biological Chemistry 281(33): 23514-23524 (2006).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, the proline at position329 (EU numbering) (P329) of a wild-type human Fc region is substituted with glycine or arginine or an amino acid residue large enough to destroy the proline sandwich within the Fc/Fc gamma receptor interface, that is formed between the P329 of the Fc and tryptophane residues W87 and W110 of FcgRIII (Sondermann et al.: Nature 406, 267-273 (20 Jul. 2000)). In a further embodiment, at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region, all according to EU numbering (U.S. Pat. No. 8,969,526 which is incorporated by reference in its entirety).

In certain embodiments, a polypeptide comprises the Fc variant of a wild-type human IgG Fc region wherein the polypeptide has P329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU numbering (U.S. Pat. No. 8,969,526 which is incorporated by reference in its entirety). In certain embodiments, the polypeptide comprising the P329G, L234A and L235A (EU numbering) substitutions exhibit a reduced affinity to the human FcγRIIIA and FcγRIIA, for down-modulation of ADCC to at least 20% of the ADCC induced by the polypeptide comprising the wild-type human IgG Fc region, and/or for down-modulation of ADCP (U.S. Pat. No. 8,969,526 which is incorporated by reference in its entirety).

In a specific embodiment the polypeptide comprising an Fc variant of a wildtype human Fc polypeptide comprises a triple mutation: an amino acid substitution at position Pro329, a L234A and a L235A mutation according to EU numbering (P329/LALA) (U.S. Pat. No. 8,969,526 which is incorporated by reference in its entirety). In specific embodiments, the polypeptide comprises the following amino acid substitutions: P329G, L234A, and L235A according to EU numbering.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

Cysteine Engineered Antibody Variants

In certain embodiments, it may be desirable to create cysteine engineered antibodies, e.g., a "THIOMAB™" or TDC, in which one or more residues of an antibody are substituted with cysteine residues. In particular embodiments, the substituted residues occur at sites of the antibody that are available for conjugation. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: K149 (Kabat numbering) of the light chain; V205 (Kabat numbering) of the light chain; A118 (EU numbering) of the heavy chain; A140 (EU numbering) of the heavy chain; L174 (EU numbering) of the heavy chain; Y373 (EU numbering) of the heavy chain; and S400 (EU numbering) of the heavy chain Fc region. In specific embodiments, the antibodies described herein comprise the HC-A140C (EU numbering) cysteine substitution. In specific embodiments, the antibodies described herein comprise the LC-K149C (Kabat numbering) cysteine substitution. In specific embodiments, the antibodies described herein comprise the HC-A118C (EU numbering) cysteine substitution. Cysteine engineered antibodies may be generated as described, e.g., in U.S. Pat. No. 7,521,541.

In certain embodiments, the antibody comprises one of the following heavy chain cysteine substitutions:

| Chain (HC/LC) | Residue | EU Mutation Site # | Kabat Mutation Site # |
|---|---|---|---|
| HC | T | 114 | 110 |
| HC | A | 140 | 136 |
| HC | L | 174 | 170 |
| HC | L | 179 | 175 |
| HC | T | 187 | 183 |
| HC | T | 209 | 205 |
| HC | V | 262 | 258 |
| HC | G | 371 | 367 |
| HC | Y | 373 | 369 |
| HC | E | 382 | 378 |
| HC | S | 424 | 420 |
| HC | N | 434 | 430 |
| HC | Q | 438 | 434 |

In certain embodiments, the antibody comprises one of the following light chain cysteine substitutions:

| Chain (HC/LC) | Residue | EU Mutation Site # | Kabat Mutation Site # |
|---|---|---|---|
| LC | I | 106 | 106 |
| LC | R | 108 | 108 |
| LC | R | 142 | 142 |
| LC | K | 149 | 149 |
| LC | V | 205 | 205 |

A nonlimiting exemplary hu7C2.v2.2. LA light chain (LC) K149C THIOMAB™ has the heavy chain and light chain amino acid sequences of SEQ ID NOs: 26 and 30, respectively. A nonlimiting exemplary hu7C2.v2.2. LA heavy chain (HC) A118C THIOMAB™ has the heavy chain and light chain amino acid sequences of SEQ ID NOs: 31 and 25, respectively.

Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Recombinant Methods and Compositions

Antibodies may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977); baby hamster kidney cells (BHK); mouse sertoli cells (TM4 cells as described, e.g., in Mather, *Biol. Reprod.* 23:243-251 (1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Monoalkylator Pyrrolobenzodiazepine Drug Moieties

An antibody-drug conjugate compound of the invention comprises a monoalkylator pyrrolobenzodiazepine drug moiety derivatized at the N10 group with a disulfide linker to the antibody.

Exemplary monoalkylator pyrrolobenzodiazepine (PBD) drug moieties, shown in Table 1a, have been prepared.

TABLE 1a

Monoalkylator pyrrolobenzodiazepine drug moieties

| No. | Structure | IUPAC Name | LC/MS M + H |
|---|---|---|---|
| DM-1 | 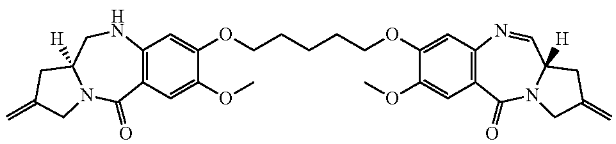 | (S)-7-methoxy-8-((5-(((S)-7-methoxy-2-methylene-5-oxo-2,3,5,10,11,11a-hexahydro-1H-benzo[e]pyrrolo[1,2-a][1,4]diazepin-8-yl)oxy)pentyl)oxy)-2-methylene-2,3-dihydro-1H-benzo[e]pyrrolo[1,2-a][1,4]diazepin-5(11aH)-one | 587 |
| DM-2 | 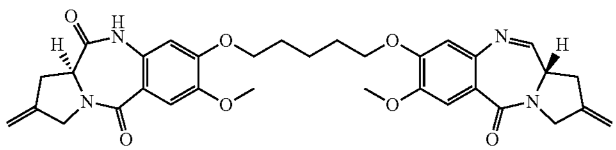 | (S)-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-2,3-dihydro-1H-benzo[e]pyrrolo[1,2-a][1,4]diazepine-5,11(10H,11aH)-dione | 601 |
| DM-3 | 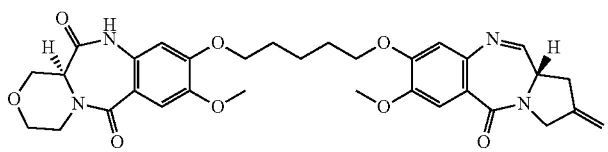 [SMILES: C=C1C[C@H]2C=Nc3cc(OCCCCCOc4cc5c(cc4OC)C(=O)N4CCOC[C@H]4C(=O)N5)c(OC)cc3C(=O)N2C1] | (S)-8-methoxy-9-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-1,3,4,12a-tetrahydro-6H-benzo[e][1,4]oxazino[4,3-a][1,4]diazepine-6,12(11H)-dione | 605 |
| DM-4 | 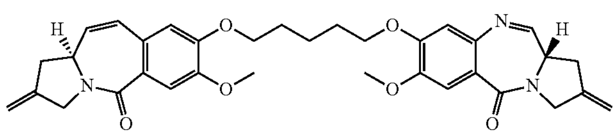 | (S)-7-methoxy-8-((5-(((S)-7-methoxy-2-methylene-5-oxo-2,3,5,11a-tetrahydro-1H-benzo[e]pyrrolo[1,2-a]azepin-8-yl)oxy)pentyl)oxy)-2-methylene-1,2,3,11a-tetrahydro-5H-benzo[e]pyrrolo[1,2-a][1,4]diazepin-5-one | 584 |
| DM-5 | 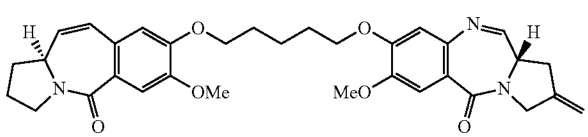 [SMILES: C=C1C[C@H]2C=Nc3cc(OCCCCCOc4cc5c(cc4OC)C(=O)N4CCC[C@H]4C=C5)c(OC)cc3C(=O)N2C1] | (S)-7-methoxy-8-((5-(((S)-7-methoxy-5-oxo-2,3,5,11a-tetrahydro-1H-benzo[e]pyrrolo[1,2-a]azepin-8-yl)oxy)pentyl)oxy)-2-methylene-1,2,3,11a-tetrahydro-5H-benzo[e]pyrrolo[1,2-a][1,4]diazepin-5-one | 572 |

TABLE 1b

Comparator drug moieties

| compound No. | Structure | IUPAC Name |
|---|---|---|
| C-1 | 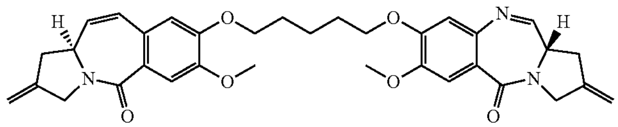 | (11aS,11a'S)-8,8'-(pentane-1,5-diylbis(oxy))bis(7-methoxy-2-methylene-1,2,3,11a-tetrahydro-5H-benzo[e]pyrrolo[1,2-a][1,4]diazepin-5-one) |
| C-2 | 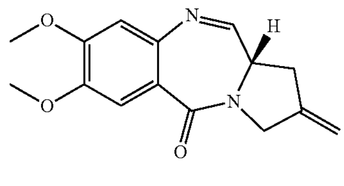 | (S)-7,8-dimethoxy-2-methylene-1,2,3,11a-tetrahydro-5H-benzo[e]pyrrolo[1,2-a][1,4]diazepin-5-one |
| C-3 | 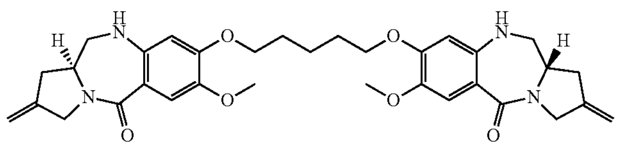 | (11aS,11a'S)-8,8-(pentane-1,5-diylbis(oxy))bis(7-methoxy-2-methylene-1,2,3,10,11,11a-hexahydro-5H-benzo[e]pyrrolo[1,2-a][1,4]diazepin-5-one) |

Monoalkylator Pyrrolobenzodiazepine, Linker-Drug Intermediates

An antibody-drug conjugate (ADC) compound of the invention may be prepared by conjugation of a monoalkylator pyrrolobenzodiazepine, linker-drug intermediate with an antibody. The thiopyridyl group of the linker-drug intermediate is displaced by a cysteine thiol of the antibody to form a disulfide linked ADC.

The monoalkylator pyrrolobenzodiazepine, linker-drug intermediate has Formula I:

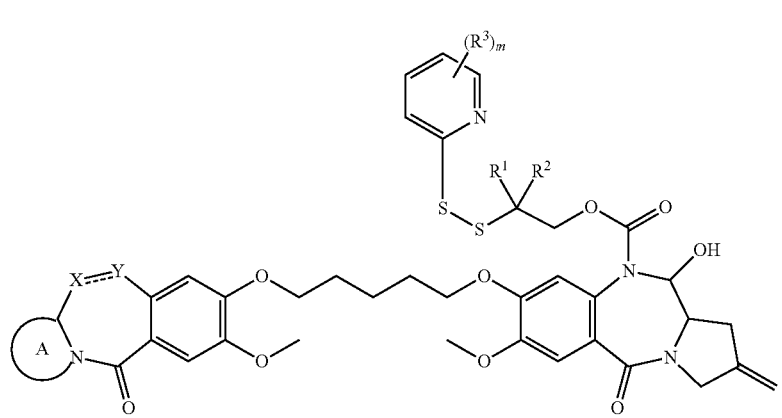

I wherein X $=$ Y is selected from $CH_2$—$CH_2$, CH=CH, C(=O)—NH, and $CH_2$—NH;

A is a 5-membered or 6-membered heterocyclic ring, optionally substituted with a group selected from F, $C_1$-$C_6$ alkyl, and =$C(R)_2$ where R is independently selected from H, F, $C_1$-$C_6$ alkyl, and $C_1$-$C_6$ fluoroalkyl;

$R^1$ and $R^2$ are independently selected from H and $C_1$-$C_6$ alkyl, or $R^1$ and $R^2$ form a 3, 4, 5, or 6-membered cycloalkyl or heterocyclyl group;

$R^3$ is independently selected from $NO_2$, Cl, F, CN, $CO_2H$ and Br; and m is 0, 1 or 2.

In an exemplary embodiment, A is a 5-membered ring.

In an exemplary embodiment, A is a 5-membered ring substituted with an exocyclic methylene group, =$CH_2$.

In an exemplary embodiment, A is a 6-membered ring.

In an exemplary embodiment, A is a morpholinyl ring.

In an exemplary embodiment, $R^1$ is —$CH_3$ and $R^2$ is H.

In an exemplary embodiment, $R^1$ and $R^2$ form cyclopropyl or cyclobutyl.

In an exemplary embodiment, $R^3$ is —$NO_2$ and m is 1.

In an exemplary embodiment, X $=$ Y is $CH_2$—$CH_2$ or CH=CH.

In an exemplary embodiment, X $=$ Y is C(=O)—NH or $CH_2$—NH.

An exemplary embodiment of monoalkylator pyrrolobenzodiazepine, linker-drug intermediate is Formula Ia:

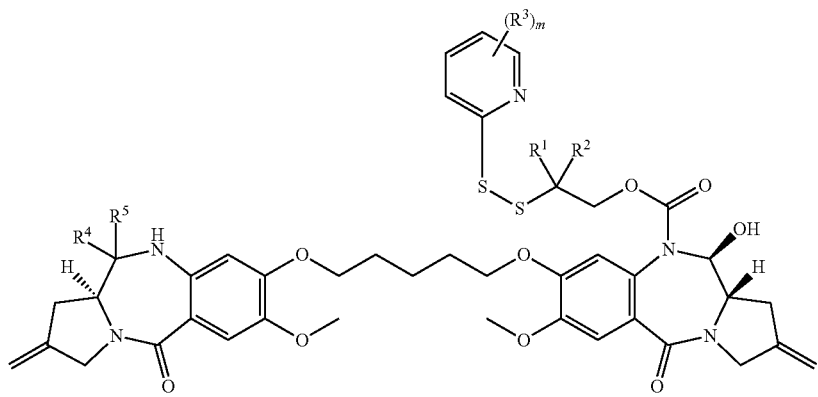

In an exemplary embodiment, $R^4$ and $R^5$ are each H.
In an exemplary embodiment, $R^4$ and $R^5$ are =O.
An exemplary embodiment of a monoalkylator pyrrolobenzodiazepine, linker-drug intermediate is Formula Ib:

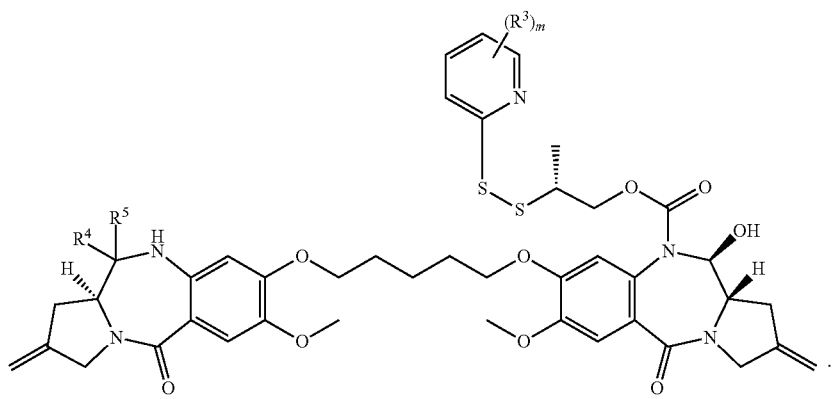

An exemplary embodiment of a monoalkylator pyrrolobenzodiazepine, linker-drug intermediate is Formula Ic:

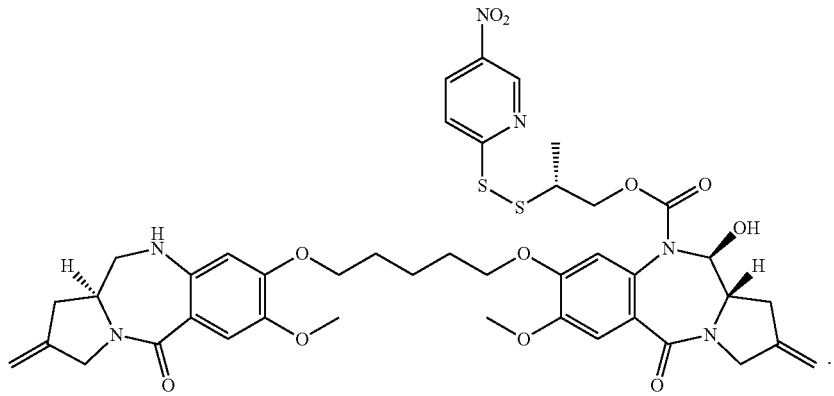

An exemplary embodiment of a monoalkylator pyrrolobenzodiazepine, linker-drug intermediate is Formula Id:

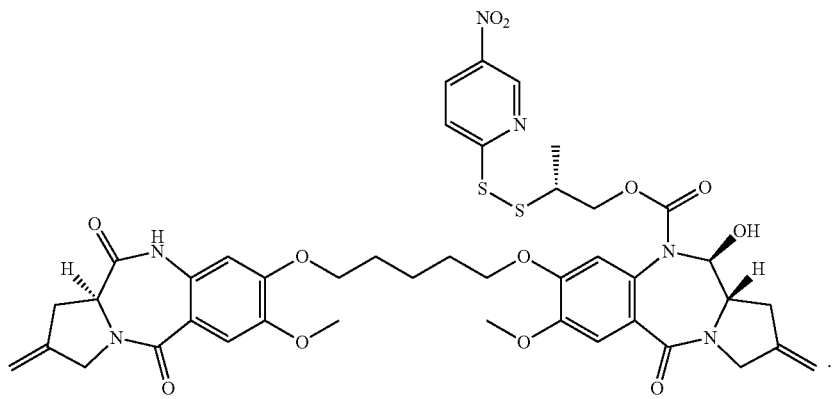

Id

Without being limited to a particular mechanism or effect, the presence of an electron-withdrawing group $R^3$ such as $NO_2$, Cl, F, CN, $CO_2H$ or Br on the pyridyl ring of the monoalkylator pyrrolobenzodiazepine, linker intermediate accelerates reaction with a cysteine thiol of a cysteine-engineered antibody. Where the cysteine thiol has been introduced at a hindered or less-reactive site on the antibody, such monoalkylator pyrrolobenzodiazepine, linker intermediate may give a more efficient conjugation reaction with an antibody relative to a corresponding unsubstituted pyridyl analog ($R^3$=H).

Exemplary monoalkylator pyrrolobenzodiazepine, linker-drug intermediates are shown in Table 2A. Comparator dialkylator pyrrolobenzodiazepine, linker-drug intermediates are shown in Table 2B. The synthesis of linker-drug intermediates and comparators are described in the Examples.

TABLE 2A

Monoalkylator pyrrolobenzodiazepine, linker-drug intermediates

| LD No. | Structure | IUPAC Name |
|---|---|---|
| LD-51 | 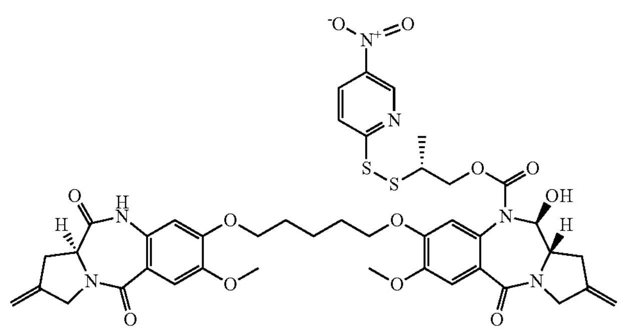 | (11S,11aS)-(R)-2-((5-nitropyridin-2-yl)disulfanyl)propyl 11-hydroxy-7-methoxy-8-((5-(((S)-7-methoxy-2-methylene-5,11-dioxo-2,3,5,10,11,11a-hexahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate |
| LD-52 | 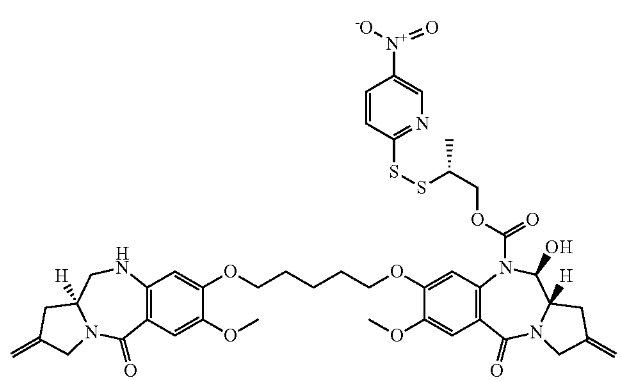 | (11S,11aS)-(R)-2-((5-nitropyridin-2-yl)disulfanyl)propyl 11-hydroxy-7-methoxy-8-((5-(((S)-7-methoxy-2-methylene-5-oxo-2,3,5,10,11,11a-hexahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate |

TABLE 2B

Comparator pyrrolobenzodiazepine linker-drug intermediates

| No. | Structure | IUPAC Name |
| --- | --- | --- |
| CLD-1 | 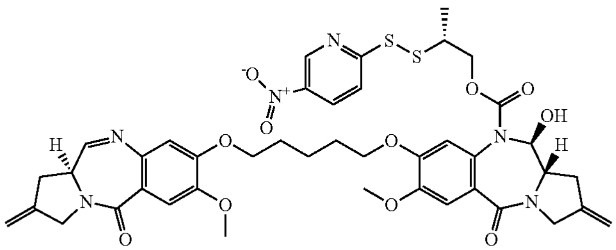 | (11S,11aS)-1-2-((5-nitropyridin-2-yl)disulfanyl)propyl 11-hydroxy-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate |
| CLD-2 | 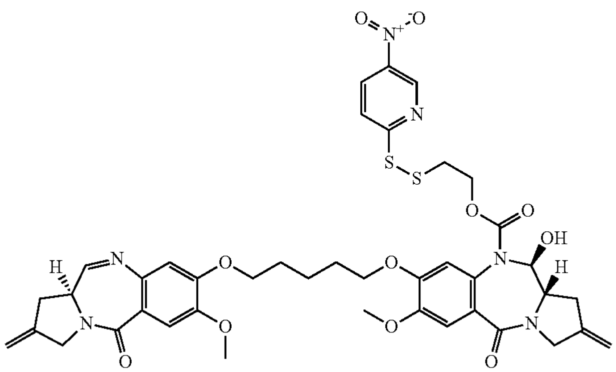 | 2-((5-nitropyridin-2-yl)disulfanyl)ethyl (11S,11aS)-11-hydroxy-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate |
| CLD-3 | 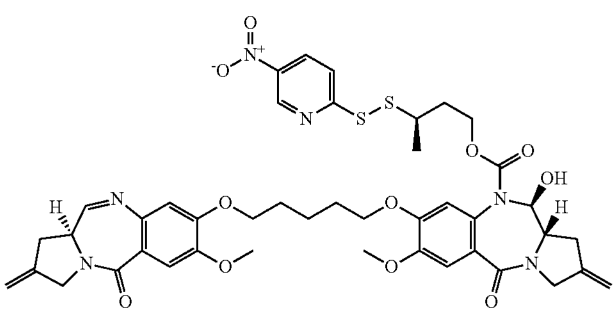 | (11S,11aS)-1-3-((5-nitropyridin-2-yl)disulfanyl)butyl 11-hydroxy-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate |
| CLD-4 | 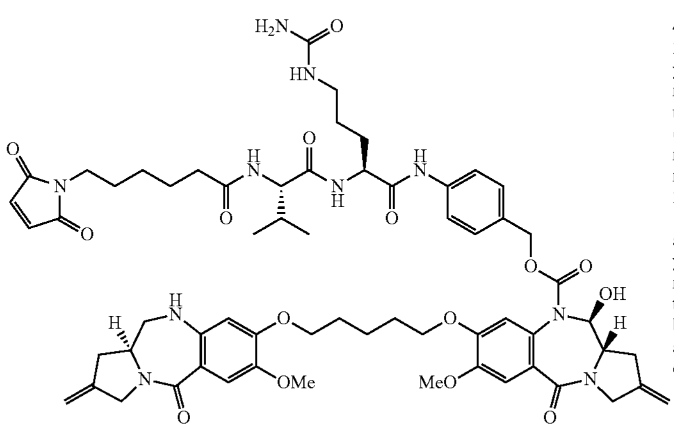 [SMILES: C=C1C[C@H]2CNc3cc(OCCCCCOc4cc5c(cc4OC)C(=O)N4CC(=C)C[C@H]4[C@H](O)N5C(=O)OCc4ccc(NC(=O)[C@H](CCCNC(N)=O)NC(=O)[C@@H](NC(=O)CCCCCN5C(=O)C=CC5=O)C(C)C)cc4)c(OC)cc3C(=O)N2C1] | 4-((S)-2-((S)-2-(6-(2,5-dioxo-2,5-dihydro-1H-pyrrol-1-yl)hexanamido)-3-methylbutanamido)-5-ureidopentanamido)benzyl (11S,11aS)-11-hydroxy-7-methoxy-8-((5-(((S)-7-methoxy-2-methylene-5-oxo-2,3,5,10,11,11a-hexahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate |

TABLE 2B-continued

Comparator pyrrolobenzodiazepine linker-drug intermediates

| No. | Structure | IUPAC Name |
| --- | --- | --- |
| CLD-5 | 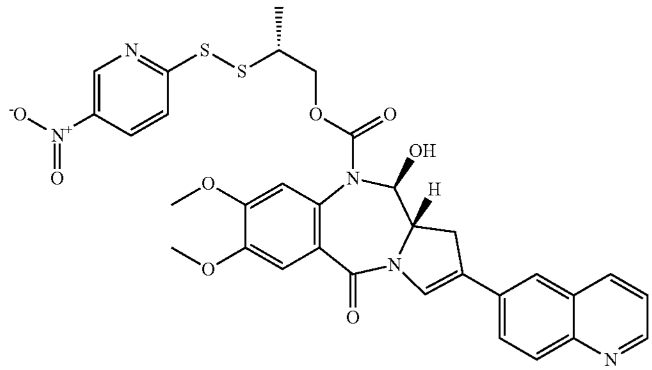 | (R)-2-((5-nitropyridin-2-yl)disulfanyl)propyl (11S,11aS)-11-hydroxy-7,8-dimethoxy-5-oxo-2-(quinolin-6-yl)-11,11a-dihydro-1H-benzo[e]pyrrolo[1,2-a][1,4]diazepine-10(5H)-carboxylate |
| CLD-6 | 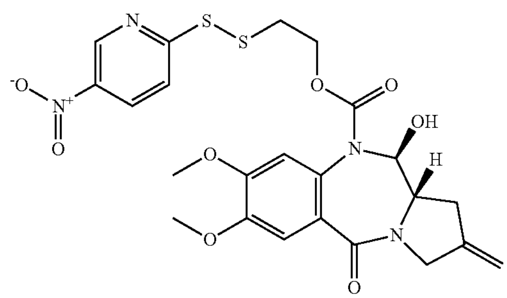 | 2-((5-nitropyridin-2-yl)disulfanyl)ethyl (11S,11aS)-11-hydroxy-7,8-dimethoxy-2-methylene-5-oxo-2,3,11,11a-tetrahydro-1H-benzo[e]pyrrolo[1,2-a][1,4]diazepine-10(5H)-carboxylate |

Antibody-Drug Conjugates (ADC)

The antibody-drug conjugate (ADC) compounds of the invention comprise an antibody specific for a tumor-associated antigen covalently attached, linked to a potent monoalkylator pyrrolobenzodiazepine drug moiety derivatized at the N10 group with a disulfide linker, and include those with biological activity. The ADC of the invention may have therapeutic activity and be effective against a number of hyperproliferative disorders, including cancer. The biological activity of the monoalkylator pyrrolobenzodiazepine drug moiety is modulated by conjugation to an antibody. The ADC of the invention selectively deliver an effective dose of the monoalkylator pyrrolobenzodiazepine drug, or toxin, to a tumor cell or site whereby greater selectivity, i.e. a lower efficacious dose, may be achieved while increasing the therapeutic index ("therapeutic window"). In an exemplary embodiment, the ADC compounds include a cysteine-engineered antibody conjugated, i.e. covalently attached by a linker, to the monoalkylator pyrrolobenzodiazepine drug moiety.

It is to be understood that where more than one nucleophilic cysteine thiol group reacts of an antibody with a drug-linker intermediate or linker reagent, then the resulting product is a mixture of ADC compounds with a distribution of one or more drug moieties attached to an antibody. The average number of drugs per antibody (DAR) may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

An antibody-drug conjugate compound of the invention has the structure of Formula II:

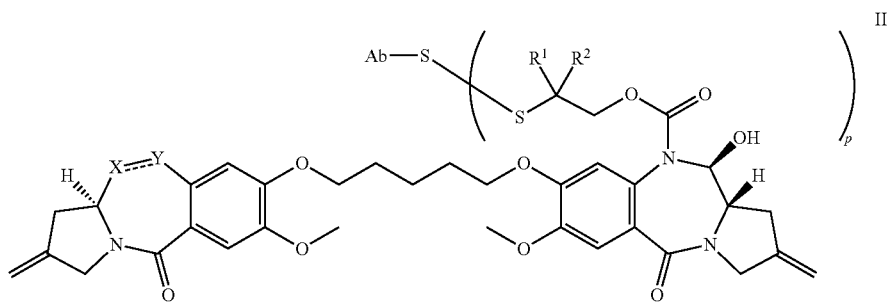

or a pharmaceutically acceptable salt thereof, wherein:
wherein:
X==Y is selected from $CH_2-CH_2$, $CH_2-C(=O)$, $CH=CH$, or $CH_2-NH$;

$R^1$ and $R^2$ are independently selected from H or $C_1$-$C_6$ alkyl, or $R^1$ and $R^2$ form a 3, 4, 5, or 6-membered cycloalkyl or heterocyclyl group;

p is an integer from 1 to 8; and

Ab is an antibody.

In an exemplary embodiment, the antibody binds to one or more tumor-associated antigens or cell-surface receptors selected from (1)-(53):

(1) BMPR1B (bone morphogenetic protein receptor-type IB);
(2) E16 (LAT1, SLC7A5);
(3) STEAP1 (six transmembrane epithelial antigen of prostate);
(4) MUC16 (0772P, CA125);
(5) MPF (MPF, MSLN, SMR, megakaryocyte potentiating factor, mesothelin);
(6) Napi2b (NAPI-3B, NPTIIb, SLC34A2, solute carrier family 34 (sodium phosphate), member 2, type II sodium-dependent phosphate transporter 3b);
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain I and short cytoplasmic domain, (semaphoring) 5B);
(8) PSCA hlg (2700050C12Rik, C530008O16Rik, RIKEN cDNA 2700050C12, RIKEN cDNA 2700050C12 gene);
(9) ETBR (Endothelin type B receptor);
(10) MSG783 (RNF124, hypothetical protein FLJ20315);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);
(12) TrpM4 (BR22450, FLJ20041, TRPM4, TRPM4B, transient receptor potential cation channel, subfamily M, member 4);
(13) CRIPTO (CR, CR1, CRGF, CRIPTO, TDGF1, teratocarcinoma-derived growth factor);
(14) CD21 (CR2 (Complement receptor 2) or C3DR (C3d/Epstein Barr virus receptor) or Hs 73792);
(15) CD79b (CD79B, CD79β, Igb (immunoglobulin-associated beta), B29);
(16) FcRH2 (IFGP4, IRTA4, SPAP1A (SH2 domain containing phosphatase anchor protein 1a), SPAP1B, SPAP1C);
(17) HER2;
(18) NCA;
(19) MDP;
(20) IL20Rα;
(21) Brevican;
(22) EphB2R;
(23) ASLG659;
(24) PSCA;
(25) GEDA;
(26) BAFF-R (B cell-activating factor receptor, BlyS receptor 3, BR3);
(27) CD22 (B-cell receptor CD22-B isoform);
(28) CD79a (CD79A, CD79α, immunoglobulin-associated alpha);
(29) CXCR5 (Burkitt's lymphoma receptor 1);
(30) HLA-DOB (Beta subunit of MHC class II molecule (Ia antigen));
(31) P2X5 (Purinergic receptor P2X ligand-gated ion channel 5);
(32) CD72 (B-cell differentiation antigen CD72, Lyb-2);
(33) LY64 (Lymphocyte antigen 64 (RP105), type I membrane protein of the leucine rich repeat (LRR) family);
(34) FcRH1 (Fc receptor-like protein 1);
(35) FcRH5 (IRTA2, Immunoglobulin superfamily receptor translocation associated 2);
(36) TENB2 (putative transmembrane proteoglycan);
(37) PMEL17 (silver homolog; SILV; D12S53E; PMEL17; SI; SL);
(38) TMEFF1 (transmembrane protein with EGF-like and two follistatin-like domains 1; Tomoregulin-1);
(39) GDNF-Ra1 (GDNF family receptor alpha 1; GFRA1; GDNFR; GDNFRA; RETL1; TRNR1; RET1L; GDNFR-alpha1; GFR-ALPHA-1);
(40) Ly6E (lymphocyte antigen 6 complex, locus E; Ly67, RIG-E, SCA-2, TSA-1);
(41) TMEM46 (shisa homolog 2 (*Xenopus laevis*); SHISA2);
(42) Ly6G6D (lymphocyte antigen 6 complex, locus G6D; Ly6-D, MEGT1);
(43) LGR5 (leucine-rich repeat-containing G protein-coupled receptor 5; GPR49, GPR67);
(44) RET (ret proto-oncogene; MEN2A; HSCR1; MEN2B; MTC1; PTC; CDHF12; Hs.168114; RET51; RET-ELE1);
(45) LY6K (lymphocyte antigen 6 complex, locus K; LY6K; HSJ001348; FLJ35226);
(46) GPR19 (G protein-coupled receptor 19; Mm.4787);
(47) GPR54 (KISS1 receptor; KISS1R; GPR54; HOT7T175; AXOR12);
(48) ASPHD1 (aspartate beta-hydroxylase domain containing 1; LOC253982);
(49) Tyrosinase (TYR; OCAIA; OCA1A; tyrosinase; SHEP3);
(50) TMEM118 (ring finger protein, transmembrane 2; RNFT2; FLJ14627);
(51) GPR172A (G protein-coupled receptor 172A; GPCR41; FLJ11856; D15Ertd747e);
(52) CD33; or
(53) CLL-1.

Exemplary antibody-drug conjugate compounds include Formula IIa:

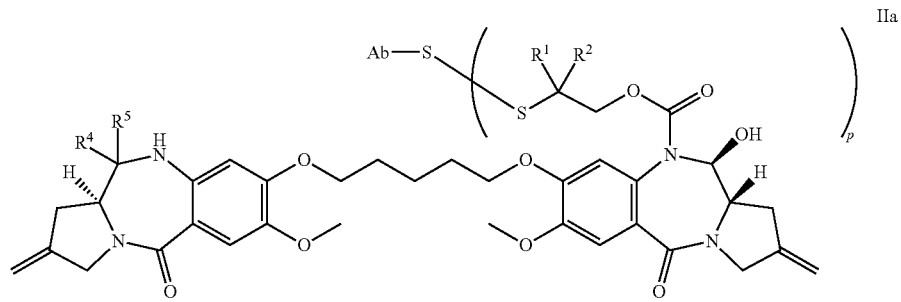

Exemplary antibody-drug conjugate compounds Formula IIa include wherein $R^4$ and $R^5$ are each H, or $R^4$ and $R^5$ are =O.

Exemplary antibody-drug conjugate compounds include Formula IIb:

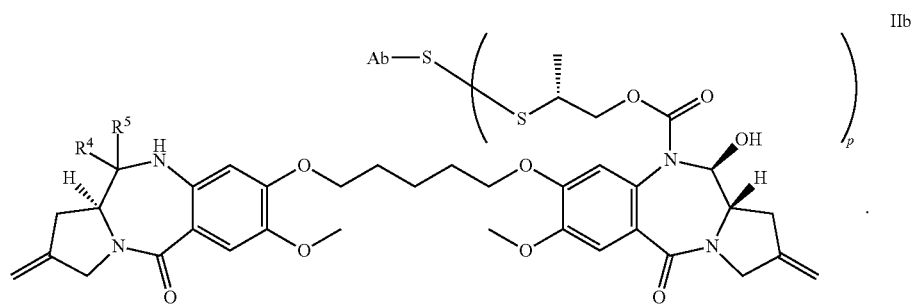

Antibody drug conjugates ADC-101-ADC-119 of Table 3A were prepared by conjugating a monoalkylator pyrrolobenzodiazepine, linker-drug intermediate LD-51 or LD-52 of Table 2A, with an antibody, including a cysteine engineered antibody. Comparator antibody-drug conjugates ADC-201-ADC-211 of Table 3B were prepared by conjugating a comparator pyrrolobenzodiazepine linker-drug intermediates CLD-1-6 of Table 2B, with an antibody, including a cysteine engineered antibody.

TABLE 3A

Monoalkylator disulfide Antibody-drug conjugates (ADC)

| ADC | ADC formula | linker-drug LD No. (Table 2A) | DAR* |
|---|---|---|---|
| ADC-101 | Thio anti-Her2 hu7C2 LC K149C-(LD-51) | 51 | 1.9 |
| ADC-102 | Thio anti-Her2 hu7C2 LC K149C-(LD-51) | 51 | 1.9 |
| ADC-103 | Thio Hu Anti-CD22 10F4v3 LC K149C-(LD-51) | 51 | 2.0 |
| ADC-104 | Thio anti-Her2 hu7C2 LC K149C-(LD-51) | 51 | 1.9 |
| ADC-105 | Thio Hu Anti-CD22 10F4v3 LC K149C-(LD-51) | 51 | 2.0 |
| ADC-106 | Thio anti-Her2 hu7C2 LC K149C-(LD-51) | 51 | 2.0 |

TABLE 3A-continued

Monoalkylator disulfide Antibody-drug conjugates (ADC)

| ADC | ADC formula | linker-drug LD No. (Table 2A) | DAR* |
|---|---|---|---|
| ADC-107 | Thio Hu Anti-CD22 10F4v3 LC K149C-(LD-52) | 52 | 1.95 |
| ADC-108 | Thio Hu-Anti-Her2 hu7C2 LC K149C-(LD-52) | 52 | 1.99 |
| ADC-109 | Thio anti-Her2 hu7C2 LC K149C-(LD-51) | 51 | 2.0 |
| ADC-110 | Thio Hu Anti-CD22 10F4v3 LC K149C-(LD-51) | 51 | 1.98 |
| ADC-111 | Thio Hu Anti-CD22 10F4v3 LC K149C HC L177C-(LD-51) | 51 | 3.6 |
| ADC-112 | Thio Hu Anti-CD22 10F4v3 LC K149C HC L177C HC Y376C-(LD-51) | 51 | 5.4 |
| ADC-113 | Thio Hu Anti-HER2 4D5 LC K149C HC L177C-(LD-51) | 51 | 3.9 |
| ADC-114 | Thio Hu Anti-HER2 4D5 LC K149C HC L177C HC Y376C-(LD-51) | 51 | |
| ADC-115 | Thio Hu Anti-Ly6E 9B12.v12 LC K149C-(LD-51) | 51 | 2.0 |
| ADC-116 | Thio Hu Anti-CD22 10F4v3 HC L177C-(LD-51) | 51 | |
| ADC-117 | Thio Hu Anti-HER2 hu7C2 HC L177C-(LD-51) | 51 | |

TABLE 3A-continued

Monoalkylator disulfide Antibody-drug conjugates (ADC)

| ADC | ADC formula | linker-drug LD No. (Table 2A) | DAR* |
|---|---|---|---|
| ADC-118 | Thio Hu Anti-CD22 10F4v3 HC Y376C-(LD-51) | 51 | |
| ADC-119 | Thio Hu Anti-HER2 hu7C2 HC Y376C-(LD-51) | 51 | |

TABLE 3B

Comparator Antibody-drug conjugates (ADC)

| ADC | ADC formula | linker-drug (Table 2B) | DAR* |
|---|---|---|---|
| ADC-201 | Thio anti-Her2 hu7C2 LC K149C-(CLD-1) | CLD-1 | 1.84 |
| ADC-202 | Thio Hu Anti-CD22 10F4v3-(CLD-1) | CLD-1 | 1.8 |
| ADC-203 | Thio Anti-Her2 hu7C2 LC K149C-(CLD-3) | CLD-3 | 2.0 |
| ADC-204 | Thio Hu Anti-CD22 10F4v3 LC K149C-MC-vc-PAB-PBD mono-amine-(CLD-4) | CLD-4 | 2.0 |

TABLE 3B-continued

Comparator Antibody-drug conjugates (ADC)

| ADC | ADC formula | linker-drug (Table 2B) | DAR* |
|---|---|---|---|
| ADC-205 | thio Anti-Her2 hu7C2 LC K149C-MC-vc-PAB-PBD mono-amine-(CLD-4) | CLD-4 | 1.9 |
| ADC-206 | Thio Hu Anti-CD22 10F4v3 LC K149C-(CLD-4) | CLD-4 | 2.0 |
| ADC-207 | Thio Hu Anti-CD22 10F4v3 LC K149C-(CLD-2) | CLD-2 | 1.96 |
| ADC-208 | Thio Hu Anti-NaPi2b 10H1.11.4B LC K149C-(CLD-2) | CLD-2 | 1.96 |

TABLE 3B-continued

Comparator Antibody-drug conjugates (ADC)

| ADC | ADC formula | linker-drug (Table 2B) | DAR* |
|---|---|---|---|
| ADC-209 | Thio Hu Anti-gD 5B6 LC K149C-(CLD-4) | CLD-4 | |
| ADC-210 | Thio Hu Anti-Ly6E 9B12.v12 LC K149C-(CLD-4) | CLD-4 | 2.0 |
| ADC-211 | Tmab-DM1 (trastuzumab emtansine) | DM1 | 3.8 |
| ADC-212 | Thio Hu anti-Ly6E LC K149C-(CLD-1) | CLD-1 | |

A118C (EU numbering)=A121C (Sequential numbering)
=A114C (Kabat numbering)
K149C (Kabat numbering) of light chain
Wild-type ("WT"), cysteine engineered mutant antibody ("thio"), light chain ("LC"), heavy chain ("HC"), 6-maleimidocaproyl ("MC"), maleimidopropanoyl ("MP"), valine-citrulline ("val-cit" or "vc"), alanine-phenylalanine ("ala-phe"), p-aminobenzyl ("PAB"), and p-aminobenzyloxycarbonyl ("PABC")

Comparator ADC-211, trastuzumab emtansine (KADCYLA®, trastuzumab-MCC-DM1 (T-DM1, Tmab-DM1), is an antibody-drug conjugate (CAS Reg. No. 139504-50-0; Phillips G. et al. (2008) Cancer Res. 68:9280-90; U.S. Pat. No. 8,142,784), and has the structure:

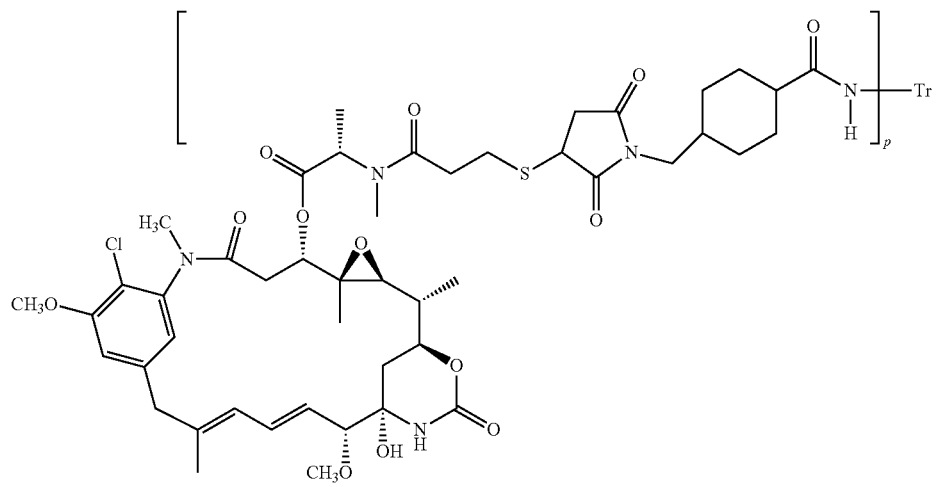

where Tr is the anti-HER2 antibody trastuzumab.

In Vitro Cell Proliferation Assays

Generally, the cytotoxic or cytostatic activity of an antibody-drug conjugate (ADC) is measured by: exposing mammalian cells having receptor proteins, e.g. HER2, to the antibody of the ADC in a cell culture medium; culturing the cells for a period from about 6 hours to about 5 days; and measuring cell viability. Cell-based in vitro assays were used to measure viability (proliferation), cytotoxicity, and induction of apoptosis (caspase activation) of the ADC of the invention.

The in vitro potency of antibody-drug conjugates (ADC) was measured by a cell proliferation assay (Example 6). The ADC of the invention showed surprising and unexpected potency in inhibition of tumor cell proliferation. Potency of the ADC was correlated with target antigen expression of the cells. The tested conjugates are capable of binding to the specific antigen expressed on the surface of cells and causing the death of those cells in vitro.

The CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713; 5,700,670). This cell proliferation assay determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

Cell-based in vitro assays are used to measure viability (proliferation), cytotoxicity, and induction of apoptosis (caspase activation) of the ADC of the invention. Generally, the cytotoxic or cytostatic activity of an antibody-drug conjugate (ADC) is measured by: exposing mammalian cells expressing antigen such as Her2 or MUC16 polypeptide to ADC in a cell culture medium; culturing the cells for a period from about 6 hours to about 5 days; and measuring cell viability. Mammalian cells useful for cell proliferation assays for anti-MUC16 ADC include: (1) a MUC16 polypeptide-expressing cell line OVCAR-3; (2) a PC3-derived cell line engineered to stably express a portion of the MUC16 polypeptide on its cell surface (PC3/MUC16); (3) the parental PC3 cell line that does not express the MUC16 polypeptide; and (4) a PC3 cell line that does not express MUC16 polypeptide but carries the vector used to drive exogenous MUC16 expression (PC3/neo).

Figure 1C:
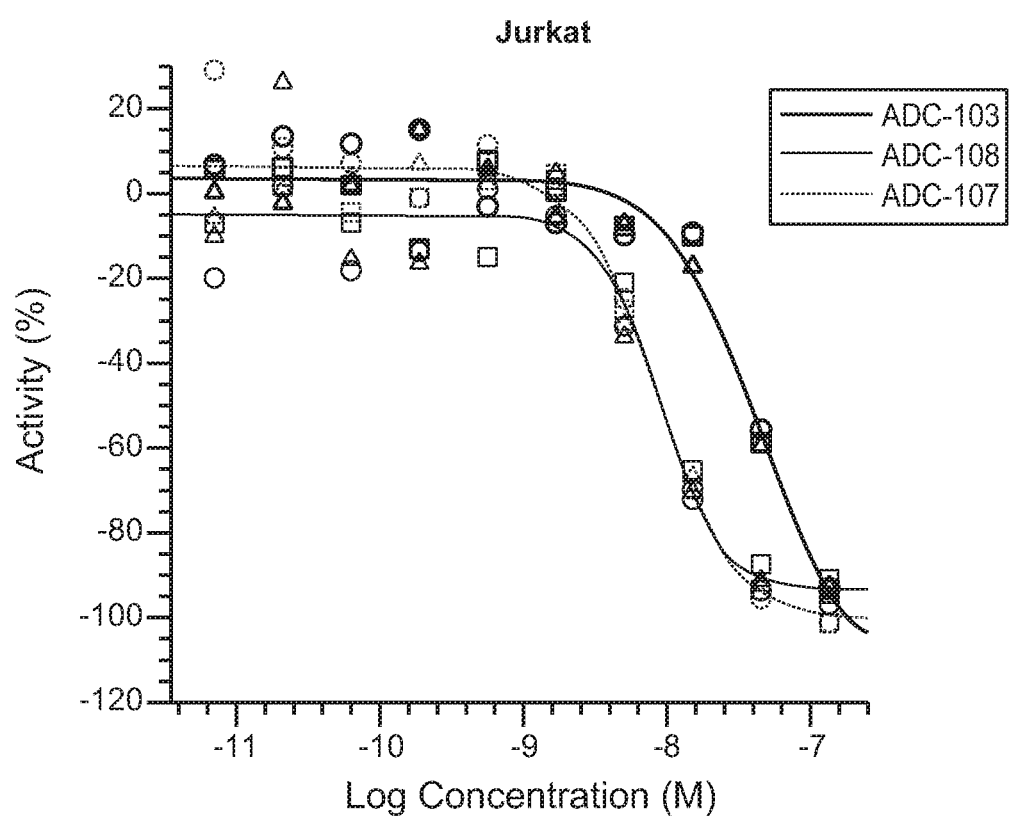
FIG. 1C shows a plot of in vitro cell viability of Jurkat cells treated with ADC-107, ADC-103 and non-target control ADC-108.
Figure 1D:
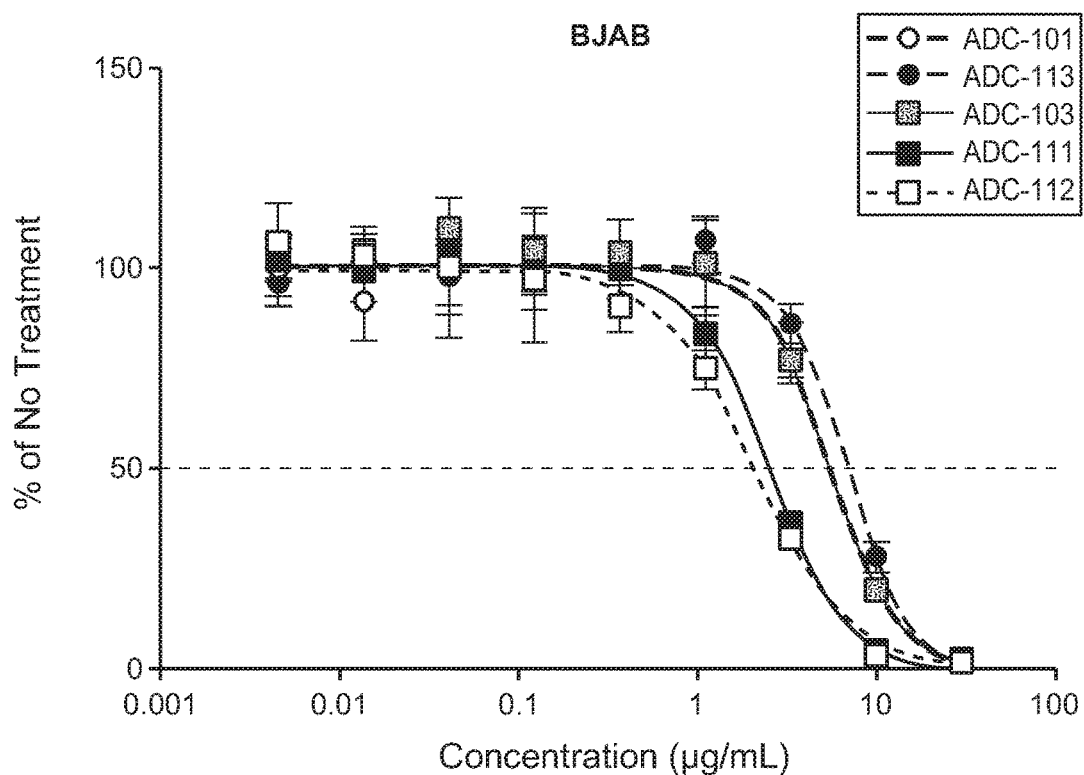
FIG. 1D shows a plot of in vitro cell viability of BJAB cells treated with ADC-101, ADC-113, ADC-103, ADC-111, and ADC-112.
Figure 1E:
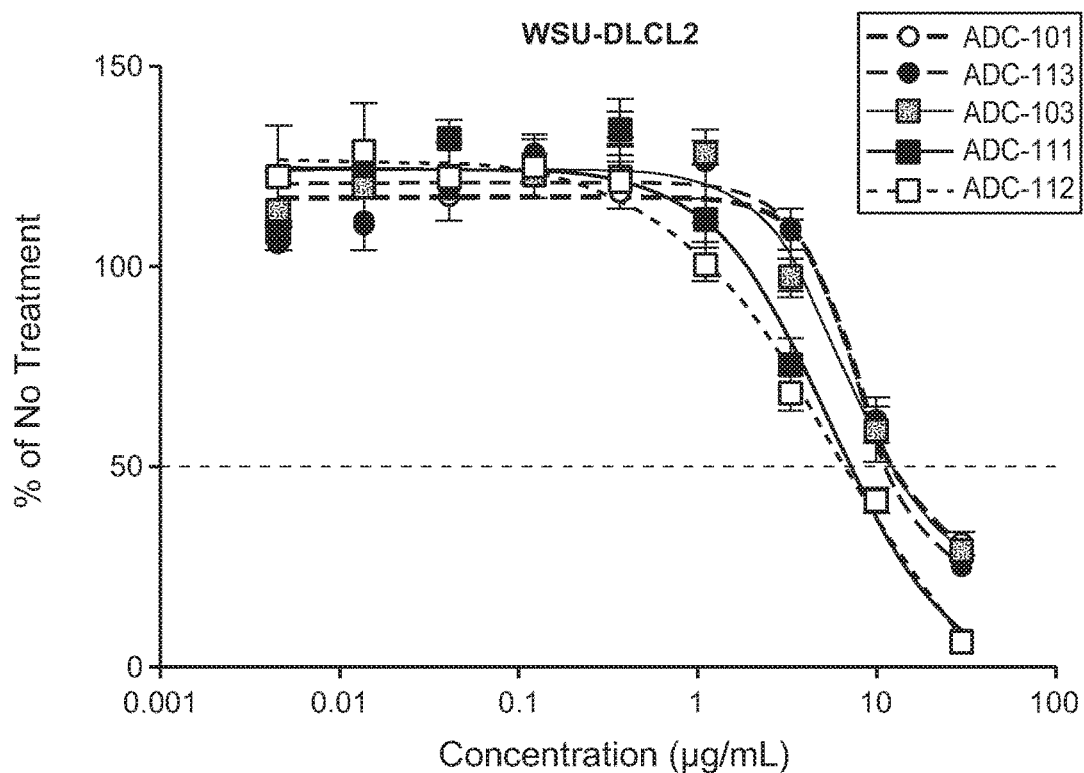
FIG. 1E shows a plot of in vitro cell viability of WSU-DLCL2 cells treated with ADC-101, ADC-113, ADC-103, ADC-111, and ADC-112.

FIGS. 1A, 1B, 1C shows Thio Hu Anti-CD22 10F4v3 LC K149C-(LD-52) ADC-107 monoamine exhibits single digit nM potency with about 4-fold difference from non-target control ADC-108 in BJAB (FIG. 1A), about 7-fold difference from non-target control in WSU-DLCL2 (FIG. 1B), and about 5-fold greater potency than non-target control ADC-108 in Jurkat (FIG. 1C). Monoamine ADC-107 is about 10-fold and about 22-fold more potent than Thio Hu Anti-CD22 10F4v3 LC K149C-(LD-51) mono-amide ADC-103 and non-target control ADC-108 in BJAB and WSU-DLCL2, respectively (FIGS. 1A-C).

TABLE 4

Figure 1F:
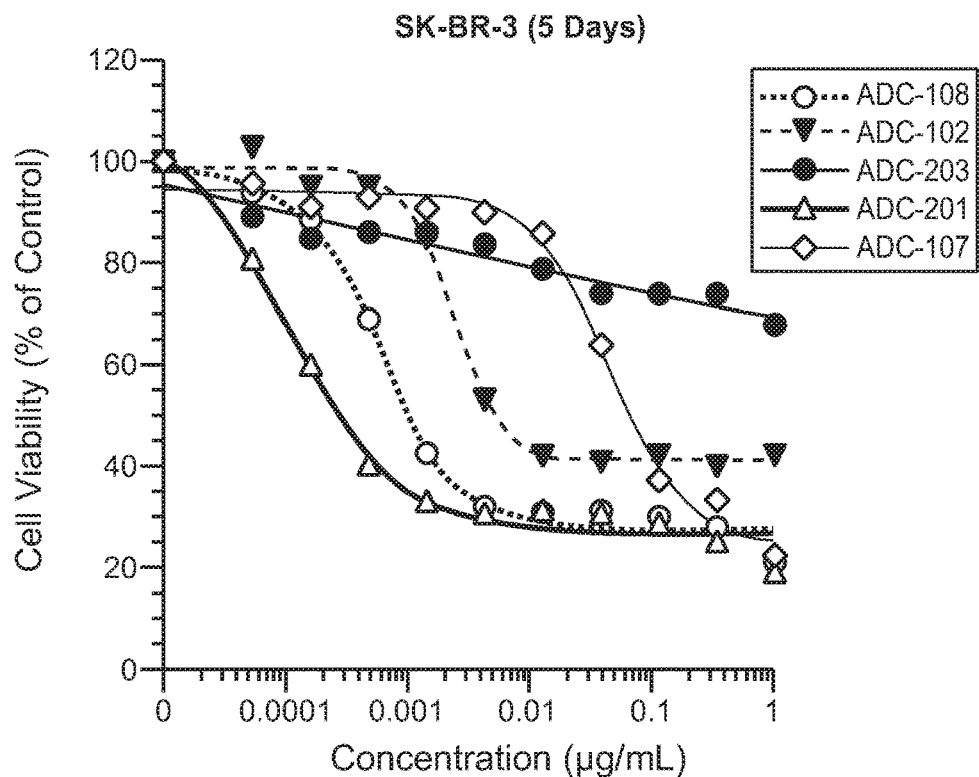
FIG. 1F shows a plot of in vitro cell viability of SK-BR-3 cells treated with ADC-108, ADC-102, ADC-203, ADC-201, and ADC-107.
Figure 1G:
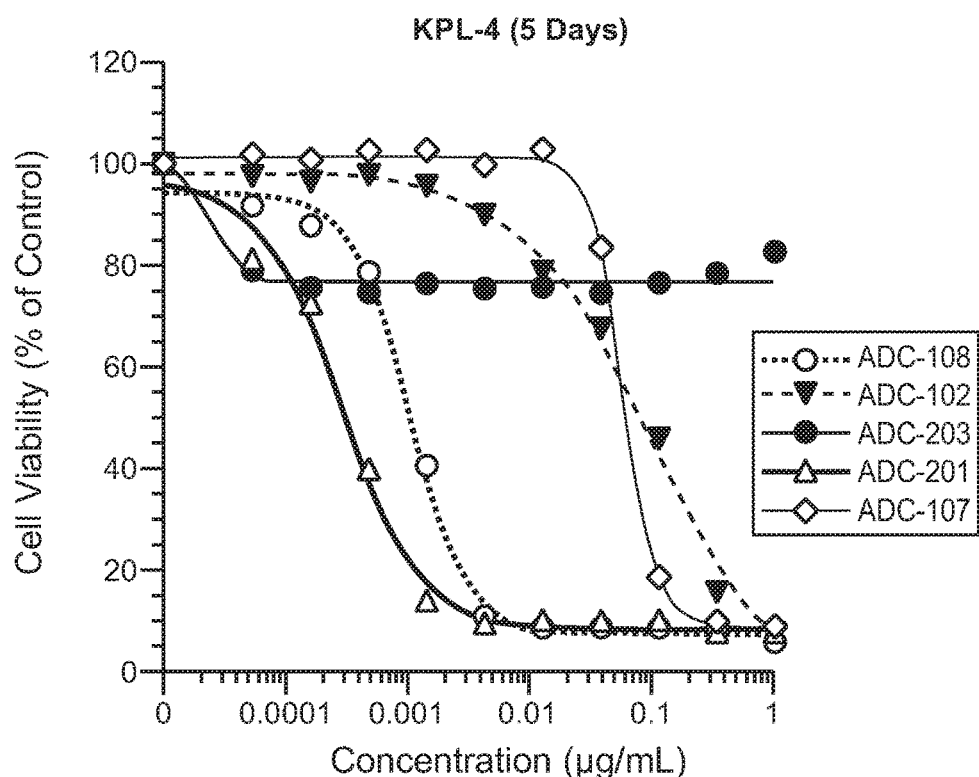
FIG. 1G shows a plot of in vitro cell viability of KPL-4 cells treated with ADC-108, ADC-102, ADC-203, ADC-201, and ADC-107.

In vitro cell proliferation assay of antibody drug conjugates (FIGS. 1F, 1G)

| ADC | Linker-drug | Target | % Aggregation | DAR | SK-BR-3 IC$_{50}$ (ng/mL) | KPL-4 IC$_{50}$ (ng/mL) |
|---|---|---|---|---|---|---|
| 108 | LD-52 | HER2 (hu7C2) | 2.28 | 1.99 | 0.6 | 1.0 |
| 107 | LD-52 | CD22 | 2.24 | 1.95 | 44.5 | 57.4 |
| 102 | LD-52 | HER2 (hu7C2) | 2.9 | 1.9 | 3.3 | 103 |
| 203 | CLD-3 | HER2 (hu7C2) | 3.2 | 2.0 | >1000 | >1000 |
| 201 | CLD-1 | HER2 (hu7C2) | 3.6 | 1.84 | 0.1 | 0.3 |

TABLE 5

In vitro potency (FIGS. 1A, 1B, 1C)

| ADC | DAR | BJAB IC50 | | WSU-DLCL2 IC50 | | Jurkat IC50 | |
|---|---|---|---|---|---|---|---|
| | | nM | ng/mL | nM | ng/mL | nM | ng/mL |
| 105 | 2 | 17.68 | 2650.34 | 34.39 | 5156.08 | 42.92 | 6434.14 |
| 107 | 1.95 | 1.70 | 254.20 | 1.56 | 234.11 | 8.70 | 1303.63 |
| 108 | 1.99 | 8.46 | 1268.70 | 11.27 | 1689.31 | 8.96 | 1342.60 |

In Vivo Efficacy

The in vivo efficacy of antibody-drug conjugates (ADC) was measured by tumor growth inhibition in mice (Example 7). The ADC of the invention showed surprising and unexpected potency in inhibition of tumor growth. Efficacy of the ADC was correlated with target antigen expression of the tumor cells.

The efficacy of antibody-drug conjugates were measured in vivo by implanting allografts or xenografts of cancer cells in rodents and treating the tumors with ADC. Variable results are to be expected depending on the cell line, the specificity of antibody binding of the ADC to receptors present on the cancer cells, dosing regimen, and other factors. The in vivo efficacy of the ADC was measured using a transgenic explant mouse model expressing moderate to high levels of a tumor-associated antigen, such as Her2, CD22, and Ly6E. Subjects were treated once with ADC and monitored over 3-6 weeks to measure the time to tumor doubling, log cell kill, and tumor shrinkage. Follow up dose-response and multi-dose experiments were conducted.

For example, the in vivo efficacy of an anti-HER2 ADC of the invention can be measured by a high expressing HER2 transgenic explant mouse model (Phillips et al (2008) Cancer Res. 68:9280-90). An allograft is propagated from the Fo5 mmtv transgenic mouse which does not respond to, or responds poorly to, HERCEPTIN® therapy. Subjects were treated once with ADC at certain dose levels (mg/kg) and placebo buffer control (Vehicle) and monitored over two weeks or more to measure the time to tumor doubling, log cell kill, and tumor shrinkage.

FIG. 2 shows the efficacy of antibody-drug conjugates, ADC-202, ADC-103, and ADC-102 in a plot of the in vivo fitted tumor volume change over time in WSU-DLCL2 xenograft model in CB-17 Fox Chase SCID mice.

FIG. 3 shows the efficacy of antibody-drug conjugates in a plot of the in vivo fitted tumor volume change over time in the Bjab-luc xenograft model in CB-17 Fox Chase SCID mice. The 0.2 and 0.4 mg/kg doses of comparator ADC-202 result in tumor regression, with the 0.1 mg/kg dose resulting in 62% TGI. The TGI range from 40-58% in the 1, 2, and 4 mg/kg doses of monoamide ADC-105 indicate these dose levels have similar response where only the highest 8 mg/kg dose shows significant activity, 89% TGI. Further, activity at 8 mg/kg falls between the 0.1 and 0.2 mg/kg dose of comparator dialkylator ADC-202, resulting in ~50× less potency. Off target control anti-Her2 hu7C2 ADC-104-monoamide at 8 mg/kg showed 2-fold less activity than off-target control, comparator anti-Her2 hu7C2 ADC-201 at 0.4 mg/kg, 18 vs 36% TGI. In body weight safety assessment, all groups exhibited weight gain.

FIG. 4 shows the efficacy of antibody-drug conjugates in a plot of the in vivo fitted tumor volume change over time WSU-DLCL2 human cell line mouse model. Efficacy for on-target, anti-CD22 ADC-107 monoamine and val-cit linkage ADC-204 were assessed at doses from 0.5-10 mg/kg. The monoamide ADC-105 was included for comparison. Off-target anti-Her2 monoamine ADC-108 and ADC-205 were used for controls. Activity for both monoamine ADC-107 and ADC-204 appear to be similar. The minimum efficacious dose (MED) for both is between 0.5 and 2 mg/kg. At the highest 10 mg/kg dose, both resulted in complete responses in 5/5 animals, a result not seen with monoamide ADC. Further, monoamine ADC results in >10 fold activity compared to monoamide ADC (compare response at 0.5 mg/kg doses monoamine vs 5 mg/kg dose monoamide). Both Her2 controls dosed at 2 mg/kg have similar response (~30% TGI). No significant weight loss for all groups.

Figure 5A:
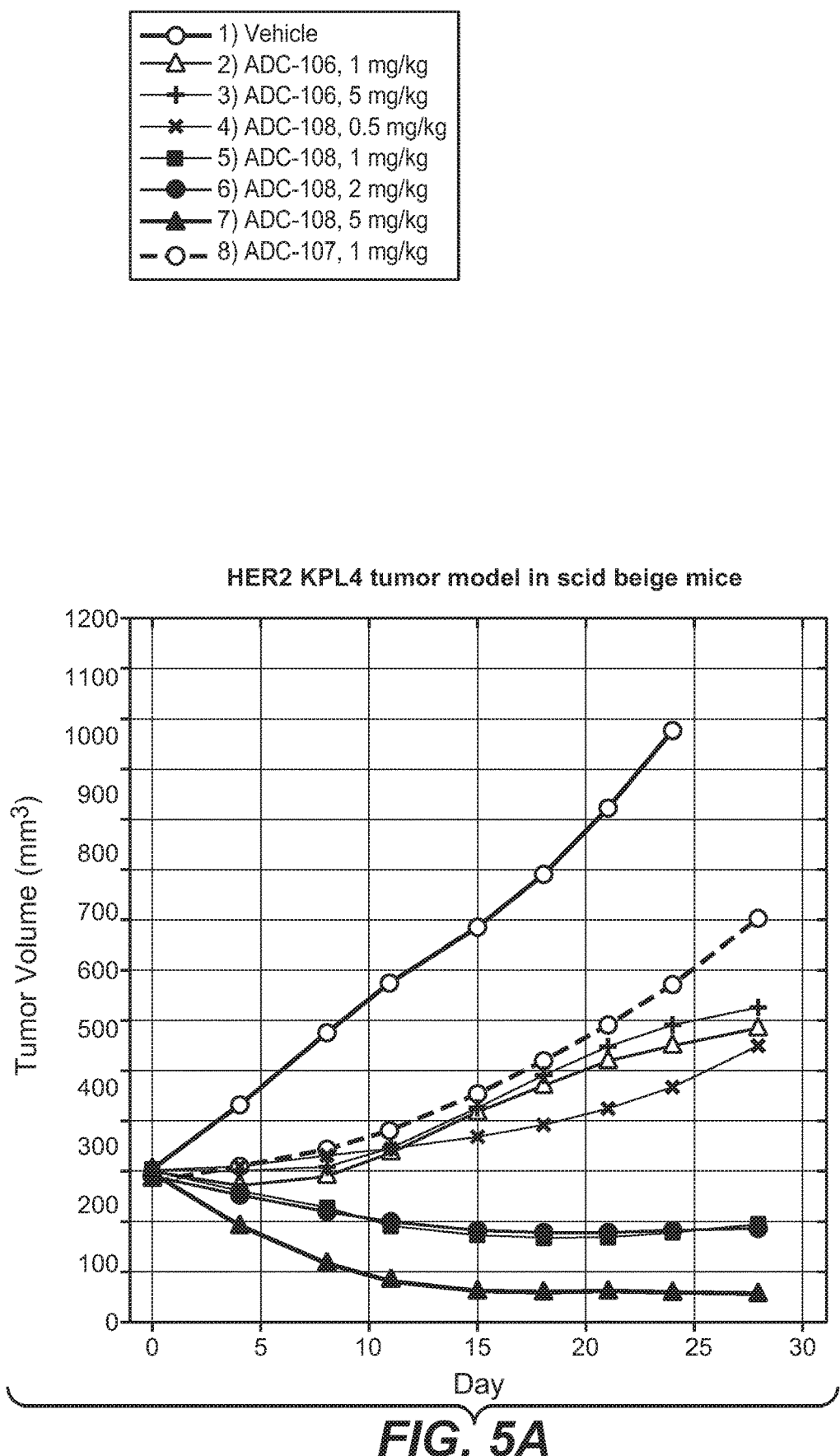
FIG. 5A shows the efficacy of antibody-drug conjugates in a plot of the in vivo fitted tumor volume change over time in HER2 KPL4 tumor model in scid beige mice, dosed IV once with the following:
1) Vehicle
2) Thio-Her2 hu7C2 LC-K149C-(LD-51) monoamide, ADC-106, 1 mg/kg
3) Thio-Her2 hu7C2 LC-K149C-(LD-51) monoamide, ADC-106, 5 mg/kg
4) Thio-Her2 hu7C2 LC-K149C-(LD-52) monoamine, ADC-108, 0.5 mg/kg
5) Thio-Her2 hu7C2 LC-K149C-(LD-52) monoamine, ADC-108, 1 mg/kg
6) Thio-Her2 hu7C2 LC-K149C-(LD-52) monoamine, ADC-108, 2 mg/kg
7) Thio-Her2 hu7C2 LC-K149C-(LD-52) monoamine, ADC-108, 5 mg/kg
8) CD22 LC-K149C-(LD-52) monoamine, ADC-107, 1 mg/kg

FIG. 5A shows the efficacy of antibody-drug conjugates, ADC-106, ADC-108, and ADC-107 in a plot of the in vivo fitted tumor volume change over time in HER2 KPL4 tumor model in scid beige mice.

FIG. 5B shows the efficacy of antibody-drug conjugates in a plot of the in vivo fitted tumor volume change over time in HER2 KPL4 tumor model in scid beige mice. Efficacy of Thio-Her2 hu7C2 LC-K149C-(LD-51) monoamide, ADC-106 and ADC-106 in combination with Tmab-DM1 was measured.

FIG. 6 shows the efficacy of antibody-drug conjugates, ADC-201, ADC-104, ADC-202, and ADC-105, and an unconjugated antibody hu7C2 in a plot of the in vivo fitted tumor volume change over time in HER2 Fo5 model in CRL nu/nu mice, dosed IV once. On-target ADC-201 and ADC-104 show tumor inhibition and dose-dependent effects. Off-target ADC-202, ADC-105, and the unconjugated antibody hu7C2 show no tumor inhibition.

FIG. 7 shows the efficacy of antibody-drug conjugates, ADC-201, ADC-104, ADC-202, ADC-105, and an unconjugated antibody hu7C2 in a plot of the in vivo fitted tumor volume change over time in HER2 KPL4 tumor model in scid beige mice. On-target ADC-201 and ADC-104 show tumor inhibition and dose-dependent effects. Off-target ADC-202, ADC-105, and the unconjugated antibody hu7C2 show little or no tumor inhibition.

FIG. 8 shows the efficacy of antibody-drug conjugates, ADC-106, ADC-18, and ADC-17 in a plot of the in vivo fitted tumor volume change over time in HER2 Fo5 model in CRL nu/nu mice. On-target ADC-106 and ADC-108 show tumor inhibition and dose-dependent effects. Off-target ADC-107 shows little or no tumor inhibition.

FIG. 9 shows the efficacy of antibody-drug conjugates ADC-104, ADC-111, ADC-112, ADC-106, and ADC-113 in a plot of the in vivo fitted tumor volume change over time in CD22-expressing WSU-DLCL2 xenograft model in CB-17 Fox Chase SCID mice. On-target ADC-104, ADC-111, ADC-112 show tumor inhibition and dose-dependent effects. Off-target ADC-106 and ADC-133 show no tumor inhibition.

FIG. 10 shows the efficacy of antibody-drug conjugates in a plot of the in vivo fitted tumor volume change over time in HCC1569X2 xenograft model. Ly6E-SG3451-mono amide has dose dependent activity, with growth delay at 6 and 12 mg/kg and tumors around stasis when dosed at 18 mg/kg. There is tumor regression seen with Ly6E-SG3451, dosed at 1 and 3 mg/kg, and Ly6E-SG3203-mono amine, dosed at 1, 3, and 6 mg/kg. The Ly6E SG3451 and SG3203-mono amine groups are clustered together.

Oligonucleotide Binding/Alkylation Assay

Pyrrolobenzodiazepine (PBD) compounds are known to form sequence-dependent, intrastrand DNA cross-links and monoalkylated adducts in addition to interstrand cross-links (Rahman K M, et al (2009) J Am Chem Soc 131:13756-13766). PBDs have a chiral C11a(S)-position which provides them with an appropriate shape to fit securely in the minor groove of DNA. In addition, an electrophilic N10-C11 moiety (i.e., interconvertible imine, carbinolamine, or carbinolamine methyl ether functionalities) can form a covalent aminal linkage between their C11-position and the nucleophilic C2-NH2 group of a guanine nucleobase. Interaction of pyrrolobenzodiazepine compounds with duplex-forming oligonucleotides of various length and sequences were studied with sequences of Pu-GAATG-Py>Pu-GATC-Py>>Pu-GATG-Py or Pu-GAATC-Py for intrastrand and interstrand cross-linking previously identified (Example 8). The oligonucleotide binding and alkylation assay is a simple model to assess the binding potential of pyrrolobenzodiazepine drug moieties in ADC to nucleic acids by HPLC separation and MS detection (Narayanaswamy M. et al (2008) Anal. Biochem. 374:173-181). Potency and efficacy of ADC may thus be correlated and predicted. Monoalkylator pyrrolobenzodiazepine drug moieties may be differentiated, such as monoamide DM-3 from monoamine DM-1, and the monoalkylators of Table 1a from comparator dialkylator pyrrolobenzodiazepine drug moieties of Table 1b, such as C-1 (Example 8).

The frequency of occurrence of selected oligonucleotide sequences that would bind/alkylate pyrrolobenzodiazepine compounds is very high and not directly proportional to the size of the chromosomes in which they occur. The pyrrolobenzodiazepine compounds in this study include monoalkylator pyrrolobenzodiazepine drug moieties from Table 1a and Comparator drug moieties from Table 1b. The study showed differential levels of drug alkylates the double-stranded oligonucleotides and the alkylating potential can be accurately assessed through disappearance of the starting duplex oligonucleotides, Pu-GAAATC-Py and Pu-GAAATG-Py, where Pu is a purine nucleotide A or G and Py is a pyrimidine nucleotide C or T. Monoamide PBD DM-2 (Table 1a) was approximately 8 times less efficient to bind/alkylate the duplex oligonucleotides than the monoamine PBD DM-1. Comparator dialkylator C-1 (Table 1b) shows 2-3 times more efficiency to covalently alkylate the duplex oligonucleotides than the monoamine DM-1. PBD monomer C-2 shows >50 times less efficiency in covalently alkylating the duplex oligonucleotides than the dimer C-1. Reduction of the imine bonds of C-1 to form C-3 completely eliminates DNA binding. Various oligo-PBD adducts were formed with different alkylators, separated by HPLC, and characterized by mass by MS analysis.

FIG. 11 shows putative adducts after reactions of a dialkylator pyrrolobenzodiazepine (PBD) dimer compound CLD-1 (top) and two monoalkylator pyrrolobenzodiazepine dimer compounds, monoamine DM-1 (middle) and monoamide DM-2 (bottom) with DNA (Rahman K M, et al (2009) *J Am Chem Soc* 131:13756-13766). Dialkylator PBD dimer compounds can form two covalent attachments (cross-link) with the C2-NH2 group of a guanine nucleobase on opposing strands of DNA duplex. Monoalkylator PBD dimer compounds can form only one covalent attachment with a guanine nucleobase, thus affecting kinetics of on/off binding and disruption of dividing cells.

Monoamide DM-2 shows 8-10 fold less binding/alkylation than monoamine DM-1 to duplex oligonucleotides, which correlates with the potency and efficacy of their ADCs in cancer cell lines and in vivo tumor xenograft models. The lower level of DNA alkylation for monoamide supports efficacy with reduced toxicity and may demonstrate a better therapeutic index. Overall, the extent of DNA binding/alkylation correlates with efficacy of PBD analogs and differentiates monoamide from monoamine PBD, and from dialkylator PBD. Optimized therapeutic indices (TI) of PBD-ADCs may be attainable through modulating DNA binding/alkylation activities of monoalkylators, and the oligo binding/alkylation method could be used to guide design and evaluation of PBD analogs with optimal antitumor efficacy with acceptable safety.

Safety/Toxicity Properties

The antibody-drug-conjugates (ADC) of the invention and comparator ADC were studied for their safety and toxicity related properties.

The anti-HER2 hu7C2 antibody ADC-108 with monoamine monoalkylator (LD-52) showed improved tolerance in CD-1 mice and improved therapeutic index (TI) relative to corresponding anti-HER2 hu7C2 antibody ADC-201 with imine dialkylator (C-1) as calculated by percent body weight change over 45 days after dosing (50, 75, 125 µg (micrograms) per kg at days 0, 7, 14. The maximum tolerated dose (MTD) for ADC-108 is 200 µg/kg whereas the MTD for ADC-201 is 75 µg/kg. Toxicity signals in rat (Sprague-Dawley) and cynomolgus monkeys may include transient decrease in reticulocytes, minor skin discolorations and flaking near injection site, vascular leak, elevated liver enzymes, nerve degeneration, bone marrow/lymphoid depletion, kidney, ocular, and lung observations, and morbidity.

The preliminary safety data suggests a significant benefit of the ADC of the invention relative to comparator ADC.

Pharmaceutical Formulations

Pharmaceutical formulations of therapeutic antibody-drug conjugates (ADC) of the invention are typically prepared for parenteral administration, i.e. bolus, intravenous, intratumor injection with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Antibody-Drug Conjugate Methods of Treatment

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant solid tumors and hematological disorders such as leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

The antibody-drug conjugates (ADC) of the invention may be administered by any route appropriate to the condition to be treated. The ADC will typically be administered parenterally, i.e. infusion, subcutaneous, intramuscular, intravenous, intradermal, intrathecal and epidural.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the ADC compounds may be used in treatment include rheumatologic disorders (such as, for example, rheumatoid arthritis, Sjögren's syndrome, scleroderma, lupus such as systemic lupus erythematosus (SLE) and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight.

Antibodies or immunoconjugates of the invention can be used either alone or in combination with other agents in a therapy. For instance, an antibody or immunoconjugate of the invention may be co-administered with at least one additional therapeutic agent.

In some embodiments, a hu7C2.v.2.2. LA antibody-drug conjugate (hu7C2 ADC) is co-administered with an additional therapeutic agent that is another antibody or immunoconjugate that binds to HER2. In some embodiments, the additional therapeutic agent is (i) an antibody or immunoconjugate that binds to domain II of HER2, and/or (ii) an antibody or immunoconjugate that binds to domain IV or HER2. In some embodiments, the additional therapeutic agent is (i) an antibody or immunoconjugate that binds to epitope 2C4, and/or (ii) an antibody or immunoconjugate that binds to epitope 4D5.

In some embodiments, a hu7C2.v.2.2. LA antibody-drug conjugate (hu7C2 ADC) is co-administered with one or more additional therapeutic agents selected from trastuzumab (Herceptin®), T-DM1 (Kadcyla®) and pertuzumab (Perjeta®). In some embodiments, an hu7C2 ADC is co-administered with trastuzumab. In some embodiments, a hu7C2 ADC is co-administered with T-DM1. In some embodiments, a hu7C2 ADC is co-administered with pertuzumab. In some embodiments, a hu7C2 ADC is co-administered with trastuzumab and pertuzumab. In some embodiments, a hu7C2 ADC is co-administered with T-DM1 and pertuzumab.

In some embodiments, the additional therapeutic agent is a PD-1 axis binding antagonist, such as a PD-L1 binding antagonist.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

Articles of Manufacture

In another embodiment of the invention, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds an antibody-drug conjugate (ADC) composition which is effective for treating the condition and may have a sterile access port (for example the container may be an intravenous solution bag or a vial having a stopper pierceable by a hypodermic injection needle). At least one active agent in the composition is an ADC. The label or package insert indicates that the composition is used for treating the condition of choice, such as cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES
Example 1
Preparation of Monoalkylator Pyrrolobenzodiazepine Drug Moieties (Table 1a)
Synthesis of (S)-7-methoxy-8-((5-(((S)-7-methoxy-2-methylene-5-oxo-2,3,5,10,11,11a-hexahydro-1H-benzo[e]pyrrolo[1,2-a][1,4]diazepin-8-yl)oxy)pentyl)oxy)-2-methylene-2,3-dihydro-1H-benzo[e]pyrrolo[1,2-a][1,4]diazepin-5(11aH)-one DM-1
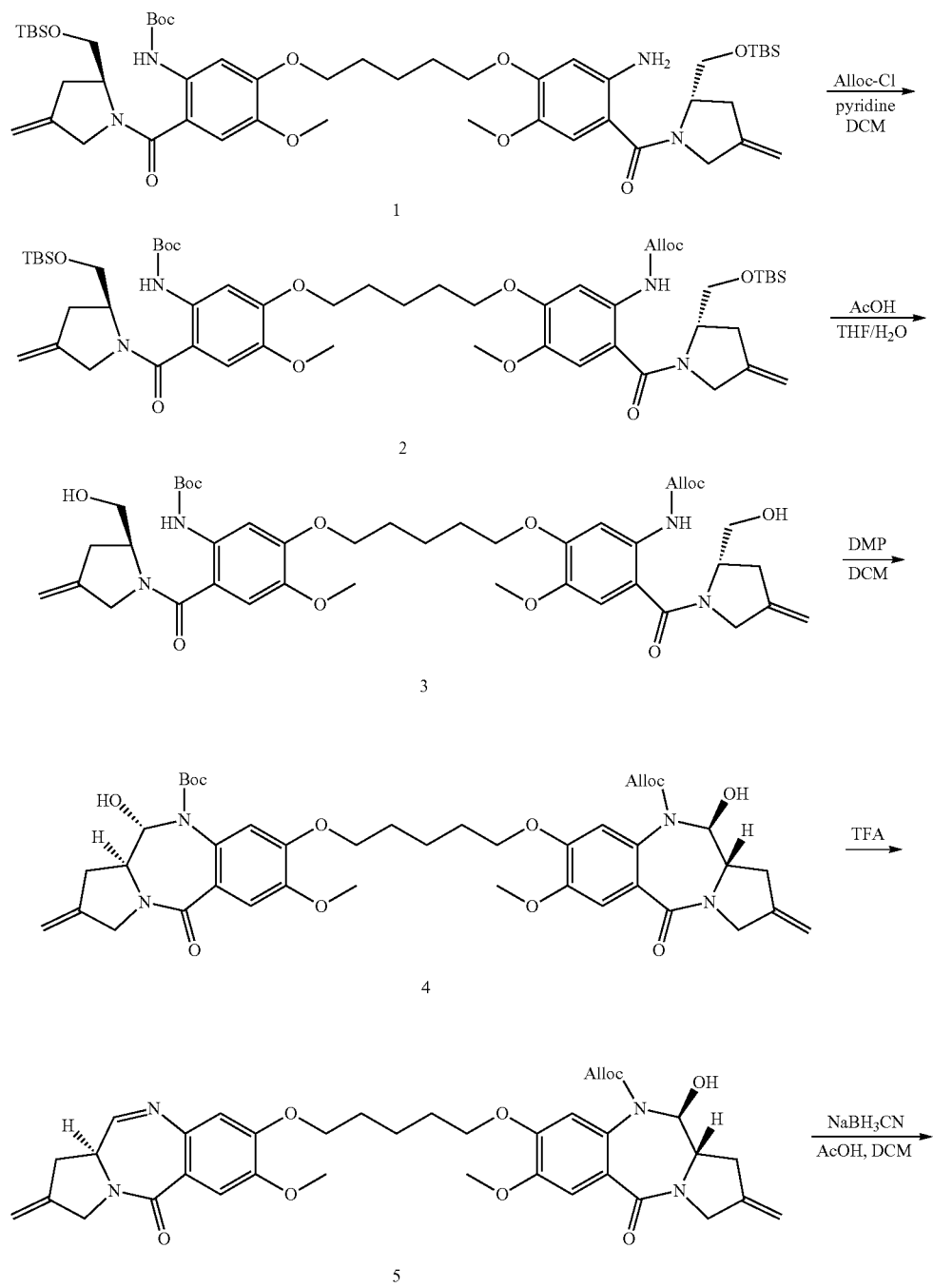

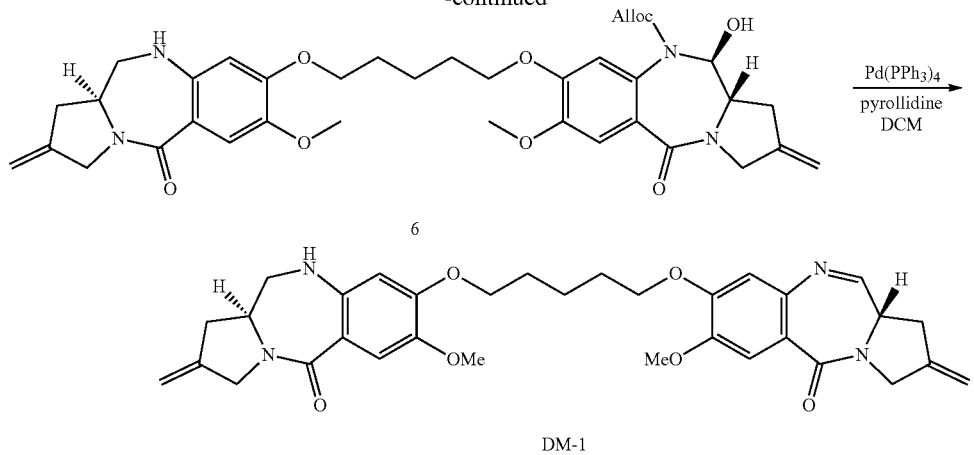

DM-1

To a solution of tert-butyl (5-((5-(5-amino-4-((S)-2-(((tert-butyldimethylsilyl)oxy)methyl)-4-methylenepyrrolidine-1-carbonyl)-2-methoxyphenoxy)pentyl)oxy)-2-((S)-2-(((tert-butyldimethylsilyl)oxy)methyl)-4-methylenepyrrolidine-1-carbonyl)-4-methoxyphenyl)carbamate 1 (0.50 g, 0.524 mmol) in DCM (5.0 mL) was added pyridine (83 mg, 1.05 mmol), followed by allyl chloroformate, Alloc-Cl (95 mg, 0.786 mmol, Sigma Aldrich, CAS Number 2937-50-0) at 16° C. The mixture was stirred for 12 h. The mixture was diluted with DCM (30 mL), and washed with aqueous HCl (1N, 5.0 mL×2), followed by aqueous NaHCO$_3$ (5 mL×2). The organic layer was concentrated to give the crude product, which was purified by flash column (20% EtOAc in petroleum ether) to afford tert-butyl (5-((5-(5-(((allyloxy)carbonyl)amino)-4-((S)-2-(((tert-butyldimethylsilyl)oxy)methyl)-4-methylenepyrrolidine-1-carbonyl)-2-methoxyphenoxy)pentyl)oxy)-2-((S)-2-(((tert-butyldimethylsilyl)oxy)methyl)-4-methylenepyrrolidine-1-carbonyl)-4-methoxyphenyl)carbamate 2 (500 mg, 92%) as a colorless oil. LCMS: (ESI, 10-80, AB, 1.5 min), RT=1.200 min, m/z=1037 [M+1]$^+$.

A solution of compound 2 (500 mg, 0.48 mmol) in HOAc/THF/H$_2$O (6 mL/3 mL/2 mL) was stirred at r.t. for 1 day. The solution was diluted with EtOAc (60 mL), washed with H$_2$O (20 mL×4), aq. NaHCO$_3$ (20 mL×2), and H$_2$O (20 mL). The organic layer was dried over Na$_2$SO$_4$, filtered, and concentrated under vacuum to afford tert-butyl (5-((5-(5-(((allyloxy)carbonyl)amino)-4-((S)-2-(hydroxymethyl)-4-methylenepyrrolidine-1-carbonyl)-2-methoxyphenoxy)pentyl)oxy)-2-((S)-2-(hydroxymethyl)-4-methylenepyrrolidine-1-carbonyl)-4-methoxyphenyl)carbamate 3 (390 g, 100%) as an oil.

To a stirred solution of compound 3 (200 mg, 0.247 mmol) in anhydrous DCM (15 mL) was added Dess Martin periodinane (419 mg, 0.988 mmol). The reaction mixture was stirred at r.t. for 2 h. It was quenched with a aq. Na$_2$SO$_3$ solution (30 mL) at 0° C., and extracted with DCM (20 mL×3). The combined organic layer was washed with brine (20 mL), dried over Na$_2$SO$_4$, filtered, and concentrated. The residue was purified by prep-TLC (DCM/MeOH=20:1) to afford allyl (11S,11aS)-8-((5-(((11S,11aS)-10-(tert-butoxycarbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)pentyl)oxy)-11-hydroxy-7-methoxy-2-methylene-5-oxo-2,3,11,11a-tetrahydro-1H-benzo[e]pyrrolo[1,2-a][1,4]diazepine-10(5H)-carboxylate 4 (80 mg, 40.2%) as colorless solid. LCMS (ESI): RT=0.709 min, M-Boc-H$_2$O+H$^+$=687.1. Method=5-95AB/1.5 min.

A solution of compound 4 (80 mg, 0.099 mmol) in TFA (2.0 mL) was stirred at 0° C. for 0.5 h. The solution was added dropwise into a saturated NaHCO$_3$ solution (120 mL) at 0° C. The mixture was extracted with DCM (20 mL×3) and the combined organic layer was dried over Na$_2$SO$_4$, filtered, and concentrated to afford crude allyl (11S,11aS)-11-hydroxy-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate 5 (50 mg, 73.5%).

To a stirred solution of compound 5 (50 mg, 0.073 mmol) in anhydrous DCM (4.0 mL) was added HOAc (13 mg, 0.219 mmol), followed by NaBH$_3$CN (23 mg, 0.365 mmol). The reaction mixture was stirred at r.t. overnight. Then the mixture was concentrated under vacuum and purified by prep-TLC (DCM/MeOH=9:1) to afford allyl (11S,11aS)-11-hydroxy-7-methoxy-8-((5-(((S)-7-methoxy-2-methylene-5-oxo-2,3,5,10,11,11a-hexahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate 6 (40 mg, 80.0%) as colorless solid. LCMS (ESI): RT=3.085 min, M+H$^+$=689.1. method=10-80AB/7 min.

To a stirred solution of compound 6 (40 mg, 0.058 mmol) in anhydrous DCM (3.0 mL) was added pyrrolidine (21 mg, 0.29 mmol), followed by Pd(PPh$_3$)$_4$ (7.0 mg, 0.006 mmol). The reaction mixture was stirred at r.t. under N$_2$ for 2 h. Then the mixture was concentrated under vacuum and purified by prep-TLC (DCM/MeOH=1:1) to afford DM-1 (12 mg, 35.3%) as an off white solid. LCMS (ESI): RT=0.651 min, M+H$^+$=587.1. method=5-95AB/1.5 min. $^1$H NMR (400 MHz, DCCl$_3$) δ 7.67 (d, J=4.4 Hz, 1H), 7.57 (s, 1H), 7.49 (s, 1H), 6.79 (s, 1H), 6.04 (s, 1H), 5.18 (d, J=11.6 Hz, 2H), 5.04 (d, J=11.2 Hz, 2H), 4.41-4.37 (m, 1H), 4.28-4.25 (m, 3H), 4.13-4.00 (m, 3H), 3.98-3.95 (m, 2H), 3.93 (s, 3H), 3.89-3.85 (m, 1H), 3.82 (s, 3H), 3.54 (d, J=30 Hz, 1H), 3.34-3.28 (dd, J=12.4, 9.2 Hz, 1H), 3.15-3.08 (m, 1H), 2.96-2.86 (m, 2H), 2.44-2.39 (dd, J=15.2, 6.0 Hz, 1H), 1.95-1.90 (m, 4H), 1.67-1.62 (m, 2H).

Synthesis of (S)-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-2,3-dihydro-1H-benzo[e]pyrrolo[1,2-a][1,4]diazepine-5,11(10H,11aH)-dione DM-2

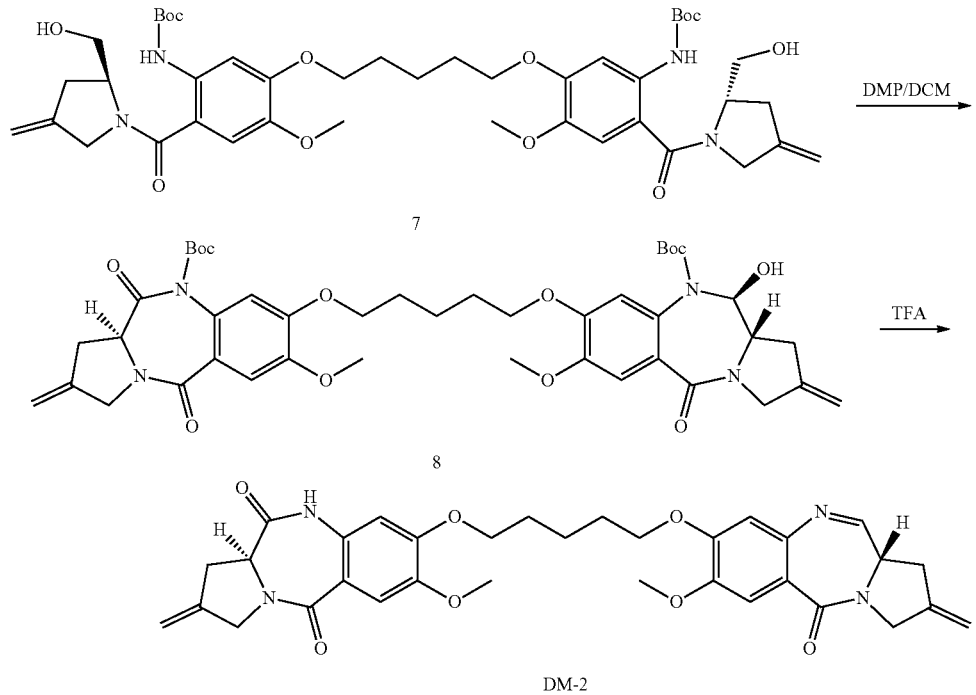

To a stirred solution of di-tert-butyl ((pentane-1,5-diylbis(oxy))bis(6-((S)-2-(hydroxymethyl)-4-methylenepyrrolidine-1-carbonyl)-4-methoxy-3,1-phenylene))dicarbamate 7 (200 mg, 0.24 mmol) in anhydrous DCM (20 mL) was added DMP (610 mg, 1.44 mmol) at 0° C. The reaction mixture was stirred at r.t. for 3 h. The mixture was diluted with EtOAc (100 mL), and quenched with aq. $Na_2SO_3$ solution (30 mL) at 0° C. The organic layer was washed with $H_2O$ (30 mL×3), aq. $NaHCO_3$ solution (30 mL), and $H_2O$ (30 mL), then dried over ($Na_2SO_4$), filtered, and concentrated. The residue was purified by prep-HPLC to afford tert-butyl (S)-8-((5-(((11S,11aS)-10-(tert-butoxycarbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)pentyl)oxy)-7-methoxy-2-methylene-5,11-dioxo-2,3,11,11a-tetrahydro-1H-benzo[e]pyrrolo[1,2-a][1,4]diazepine-10(5H)-carboxylate 8 (58 mg, 30.0%) as a white solid. LCMS (ESI): RT=0.748 min, M+Na$^+$=841.4. method=5-95AB/1.5 min.

A solution of compound 8 (58 mg, 0.07 mmol) in 95% TFA/$H_2O$ (2.0 mL) was stirred at 0° C. for 2 h. Then the solution was added dropwise into saturated $NaHCO_3$ solution (120 mL) at 0° C. The mixture was extracted with DCM (20 mL×3). The combined organic layer was dried over $Na_2SO_4$, filtered, concentrated and purified by prep-HPLC to afford DM-2 (15.7 mg, 38%) as a white solid. $^1$H NMR (400 MHz, CDCl$_3$) δ ppm 1.65-1.73 (m, 2 H) 1.89-2.00 (m, 4H) 2.77-2.89 (m, 1 H) 2.91-3.00 (m, 1 H) 3.08-3.19 (m, 1 H) 3.46 (d, J=16.6 Hz, 1 H) 3.91 (s, 3 H) 3.94 (s, 3 H) 4.02 (t, J=6.5 Hz, 2 H) 4.06-4.19 (m, 2 H) 4.20-4.26 (m, 2 H) 4.30 (s, 2 H) 4.43 (d, J=15.6 Hz, 1 H) 5.09-5.26 (m, 4 H) 6.41 (s, 1 H) 6.80 (s, 1 H) 7.43 (s, 1 H) 7.51 (s, 1 H) 7.71 (d, J=4.5 Hz, 1 H) 7.83 (s, 1 H).

Synthesis of (S)-8-methoxy-9-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-1,3,4,12a-tetrahydro-6H-benzo[e][1,4]oxazino[4,3-a][1,4]diazepine-6,12(11H)-dione DM-3

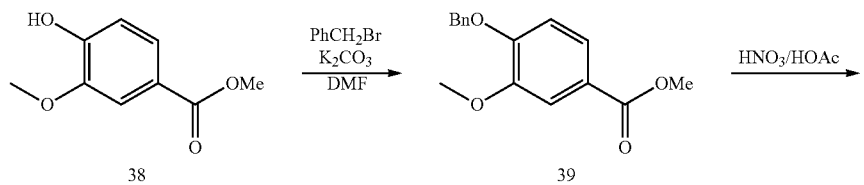

-continued
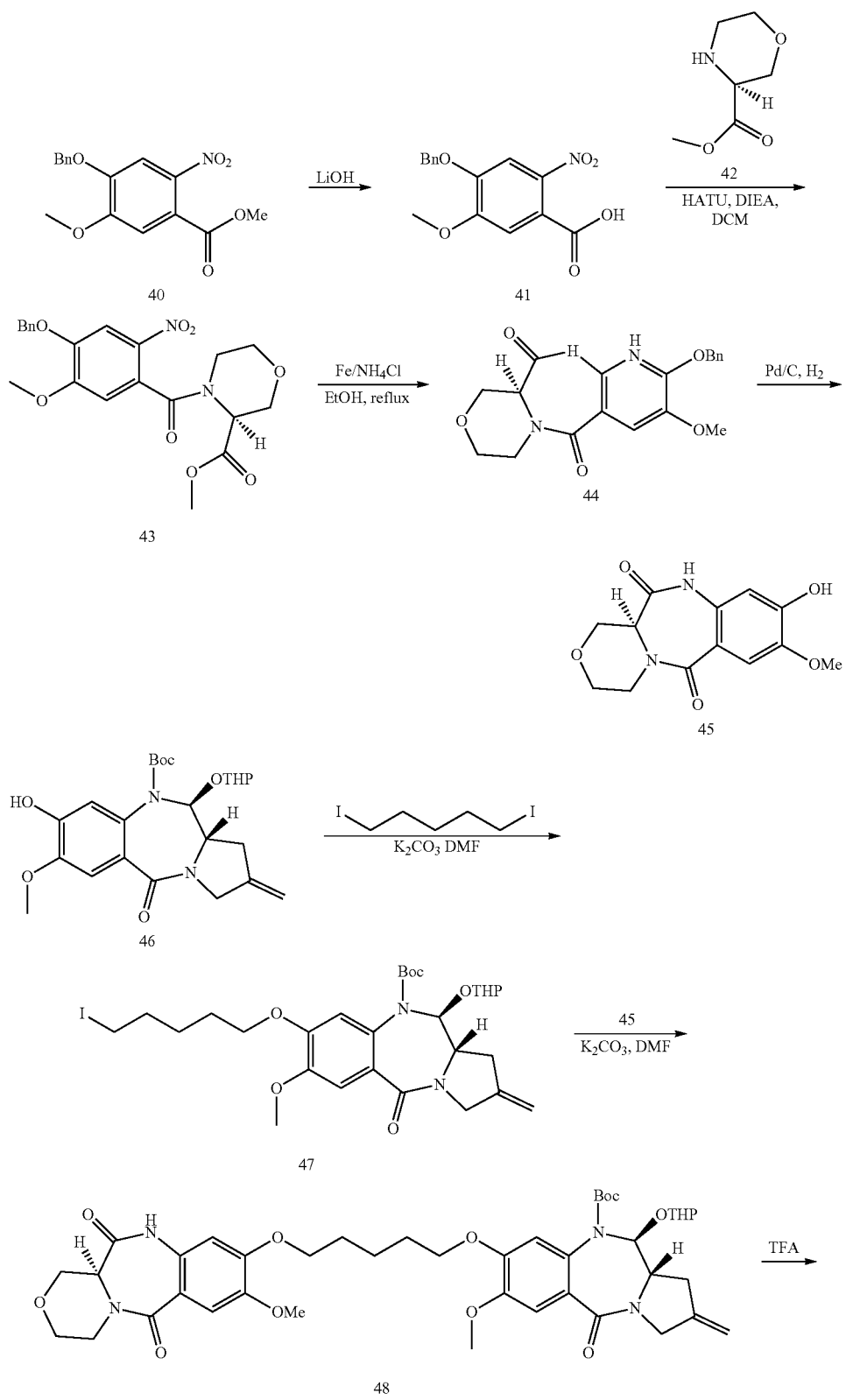

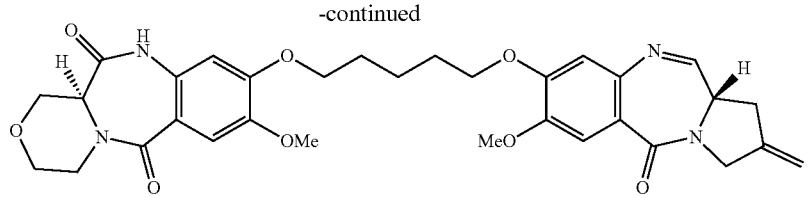

DM-3

A solution of methyl 4-hydroxy-3-methoxybenzoate 38 (3.0 g, 16.5 mmol) in DMF (100 mL) was added benzyl bromide (4.22 g, 24.7 mmol) and K₂CO₃ (4.56 g, 32.9 mmol). The reaction mixture was stirred at 100° C. for 3 h. The mixture was concentrated in vacuo and was dissolved in water (50 mL), extracted with EtOAC (30 mL×2), washed with NaCl (30 mL), dried over Na₂SO₄. It was concentrated and purified by silica chromatography (0-30% EtOAc in petroleum ether) to give methyl 4-(benzyloxy)-3-methoxybenzoate 39 (3.8 g, 13.5 mmol, 82.2% yield) as a white solid. LCMS (5-95AB/1.5 min): RT=0.787 min, [M+H]+ 272.9

A solution of 39 (2.0 g, 7.34 mmol) in HOAc (5.0 mL) was added to a mixture of HOAc (5.0 mL) and HNO₃ (20.6 mL, 441 mmol) at 0° C. The reaction mixture was stirred at 20° C. for 30 min. The mixture was poured into ice water (100 mL) and adjust pH to 5-6. The mixture was filtered, and the filtrates was concentrated to give methyl 4-(benzyloxy)-5-methoxy-2-nitrobenzoate 40 (2.3 g, 7.25 mmol, 98.7% yield) as a yellow solid.

A solution of 40 (2.3 g, 7.25 mmol) in MeOH (20 mL) was added a solution of LiOH (2.25 mL, 36.24 mmol) in water (5 mL). The reaction mixture was stirred at 20° C. for 2 h. The mixture was poured into water (50 mL), and washed with EtOAc (50 mL). The water phase was adjust pH to 3-4 with 2M HCl, and extracted with EtOAc (50 mL×3). It was washed with NaCl (25 mL), dried over Na₂SO₄ and concentrated in vacuo to give crude 4-(benzyloxy)-5-methoxy-2-nitrobenzoic acid 41 (2.0 g, 6.59 mmol, 91% yield) as white solid.

A mixture of 41 (460.0 mg, 1.52 mmol) and methyl (S)-morpholine-3-carboxylate 42, CAS Reg. No. 741288-31-3, Hicks, F. et al, (2013) Organic Process Research & Development, 17(5):829-837, (330 mg, 2.28 mmol) and diisopropylethylamine, DIEA (392 mg, 3.03 mmol) in DCM (30 mL) was added HATU (865 mg, 2.28 mmol). The reaction solution was stirred at 20° C. for 8 h. The solution was concentrated in vacuo and purified by chromatography on silica (0-50% EtOAC in petroleum ether) to give methyl (S)-4-(4-(benzyloxy)-5-methoxy-2-nitrobenzoyl)morpholine-3-carboxylate 43 (520 mg, 1.21 mmol, 79.7% yield) as a yellow oil. LCMS (5-95AB/1.5 min): R$_T$=0.731 min, [M+Na]⁺453.0

A solution of NH₄Cl (646 mg, 12.1 mmol) in EtOH (20 mL) and water (15 mL) was added 43 (520 mg, 1.21 mmol) and iron (539 mg, 9.67 mmol). After the reaction mixture was stirred at 90° C. for 12 h, it was filtered, and the filtrates was extracted with EtOAc (50 mL×3) washed with NaCl (20 mL), dried over Na₂SO₄ and concentrated in vacuo. The reaction mixture was purified by chromatography on silica (0-30% EtOAc in petroleum ether) to give (S)-9-(benzyloxy)-8-methoxy-1,3,4,12a-tetrahydro-6H-benzo[e][1,4]oxazino[4,3-a][1,4]diazepine-6,12(11H)-dione 44 (320 mg, 0.84 mmol, 69.7% yield) as a white solid. LCMS (5-95AB/1.5 min): RT=0.638 min, [M+H]+368.9

A solution of 44 (260 mg, 0.71 mmol) in DCM (10 mL) and MeOH (1.0 mL) was added 10% palladium on charcoal (26.0 mg, 0.020 mmol). The reaction mixture was stirred at 18° C. for 1 h under H₂ (15 psi). The reaction mixture was filtrated and concentrated in vacuo to give (S)-9-hydroxy-8-methoxy-1,3,4,12a-tetrahydro-6H-benzo[e][1,4]oxazino[4,3-a][1,4]diazepine-6,12(11H)-dione 45 (100 mg, 0.359 mmol, 50.9% yield) as a white solid.

A solution of tert-butyl (11S,11aS)-8-hydroxy-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate 46 (200 mg, 0.43 mmol) in DMF (5.0 mL) was added K₂CO₃ (60 mg, 0.43 mmol) and 1,5-diiodopentane (703 mg, 2.17 mmol). The reaction mixture was stirred at 90° C. for 12 h. The reaction mixture was concentrated and purified by silica chromatography (0-50% EtOAc in petroleum ether) to give tert-butyl (11S,11aS)-8-((5-iodopentyl)oxy)-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate 47 (129 mg, 0.191 mmol, 43.9% yield) as a yellow oil. LCMS (5-95AB/1.5 min): RT=0.907 min, [M+H]+657.1

A mixture of 47 (100 mg, 0.150 mmol), 45 (50.9 mg, 0.18 mmol) and K₂CO₃ (31.6 mg, 0.23 mmol) in DMF (5.0 mL). The mixture was stirred at 90° C. for 3 h. The mixture was concentrated in vacuo and purified by chromatography (0-5% MeOH in DCM Rf=0.4) to give tert-butyl (11S,11aS)-7-methoxy-8-((5-(((S)-8-methoxy-6,12-dioxo-3,4,6,11,12,12a-hexahydro-1H-benzo[e][1,4]oxazino[4,3-a][1,4]diazepin-9-yl)oxy)pentyl)oxy)-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate 48 (75 mg, 0.093 mmol, 61% yield) as a colorless oil.

Compound 48 (75.0 mg, 0.090 mmol) was added TFA (1.9 mL) and water (0.10 mL) at 0° C. The mixture was stirred at 17° C. for 1h. The reaction mixture was poured into saturated NaHCO₃ (200 mL) and extracted with DCM (100 mL×3) washed with brine (50 mL) dried and purified by prep-TLC (4% methanol in DCM Rf=0.5) to give DM-3 (18.9 mg, 0.030 mmol, 32.3% yield) as a white solid. LCMS (5-95AB/1.5 min): RT=0.633 min, [M+H]⁺ 605.2. ¹H NMR (400 MHz, CDCl₃) δ 8.16 (s, 1H), 7.64 (d, J=4.4 Hz, 1H), 7.43 (s, 1H), 7.22 (d, J=23.2 Hz, 1H), 6.73 (d, J=2.4 Hz, 1H), 6.35 (d, J=2.8 Hz, 1H), 5.11 (d, J=10.8 Hz, 2H), 4.41 (s, 3H), 4.38 (s, 2H), 4.22 (s, 3H), 4.05 (s, 3H), 4.04 (s, 3H), 4.02 (s, 3H), 3.95-3.92 (m, 1H), 3.86 (s, 1H), 3.83-3.62 (m, 1H), 3.18 (s, 1H), 2.88 (d, J=30.8 Hz, 1H), 1.86 (s, 4H) 1.79-1.62 (m, 2H).

Synthesis of (S)-7-methoxy-8-((5-(((S)-7-methoxy-5-oxo-2,3,5,11a-tetrahydro-1H-benzo[e]pyrrolo[1,2-a]azepin-8-yl)oxy)pentyl)oxy)-2-methylene-1,2,3,11a-tetrahydro-5H-benzo[e]pyrrolo[1,2-a][1,4]diazepin-5-one DM-5
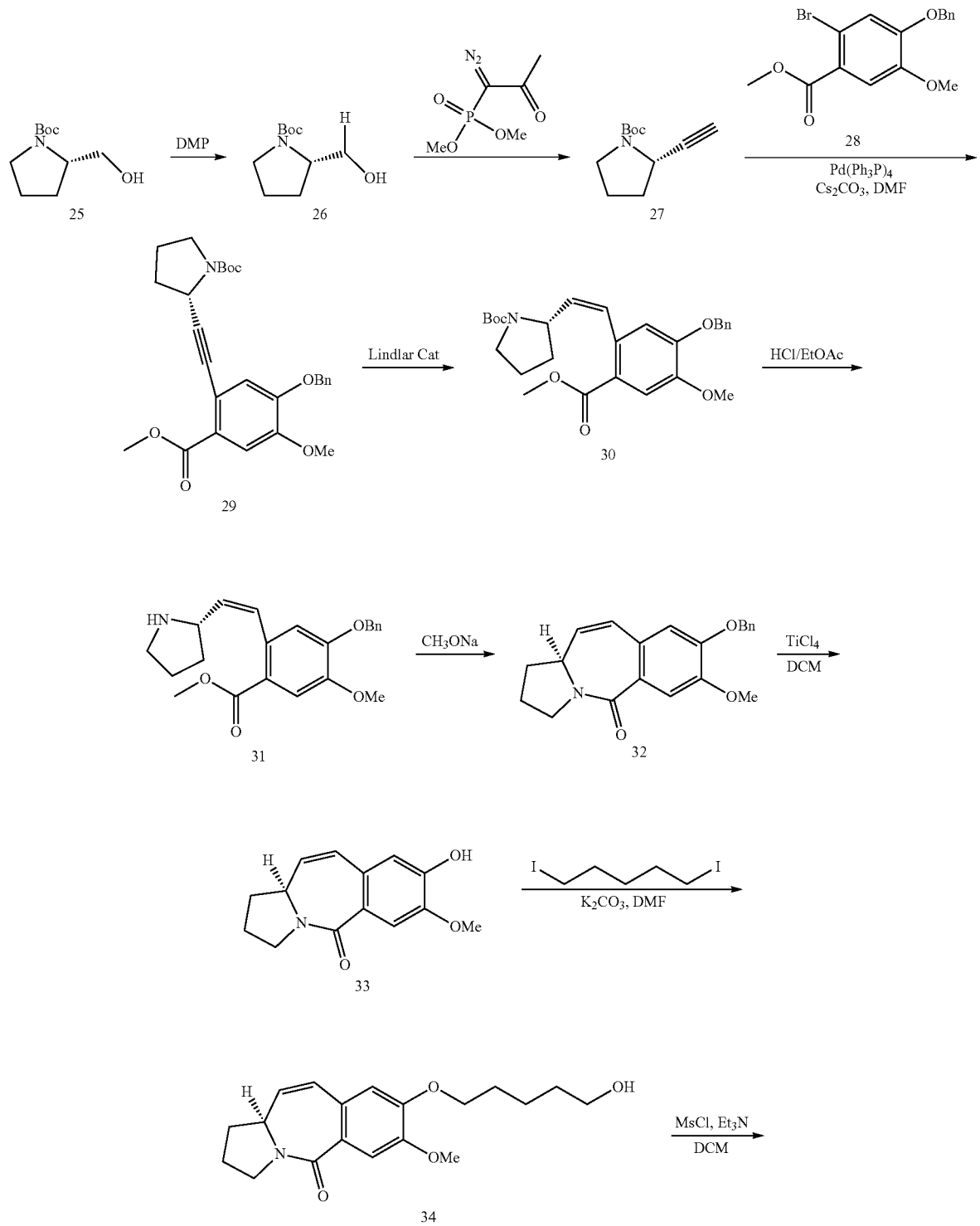

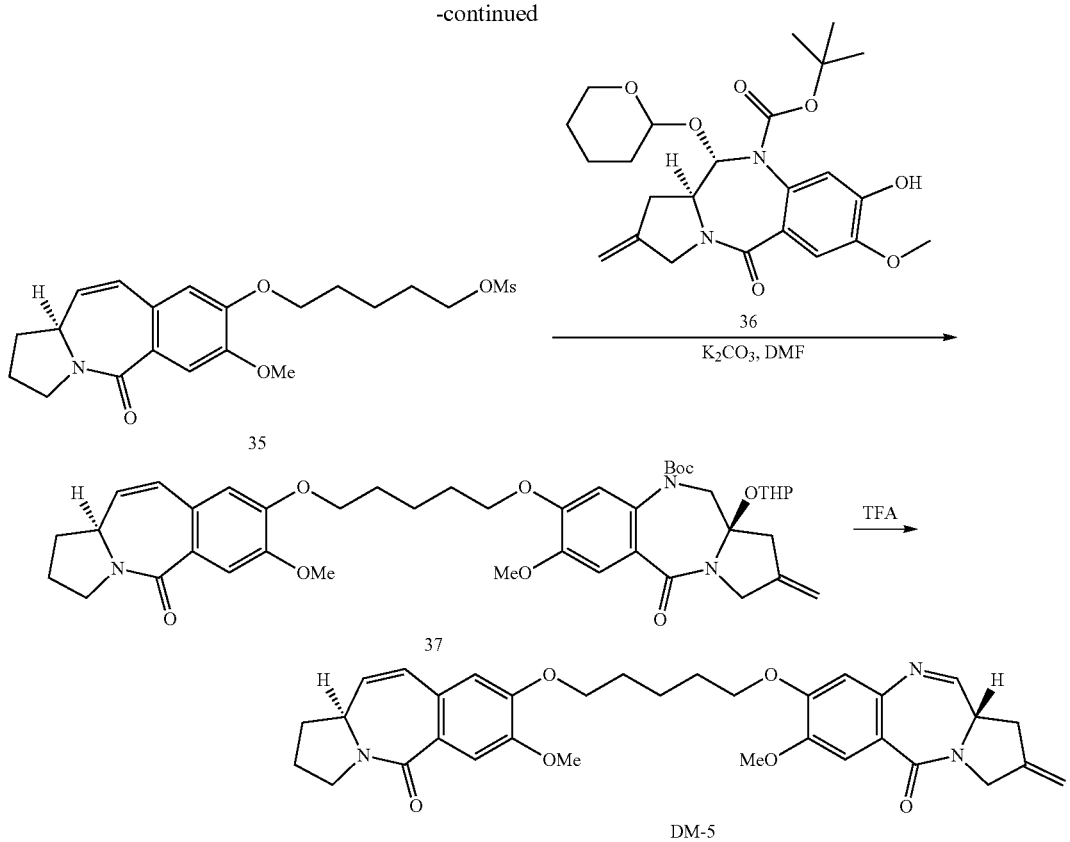

To a solution of tert-butyl (S)-2-(hydroxymethyl)pyrrolidine-1-carboxylate 25 (3.0 g, 14.9 mmol) in DCM (80 mL) was added Dess Martin periodinane, DMP (9.48 g, 22.4 mmol). After the mixture was stirred at 0° C. for 1 h, it was added $Na_2S_2O_3$ (50 mL)/$NaHCO_3$ (50 mL) and MTBE (130 mL). The organic phase was washed with water (60 mL×3) and concentrated to give tert-butyl (S)-2-formylpyrrolidine-1-carboxylate 26 (2.9 g, 14.6 mmol, 97.6% yield) as a colorless oil.

To a solution of Compound 26 (2.9 g, 14.6 mmol) and dimethyl (1-diazo-2-oxo-propyl) phosphonate in MeOH (20 mL) was added $K_2CO_3$ (6.03 g, 43.7 mmol). After the reaction mixture was stirred at 20° C. for 1 h, it was concentrated in vacuo, the residue was purified by column chromatography (10% EtOAc in PE) to give tert-butyl (S)-2-ethynylpyrrolidine-1-carboxylate 27 (2.0 g, 10.24 mmol, 70.4% yield) as a colorless oil.

To a solution of Compound 27 (2.0 g, 10.2 mmol) and methyl 4-(benzyloxy)-2-bromo-5-methoxybenzoate 28 (5.4 g, 15.4 mmol) in DMF (50 mL) was added $Cs_2CO_3$ (3.97 g, 20.5 mmol) and $Pd(PPh_3)_4$ (785 mg, 1.54 mmol). The mixture was stirred at 95° C. under $N_2$ for 1 h. The mixture was concentrated and purified by flash column chromatography (20% EtOAc in PE) to give tert-butyl (S)-2-((5-(benzyloxy)-4-methoxy-2-(methoxycarbonyl)phenyl)ethynyl)pyrrolidine-1-carboxylate 29 (1.60 g, 2.44 mmol, 23.8% yield) as a colorless oil. LCMS (5-95AB/1.5 min): RT=0.994 min, [M+H-56]$^+$410.0

To a solution of Compound 29 (2.0 g, 4.3 mmol) in MeOH (10 mL) was added Pd/$CaCO_3$ (200.0 mg, 21.5 mmol). The mixture was stirred at 30° C. for 1 h under $H_2$ (1 atm). The mixture was filtered and the filtrate was concentrated to give the crude product, which was purified by flash column chromatography (10% EtOAc in PE) to give tert-butyl (S,Z)-2-(5-(benzyloxy)-4-methoxy-2-(methoxycarbonyl) styryl)pyrrolidine-1-carboxylate 30 (1.0 g, 2.14 mmol, 49.8% yield) as a white solid. LCMS (5-95AB/1.5 min): RT=0.983 min, [M+Na]$^+$490.1

To a solution of Compound 30 (0.9 g, 1.92 mmol) in EtOAc (10 mL) was added HCl/EtOAc (6.0 mL). After the mixture was stirred at 25° C. for 1 h, it was concentrated to give methyl (S,Z)-4-(benzyloxy)-5-methoxy-2-(2-(pyrrolidin-2-yl)vinyl)benzoate 31 (0.77 g, 1.90 mmol, 99% yield) as a white solid.

To a solution of Compound 31 (0.77 g, 1.91 mmol) in MeOH (30 mL) was added NaOMe (1.03 g, 19.06 mmol). The mixture was stirred at 30° C. for 2 h. The mixture was concentrated and purified by flash column chromatography (25-75% EtOAc in PE) to give (S)-8-(benzyloxy)-7-methoxy-1,2,3,11a-tetrahydro-5H-benzo[e]pyrrolo[1,2-a]azepin-5-one 32 (0.60 g, 1.79 mmol, 93.8% yield) as a yellow oil. $^1$H NMR (400 MHz, $CDCl_3$) δ ppm 1.89-2.11 (m, 3 H) 2.18-2.33 (m, 1 H) 3.59 (dt, J=12.0, 7.6 Hz, 1 H) 3.80 (dt, J=11.5, 5.8 Hz, 1 H) 3.90-3.96 (m, 1 H) 3.97 (s, 3 H) 5.19 (s, 2 H) 5.86 (dd, J=10.0, 4.8 Hz, 1 H) 6.53 (dd, J=10.0, 2.0 Hz, 1 H) 6.69 (s, 1 H) 7.29-7.35 (m, 1 H) 7.36-7.41 (m, 2 H) 7.42-7.48 (m, 2 H) 7.62 (s, 1 H)

To a solution of Compound 32 (580 mg, 1.73 mmol) in DCM (50 mL) was added $TiCl_4$ (656 mg, 3.46 mmol). The mixture was stirred at 30° C. for 12 h. The mixture was added 1M HCl (20 mL) and EtOAc (100 mL). The organic layer was washed with water (50 mL×3) and concentrated to give (S)-8-hydroxy-7-methoxy-1,2,3,11a-tetrahydro-5H-benzo[e]pyrrolo[1,2-a]azepin-5-one 33 (250 mg, 0.44 mmol, 25.3% yield) as a yellow solid.

A solution of Compound 33 (50.0 mg, 0.20 mmol) in DMF (5.0 mL) was added K₂CO₃ (42.26 mg, 0.31 mmol) and 1,5-diiodopentane (333 mg, 1.0 mmol). The reaction mixture was stirred at 90° C. for 3 h. The reaction mixture was purified by silica chromatography (0-50% EtOAC in petroleum ether) to give (S)-8-((5-hydroxypentyl)oxy)-7-methoxy-1,2,3,11a-tetrahydro-5H-benzo[e]pyrrolo[1,2-a]azepin-5-one 34 (60 mg, 0.178 mmol, 87.6% yield) as an oil. LCMS (5-95AB/1.5 min): RT=0.765 min, [M+H]+332.0

To a solution of Compound 34 (60.0 mg, 0.18 mmol) in DCM (6.0 mL) was added triethylamine (55 mg, 0.54 mmol) and methanesulfonyl chloride, MsCl (41 mg, 0.36 mmol). After the mixture was stirred at 35° C. for 1 h, EtOAc (80 mL) and washed with water (50 mL×3). The organic layer was concentrated to give (S)-5-((7-methoxy-5-oxo-2,3,5,11a-tetrahydro-1H-benzo[e]pyrrolo[1,2-a]azepin-8-yl)oxy)pentyl methanesulfonate 35 (70 mg) as a colorless oil. LCMS (5-95AB/1.5 min): RT=0.679 min, [M+H]⁺410.0

To a solution of Compound 35 (70 mg, 0.17 mmol) and tert-butyl (11S,11aS)-8-hydroxy-7-methoxy-2-methylene-5-oxo-11-((tetrahydro-2H-pyran-2-yl)oxy)-2,3,11,11a-tetrahydro-1H-benzo[e]pyrrolo[1,2-a][1,4]diazepine-10(5H)-carboxylate 36 (87 mg, 0.19 mmol) in DMF (5.0 mL) was added K₂CO₃ (47 mg, 0.34 mmol) and KI (5.68 mg, 0.030 mmol). The mixture was stirred at 90° C. for 3 h, and purified by prep-HPLC (HCOOH) to give tert-butyl (11aR)-7-methoxy-8-((5-(((S)-7-methoxy-5-oxo-2,3,5,11a-tetrahydro-1H-benzo[e]pyrrolo[1,2-a]azepin-8-yl)oxy)pentyl)oxy)-2-methylene-5-oxo-11a-((tetrahydro-2H-pyran-2-yl)oxy)-2,3,11,11a-tetrahydro-1H-benzo[e]pyrrolo[1,2-a][1,4]diazepine-10(5H)-carboxylate 37 (70 mg, 0.084 mmol, 49.2% yield) as a white solid. LCMS (5-95AB/1.5 min): RT=0.845 min, [M+H]⁺774.4

A solution of Compound 37 (50 mg, 0.060 mmol) in TFA (1.9 mL) and water (0.10 mL) was stirred at 35° C. for 1 h. The mixture was partitioned between sat.NaHCO₃ (30 mL) and EtOAc (50 mL). The organic layer was washed with water (30 mL×2) and brine (30 mL) and dried over Na₂SO₄. It was concentrated and purified by prep-TLC (5% MeOH in DCM, Rf=0.5) to give DM-5 (20 mg, 0.034 mmol, 53.1% yield) as a white solid. LCMS (5-95AB/1.5 min): RT=0.825 min, [M+H]⁺572.1. ¹H NMR (400 MHz, CDCl₃) δppm 1.65-1.75 (m, 3 H) 1.88-2.10 (m, 8 H) 2.19-2.31 (m, 1 H) 2.82-3.29 (m, 2 H) 3.60 (dt, J=11.9, 7.5 Hz, 1 H) 3.81 (dt, J=11.6, 5.9 Hz, 1 H) 3.86-3.91 (m, 1 H) 3.94 (s, 6 H) 3.97 (br. s., 1 H) 4.01-4.18 (m, 4 H) 4.30 (s, 2 H) 5.19 (d, J=10.6 Hz, 2 H) 5.89 (dd, J=9.9, 5.1 Hz, 1 H) 6.53-6.63 (m, 1 H) 6.66 (s, 1 H) 6.81 (s, 1 H) 7.51 (s, 1 H) 7.59 (s, 1 H) 7.68 (d, J=4.4 Hz, 1H)

Example 2

Preparation of Monoalkylator Pyrrolobenzodiazepine Linker-drug Intermediates (Table 2A)

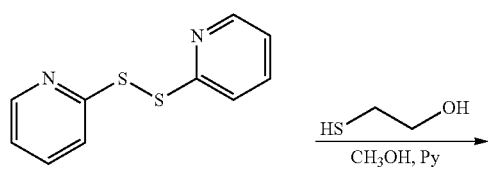

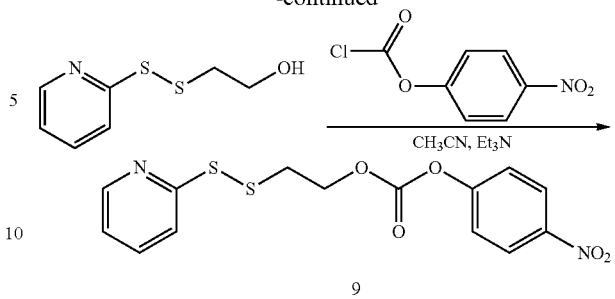

1,2-Di(pyridin-2-yl)disulfane and 2-mercaptoethanol were reacted in pyridine and methanol at room temperature to give 2-(pyridin-2-yldisulfanyl)ethanol. Acylation with 4-nitrophenyl carbonochloridate in triethylamine and acetonitrile gave 4-nitrophenyl 2-(pyridin-2-yldisulfanyl)ethyl carbonate 9.

To a mixture of 1,2-bis(5-nitropyridin-2-yl)disulfane 10 (1.0 g, 3.22 mmol) in anhydrous DMF/MeOH (25 mL/25 mL) was added HOAc (0.1 mL), followed by 2-aminoethanethiol hydrochloride 11 (183 mg, 1.61 mmol). After the reaction mixture was stirred at r.t. overnight, it was concentrated under vacuum to remove the solvent, and the residue was washed with DCM (30 mL×4) to afford 2-((5-nitropyridin-2-yl)disulfanyl)ethanamine hydrochloride 12 as pale yellow solid (300 mg, 69.6%). ¹H NMR (400 MHz, DMSO-d₆) δ 9.28 (d, J=2.4 Hz, 1H), 8.56 (dd, J=8.8, 2.4 Hz, 1H), 8.24 (s, 4H), 8.03 (d, J=8.8 Hz, 1H), 3.15-3.13 (m, 2H), 3.08-3.06 (m, 2H)

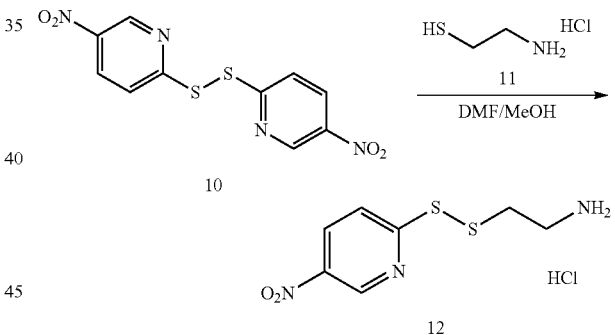

A solution of 1,2-bis(5-nitropyridin-2-yl)disulfane 10 (9.6 g, 30.97 mmol) and 2-mercaptoethanol (1.21 g, 15.49 mmol) in anhydrous DCM/CH₃OH (250 mL/250 mL) was stirred at r.t. under N₂ for 24 h. After the mixture was concentrated under vacuum, and the residue was diluted with DCM (300 mL). MnO₂ (10 g) was added and the mixture was stirred at r.t. for another 0.5 h. The mixture was purified by column chromatography on silica gel (DCM/MeOH=100/1 to 100/1) to afford 2-((5-nitropyridin-2-yl)disulfanyl)ethanol 13 (2.2 g, 61.1%) as brown oil. ¹H NMR (400 MHz, CDCl₃) δ 9.33 (d, J=2.8 Hz, 1H), 8.38-8.35 (dd, J=9.2, 2.8 Hz, 1H), 7.67 (d, J=9.2 Hz, 1H), 4.10 (t, J=7.2 Hz, 1H), 3.81-3.76 (q, 2H), 3.01 (t, J=5.2 Hz, 2H).

To a solution of 13 (500 mg, 2.15 mmol) in anhydrous DMF (10 mL) was added DIEA (834 mg, 6.45 mmol), followed by PNP carbonate (bis(4-nitrophenyl) carbonate, 1.31 g, 4.31 mmol). The reaction solution was stirred at r.t for 4 h and the mixture was purified by prep-HPLC (FA) to afford 4-nitrophenyl 2-((5-nitropyridin-2-yl)disulfanyl)ethyl carbonate 14 (270 mg, 33.1%) as light brown oil. $^1$H NMR (400 MHz, CDCl$_3$) δ 9.30 (d, J=2.4 Hz, 1H), 8.43-8.40 (dd, J=8.8, 2.4 Hz, 1H), 8.30-8.28 (m, 2H), 7.87 (d, J=8.8 Hz, 1H), 7.39-7.37 (m, 2H), 4.56 (t, J=6.4 Hz, 2H), 3.21 (t, J=6.4 Hz, 2H).
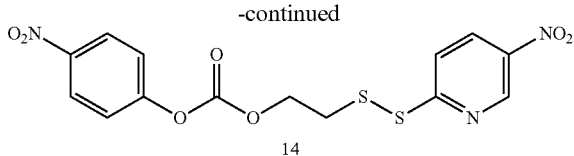
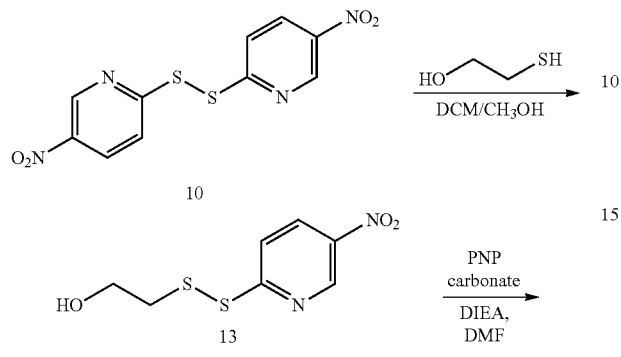
Synthesis of (11S,11aS)-(R)-2-((5-nitropyridin-2-yl)disulfanyl)propyl 11-hydroxy-7-methoxy-8-((5-(((S)-7-methoxy-2-methylene-5,11-dioxo-2,3,5,10,11,11a-hexahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate (LD-51)
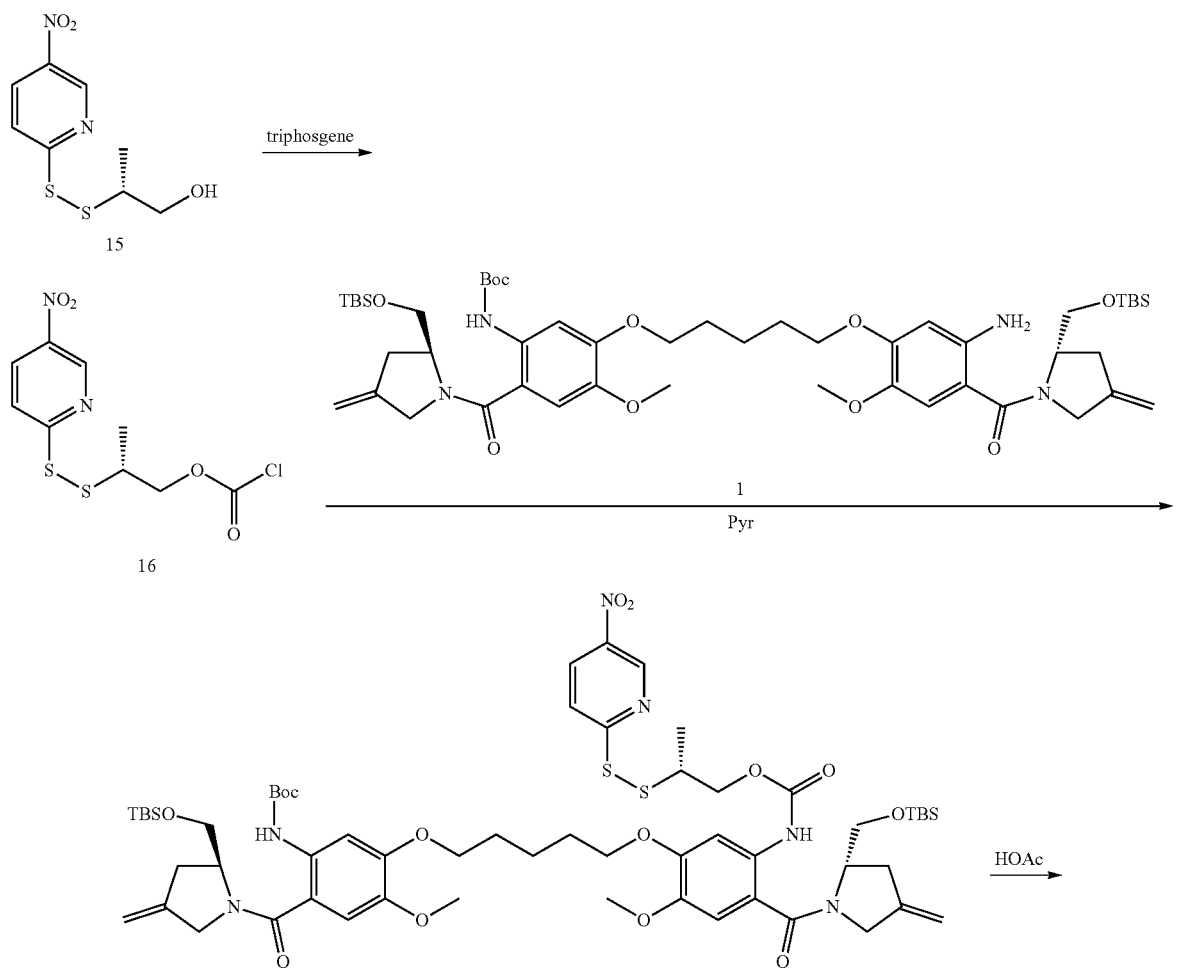

-continued
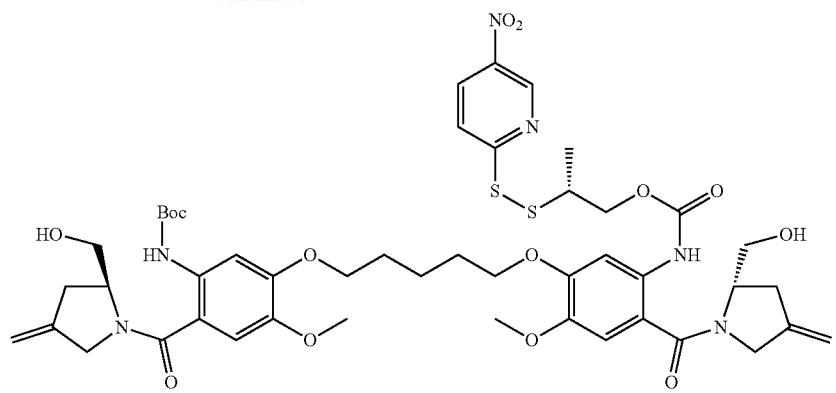
18
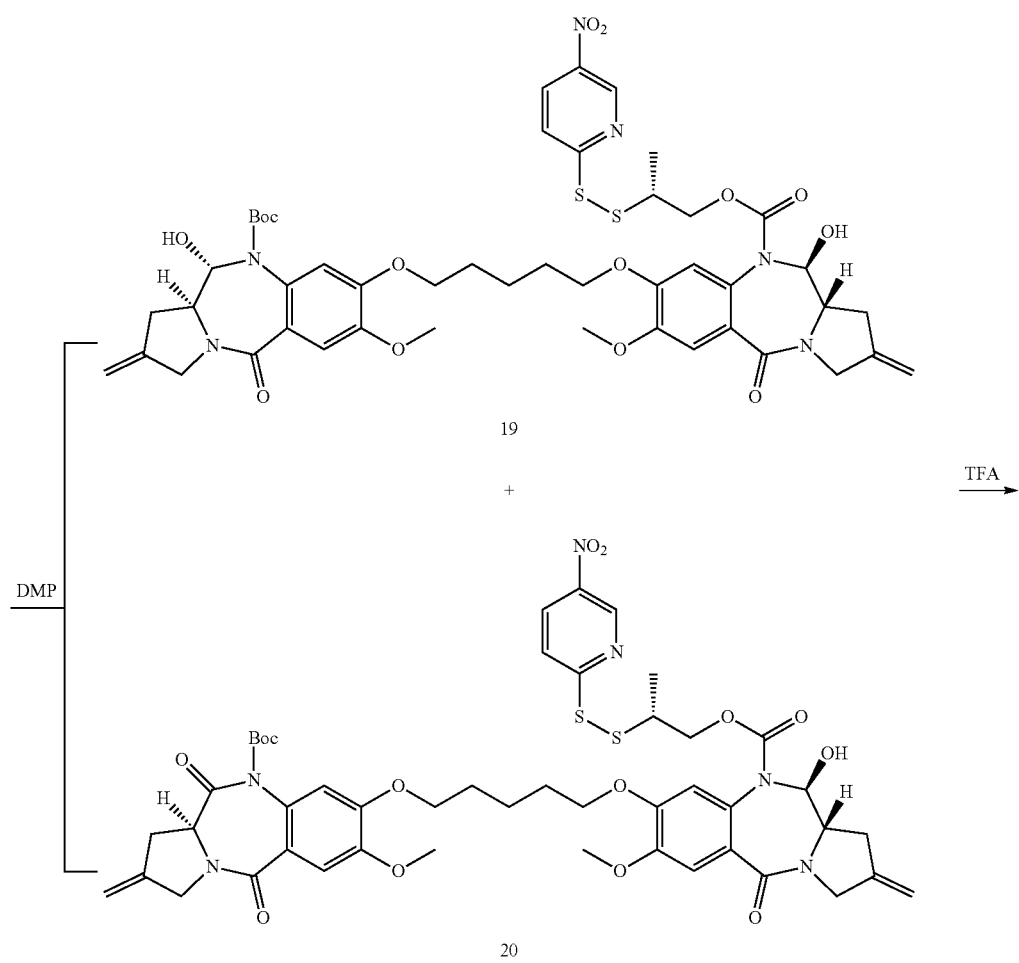

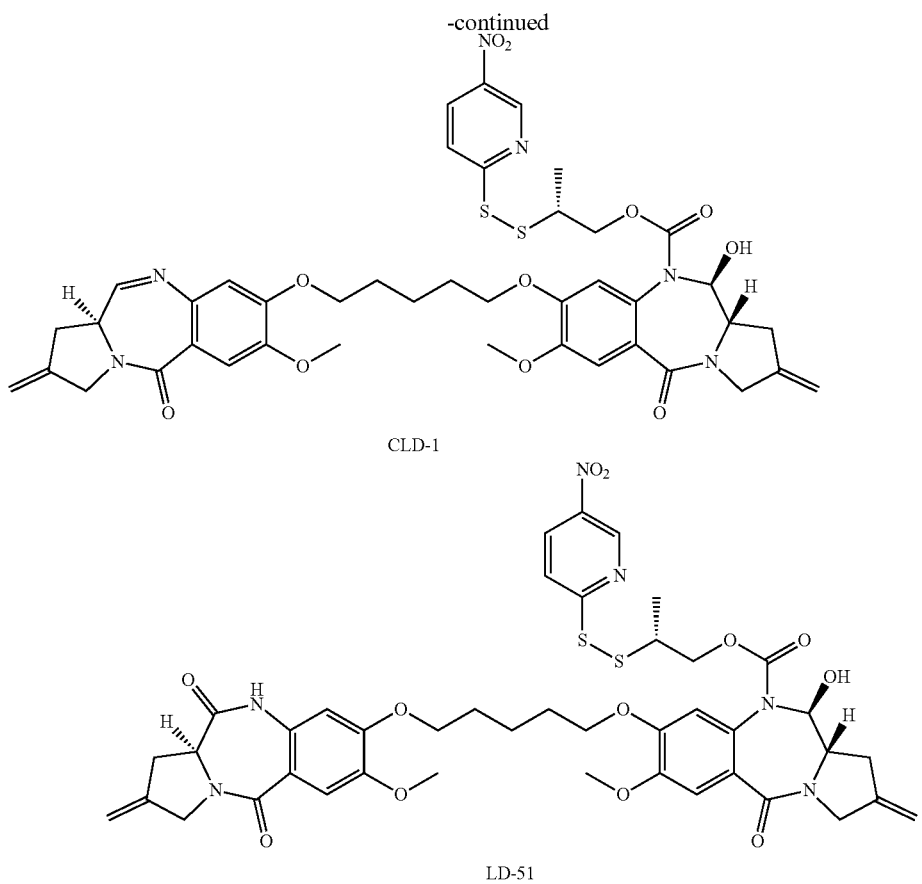

CLD-1

LD-51

Sulfuryl chloride (2.35 mL of a 1.0M solution in DCM, 2.35 mmol) was added drop-wise to a stirred suspension of 5-nitropyridine-2-thiol (334 mg, 2.14 mmol) in dry DCM (7.5 mL) at 0° C. (ice/acetone) under an argon atmosphere. The reaction mixture turned from a yellow suspension to a yellow solution and was allowed to warm to room temperature then stirred for 2 hours after which time the solvent was removed by evaporation in vacuo to provide a yellow solid. The solid was re-dissolved in DCM (15 mL) and treated drop-wise with a solution of (R)-2-mercaptopropan-1-ol (213 mg, 2.31 mmol) in dry DCM (7.5 mL) at 0° C. under an argon atmosphere. The reaction mixture was allowed to warm to room temperature and stirred for 20 hours at which point analysis by LC/MS revealed substantial product formation at retention time 1.41 minutes (ES+) m/z 247 ([M+H]+, ~100% relative intensity). The precipitate was removed by filtration and the filtrate evaporated in vacuo to give an orange solid which was treated with $H_2O$ (20 mL) and basified with ammonium hydroxide solution. The mixture was extracted with DCM (3×25 mL) and the combined extracts washed with $H_2O$ (20 mL), brine (20 mL), dried ($MgSO_4$), filtered and evaporated in vacuo to give the crude product. Purification by flash chromatography (gradient elution in 1% increments: 100% DCM to 98:2 v/v DCM/MeOH) gave (R)-2-((5-nitropyridin-2-yl)disulfanyl)propan-1-ol 15 as an oil (111 mg, 21% yield).

To a solution of triphosgene, $Cl_3COCOOCCl_3$, Sigma Aldrich, CAS Reg. No. 32315-10-9 (241 mg, 0.812 mmol) in DCM (10 mL) was added a solution of (R)-2-((5-nitropyridin-2-yl)disulfanyl)propan-1-ol 15 (500 mg, 2.03 mmol) and pyridine (153 mg, 1.93 mmol) in DCM (10 mL) dropwise at 20° C. After the reaction mixture was stirred at 20° C. for 30 min, it was concentrated and (R)-2-((5-nitropyridin-2-yl)disulfanyl)propyl carbonochloridate 16 was used directly in the next step without further purification.

A solution of compound 16 (626 mg, 2.03 mmol) in DCM (10 mL) was added drop-wise to a solution of tert-butyl (5-((5-(5-amino-4-((S)-2-(((tert-butyldimethylsilyl)oxy)methyl)-4-methylenepyrrolidine-1-carbonyl)-2-methoxyphenoxy)pentyl)oxy)-2-((S)-2-(((tert-butyldimethylsilyl)oxy)methyl)-4-methylenepyrrolidine-1-carbonyl)-4-methoxyphenyl)carbamate 1 (1.50 g, 1.57 mmol) and pyridine (161 mg, 2.05 mmol) at 20° C. The reaction mixture was stirred at 20° C. for 3 h. The solvent was removed and the residue was purified by flash column (EtOAc in petroleum ether 0~30%) to give tert-butyl (2-((S)-2-(((tert-butyldimethylsilyl)oxy)methyl)-4-methylenepyrrolidine-1-carbonyl)-5-((5-(4-((S)-2-(((tert-butyldimethylsilyl)oxy)methyl)-4-methylenepyrrolidine-1-carbonyl)-2-methoxy-5-((((R)-2-((5-nitropyridin-2-yl)disulfanyl)propoxy)carbonyl)amino)phenoxy)pentyl)oxy)-4-methoxyphenyl)carbamate 17 (1.6 g, 83%) as a yellow foam. LCMS (5-95AB/1.5 min): RT=1.360 min, [M+Na]+ 1247.4

To a solution of compound 17 (900 mg, 0.734 mmol) in $THF/H_2O$ (10 mL/10 mL) was added HOAc (15 mL) at 20° C. The reaction mixture was stirred at 20° C. for 24 h. The reaction mixture was diluted with EtOAc (50 mL) and washed with water (2×20 mL), Saturated aq. $NaHCO_3$ (30 mL) and brine (30 mL). It was dried and concentrated to give the crude product which was purified by flash chromatography (DCM:MeOH=100:1~20:1) to give tert-butyl (2-((S)-2-(hydroxymethyl)-4-methylenepyrrolidine-1-carbonyl)-5-((5-(4-((S)-2-(hydroxymethyl)-4-methylenepyrrolidine-1-carbonyl)-2-methoxy-5-((((R)-2-((5-nitropyridin-2-yl)disulfanyl)propoxy)carbonyl)amino)phenoxy)pentyl)oxy)-4-methoxyphenyl)carbamate 18 (700 mg, 95.6%) as a yellow foam. LCMS (5-95AB/1.5 min): RT=0.978 min, [M+H]+ 997.6

To a solution of compound 18 (700 mg, 0.702 mmol) in DCM (40 mL) was added Dess-Martin periodinane, DMP, 1,1,1-Tris(acetyloxy)-1,1-dihydro-1,2-benziodoxol-3-(1H)-one, Sigma Aldrich, CAS Reg. No. 87413-09-0 (1.19 mg, 2.81 mmol) at 20° C. The reaction mixture was stirred at 20° C. for 1 h. The reaction was quenched with a saturate solution of $NaHCO_3/Na_2SO_3$ (20 mL/20 mL) and extracted with DCM (3×10 mL). The combined organic layer was washed with $NaHCO_3/Na_2SO_3$ (10 mL/10 mL), brine (20 mL), dried and concentrated to give a mixture of tert-butyl (11S,11aS)-11-hydroxy-8-((5-(((11S,11aS)-11-hydroxy-7-methoxy-2-methylene-10-(((R)-2-((5-nitropyridin-2-yl)disulfanyl)propoxy)carbonyl)-5-oxo-2,3,5,10,11,11a-hexahydro-1H-benzo[e]pyrrolo[1,2-a][1,4]diazepin-8-yl)oxy)pentyl)oxy)-7-methoxy-2-methylene-5-oxo-2,3,11,11a-tetrahydro-1H-benzo[e]pyrrolo[1,2-a][1,4]diazepine-10(5H)-carboxylate 19 (LCMS (5-95AB/1.5 min): RT=0.912 min, [M+Na]+1015.3) and tert-butyl (S)-8-((5-(((11S,11aS)-1-hydroxy-7-methoxy-2-methylene-10-(((R)-2-((5-nitropyridin-2-yl)disulfanyl)propoxy)carbonyl)-5-oxo-2,3,5,10,11,11a-hexahydro-1H-benzo[e]pyrrolo[1,2-a][1,4]diazepin-8-yl)oxy)pentyl)oxy)-7-methoxy-2-methylene-5,11-dioxo-2,3,11,11a-tetrahydro-1H-benzo[e]pyrrolo[1,2-a][1,4]diazepine-10(5H)-carboxylate 20 which was used in the next step directly.

Cold TFA (8 mL) was added to a crude mixture of 19 and 20 (600 mg, 0.604 mmol) at 0° C. The reaction mixture was stirred at 0° C. for 30 min. The reaction mixture was added dropwise to a cold saturate aq. $NaHCO_3$ (150 mL) at 0° C. and extracted with DCM (4×40 mL). The combined organic layer was washed with brine (50 mL), dried and concentrated to give the crude product which was purified by pre-TLC (DCM:MeOH=15:1) to separate pure LD-51 (28 mg, 5.2%) as a yellow foam. LCMS: (5-95, AB, 1.5 min), 0.739 min, m/z=891.2 (M+1). $^1$H NMR (400 MHz, $CDCl_3$) δ 9.26 (s, 1H), 8.31 (d, J=6.8 H, 1 Hz), 8.18 (s, 1H), 7.62 (d, J=8.4 Hz, 1H), 7.41 (s, 1H), 7.18 (s, 1H), 6.77 (s, 1H), 6.41 (s, 1H), 5.60 (d, J=10.0 Hz, 1H), 5.20-5.06 (m, 4H), 4.50-3.81 (m, 18H), 3.70-3.60 (m, 1H), 3.50-3.40 (m, 1H), 3.18 (br, 1H), 2.98-2.62 (m, 6H), 1.95-1.86 (m, 4H), 1.70-1.52 (m, 2H), 1.17 (d, J=6.4 Hz, 3H).

Synthesis of (11S,11aS)-(R)-2-((5-nitropyridin-2-yl)disulfanyl)propyl 11-hydroxy-7-methoxy-8-((5-(((S)-7-methoxy-2-methylene-5-oxo-2,3,5,10,11,11a-hexahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate (LD-52)

To a solution of CLD-1 (45 mg, 0.050 mmol) in THF (3.0 mL) was added $NaBH_3CN$ (3 mg, 0.050 mmol) and HOAc (0.05 mL) at 0° C. The mixture was stirred at 0° C. for 2 min. The reaction solution was purified by prep-TLC (7% methanol in DCM, Rf=0.5) to afford LD-52 (20 mg, 0.022 mmol, 42.1% yield) as a white solid. LCMS (5-95AB/1.5 min): RT=0.878 min, [M+H]+877.2. 1H NMR (400 MHz, $CDCl_3$) δ 9.19 (s, 1H), 8.27 (d, J=6.8 Hz, 1H), 7.58 (d, J=8.8 Hz, 1H), 7.53 (s, 1H), 7.24 (s, 1H), 6.69 (s, 1H), 6.02 (s, 1H), 5.56 (d, J=9.7 Hz, 1H), 5.12 (s, 2H), 5.05 (d, J=11.2 Hz, 2H), 4.54 (br.s, 1H), 4.42-4.38 (m, 1H), 4.29-4.22 (m, 4H), 4.13-4.09 (m, 1H), 4.02-3.39 (m, 8H), 3.79 (s, 3H), 3.63 (t, J=8.0 Hz, 1H), 3.53 (d, J=11.9 Hz, 1H), 3.37-3.31 (m, 1H), 3.16-3.14 (m, 1H), 2.94-2.88 (m, 2H), 2.74-2.71 (m, 1H), 2.44-2.39 (m, 1H), 1.93-1.85 (m, 4H), 1.66-1.56 (m, 2H), 1.24-1.14 (m, 3H)

Example 3

Preparation of Comparator Pyrrolobenzodiazepine Linker-drug Intermediates (Table 2B)

Synthesis of (R)-2-((5-nitropyridin-2-yl)disulfanyl)propyl (11S,11aS)-11-hydroxy-7-methoxy-8-((5-(((S)-7-methoxy-2-methylene-5-oxo-2,3,5,10,11,11a-hexahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate (CLD-1)

To a solution of 18 (50 mg, 0.050 mmol) in DCM (2.0 mL) was added DMP (149 mg, 0.35 mmol) at 25° C. The reaction mixture was stirred at 25° C. for 2 h. The reaction was diluted with DCM (5 mL) and quenched with a saturate solution of $NaHCO_3/Na_2SO_3$ (2 mL/2 mL) and extracted with DCM (2×5 mL). The combined organic layer was washed with $NaHCO_3/Na_2SO_3$ (2 mL/2 mL), brine (5 mL), dried and concentrated. The residue was purified by pre-TLC (DCM:MeOH=20:1) to give tert-butyl (11S,11aS)-11-hydroxy-8-((5-(((11S,11aS)-11-hydroxy-7-methoxy-2-methylene-10-(((R)-2-((5-nitropyridin-2-yl)disulfanyl)propoxy)carbonyl)-5-oxo-2,3,5,10,11,11a-hexahydro-1H-benzo[e]pyrrolo[1,2-a][1,4]diazepin-8-yl)oxy)pentyl)oxy)-7-methoxy-2-methylene-5-oxo-2,3,11,11a-tetrahydro-1H-benzo[e]pyrrolo[1,2-a][1,4]diazepine-10(5H)-carboxylate 19 which was used directly in the next step. LCMS: (5-95, AB, 1.5 min), 0.830 min, m/z=1013.4 (M+23).

Cold TFA (1 mL) was added to 19 (20 mg, 0.020 mmol) at 0° C. The reaction mixture was stirred at 0° C. for 20 min. The reaction mixture was added dropwise to a cold saturate aq. $NaHCO_3$ (20 mL) at 0° C. and extracted with DCM (3×15 mL). The combined organic layer was washed with brine (15 mL), dried and concentrated to give the crude product which was purified by pre-TLC (DCM:MeOH=15:1) to give CLD-1 (4 mg, 23%) as a gray solid. LCMS: (5-95, AB, 1.5 min), 0.89 min, m/z=873.6 (M+1). $^1$H NMR (400 MHz, $CDCl_3$) δ 9.22 (s, 1H), 8.38 (d, J=8.8 Hz, 1H), 7.78 (d, J=8.8 Hz, 1H), 7.68 (d, J=4.4 Hz, 1H), 7.49 (s, 1H), 7.33 (s, 1H), 6.82 (s, 1H), 6.77 (s, 1H), 5.20-5.13 (m, 4H), 4.36-4.26 (m, 5H), 4.20-3.95 (m, 7H), 4.89-3.70 (m, 8H), 3.50-2.70 (m, 5H), 2.05-1.82 (m, 4H), 1.40-1.15 (m, 3H).

Synthesis of 4-((S)-2-((S)-2-(6-(2,5-dioxo-2,5-di-hydro-1H-pyrrol-1-yl)hexanamido)-3-methylbutanamido)-5-ureidopentanamido)benzyl (11S,11aS)-11-hydroxy-7-methoxy-8-((5-(((S)-7-methoxy-2-methylene-5-oxo-2,3,5,10,11,11a-hexahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate CLD-4
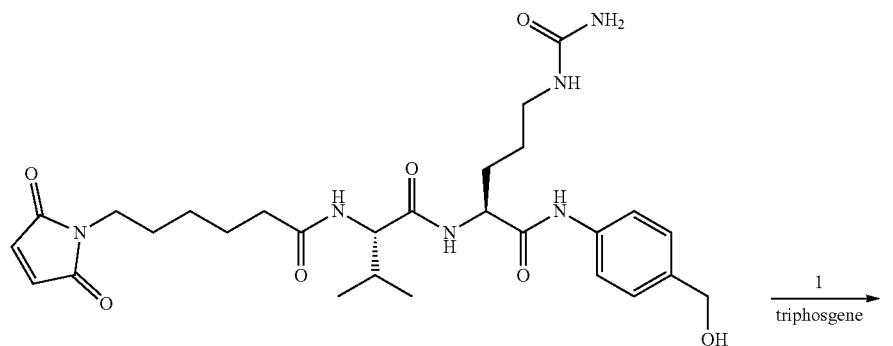
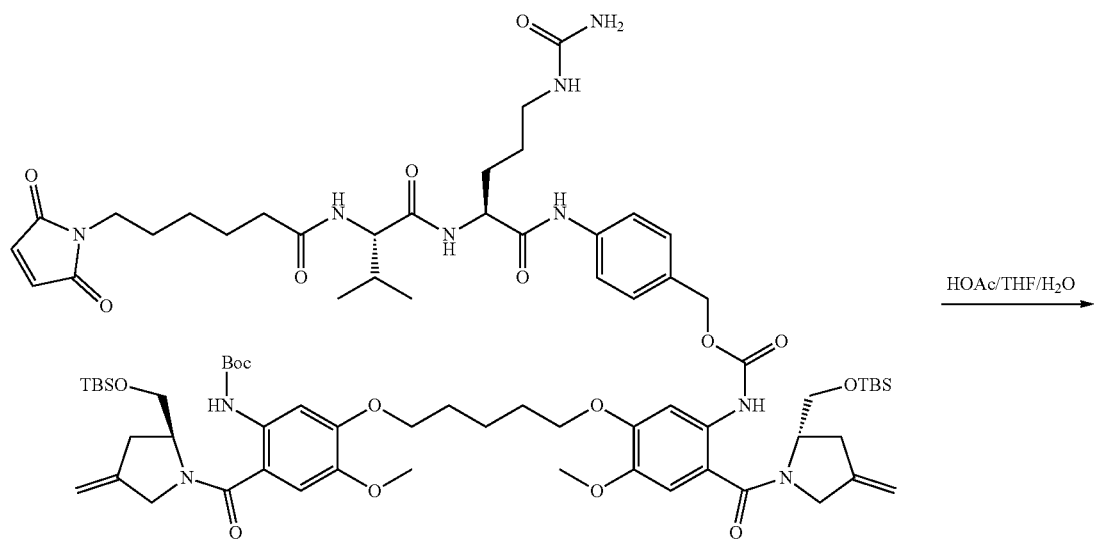

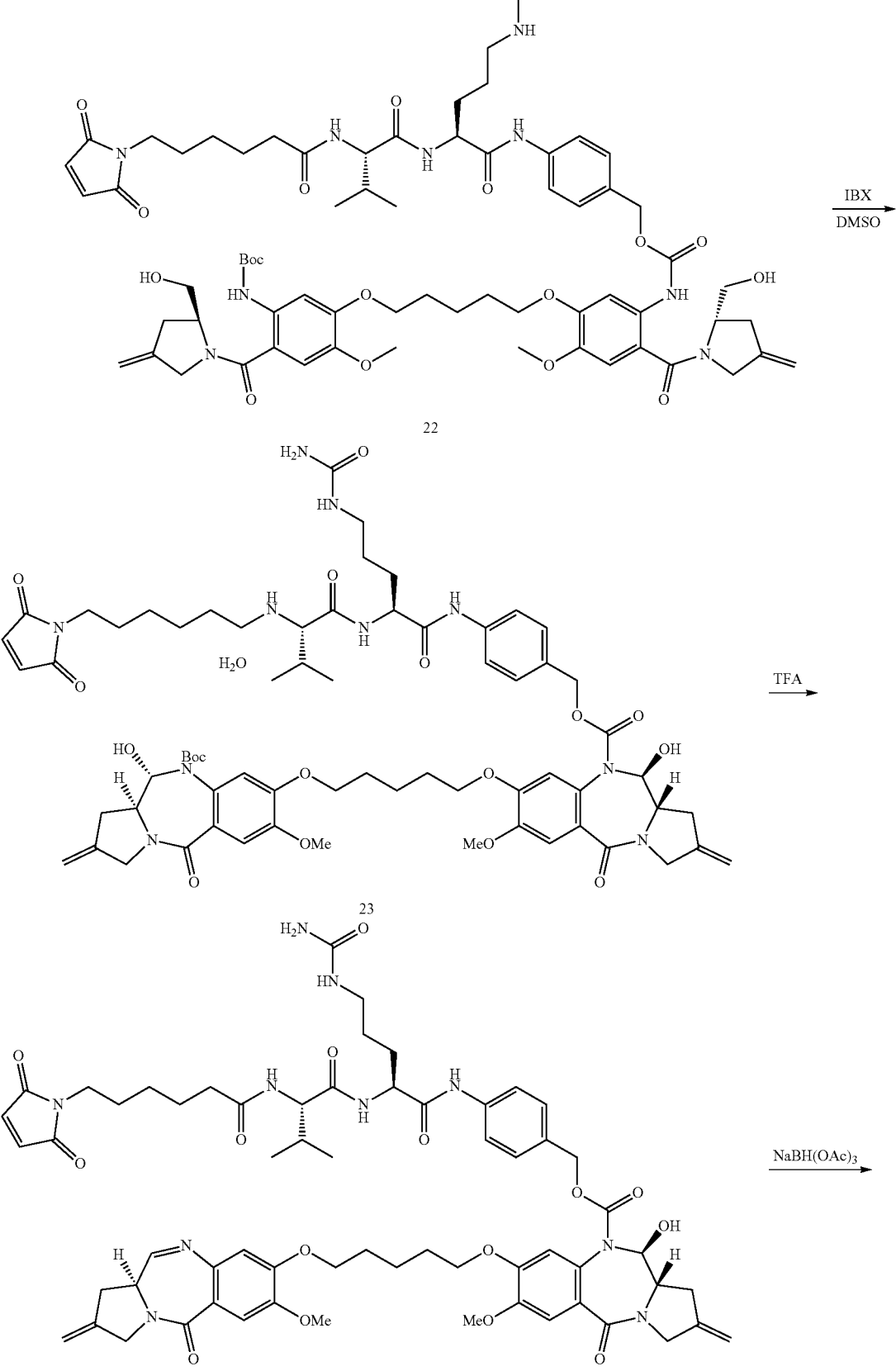

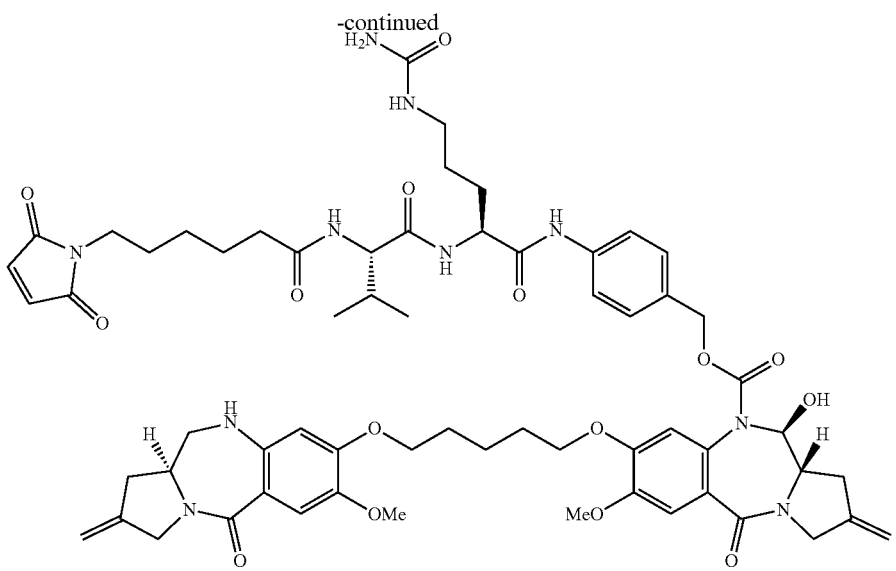

CLD-4

To a solution of triphosgene (156 mg, 0.52 mmol) in DCM (20 mL) was added a solution of 1 (1.0 g, 1.05 mmol) and Et₃N (318 mg, 3.15 mmol) in DCM (5.0 mL). The mixture was stirred at 0° C. for 1 h, and concentrated to give the crude intermediate, which was added (0.88 g, 1.53 mmol) in DCM (20 mL) was added to a mixture of triethylamine (310 mg, 3.07 mmol) and 6-(2,5-dioxo-2,5-dihydro-1H-pyrrol-1-yl)-N—((S)-1-(((S)-1-((4-(hydroxymethyl)phenyl)amino)-1-oxo-5-ureidopentan-2-yl)amino)-3-methyl-1-oxobutan-2-yl)hexanamide, MC-VC-PAB (1.0 g, 1.02 mmol) in DMF (10 mL) at 0° C. The mixture was diluted with DCM (40 mL), washed with water (2×30 mL). The organic layer was dried over Na₂SO₄, concentrated and purified by chromatography on silica (0-10% MeOH in DCM) to give tert-butyl (2-((S)-2-(((tert-butyldimethylsilyl)oxy)methyl)-4-methylenepyrrolidine-1-carbonyl)-5-((5-(4-((S)-2-(((tert-butyldimethylsilyl)oxy)methyl)-4-methylenepyrrolidine-1-carbonyl)-5-(((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)-2-methoxyphenoxy)pentyl)oxy)-4-methoxyphenyl)carbamate 21 (1.0 g, 0.64 mmol, 62.4% yield) as a yellow solid.

To a solution of Compound 21 (1.0 g, 0.64 mmol) in THF (6.0 mL) was added water (6.0 mL) and acetic acid (9.0 mL). The mixture was stirred at 20° C. for 12 h. The mixture was added EtOAc (100 mL) and the organic layer was washed with water (50 mL×3) and sat. NaHCO₃ (50 mL) and concentrated to give tert-butyl (5-((5-(5-(((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)-4-((S)-2-(hydroxymethyl)-4-methylenepyrrolidine-1-carbonyl)-2-methoxyphenoxy)pentyl)oxy)-2-((S)-2-(hydroxymethyl)-4-methylenepyrrolidine-1-carbonyl)-4-methoxyphenyl)carbamate 22 (700 mg, 0.53 mmol, 82.1% yield) as a white solid.

To a solution of 22 (597 mg, 0.45 mmol) in DMSO (5.0 mL) was added 2-iodoxybenzoic acid, IBX (126 mg, 0.45 mmol) at 18° C. The reaction mixture was stirred at 37° C. for 8 h and purified by prep-HPLC (acetonitrile 40-70%/0.225% FA in water) to give tert-butyl (11S,11aS)-8-((5-(((11S,11aS)-10-(((4-((S)-2-((S)-2-((6-(2,5-dioxo-2,5-dihydro-1H-pyrrol-1-yl)hexyl)amino)-3-methylbutanamido)-5-ureidopentanamido)benzyl)oxy)carbonyl)-11-hydroxy-7-methoxy-2-methylene-5-oxo-2,3,5,10,11,11a-hexahydro-1H-benzo[e]pyrrolo[1,2-a][1,4]diazepin-8-yl)oxy)pentyl)oxy)-11-hydroxy-7-methoxy-2-methylene-5-oxo-2,3,11,11a-tetrahydro-1H-benzo[e]pyrrolo[1,2-a][1,4]diazepine-10(5H)-carboxylate hydrate 23 (120 mg, 0.089 mmol, 19.8% yield) as a white solid.

A solution of 23 (100 mg, 0.080 mmol) in TFA (4.0 mL) was stirred at 0° C. for 30 min then added to cold sat..NaHCO₃ (40 mL). It was extracted with EtOAc (60 mL×3). The combined organic layers were concentrated to give the 4-((S)-2-((S)-2-(6-(2,5-dioxo-2,5-dihydro-1H-pyrrol-1-yl)hexanamido)-3-methylbutanamido)-5-ureidopentanamido) benzyl (11S,11aS)-11-hydroxy-7-methoxy-8-((5-(((S)-7-methoxy-2-methylene-5-oxo-2,3,5,11a-tetrahydro-1H-benzo[e]pyrrolo[1,2-a][1,4]diazepin-8-yl)oxy)pentyl)oxy)-2-methylene-5-oxo-2,3,11,11a-tetrahydro-1H-benzo[e]pyrrolo[1,2-a][1,4]diazepine-10(5H)-carboxylate 24 (90 mg) as a yellow solid, which was used in the next step directly.

To a solution of Compound 24 (90 mg, 0.070 mmol) in DMF (4.0 mL) was added Sodium triacetoxyborohydride (9.42 mg, 0.1500 mmol). Sodium cyanoborohydride can also be used as reducing agent. The mixture stirred at 20° C. for 30 min. The resulting residue was purified by prep-HPLC (acetonitrile 0-40/0.1% HCl in water) to afford CLD-4 (28 mg, 0.022 mmol, 29.5% yield) as white solid. LCMS: (5-95, AB, 1.5 min), 0.832 min, m/z=602.7, 1203.6 (M+1)

Example 4

Preparation of Cysteine Engineered Antibodies for Conjugation by Reduction and Reoxidation Light chain amino acids are numbered according to Kabat (Kabat et al., *Sequences of proteins of immunological interest*, (1991) 5th Ed., US Dept of Health and Human Service, National Institutes of Health, Bethesda, Md.). Heavy chain amino acids are numbered according to the EU numbering system (Edelman et al (1969) Proc. Natl. Acad. of Sci. 63(1):78-85), except where noted as the Kabat system. Single letter amino acid abbreviations are used.

Full length, cysteine engineered monoclonal antibodies (THIOMAB™) expressed in CHO cells bear cysteine adducts (cystines) or are glutathionylated on the engineered cysteines due to cell culture conditions. As is, THIOMAB™s purified from CHO cells cannot be conjugated to Cys-reactive linker-drug intermediates. Cysteine engineered antibodies may be made reactive for conjugation with linker-drug intermediates of the invention, such as those in Table 2A, by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.) followed by re-formation of the inter-chain disulfide bonds (re-oxidation) with a mild oxidant such as dehydroascorbic acid. Full length, cysteine engineered monoclonal antibodies (THIOMAB™) expressed in CHO cells (Gomez et al (2010) Biotechnology and Bioeng. 105(4):748-760; Gomez et al (2010) Biotechnol. Prog. 26:1438-1445) were reduced, for example, with about a 50 fold excess of DTT overnight in 50 mM Tris, pH 8.0 with 2 mM EDTA at room temperature, which removes Cys and glutathione adducts as well as reduces interchain disulfide bonds in the antibody. Removal of the adducts was monitored by reverse-phase LCMS using a PLRP-S column. The reduced THIOMAB™ was diluted and acidified by addition to at least four volumes of 10 mM sodium succinate, pH 5 buffer.

Alternatively, the antibody was diluted and acidified by adding to at least four volumes of 10 mM succinate, pH 5 and titration with 10% acetic acid until pH was approximately five. The pH-lowered and diluted THIOMAB™ was subsequently loaded onto a HiTrap S cation exchange column, washed with several column volumes of 10 mM sodium acetate, pH 5 and eluted with 50 mM Tris, pH 8.0, 150 mM sodium chloride. Disulfide bonds were reestablished between cysteine residues present in the parent Mab by carrying out reoxidation. The eluted reduced THIOMAB™ described above is treated with 15× dehydroascorbic acid (DHAA) for about 3 hours or, alternatively, with 200 nM to 2 mM aqueous copper sulfate ($CuSO_4$) at room temperature overnight. Other oxidants, i.e. oxidizing agents, and oxidizing conditions, which are known in the art may be used. Ambient air oxidation may also be effective. This mild, partial reoxidation step forms intrachain disulfides efficiently with high fidelity. Reoxidation was monitored by reverse-phase LCMS using a PLRP-S column. The reoxidized THIOMAB™ was diluted with succinate buffer as described above to reach pH approximately 5 and purification on an S column was carried out as described above with the exception that elution was performed with a gradient of 10 mM succinate, pH 5, 300 mM sodium chloride (buffer B) in 10 mM succinate, pH 5 (buffer A). To the eluted THIOMAB™, EDTA was added to a final concentration of 2 mM and concentrated, if necessary, to reach a final concentration of more than 5 mg/mL. The resulting THIOMAB™, ready for conjugation, was stored at −20 C in aliquots. Liquid chromatography/Mass Spectrometric Analysis was performed on a 6200 series TOF or QTOF Agilent LC/MS. Samples were chromatographed on a PRLP-S®, 1000 A, microbore column (50 mm×2.1 mm, Polymer Laboratories, Shropshire, UK) heated to 80° C. A linear gradient from 30-40% B (solvent A: 0.05% TFA in water, solvent B: 0.04% TFA in acetonitrile) was used and the eluent was directly ionized using the electrospray source. Data were collected and deconvoluted by the MassHunter software. Prior to LC/MS analysis, antibodies or drug conjugates (50 micrograms) were treated with PNGase F (2 units/ml; PROzyme, San Leandro, Calif.) for 2 hours at 37° C. to remove N-linked carbohydrates.

Alternatively, antibodies or drug conjugates were partially digested with LysC (0.25 g per 50 μg (microgram) antibody or conjugate) for 15 minutes at 37° C. to give a Fab and Fc fragment for analysis by LCMS. Peaks in the deconvoluted LCMS spectra were assigned and quantitated. Drug-to-antibody ratios (DAR) were calculated by calculating the ratio of intensities of the peak or peaks corresponding to drug-conjugated antibody relative to all peaks observed.

Example 5

Conjugation of Linker-drug Intermediates to Antibodies

After the reduction and reoxidation procedures of Example 2, the cysteine-engineered antibody (THIOMAB™), in 10 mM succinate, pH 5, 150 mM NaCl, 2 mM EDTA, is pH-adjusted to pH 7.5-8.5 with 1M Tris. An excess, from about 3 molar to 20 equivalents of a linker-drug intermediate with a thiol-reactive pyridyl disulfide group, including but not limited to those in Table 2A, is dissolved in DMF or DMA and added to the reduced, reoxidized, and pH-adjusted antibody. The reaction is incubated at room temperature or 37 C and monitored until completion (1 to about 24 hours), as determined by LC-MS analysis of the reaction mixture. When the reaction is complete, the conjugate is purified by one or any combination of several methods, the goal being to remove remaining unreacted linker-drug intermediate and aggregated protein (if present at significant levels). For example, the conjugate may be diluted with 10 mM histidine-acetate, pH 5.5 until final pH is approximately 5.5 and purified by S cation exchange chromatography using either HiTrap S columns connected to an Akta purification system (GE Healthcare) or S maxi spin columns (Pierce). Alternatively, the conjugate may be purified by gel filtration chromatography using an S200 column connected to an Akta purification system or Zeba spin columns. Alternatively, dialysis may be used. The THIOMAB drug conjugates were formulated into 20 mM His/acetate, pH 5, with 240 mM sucrose using either gel filtration or dialysis. The purified conjugate is concentrated by centrifugal ultrafiltration and filtered through a 0.2-μm filter under sterile conditions and frozen for storage. The antibody-drug conjugates were characterized by BCA assay to determine protein concentration, analytical SEC (size-exclusion chromatography) for aggregation analysis and LC-MS after treatment with Lysine C endopeptidase (LysC) to calculate DAR.

Size exclusion chromatography is performed on conjugates using a Shodex KW802.5 column in 0.2M potassium phosphate pH 6.2 with 0.25 mM potassium chloride and 15% IPA at a flow rate of 0.75 ml/min. Aggregation state of the conjugate was determined by integration of eluted peak area absorbance at 280 nm.

LC-MS analysis may be performed on ADC using an Agilent QTOF 6520 ESI instrument. As an example, the antibody-drug conjugate is treated with 1:500 w/w Endoproteinase Lys C (Promega) in Tris, pH 7.5, for 30 min at 37° C. The resulting cleavage fragments are loaded onto a 1000Å(Angstrom), 8 μm (micron) PLRP-S (highly cross-linked polystyrene) column heated to 80° C. and eluted with a gradient of 30% B to 40% B in 5 minutes. Mobile phase A was H$_2$O with 0.05% TFA and mobile phase B was acetonitrile with 0.04% TFA. The flow rate was 0.5 ml/min. Protein elution was monitored by UV absorbance detection at 280 nm prior to electrospray ionization and MS analysis. Chromatographic resolution of the unconjugated Fc fragment, residual unconjugated Fab and drugged Fab was usually achieved. The obtained m/z spectra were deconvoluted using Mass Hunter™ software (Agilent Technologies) to calculate the mass of the antibody fragments.

By these procedures, cysteine engineered, antibody drug conjugates of Table 3A and 3B were prepared.

Example 6

In Vitro Cell Proliferation Assay

Efficacy of ADC was measured by a cell proliferation assay employing the following protocol (CELLTITER GLO™ Luminescent Cell Viability Assay, Promega Corp. Technical Bulletin TB288; Mendoza et al (2002) Cancer Res. 62:5485-5488). The protocol is a modification of the CELLTITER GLO™ Luminescent Cell assay:
1. An aliquot of 100 µl of cell culture containing about 10$^4$ cells (SKBR-3, BT474, MCF7 or MDA-MB-468) in medium was deposited in each well of a 96-well, opaque-walled plate.
2. Control wells were prepared containing medium and without cells.
3. ADC was added to the experimental wells and incubated for 3-5 days.
4. The plates were equilibrated to room temperature for approximately 30 minutes.
5. A volume of CELLTITER GLO™ Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Data are plotted as the mean of luminescence for each set of replicates, with standard deviation error bars, as seen in FIGS. 1A-E.

Media: SK-BR-3 grow in 50/50/10% FBS/glutamine/250 µg/mL G-418 OVCAR-3 grow in RPMI/20% FBS/glutamine.

Example 7

Tumor Growth Inhibition, In Vivo Efficacy in Xenograft Mice

Tumors were established and allowed to grow to 150-200 mm$^3$ in volume (as measured using calipers) before a single treatment on day 0. Tumor volume was measured using calipers according to the formula: V (mm$^3$)=0.5A×B$^2$, where A and B are the long and short diameters, respectively. Mice were euthanized before tumor volume reached 3000 mm$^3$ or when tumors showed signs of impending ulceration. Data collected from each experimental group (10 mice per group) were expressed as mean±SE.

Inoculate n=150 mice with HER2 KPL-4 cells at 3 million cells/mouse suspended in HBSS/matrigel, in the thoracic mammary fat pad at a volume of 0.2 ml. When tumors have reached a mean tumor volume of 100-250 mm3, they will be grouped out into 10 groups of 8-10 mice each. A single treatment will be administered intravenously via the tail vein on Day 0. Volume not to exceed 0.3 ml, needle size 28 or 29 gauge.

The HCC1569 cell line expresses Ly6E and was obtained from ATCC (American Type Culture Collection; Manassas, Va.) and a sub-line HCC1569X2 was generated at Genentech for optimal growth in mice. Female C.B-17 SCID-beige mice (Charles River Laboratory) were each inoculated in the thoracic mammary fat pad area with 5 million HCC1569X2 cells suspended in HBSS/matrigel (1:1 ratio). When the xenograft tumors reached an average tumor volume of 100-300 mm$^3$ (referred to as Day 0), animals were randomized into groups of 5 mice each and received a single intravenous injection of the antibody-drug conjugate through tail vein. Tumors and body weights of mice were measured 1-2 times a week throughout the study. Mice were promptly euthanized when body weight loss was >20% of their starting weight. All animals were euthanized before tumors reached 3000 mm$^3$ or showed signs of impending ulceration. Tumor volume was measured in two dimensions (length and width) using calipers and the tumor volume was calculated using the formula: Tumor size (mm$^3$)=(longer measurement×shorter measurement$^2$)×0.5 (WO 2013/177055).

The Fo5 mouse mammary tumor model was employed to evaluate the in vivo efficacy of antibody-drug conjugates of the invention after single dose intravenous injections, and as described previously (Phillips G D L, Li G M, Dugger D L, et al. Targeting HER2-Positive Breast Cancer with Trastuzumab-DM1, an Antibody-Cytotoxic Drug Conjugate. (2008) Cancer Res. 68:9280-90), incorporated by reference herein. Anti-Her2 ADC were tested with the Fo5 model, a transgenic mouse model in which the human HER2 gene is over-expressed in mammary epithelium under transcriptional regulation of the murine mammary tumor virus promoter (MMTV-HER2) as shown in FIGS. 3 and 5. The HER2 over-expression causes spontaneous development of a mammary tumor. The mammary tumor of one of these founder animals (founder #5 [Fo5]) has been propagated in subsequent generations of FVB mice by serial transplantation of tumor fragments (~2×2 mm in size). All studies were conducted in accordance with the Guide for the Care and Use of Laboratory Animals. Each antibody-drug conjugate (single dose) was dosed in nine animals intravenously at the start of the study, and 14 days post-transplant. Initial tumor size was about 200 mm$^3$ volume. Measurements of tumor growth inhibition over time by antibody-drug conjugates of the invention and controls are shown in FIGS. 2-8.

Another mammary fat pad transplant efficacy model may be employed as described (Chen et al. (2007) Cancer Res 67:4924-4932), evaluating tumor volume after a single intravenous dose and using tumors excised from a mouse bearing an intraperitoneal tumor, then serially passaged into the mammary fat pads of recipient mice.

The cell killing activities of anti-CD22 and anti-Napi ADCs were determined in CD22 or Napi-expressing cell lines following 5-day incubations and in xenograft mice.

Example 8

Oligonucleotide Binding/Alkylation Assay

Interaction of pyrrolobenzodiazepine compounds with duplex-forming oligonucleotides of various length and sequences were studied with sequences of Pu-GAATG-Py>Pu-GATC-Py>>Pu-GATG-Py or Pu-GAATC-Py, where Pu is a purine nucleotide A or G and Py is a pyrimidine nucleotide C or T, for intrastrand and interstrand cross-linking previously identified (Rahman K M, et al (2009) *J Am Chem Soc* 131:13756-13766). The interstrand G duplex, 5'-TATAGAAATCTATA-3' and 3'-ATATCTTTAGATAT-5', and the intrastrand G duplex, 5'-TATAGAAATGTATA-3' and 3'-ATATCTTTACATAT-5' were studied by the following procedure:

The compounds at 100 µM were incubated with 50 µM double strand deoxyoligonucleotides (DNA) for 1 hour in 10 mM Bis-Tris, pH 7.1 at 37° C. The samples were analyzed by LC/MS/UV on Sciex TripleTOF 5600 on a Hypersil Gold C18 column (100×2.1, 1.9 µM, Thermo Scientific). The column was eluted at 0.4 mL/min by a gradient of buffer A (50 mM hexafluoro-isopropanol and 15 mM diethylamine) to buffer B (50% A and 50% of 1:1 methanol:acetonitrile), 5% to 25% B in 8 min, to 75% B in 5 min, and to 95% B in 1 min.

Example 9

Safety/Toxicity Study in Cynomolgus Monkeys

Antibody-drug conjugates of the invention were evaluated for toxicity in cynomolgus monkeys, including pulmonary effects of antigen-dependent toxicity due to expression in the lung.

Study Design:

Regimen: IV dosing twice, on days 1 and 22 to assess toxicity over 2 full cycles. 10 day lead in (1M per group), dosed 10 days prior to remaining 1M/2F to mitigate risk of acute morbidity/mortality Potential clinical observations may include skin redness, black discoloration of the skin, sloughing/scaling, ulcers, facial swelling/edema, lean body condition, lack of appetite, and general moribundity.

Potential clinical pathology changes associated with antibody-drug conjugate dosing in cynomolgus monkeys may include increase in urea nitrogen and creatinine combined with inadequately concentrated urine, alterations in sodium, chloride, and potassium likely related to impaired renal tubular function, lung alveolar degeneration, and dose-responsive changes in hematology parameters and inflammation.

Major organ toxicities may include kidney, eye, skin/SQ/muscle, bone marrow, lung, lymphoid organs (splenic and thymic lymphoid depletion).

Dose-dependent increase in severity of pathology findings may allow for comparison of safety/toxicity properties of antibody-drug conjugates and control compounds.

Example 10

Efficacy in Mice

The efficacy of anti-Her2 antibody-drug conjugates was investigated in a mouse allograft model of MMTV-HER2 Founder #5 (murine mammary tumor), or a mouse xenograft model of KPL4, HCC1569X2 (human breast cancer).

The MMTV-HER2 Founder #5 (Fo5) model (developed at Genentech) is a transgenic mouse model in which the human HER2 gene, under transcriptional regulation of the murine mammary tumor virus promoter (MMTV-HER2), is overexpressed in mammary epithelium. The overexpression causes spontaneous development of mammary tumors that overexpress the human HER2 receptor. The mammary tumor from one of the founder animals (founder #5, Fo5) was surgically implanted into the thoracic mammary fat pad of female nu/nu or FVB mice (Charles River Laboratories) as tumor fragments of approximately 15-30 mm$^3$ in size.

The KPL4 breast cancer cell line was obtained from Dr. J. Kurebayashi lab (Japan). The HCC1569 breast cancer cell line was obtained from ATCC (American Type Culture Collection; Manassas, Va.) and a sub-line HCC1569X2 was generated at Genentech for optimal growth in mice. Both cell lines express HER2 as determined by FACS and IHC. To establish the model, female C.B-17 SCID-beige mice (Charles River Laboratories) were each inoculated in the thoracic mammary fat pad area with 3 million KPL4 cells or 5 million HCC1569X2 cells suspended in HBSS/matrigel (1:1 ratio).

Figure 13:
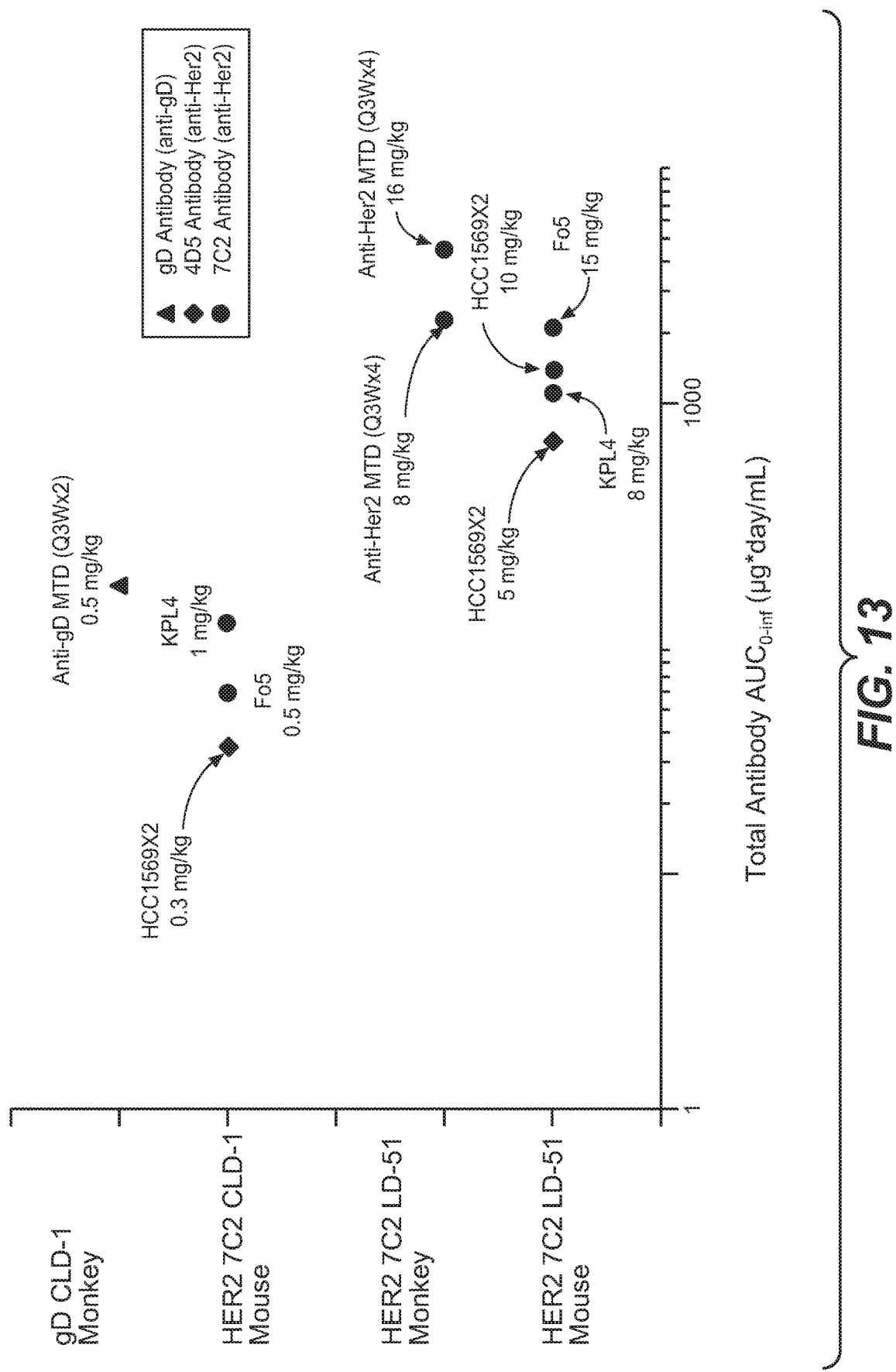
FIG. 13 shows an exposure based therapeutic index assessment of a HER2 LC K149C LD-51 ADC with a HER2 LC K149C CLD-1 ADC.

When tumors reached an average tumor volume of 100-300 mm$^3$, animals were randomized into groups of 5-10 mice each and received a single intravenous injection of the ADCs (referred to as Day 0). Tumors and body weights of mice were measured 1-2 times a week throughout the study. Mice were promptly euthanized when body weight loss was >20% of their starting weight. All animals were euthanized before tumors reached 3000 mm$^3$ or showed signs of impending ulceration. Tumor volume was measured in two dimensions (length and width) using calipers and the tumor volume was calculated using the formula: Tumor size (mm$^3$)=0.5×(length×width×width). Data from this test is shown in FIGS. 12 and 13.

Example 11

Toxicology in Cynomolgus Monkeys

Anti-HER2 hu7C2 LC:K149C-LD-51 Cynomolgus Monkey Toxicology Study

An exploratory dose-escalation toxicology study was conducted in cynomolgus monkeys. Animals received two or four q3w slow IV bolus doses of anti-HER2 hu7C2 LC:K149C-LD-51 starting at a dose level of 1 mg/kg. Dose escalations were staggered by 2-3 weeks. The study design is summarized in Table 7 below.

TABLE 7

Design of Anti-HER2-LD51 LC:K149C cynomolgus monkey toxicology study

| Test article | N/sex | Dose (mg/kg) | Dosing Regimen |
|---|---|---|---|
| Vehicle | 2M/2F | 0 | 2X q3w |
| Anti-HER2-LD51 | 1M | 1 | 2X q3w |
| Anti-HER2-LD51 | 1M | 2 | 2X q3w |
| Anti-HER2-LD51 | 1M | 4 | 2X q3w |
| Anti-HER2-LD51 | 1M | 8 | 2X q3w |
| Anti-HER2-LD51 | 2M/2F | 16 | 2X q3w |
| Anti-HER2-LD51 | 2M/2F | 16 | 4X q3w |
| Anti-HER2-LD51 | 2M/2F | 24 | 2X q3w |
| Anti-HER2-LD51 | 1M | 36 | 2X q3w |

Toxicity was assessed by clinical and ophthalmic exams and clinical pathology (hematology, serum chemistry, coagulation and urinalysis; approximately weekly throughout the study). Gross and microscopic histopathology was conducted on tissues collected at necropsy three weeks after the last dose.

In animals administered four q3w doses of 16 mg/kg Anti-HER2 hu7C2 LC:K149C-LD-51, histological findings were generally more severe than those observed after two doses of 16 mg/kg. Renal tubular degeneration (mild-moderate), lymphoid depletion (thymus, spleen, lymph nodes; mild-moderate), skin pigmentation/hyperkeratosis (mild), small intestine mucosa (mild), and mild lung alveolar degeneration/fibroplasia (mild) were observed.

Major target organs of Anti-HER2 hu7C2 LC:K149C-LD-51 in the cynomolgus monkey are kidney, bone marrow, skin, lung, lymphoid organs (spleen, thymus, lymph nodes), small intestine, and eye (cornea). The maximum tolerated dose (MTD) as a 2X q3w regimen is 16 mg/kg, while the MTD as a 4× q3w regimen is 8 mg/kg.

No studies of anti-HER2-CLD-1 were conducted in monkeys. However, the 2X q3w dose MTD of CLD-1 when conjugated to other cysteine engineered antibodies was determined in the cynomolgus monkey. The MTD of 2 q3w doses of anti-NaPi2b-CLD-1 was 0.5 mg/kg, while that of the non-targeting conjugate gD-CLD-1 was 0.5 mg/kg. The similar target organ effects observed suggests that the toxicities are largely antigen-independent and attributable to CLD-1 or LD-51. The increased MTD of LD-51 conjugates compared with the CLD-1 conjugates indicates the improve tolerability of LD-51 compared to CLD-1. The data for these tests is shown in FIGS. 12 and 13.

Example 12

C-1 and DM-2 Rat Toxicology Study

An exploratory single dose toxicology study was conducted in rats comparing the C-1 (PBD bis alkylator) and DM-2 (PBD monoalkylator) free drugs. Animals received a single IV dose of C-1, DM-2, or vehicle and were monitored for a 7-day recovery period. The study design is summarized in Table 8 below.

TABLE 8

Design of C-1 and DM-2 free drug rat toxicology study

| Test article | N/sex | Dose (mg/kg) |
|---|---|---|
| Vehicle | 5F | 0 |
| C-1 | 5F | 0.05 |
| C-1 | 5F | 0.1 |
| C-1 | 5F | 0.2 |
| DM-2 | 5F | 0.5 |
| DM-2 | 5F | 1 |
| DM-2 | 5F | 2 |

Toxicity was assessed by clinical observations and clinical pathology (hematology and clinical chemistry at 72 and 168 hours post-dose). In general, results were similar for DM-2 at ten times the dose level of C-1. For C-1, a dose-dependent decrease in reticulocytes was observed at all doses at 72 hours, recovering in the 0.05 and 0.1 mg/kg groups by 168 hrs. post-dose. At the 0.2 mg/kg dose, clinical pathology changes indicative of liver and kidney toxicity were observed. Doses of 0.05 and 0.1 mg/kg well tolerated with no clinical signs.

The 0.5 and 1 mg/kg dose levels of DM-2 were well tolerated, resulting in no clinical signs or early euthanasias. Animals administered 2 mg/kg lost approximately 14% of their body weight from Day 2 to 4 and were euthanized in moribund condition on Day 4. A dose-dependent decrease in reticulocytes was observed at all doses of DM-2 72 hours post-dose, which recovered in the 0.5 and 1 mg/kg groups by 168 hours post-dose. At the 2 mg/kg dose, clinical pathology changes indicative of liver and kidney toxicity were observed.

In summary, the toxicity profile resulting from a single dose of C-1 or DM-2 was similar, with C-1 approximately ten times as potent as DM-2. The main target organs of both test articles were bone marrow, kidney, and liver. The MTDs of C-1 and DM-2 were 0.1 and 1 mg/kg, respectively, as a single IV dose in rats. The results of this study indicate the improved tolerability of DM-2 compared to C-1.

Example 13

In Vitro Activity in HER2 Positive Breast Cancer Cell Lines SK-BR-3 and KPL-4

Cells were plated in 96-well plates and allowed to adhere overnight at 37° C. in a humidified atmosphere of 5% $CO_2$. Medium was then removed and replaced by fresh culture medium containing various concentrations of each drug. Cell Titer-Glo (Promega Corp.) was added to the wells at 5 days after drug administration and the luminescent signal was measured using EnVision Multilabel Plate Reader (PerkinElmer). The compounds tested were anti-HER2 hu7C2 LC:K149C CLD-7; anti-HER2 hu7C2 LC:K149C CLD-8; anti-HER2 hu7C2 LC:K149C CLD-9; and anti-HER2 hu7C2 LC:K149C LD-51

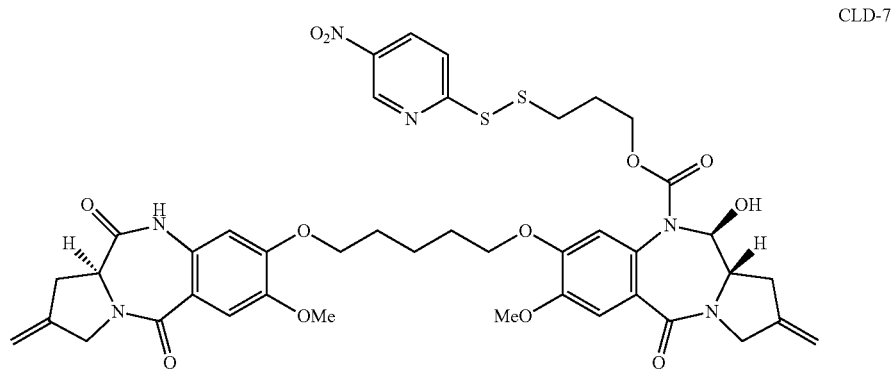

CLD-7

-continued

CLD-8

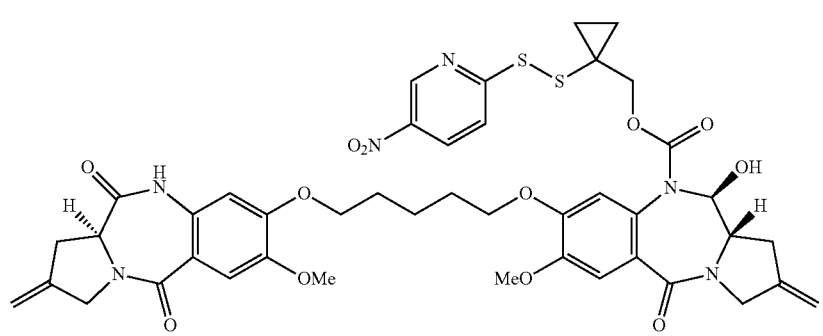

CLD-9

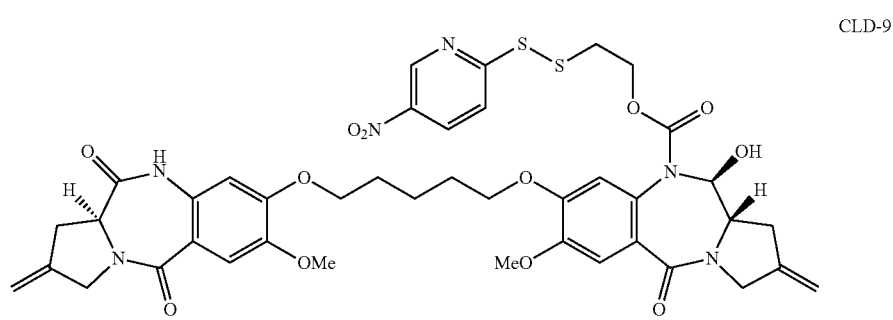

Figure 14:
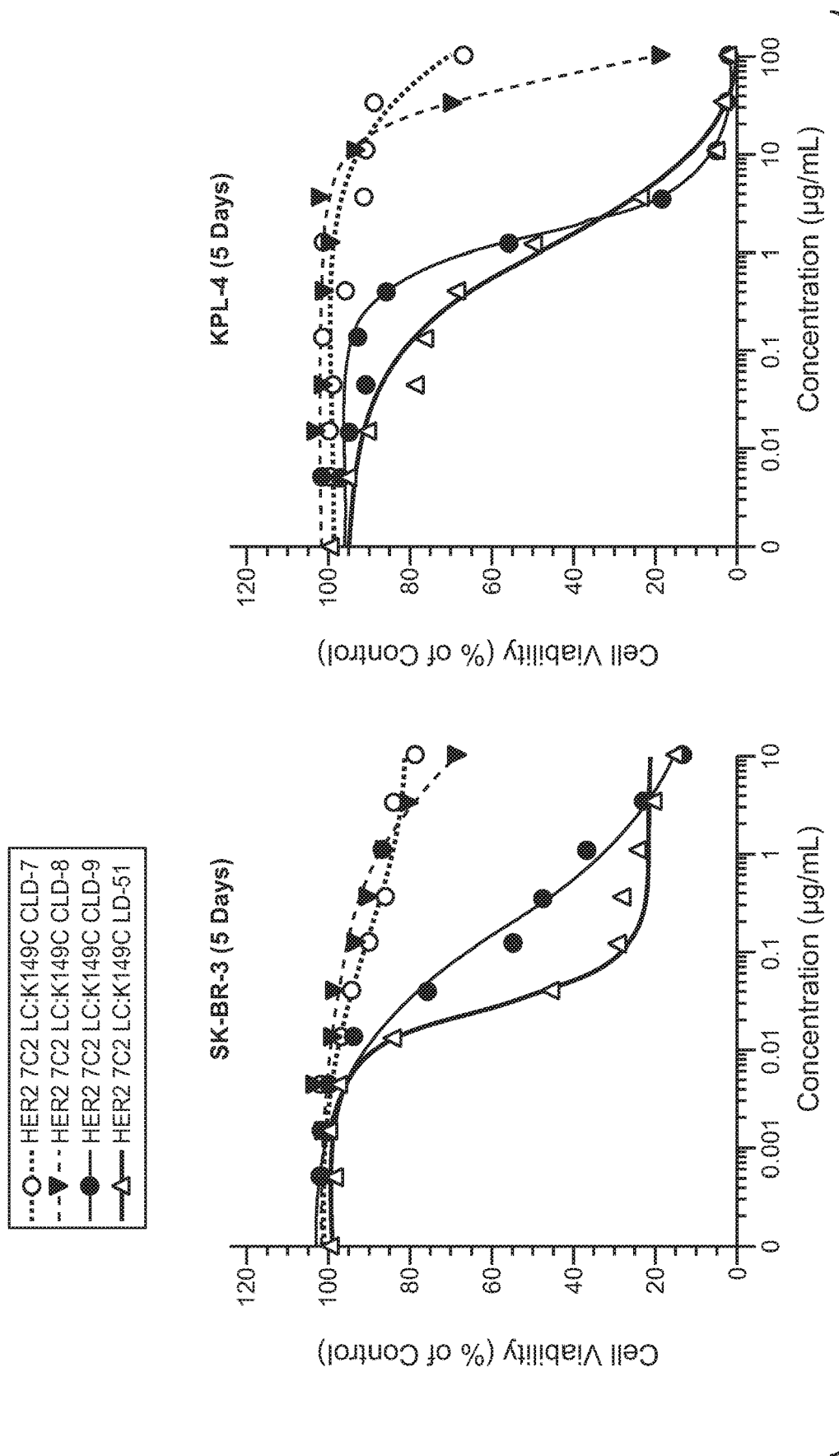
FIG. 14 shows cell viability assay data with several HER2 hu7C2 LC K149C ADCs with different linkers.

The data from this test is shown in FIG. 14 and the Table 9 below.

TABLE 9

| Linker-drug | Target | DAR | SK-BR-3 IC$_{50}$ ng/mL | nM | KPL-4 IC$_{50}$ ng/mL | nM |
|---|---|---|---|---|---|---|
| CLD-7 | HER2 (7C2) | 1.9 | >10,000 | >67 | >100,000 | >67 |
| CLD-8 | HER2 (7C2) | 1.94 | >10,000 | >67 | 63,000 | 422 |
| CLD-9 | HER2 (7C2) | 2.0 | 180 | 1.2 | 1480 | 9.9 |
| LD-51 | HER2 (7C2) | 1.9 | 27.7 | 0.19 | 1240 | 8.3 |

Example 14

In Vivo Mouse Allograft Efficacy

The efficacy of the anti-Her2 antibody-drug conjugates (ADCs) was investigated in a mouse allograft model of MMTV-HER2 Founder #5 (murine mammary tumor). The MMTV-HER2 Founder #5 (Fo5) model (developed at Genentech) is a transgenic mouse model in which the human HER2 gene, under transcriptional regulation of the murine mammary tumor virus promoter (MMTV-HER2), is overexpressed in mammary epithelium. The overexpression causes spontaneous development of mammary tumors that overexpress the human HER2 receptor. The mammary tumor from one of the founder animals (founder #5, Fo5) has been propagated in FVB mice (Charles River Laboratories) by serial transplantation of tumor fragments.

Figure 15:
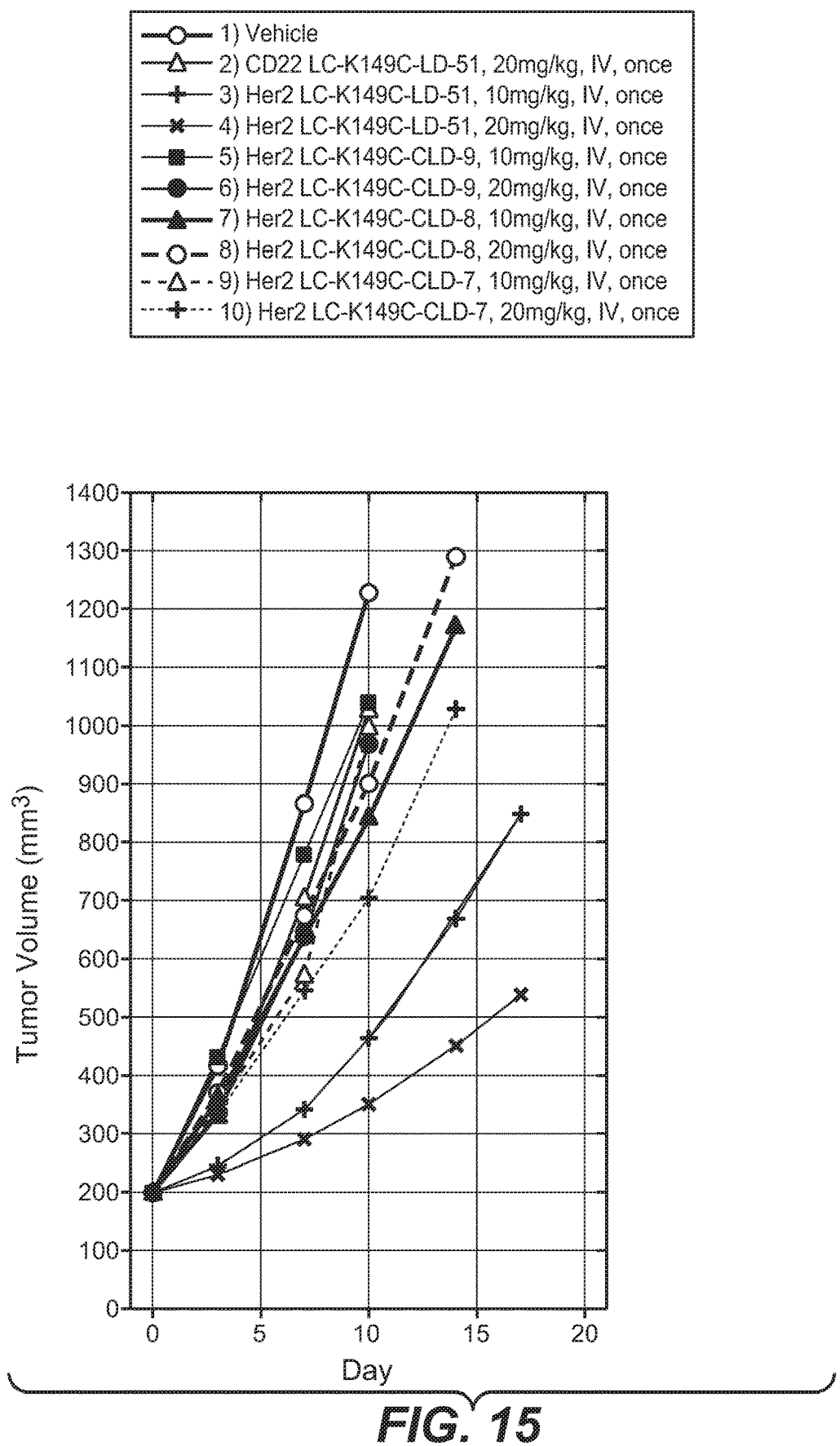
FIG. 15 shows tumor volume over time for various ADCs in a mouse allograft tumor model.

For efficacy studies, the Fo5 transgenic mammary tumor was surgically transplanted into the thoracic mammary fat pad of female nu/nu mice (Charles River Laboratories; Hollister, Calif.) as tumor fragments of approximately 15-30 mm$^3$ in size. When the allograft tumors reached an average tumor volume of 100-300 mm3 (referred to as Day 0), animals were randomized into groups of 7 mice each and received a single intravenous injection of the ADCs. Tumors and body weights of mice were measured 1-2 times a week throughout the study. Mice were promptly euthanized when body weight loss was >20% of their starting weight. All animals were euthanized before tumors reached 3000 mm3 or showed signs of impending ulceration. Tumor volume was measured in two dimensions (length and width) using calipers and the tumor volume was calculated using the formula: Tumor size (mm$^3$)=0.5×(length×width×width). The data from this study is shown in FIG. 15. Among the 4 anti-Her2 ADCs, only anti-Her2-LD-51 demonstrated clear anti-tumor activity when compared to the vehicle group. The efficacy of anti-Her2-LD-51 was target-dependent as the corresponding non target control anti-CD22-LD-51 had no effect on the tumor growth.

Example 15

Synthesis of DM-4, C-1, C-2, C-3, CLD-2, CLD, 3, CLD-5 and CLD-6

The synthetic procedure for making C-1, C-2, C-3 and CLD-2 can be found in the following documents: C-1: Journal of Medicinal Chemistry (2004), 47(5), 1161-1174; C-2: Bioorganic & Medicinal Chemistry Letters (2000), 10(16), 1845-1847 or PCT Int. Appl. WO 2000012508; C-3: PCT Int. Appl. WO 2015155753; and CLD-2 US 20160074527.

Synthesis of CLD-7
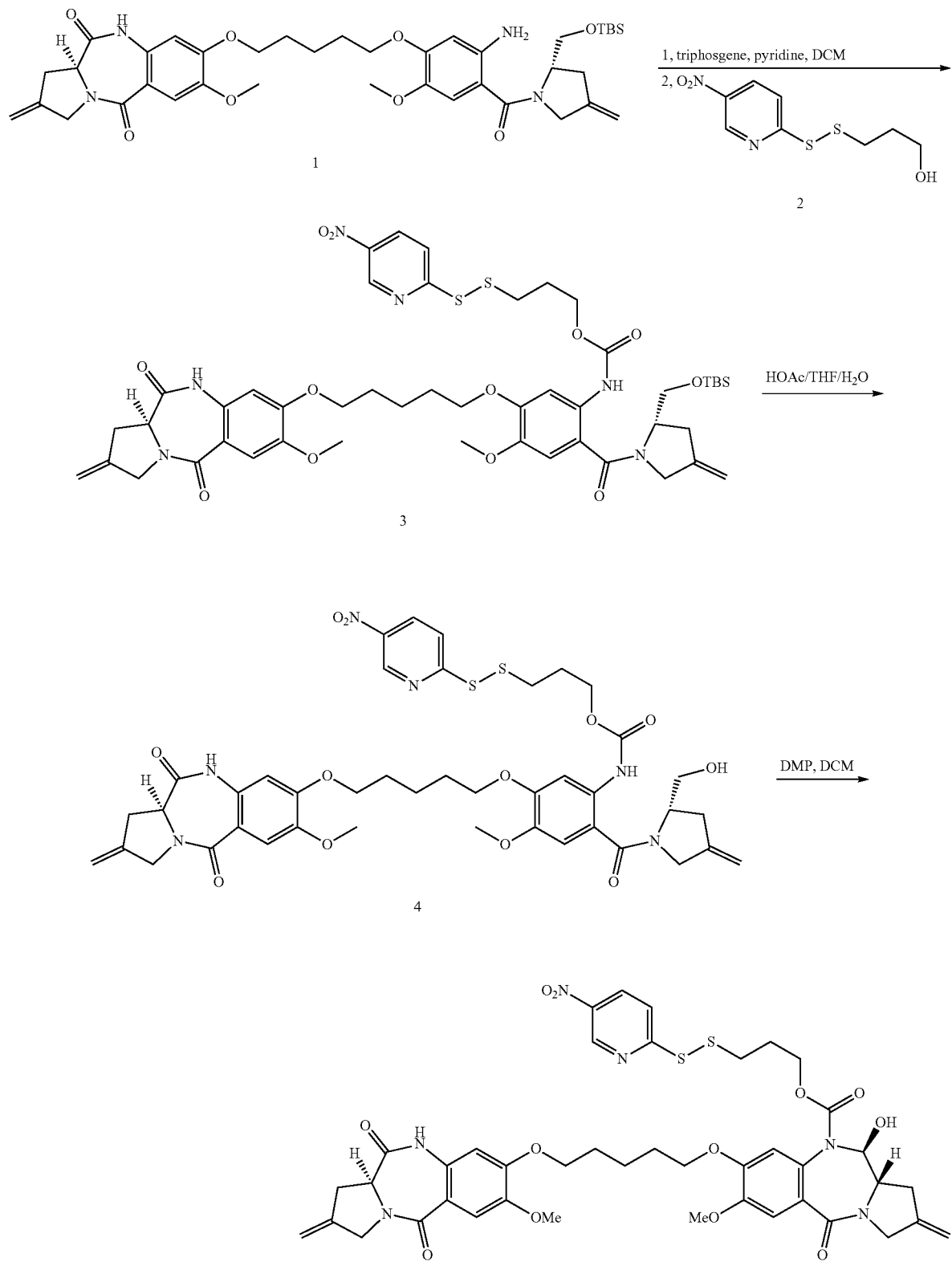

Experimental

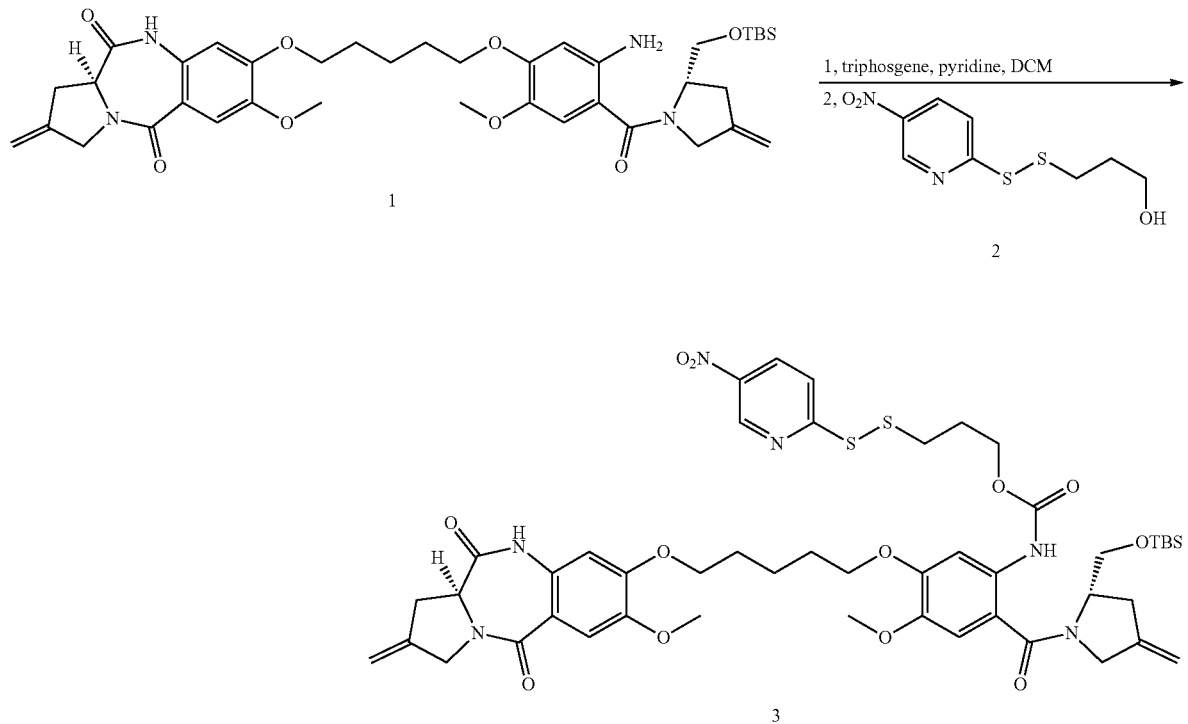

To a solution of triphosgene (60.6 mg, 0.200 mmol) in DCM (15 mL) was added a solution of pyridine (129 mg, 1.63 mmol) and 2 (55.3 mg, 0.220 mmol) in DCM (15 mL). The mixture was stirred at 0° C. for 10 min, TLC (25% EtOAc in petroleum ether, $R_f$=0.5) showed starting material was consumed. The mixture was concentrated to dryness and dissolved in DCM (10 mL) and added to a solution of compound 1 (150.0 mg, 0.200 mmol) and Et$_3$N (103.3 mg, 1.02 mmol) in DCM (15 mL). The mixture was stirred at 0° C. for 1 h. TLC (50% EtOAc in petroleum ether) showed starting material was consumed. The mixture was concentrated, and the crude was purified by flash column chromatography on silica (0-33% EtOAc in petroleum ether). It was concentrated to give 3 (180.0 mg, 81%) as yellow solid. LCMS (5-95AB/1.5 min): RT=1.014 min, [M+H]+1007.1.

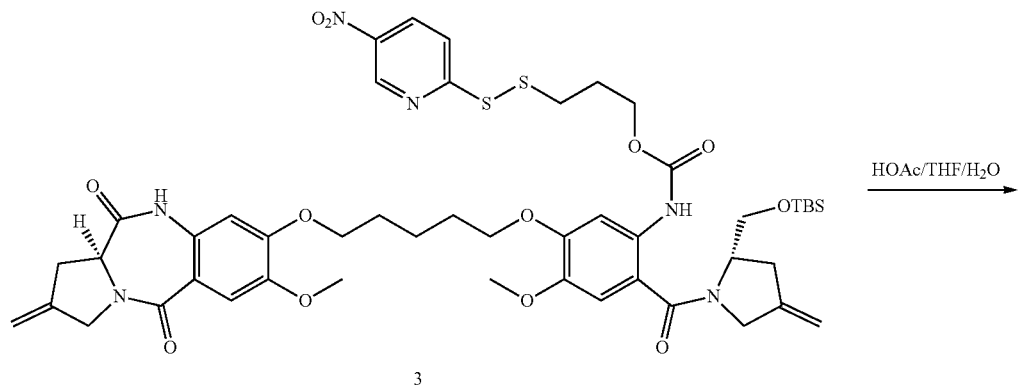

-continued

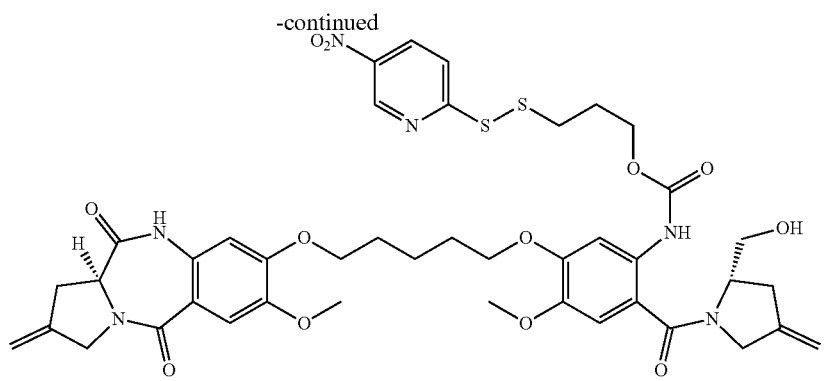

4

To a solution of HOAc (5.0 mL, 87 mmol) in a mixture of THF (3.0 mL) and water (3.0 mL) was added 3 (150.0 mg, 0.1500 mmol). The reaction solution was stirred at 40° C. for 16 h. The solution was concentrated to remove the solvent and the residue was diluted with EtOAc (100 mL), washed with H$_2$O (30 mL×4), dried over Na$_2$SO$_4$, filtered, and concentrated. The residue was purified by prep-TLC (5% MeOH in DCM, R$_f$=0.5) to give 4 (100 mg, 75%) as a yellow solid. LCMS (5-95AB/1.5 min): RT=0.776 min, [M+H]+893.2.

To a solution of DMP (22.8 mg, 0.0500 mmol) in anhydrous DCM (10.0 mL) was added Compound 4 (40.0 mg, 0.0400 mmol). The reaction mixture was stirred at 18° C. for 1 h. The mixture was diluted with DCM (50 mL), filtered. The filtrate was washed with Na$_2$SO$_3$ (30 mL×3), dried over Na$_2$SO$_4$, filtered, and concentrated in vacuo. The residue was purified by prep-TLC (5% MeOH in DCM, R$_f$=0.5) to give CLD-7 (GNT_B343_867-1) (20 mg, 50%) as a yellow solid. LCMS (5-95AB/1.5 min): RT=0.761 min, [M+H]+ 891.0 showed 96% of desired product. HPLC (10-80AB/15 min): RT=8.40 min, showed 94.9% of desired product.

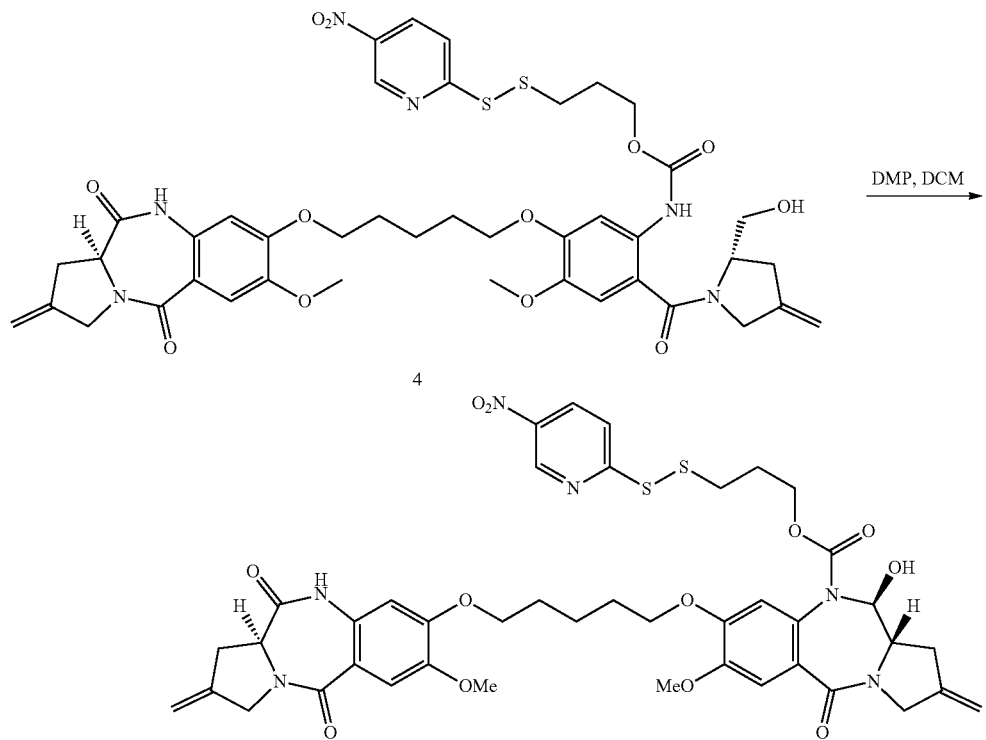

Synthesis of CLD-8
Scheme
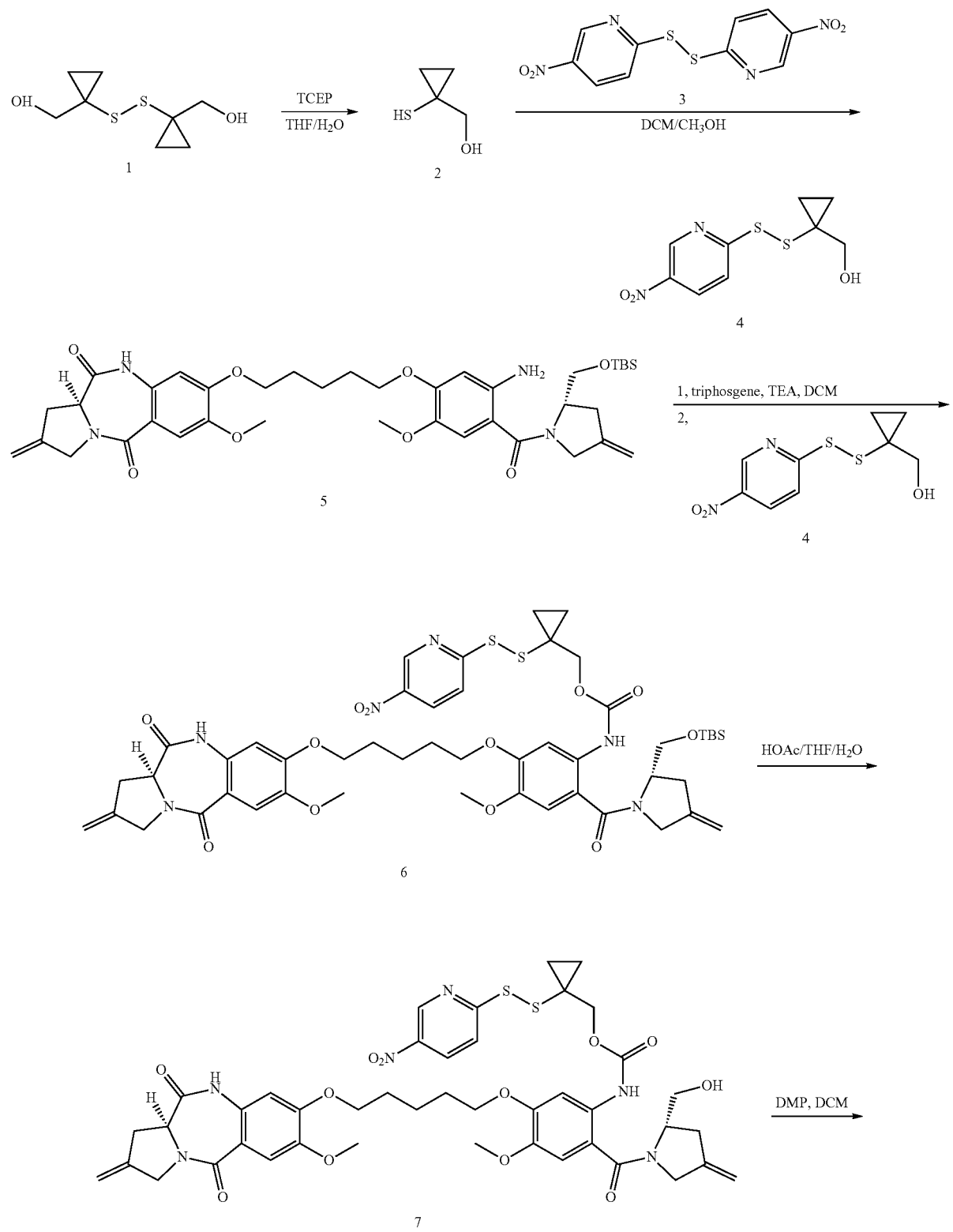

-continued

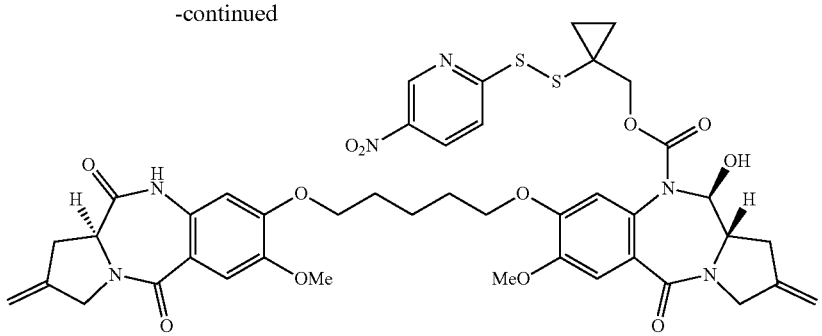

GNT_B343_866-1

Experimental

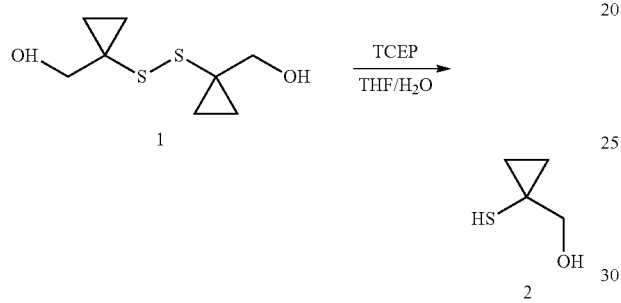

To a solution of compound 1 (40.0 mg, 0.190 mmol) in THF (5.0 mL)/water (5.0 mL) was added TCEP (277.9 mg, 0.970 mmol). The reaction mixture was stirred at 16° C. for 48 h. The solution was diluted with $H_2O$ (10 mL), extracted with DCM (20 mL×3). The combined organic layers were dried over $Na_2SO_4$, filtered, and used in the next step directly.

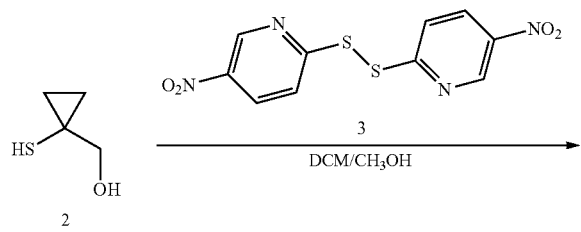

To a solution of compound 2 (40.0 mg, 0.380 mmol) in a mixture of DCM (25 mL) and MeOH (25 mL) was added compound 3 (238.3 mg, 0.770 mmol). The reaction solution was stirred at 16° C. for 16 h, and $MnO_2$ (500 mg) was added, and the mixture was stirred for 0.5 h. The mixture was filtered and the filtrate was concentrated in vacuo. The residue was diluted with MeOH (5 mL), filtered again to remove most of remaining compound 3, the filtrate was concentrated, and purified by prep-TLC (33% EtOAc in petroleum ether, $R_f$=0.5) to give compound 4 (50 mg, 0.157 mmol, 40.8% yield) as a colorless oil. LCMS (5-95AB/1.5 min): $R_T$=0.805 min, [M+H]⁺ 258.9 showed 81% of DP.

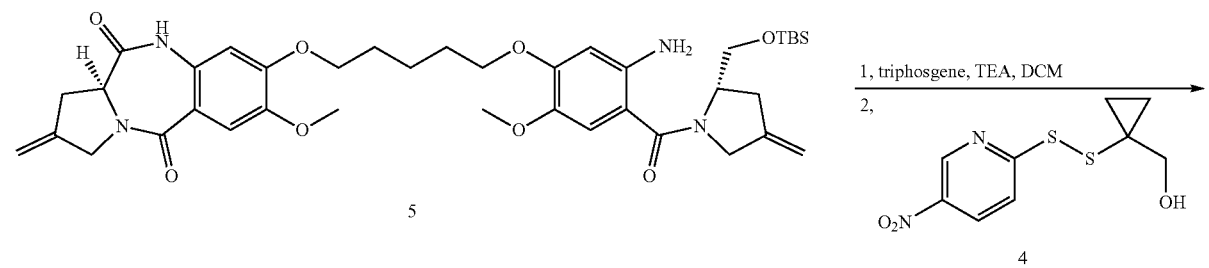

-continued

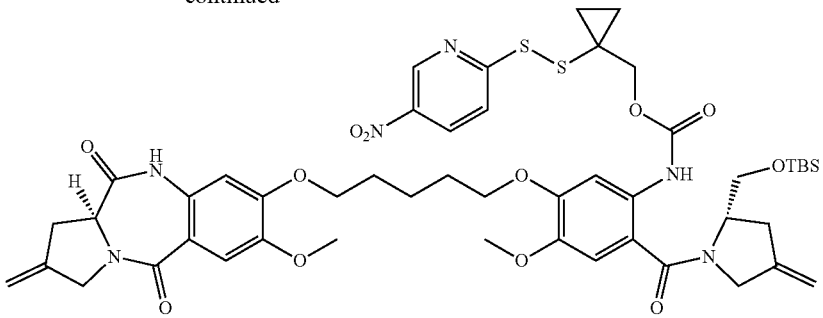

6

To a stirred mixture of triphosgene (64.6 mg, 0.220 mmol) and 4 Å MS (30 mg) in anhydrous DCM (8 mL) was added a solution of compound 5 (160.0 mg, 0.220 mmol) and triethylamine (110.1 mg, 1.09 mmol) in anhydrous DCM (8 mL) slowly. The reaction mixture was stirred at 16° C. for 1 h, and the mixture was concentrated in vacuo to remove the solvent. It was dissolved in anhydrous DCM (10.0 mL) and triethylamine (65.8 mg, 0.650 mmol) was added, followed by a solution of compound 4 (50.0 mg, 0.190 mmol) in anhydrous DCM (5.0 mL). The reaction mixture was stirred at 16° C. for 16 h. The mixture was filtered, the filtrate was concentrated and purified by prep-TLC (10% MeOH in DCM, $R_f$=0.8) to give compound 6 (100 mg, 0.0814 mmol, 37.6% yield) as a yellow solid. LCMS (5-95AB/1.5 min): $R_T$=1.119 min, [M+H]$^+$ 1019.4 showed 83% of desired product.

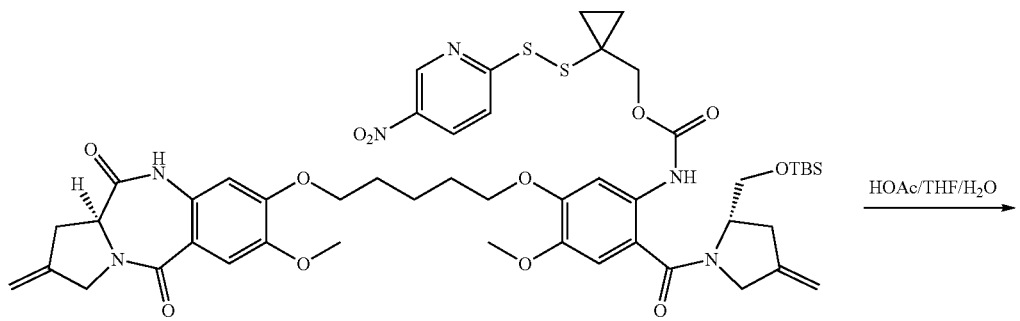

6

HOAc/THF/H$_2$O →

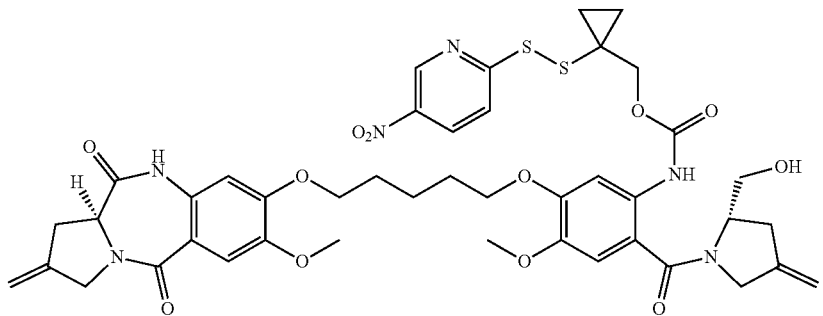

7

A solution of compound 6 (100.0 mg, 0.1000 mmol) in a mixture of acetic acid (3.0 mL), THF (2.0 mL) and water (1.0 mL) was stirred at 16° C. for 48 h. The solution was concentrated in vacuo, and the residue was diluted with DCM (30 mL), washed with H$_2$O (20 mL×3), dried, filtered, and concentrated. The residue was purified by prep-TLC (10% MeOH in DCM, $R_f$=0.5) to give compound 7 (55 mg, 0.0602 mmol, 61.3% yield) as a yellow solid. LCMS (5-95AB/1.5 min): RT=0.892 min, [M+H]$^+$ 905.2 showed 99% of desired product.

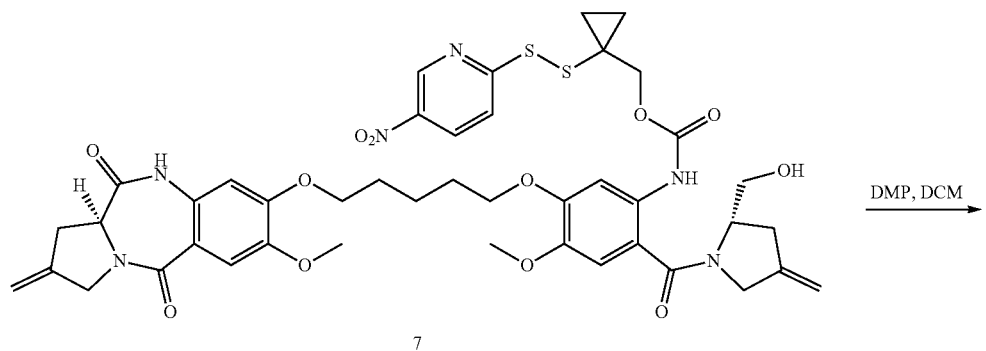

7

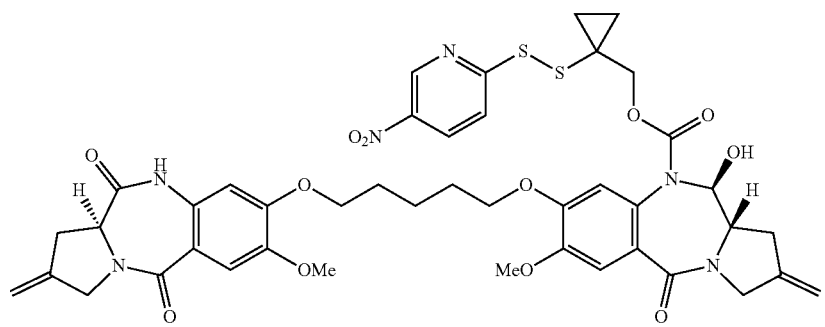

GNT_B343_866-1

To a mixture of compound 7 (55 mg, 0.060 mmol) and 4 Å MS (30 mg) in anhydrous DCM (6.0 mL) was added DMP (44.0 mg, 0.104 mmol). The reaction mixture was stirred at 16° C. for 1 h. The mixture was diluted with EtOAc (30 mL), quenched with saturated $Na_2SO_3$ solution (30 mL), and extracted with EtOAc (30 mL×3). The combined organic layers were dried over $Na_2SO_4$, filtered, and concentrated. The residue was purified by prep-TLC (10% MeOH in DCM, $R_f$=0.5) to give CLD-8 (GNT_B343_866-1) (42 mg, 77% yield) as pale yellow solid. LCMS (5-95AB/1.5 min): $R_T$=0.868 min, [M+H]$^+$ 903.2 showed 98% of the desired product.

Synthesis of CLD-9

Scheme

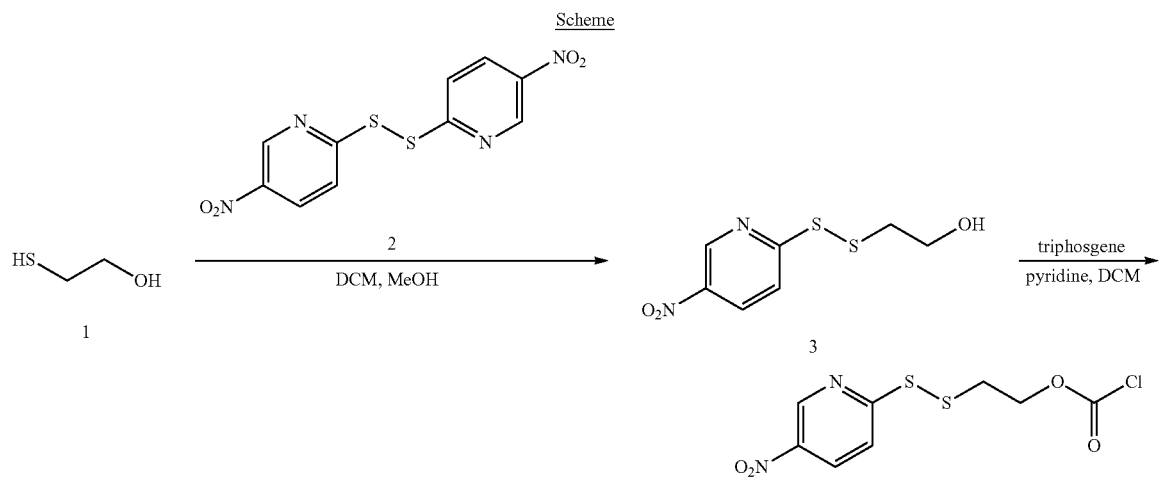

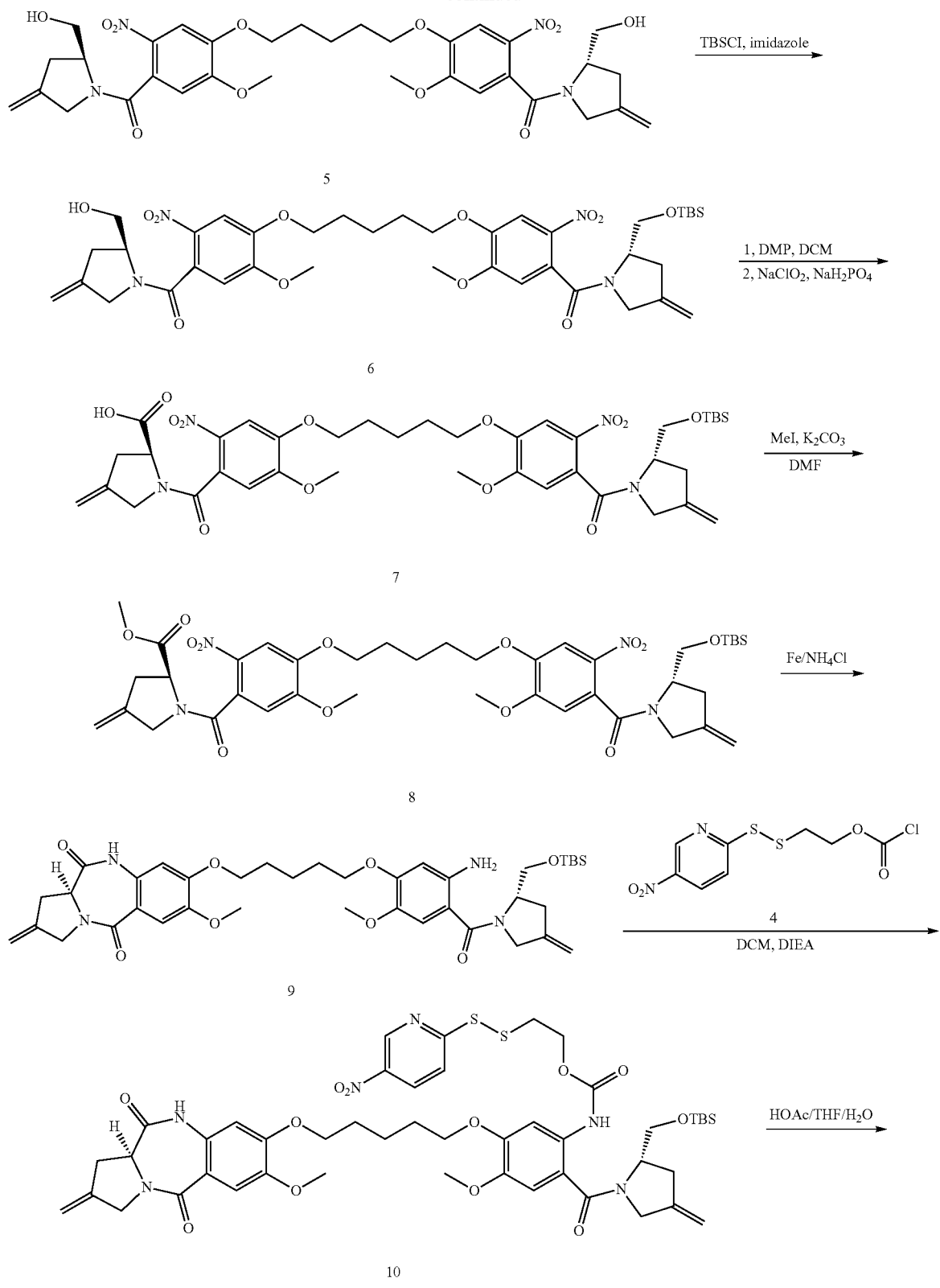

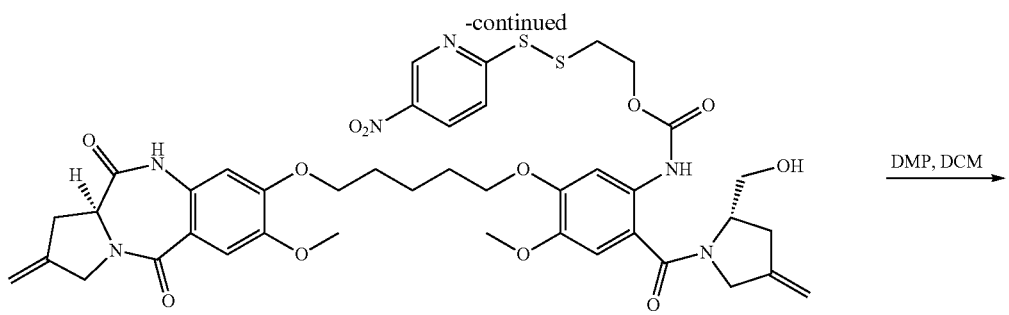

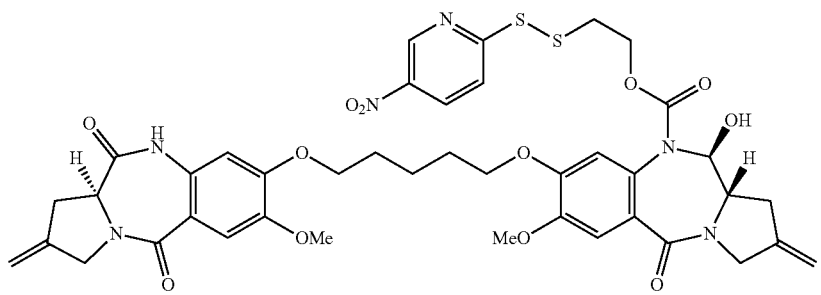

GNT_B343_865-1

Experimental

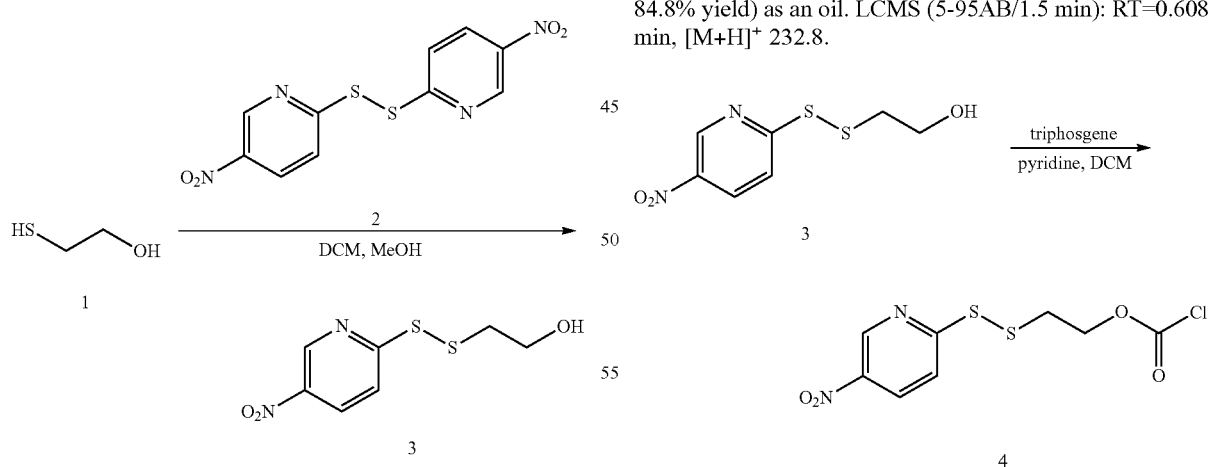

To a solution of compound 2 (2383 mg, 7.68 mmol) in DCM (10 mL)/MeOH (10 mL) was added compound 1 (300 mg, 3.84 mmol). The solution was stirred at 16° C. for 2 h. MnO$_2$ (5.0 g) was added into the solution, the mixture was stirred at 16° C. for 30 min. The mixture was filtered and the filtrate was concentrated in vacuo and the residue was washed with MeOH (15 mL), filtered and concentrated. The crude product was purified by flash column chromatography on silica (DCM) to give compound 3 (800 mg, 3.25 mmol, 84.8% yield) as an oil. LCMS (5-95AB/1.5 min): RT=0.608 min, [M+H]$^+$ 232.8.

Compound 3 (65.0 mg, 0.280 mmol) and pyridine (88.5 mg, 1.12 mmol) in anhydrous DCM (5.0 mL) was added drop-wise to a triphosgene (41.5 mg, 0.140 mmol) solution in anhydrous DCM (5.0 mL) at 0° C. The solution was stirred at 0° C. for 10 min, and the mixture was concentrated to give the crude compound 4 as a white solid, which was used for the next step.

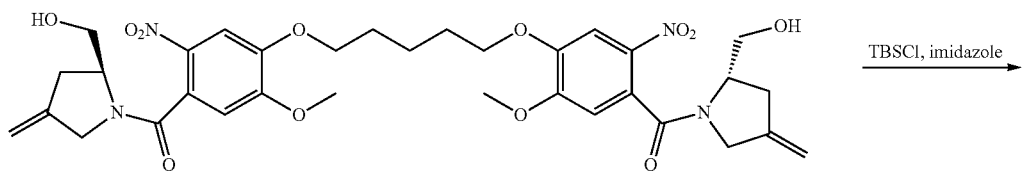

5

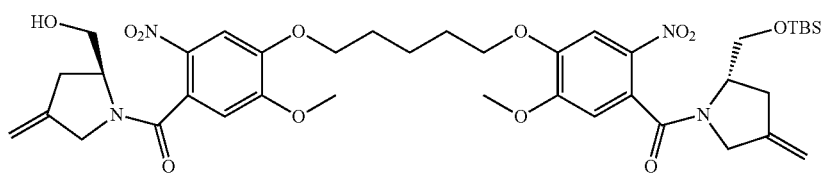

6

To a solution of compound 5 (4000 mg, 5.84 mmol) in anhydrous DCM (80 mL) was added imidazole (2.38 g, 35.1 mmol), followed by TBSCl (1.761 g, 11.7 mmol). The reaction mixture was stirred at 40° C. for 3 h. The mixture was diluted with DCM (100 mL), washed with H$_2$O (50 mL×3), dried over Na$_2$SO$_4$, filtered, and concentrated. The residue was purified by flash column chromatography on silica (0-3.3% MeOH in DCM) to give compound 6 (2.50 g, 3.13 mmol, 53.6% yield) as a pale yellow solid.
LCMS (5-95AB/1.5 min): RT=0.945 min, [M+H]$^+$ 799.2.

quenched with sat. Na$_2$SO$_3$ solution (200 mL), sat. Na$_2$SO$_3$/NaHCO$_3$ solution (v/v=1:1, 200 mL) and brine. The organic layer was dried over Na$_2$SO$_4$, filtered, and concentrated to give crude oil, which was dissolved in $^t$BuOH (40 mL, 2.88 mmol)/water (20 mL) and then treated with 2-methyl-2-butene (30 mL, 2.88 mmol) and sodium dihydrogenphasphate (1.382 mg, 11.5 mmol) successively at 10° C. After it was stirred at 10° C. for 0.5 h, the reaction mixture was stirred with sodium chlorite (1.56 g, 17.3 mmol) at 10° C. for 1 h. The mixture was diluted with EtOAc (300 mL), and

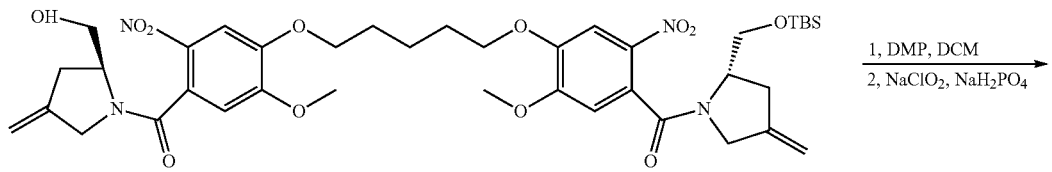

6

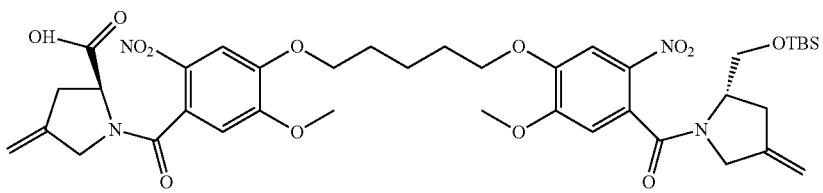

7

To a solution of compound 6 (2.30 g, 2.88 mmol) in anhydrous DCM (100 mL) was added DMP (4.88 g, 11.52 mmol). The reaction mixture was stirred at 10° C. for 2 h. It was filtered, the filtrate was diluted with EtOAc (600 mL), washed with water (100 mL) and brine (100 mL). The organic layer was dried over Na$_2$SO$_4$, filtered, and concentrated in vacuo to give compound 7 (2.0 g, 2.46 mmol, 85.5% yield) as crude product. LCMS (5-95AB/1.5 min): RT=0.929 min, [M+H]$^+$ 813.2.

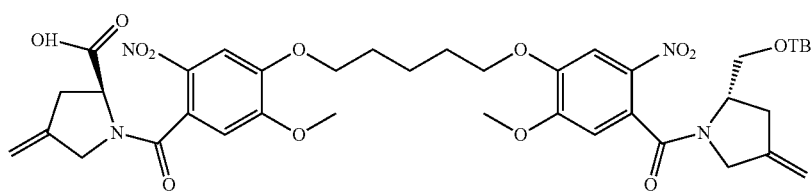

7

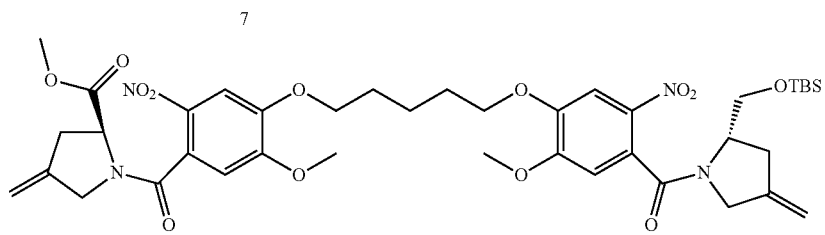

8

To a solution of compound 7 (2.0 g, 2.46 mmol) in DMF (20 mL) was added $K_2CO_3$ (680 mg, 4.92 mmol), followed by MeI (3.95 g, 27.8 mmol). The reaction mixture was stirred at 10° C. for 1 h. The mixture was diluted with EtOAc (200 mL), washed with brine (40 mL×5), then dried over $Na_2SO_4$, filtered, and concentrated in vacuo to give compound 8 (2.0 g, 2.42 mmol, 98.3% yield) as a yellow oil. LCMS (5-95AB/1.5 min): RT=0.975 min, [M+H]$^+$ 827.2.

added $NH_4Cl$ (2.59 g, 48.7 mmol). The reaction mixture was stirred at 70° C. for 2 h. The mixture was filtered, the filtrate was concentrated in vacuo to remove EtOH, and the water slurry was extracted with EtOAc (50 mL×3). The combined EtOAc layers were dried over $Na_2SO_4$, filtered, concentrated and purified by flash column chromatography on silica (3-5% MeOH in DCM, Rf=0.5) to give compound 9 (1.5 g,

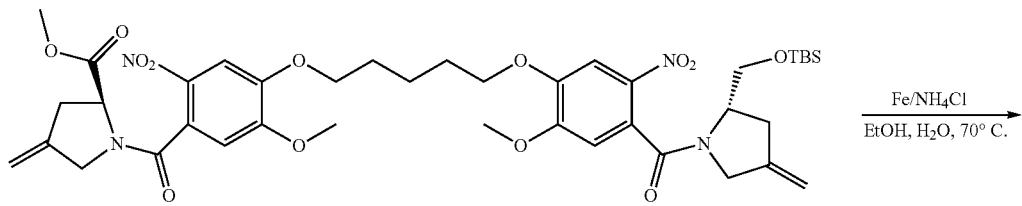

8

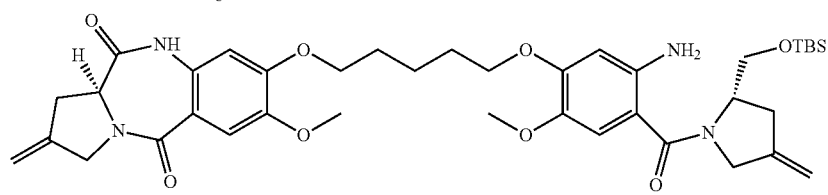

9

To a mixture of compound 8 (2.0 g, 2.42 mmol) and iron (1.35 g, 24.2 mmol) in EtOH (20 mL)/water (10 mL) was 1.89 mmol, 78.1% yield) as a yellow solid. LCMS (5-95AB/1.5 min): RT=0.845 min, [M+H]$^+$ 735.3.

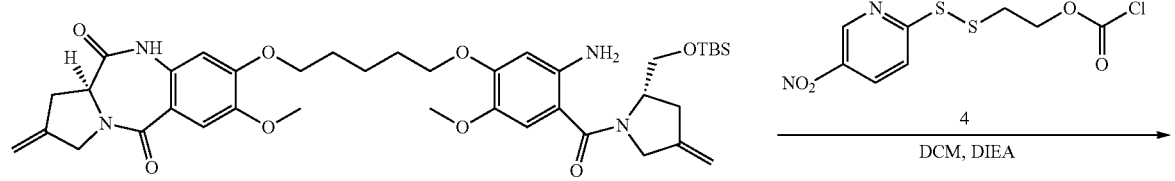

9

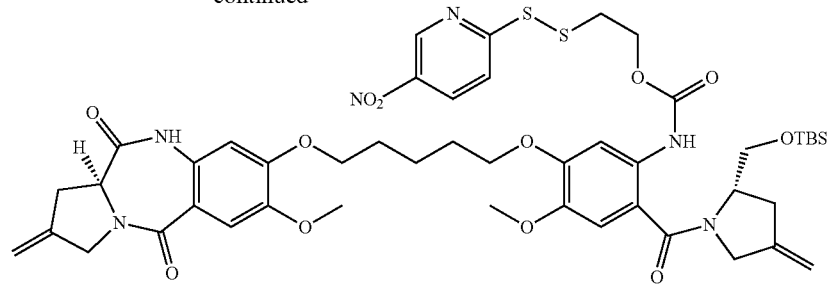

10

To a solution of compound 9 (100 mg, 0.140 mmol) and DIEA (68.8 mg, 0.680 mmol) in DCM (15 mL) was added compound 4 (80.2 mg, 0.270 mmol) and the reaction was stirred at 0° C. for 1 h. The mixture was concentrated and the residue was purified by flash column chromatography on silica (0-5% MeOH in DCM, Rf=0.5) to give compound 10 (130 mg, 0.117 mmol, 85.8% yield) as a yellow oil. LCMS (5-95AB/1.5 min): RT=0.985 min, [M+H]$^+$ 993.4

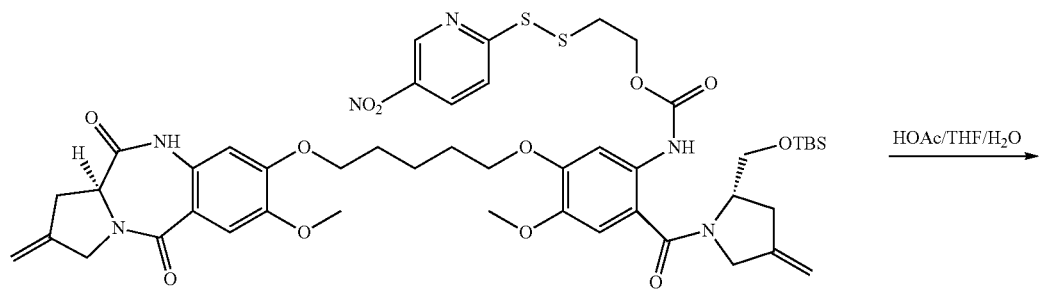

10

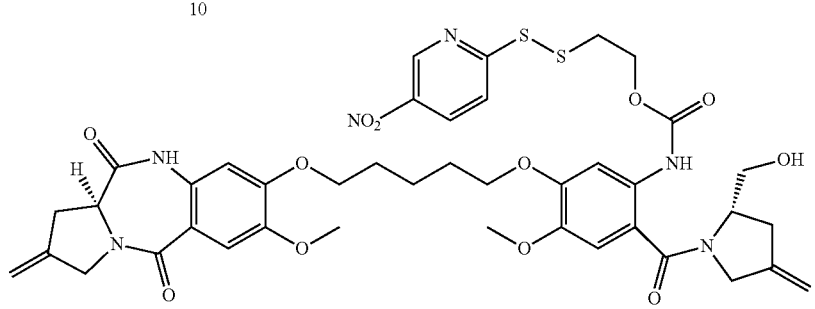

11

To a solution of acetic acid (6.0 mL, 105 mmol) in THF (6.0 mL)/water (3.0 mL) was added compound 10 (130 mg, 0.130 mmol). The reaction solution was stirred at 40° C. for 24 h. The solution was concentrated in vacuo to remove the solvent, the residue was diluted with EtOAc (30 mL), washed with H$_2$O (10 mL×4), dried over Na$_2$SO$_4$, filtered, and concentrated in vacuo. The residue was purified by prep-TLC (8% MeOH in DCM, R$_f$=0.5) to give compound 11 (60 mg, 0.0683 mmol, 52.2% yield) as a yellow oil. LCMS (5-95AB/1.5 min): RT=0.763 min, [M+H]$^+$ 879.0

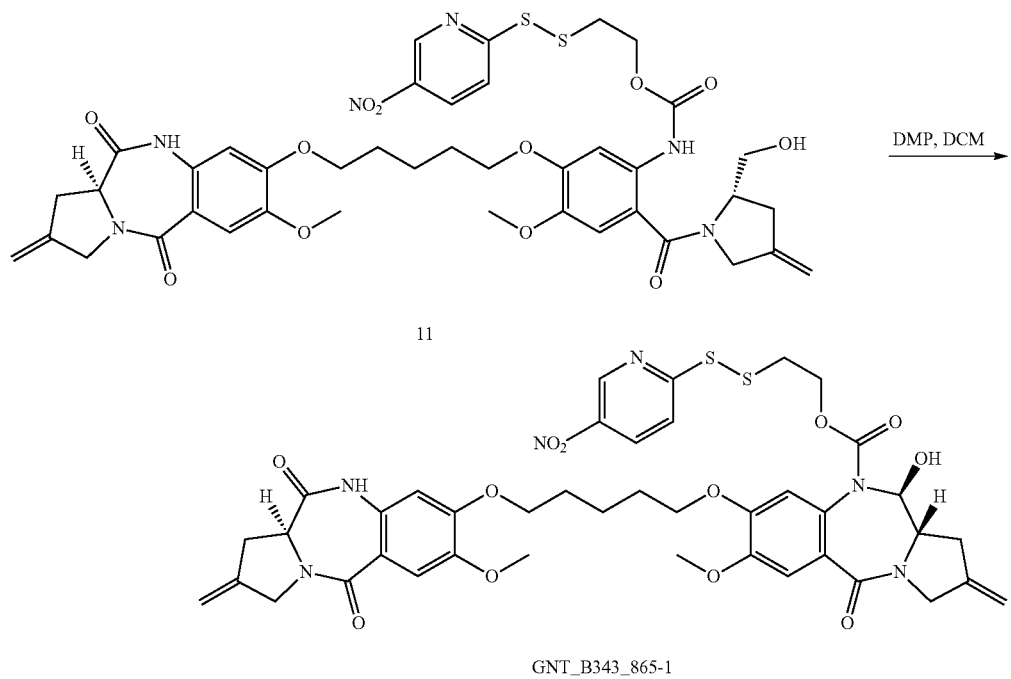

11

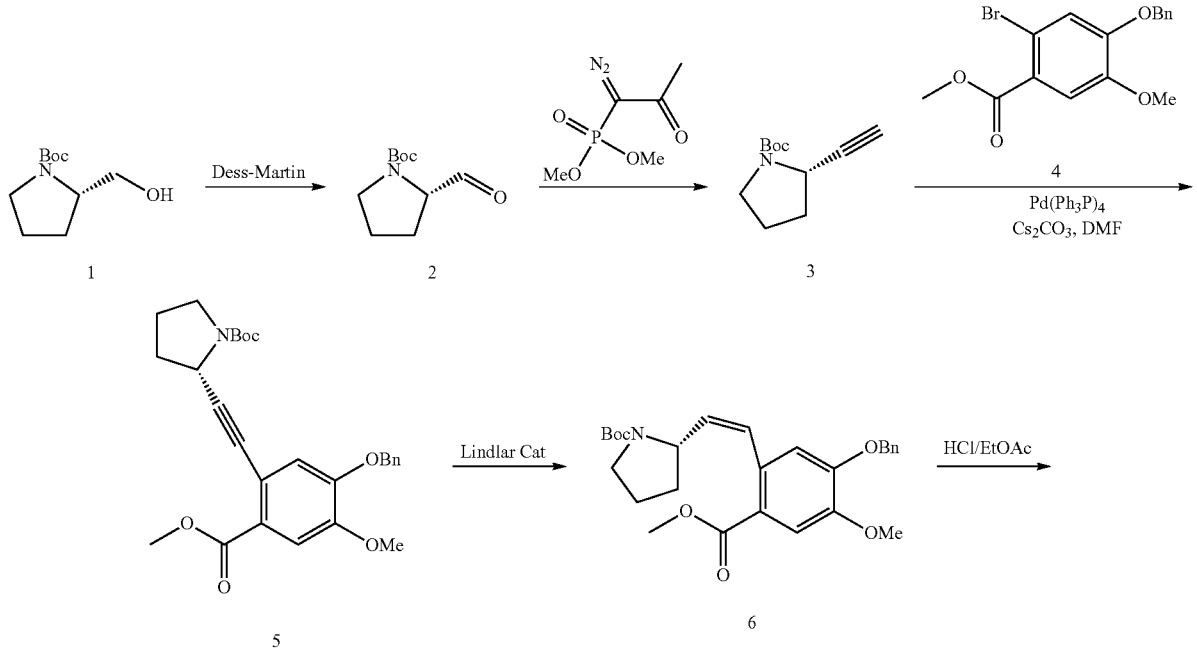

GNT_B343_865-1

To a solution of compound 11 in anhydrous DCM (5 mL) was added DMP (17.4 mg, 0.0400 mmol). The reaction mixture was stirred at 18° C. for 1 h. The mixture was diluted with DCM (50 mL), filtered. The filtrate was washed with Na$_2$SO$_3$ (30 mL×3), dried over Na$_2$SO$_4$, filtered, and concentrated in vacuo. The crude product was purified by prep-TLC (5% MeOH in DCM, Rf=0.5) to give CLD-9 (GNT_B343_865-1) (12.2 mg, 0.0136 mmol, 39.9% yield) as a pale yellow solid. LCMS (5-95AB/1.5 min): RT=0.739 min, [M+H]$^+$ 877.2

Synthesis of DM-4

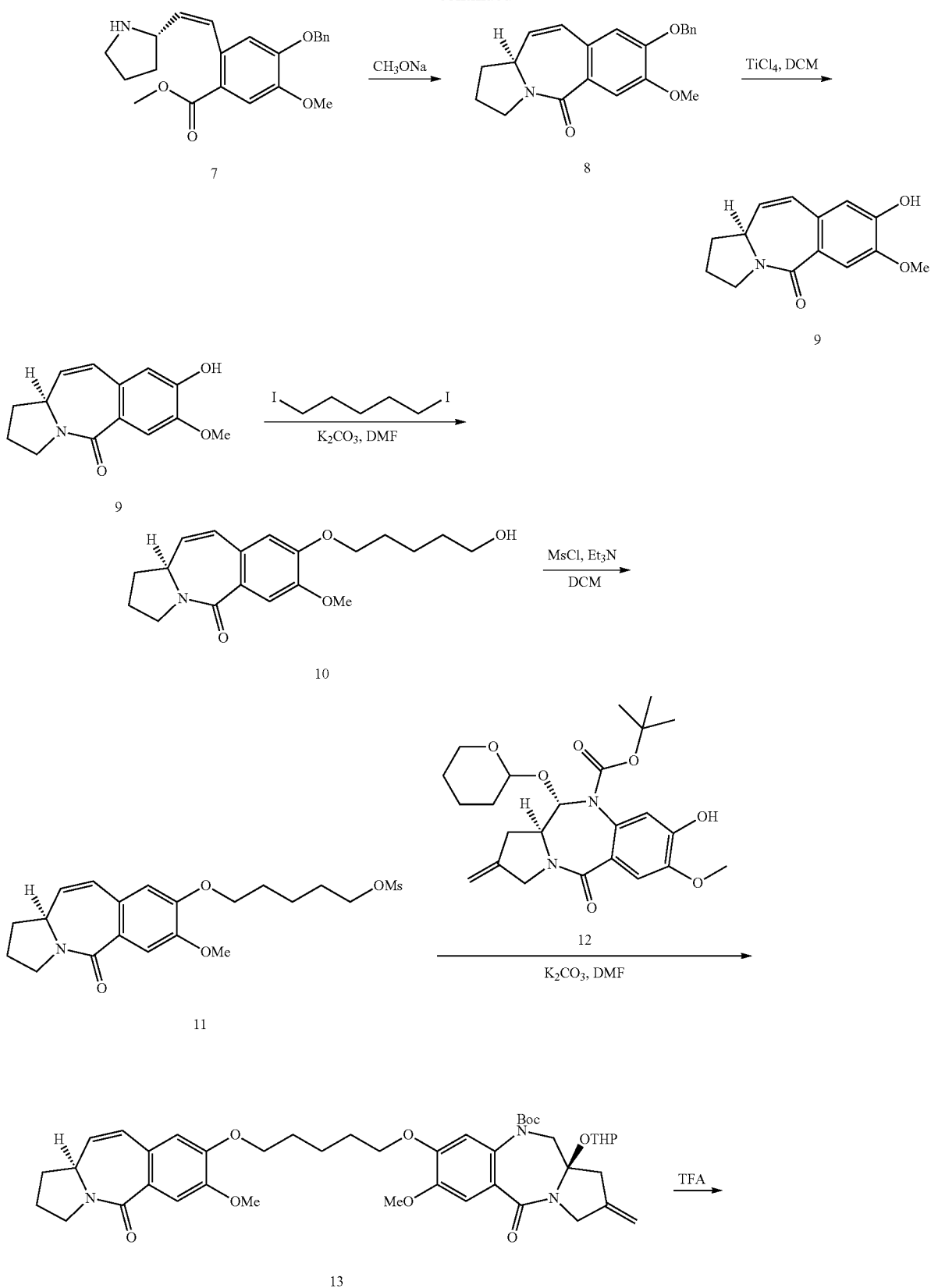

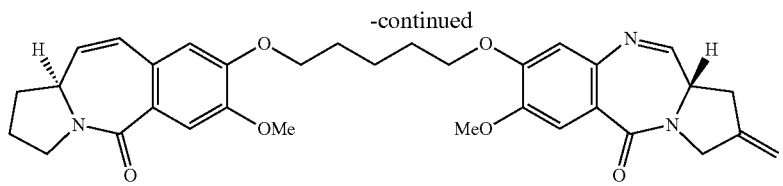

GNT_B343_655-1

Experimental

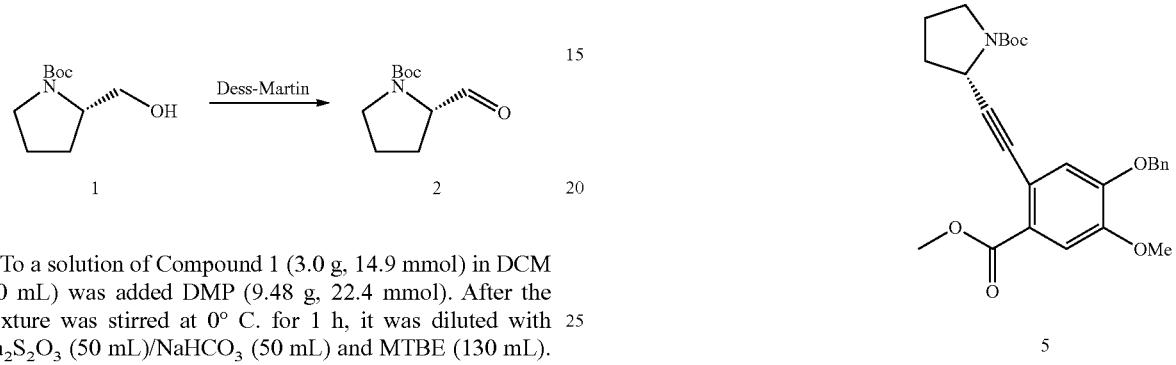

To a solution of Compound 1 (3.0 g, 14.9 mmol) in DCM (80 mL) was added DMP (9.48 g, 22.4 mmol). After the mixture was stirred at 0° C. for 1 h, it was diluted with $Na_2S_2O_3$ (50 mL)/$NaHCO_3$ (50 mL) and MTBE (130 mL). The organic phase was washed with water (60 mL×3) and concentrated to give the Compound 2 (2.9 g, 14.6 mmol, 97.6% yield) as a colorless oil.

To a solution of Compound 2 (2.9 g, 14.6 mmol) and dimethyl (1-diazo-2-oxo-propyl) phosphonate in MeOH (20 mL) was added $K_2CO_3$ (6.03 g, 43.7 mmol). After the reaction mixture was stirred at 20° C. for 1 h, it was concentrated in vacuo, and the residue was purified by flash column chromatography on silica (10% EtOAc in PE) to give the product Compound 3 (2.0 g, 10.24 mmol, 70.4% yield) as a colorless oil.

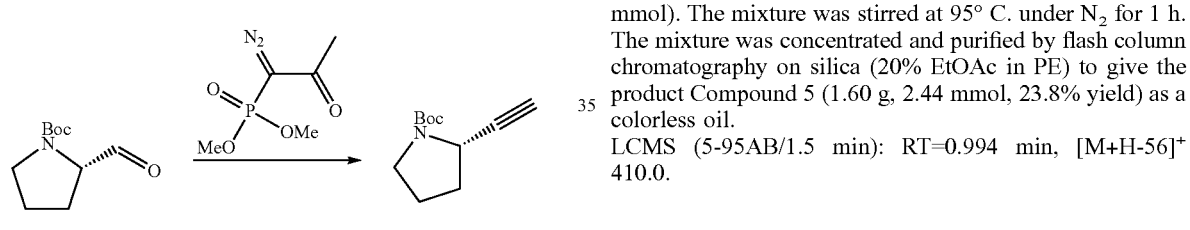

To a solution of Compound 3 (2.0 g, 10.2 mmol) and Compound 4 (5.4 g, 15.4 mmol) in DMF (50 mL) was added $Cs_2CO_3$ (3.97 g, 20.5 mmol) and $Pd(PPh_3)_4$ (785 mg, 1.54 mmol). The mixture was stirred at 95° C. under $N_2$ for 1 h. The mixture was concentrated and purified by flash column chromatography on silica (20% EtOAc in PE) to give the product Compound 5 (1.60 g, 2.44 mmol, 23.8% yield) as a colorless oil.
LCMS (5-95AB/1.5 min): RT=0.994 min, $[M+H-56]^+$ 410.0.

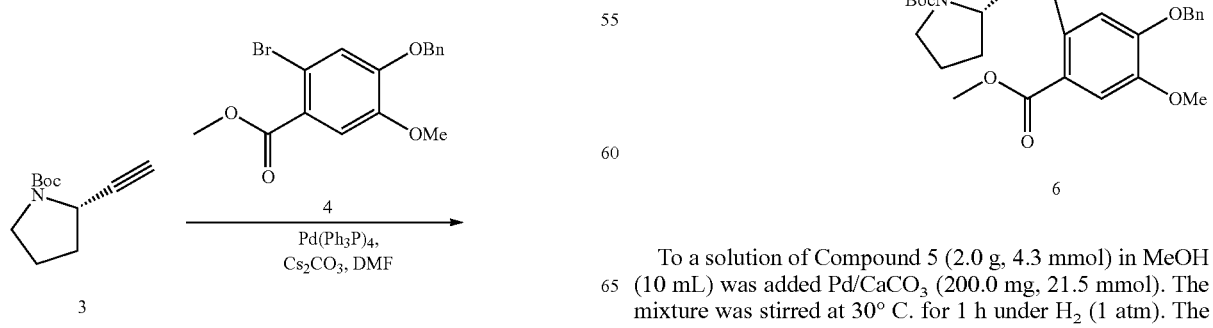

To a solution of Compound 5 (2.0 g, 4.3 mmol) in MeOH (10 mL) was added $Pd/CaCO_3$ (200.0 mg, 21.5 mmol). The mixture was stirred at 30° C. for 1 h under $H_2$ (1 atm). The mixture was filtered and the filtrate was concentrated to give the crude product, which was purified by flash column chromatography on silica (10% EtOAc in PE) to give the product Compound 6 (1.0 g, 2.14 mmol, 49.8% yield) as a white solid. LCMS (5-95AB/1.5 min): RT=0.983 min, [M+Na]⁺490.1.

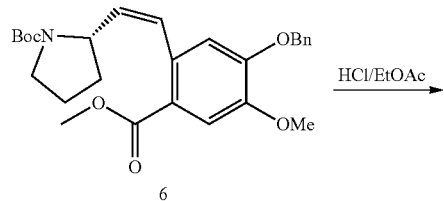

To a solution of Compound 6 (0.90 g, 1.92 mmol) in EtOAc (10 mL) was added HCl/EtOAc (6.0 mL). After the mixture was stirred at 25° C. for 1 h, it was concentrated to give the crude product Compound 7 (0.77 g, 1.90 mmol, 99% yield) as a white solid.

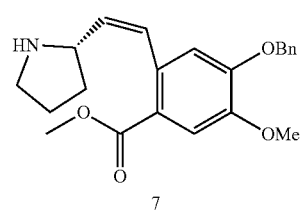

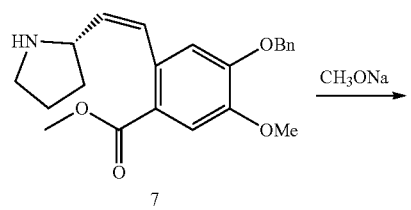

To a solution of Compound 7 (0.77 g, 1.91 mmol) in MeOH (30 mL) was added NaOMe (1.03 g, 19.06 mmol). The mixture was stirred at 30° C. for 2 h. The mixture was concentrated and purified by flash column chromatography on silica (25-75% EtOAc in PE) to give the product Compound 8 (0.60 g, 1.79 mmol, 93.8% yield) as a yellow oil. $^1$H NMR (400 MHz, CDCl$_3$) δ ppm 1.89-2.11 (m, 3 H) 2.18-2.33 (m, 1H) 3.59 (dt, J=12.0, 7.6 Hz, 1 H) 3.80 (dt, J=11.5, 5.8 Hz, 1 H) 3.90-3.96 (m, 1 H) 3.97 (s, 3 H) 5.19 (s, 2 H) 5.86 (dd, J=10.0, 4.8 Hz, 1 H) 6.53 (dd, J=10.0, 2.0 Hz, 1 H) 6.69 (s, 1 H) 7.29-7.35 (m, 1 H) 7.36-7.41 (m, 2 H) 7.42-7.48 (m, 2 H) 7.62 (s, 1 H)

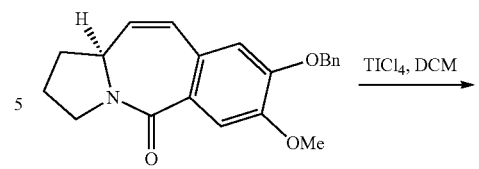

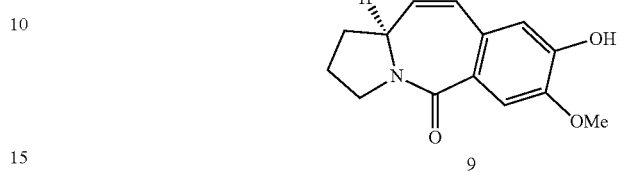

To a solution of Compound 8 (580 mg, 1.73 mmol) in DCM (50 mL) was added TiCl$_4$ (656 mg, 3.46 mmol). The mixture was stirred at 30° C. for 12 h. The mixture was added HCl (1.0 M, 20 mL) and EtOAc (100 mL). The organic layer was washed with water (50 mL×3) and concentrated to give the crude product Compound 9 (250 mg, 0.44 mmol, 25.3% yield) as a yellow solid.

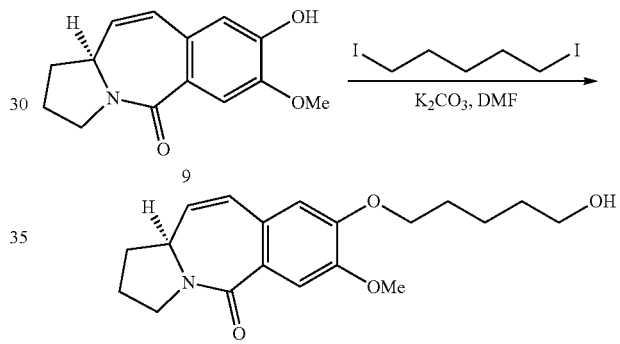

A solution of Compound 9 (50.0 mg, 0.20 mmol) in DMF (5.0 mL) was added K$_2$CO$_3$ (42.26 mg, 0.31 mmol) and 1,5-diiodopentane (333 mg, 1.0 mmol). The reaction mixture was stirred at 90° C. for 3 h. The reaction mixture was purified by silica column chromatography (0-50% EtOAC in petroleum ether) to give Compound 10 (60 mg, 0.178 mmol, 87.6% yield) as an oil. LCMS (5-95AB/1.5 min): RT=0.765 min, [M+H]⁺332.0

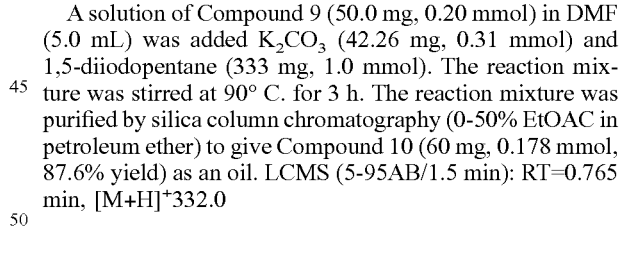

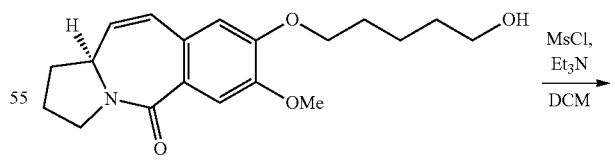

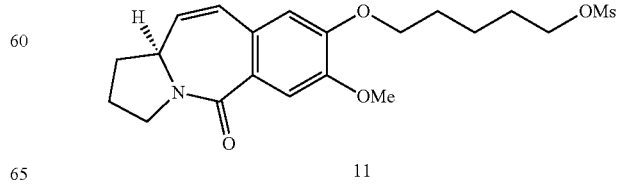

To a solution of Compound 10 (60.0 mg, 0.18 mmol) in DCM (6.0 mL) was added triethylamine (55 mg, 0.54 mmol) and MsCl (41 mg, 0.36 mmol). After the mixture was stirred at 35° C. for 1 h, it was diluted with EtOAc (80 mL) and washed with water (50 mL×3). The organic layer was concentrated to give the crude product (70 mg) as a colorless oil. LCMS (5-95AB/1.5 min): RT=0.679 min, [M+H]⁺410.0

A solution of Compound 13 (50 mg, 0.060 mmol) in a mixture of TFA (1.9 mL) and water (0.10 mL) was stirred at 35° C. for 1 h. The mixture was partitioned between sat-.NaHCO₃ (30 mL) and EtOAc (50 mL). The organic layer was washed with water (30 mL×2), brine (30 mL) and dried over Na₂SO₄. It was concentrated and purified by prep-TLC (5% MeOH in DCM, Rf=0.5) to give the product DM-4

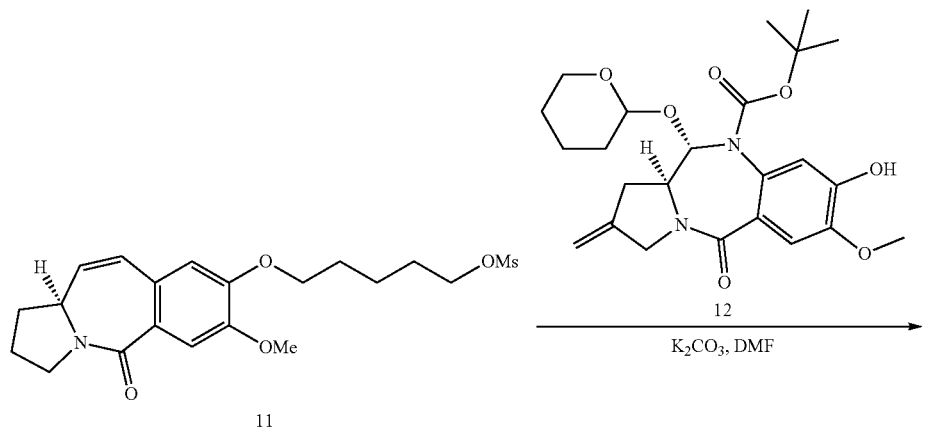

To a solution of Compound 11 (70 mg, 0.17 mmol) and Compound 12 (87 mg, 0.19 mmol) in DMF (5.0 mL) was added K₂CO₃ (47 mg, 0.34 mmol) and KI (5.68 mg, 0.030 mmol). The mixture was stirred at 90° C. for 3 h, and purified by prep-HPLC (HCOOH) to give the product Compound 13 (70 mg, 0.084 mmol, 49.2% yield) as a white solid. LCMS (5-95AB/1.5 min): RT=0.845 min, [M+H]⁺774.4.

(GNT_B343_655-1) (20 mg, 0.034 mmol, 53.1% yield) as a white solid. LCMS (5-95AB/1.5 min): RT=0.825 min, [M+H]⁺572.1. ¹H NMR (400 MHz, CDCl₃) δppm 1.65-1.75 (m, 3H) 1.88-2.10 (m, 8H) 2.19-2.31 (m, 1H) 2.82-3.29 (m, 2H) 3.60 (dt, J=11.9, 7.5 Hz, 1H) 3.81 (dt, J=11.6, 5.9 Hz, 1H) 3.86-3.91 (m, 1H) 3.94 (s, 6H) 3.97 (br. s., 1H) 4.01-4.18 (m, 4H) 4.30 (s, 2H) 5.19 (d, J=10.6 Hz, 2H) 5.89 (dd, J=9.9, 5.1 Hz, 1H) 6.53-6.63 (m, 1H) 6.66 (s, 1H) 6.81 (s, 1H) 7.51 (s, 1H) 7.59 (s, 1H) 7.68 (d, J=4.4 Hz, 1H)

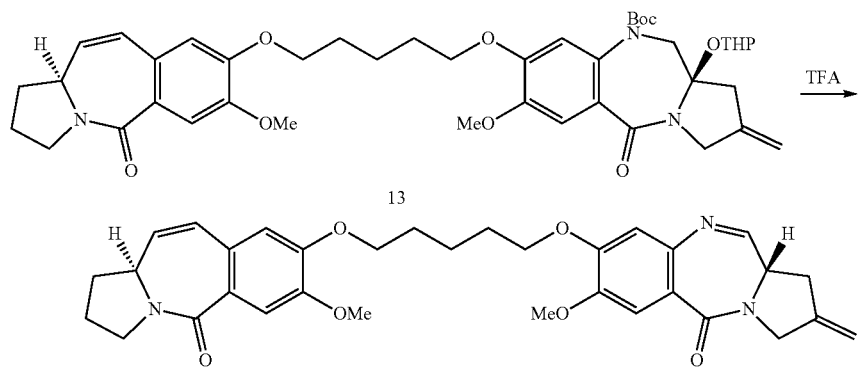

Synthesis of CLD-3
Scheme
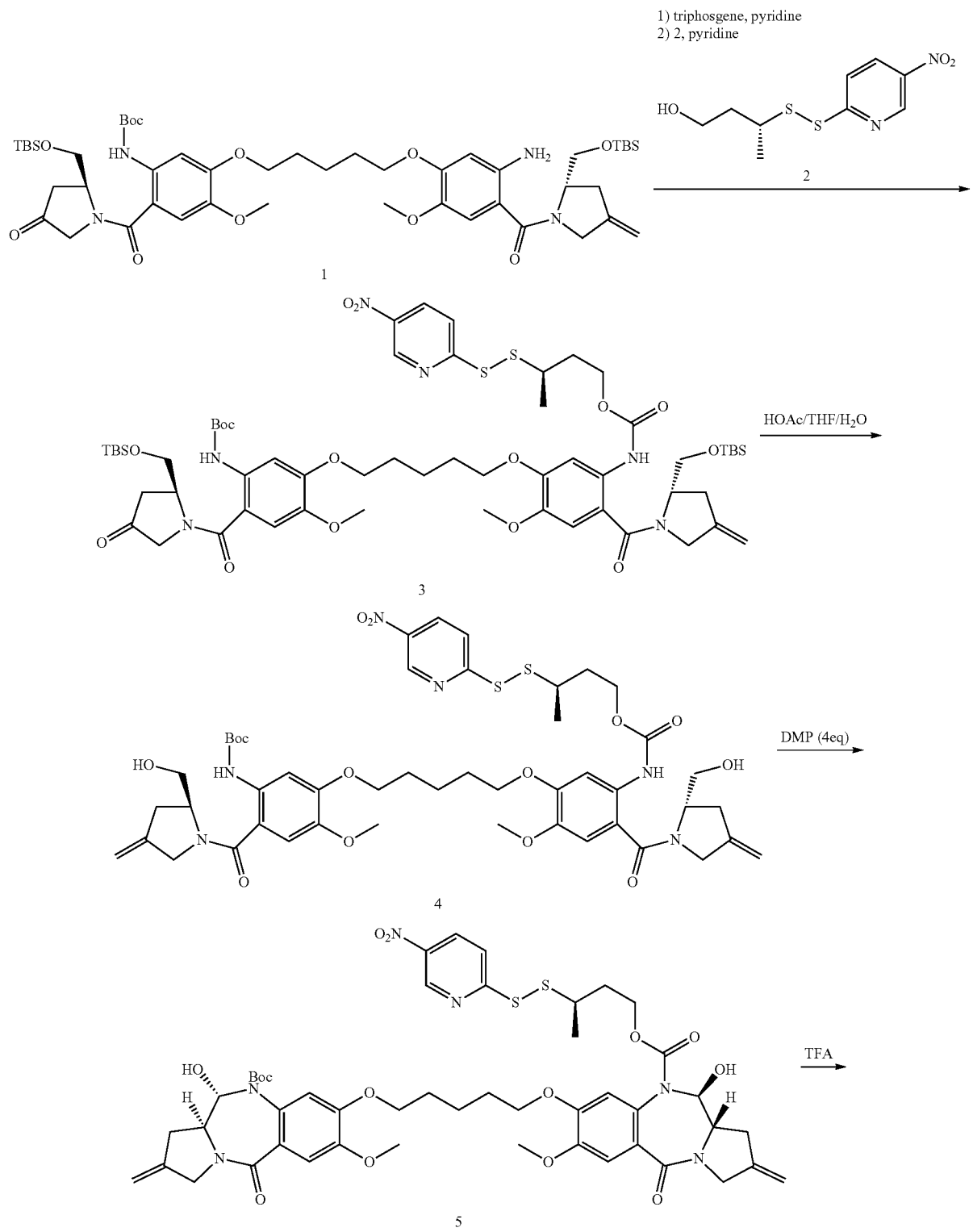

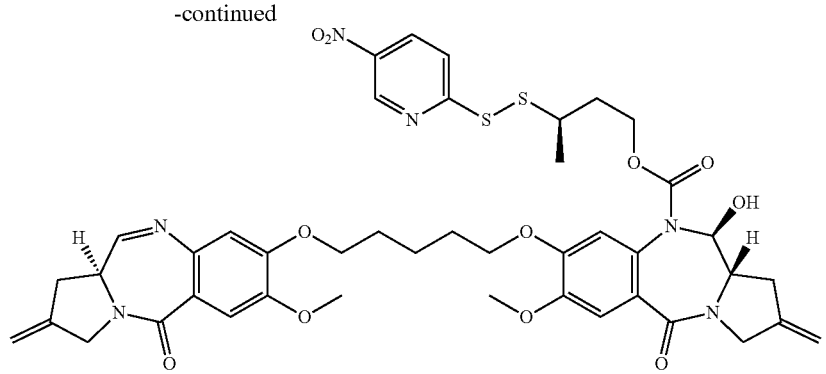

GNT_B343_427

Synthesis of INT02:

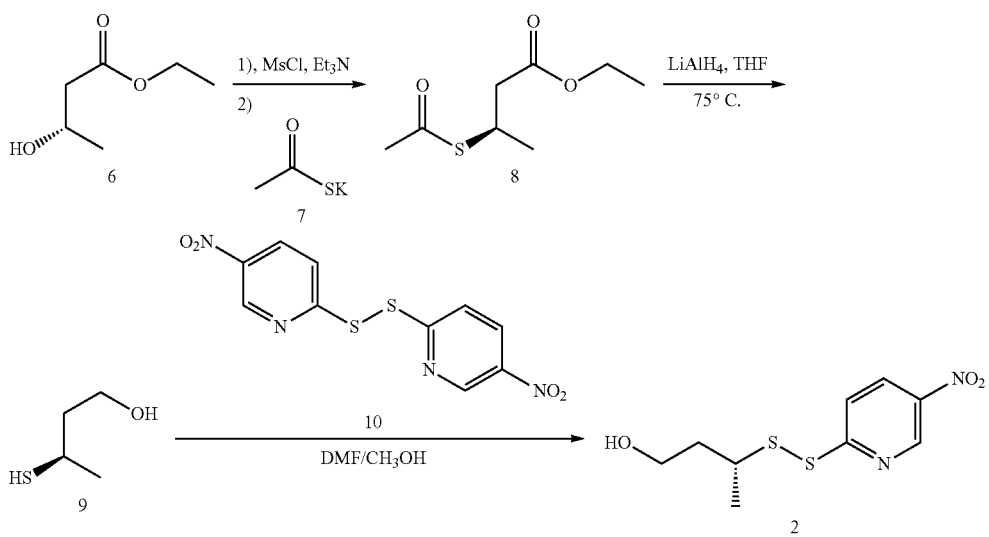

Experimental

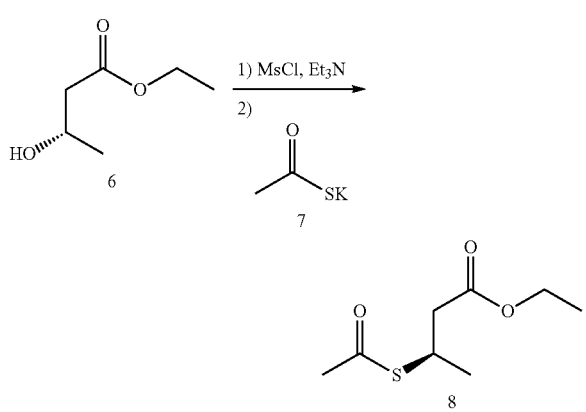

To a solution of compound 6 (5.00 g, 37.83 mmol) and Et₃N (11.49 g, 113.50 mmol) in DCM (100 mL) was added MsCl (8.97 g, 78.32 mmol) dropwise at 0° C. After it was stirred at 25° C. for 2 h under N₂, the reaction mixture was poured into ice water (200 mL), and extracted with DCM (100 mL×2). The organic phase was washed with brine, dried over Na₂SO₄ and concentrated in vacuo to give the crude product (7.0 g, 95%) as a yellow oil. It was mixed with KSAc (6.59 g, 57.66 mmol) in acetone/water (50 mL/50 mL) and was stirred at 25° C. for 10 h. The reaction mixture was concentrated and purified by flash column chromatography on silica (PE/EtOAc=100/1~40/1) to give pure compound 8 (1.0 g, 14.6%) as a yellow oil.

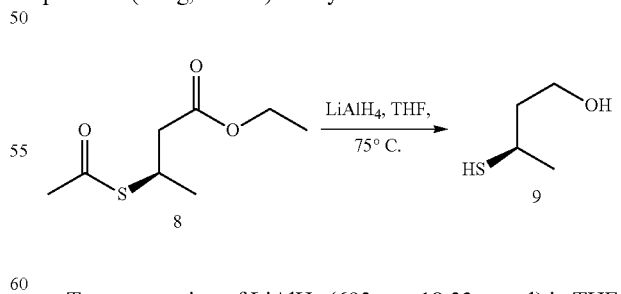

To a suspension of LiAlH₄ (692 mg, 18.23 mmol) in THF (20 mL) was added a solution of compound 8 (867 mg, 4.56 mmol) in THF (5 mL) at 0° C. under N₂. The reaction mixture was stirred at 75° C. under reflux for 2 h. The reaction mixture was quenched by EtOAc (3.0 mL) and HCl solution (2.0 M, 5 mL) at 0° C. The reaction mixture was used in the next step directly.

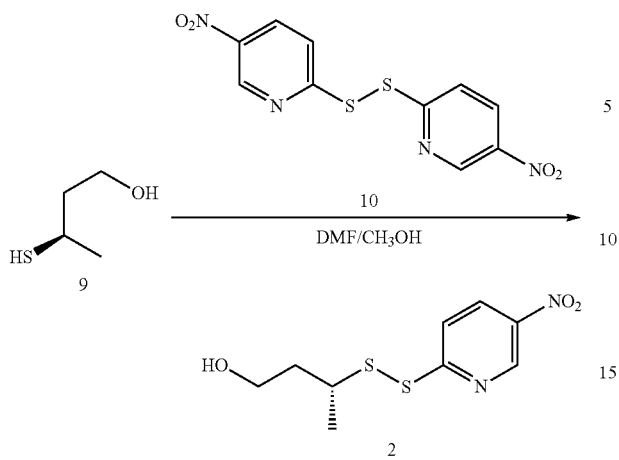

To a solution of compound 10 (2.84 g, 9.12 mmol) in DCM/MeOH (25 mL/25 mL) was added a solution of compound 9 (from above step) at 25° C. The mixture was stirred at 25° C. for 10 h. The reaction mixture was added $MnO_2$ (3.4 g, 39.6 mmol) and filtered. The filtrate was concentrated in vacuo and purified by flash column chromatography on silica (DCM) and SFC to give the compound 2 (0.80 g, 67.4%) as a yellow oil. LCMS (5-95 AB, 1.5 min): RT=1.020 min, M+H$^+$=260.9.

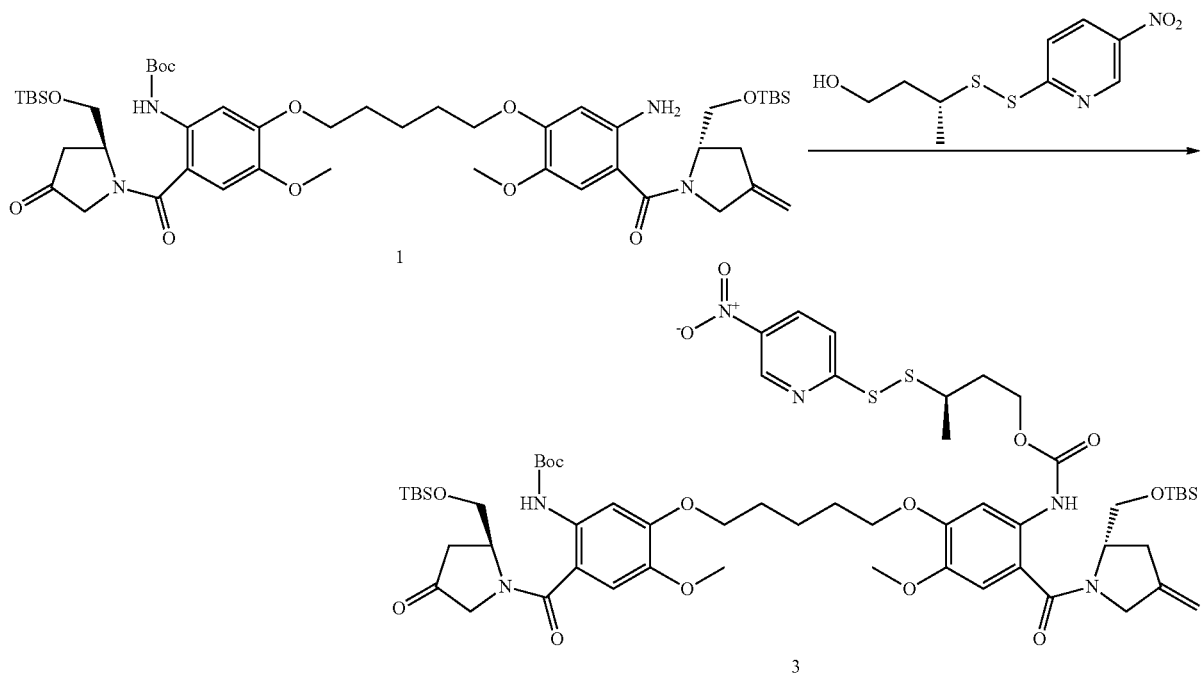

To a solution of triphosgene (46 mg, 0.16 mmol) in DCM (3.0 mL) was added a solution of compound 2 (100 mg, 0.38 mmol) and pyridine (30 mg, 0.38 mmol) in DCM (3 mL) dropwise at 0° C. The reaction mixture was stirred at 0° C. for 15 min, and was added to a solution of compound 1 (280 mg, 0.29 mmol) and pyridine (30 mg, 0.38 mmol) in DCM (4.0 mL) dropwise at 26° C. The reaction mixture was stirred at 26° C. for 2 h. The solvent was removed and the residue was purified by prep-TLC (solvent: 30% EtOAc in petroleum ether) to give compound 3 (300 mg, 82.4%) as a yellow foam. LCMS (5-95AB/1.5 min): RT=1.248 min, [M+H]$^+$1239.5

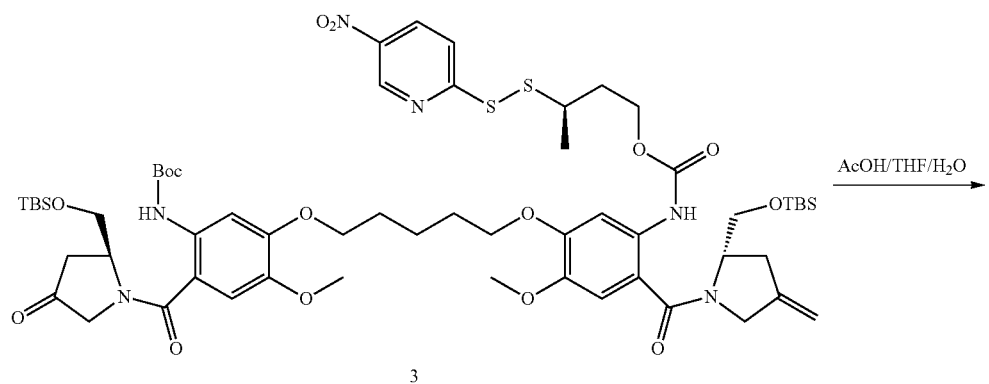
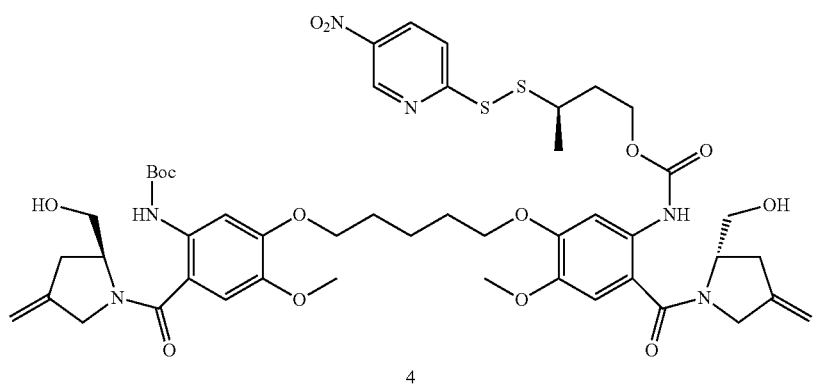
To a solution of compound 3 (312 mg, 0.24 mmol) in THF/H₂O (4 mL/4 mL) was added HOAc (6.0 mL) at 26° C. After the reaction mixture was stirred at 26° C. for 24 h, it was diluted with EtOAc (20 mL) and washed with water (2×10 mL), sat. aq. NaHCO₃ (15 mL) and brine (15 mL). It was dried, concentrated and purified by flash column chromatography on silica (0-5% MeOH in DCM) to afford compound 4 (240 mg, 97.1%) as a yellow foam. LCMS (5-95AB/1.5 min): RT=0.876 min, [M+H]+1011.3.
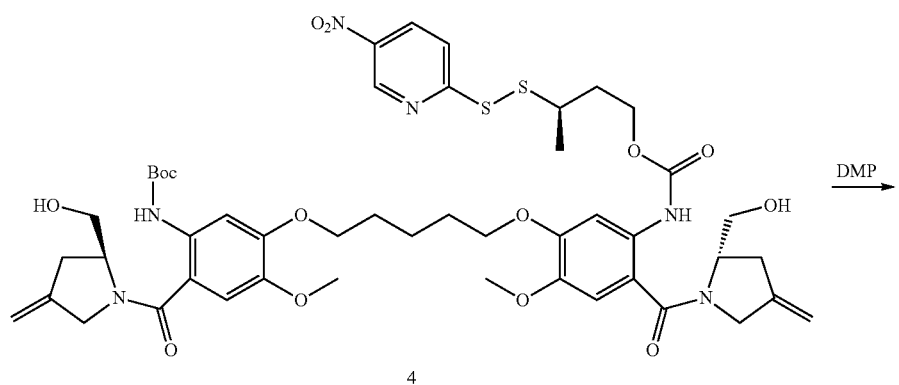

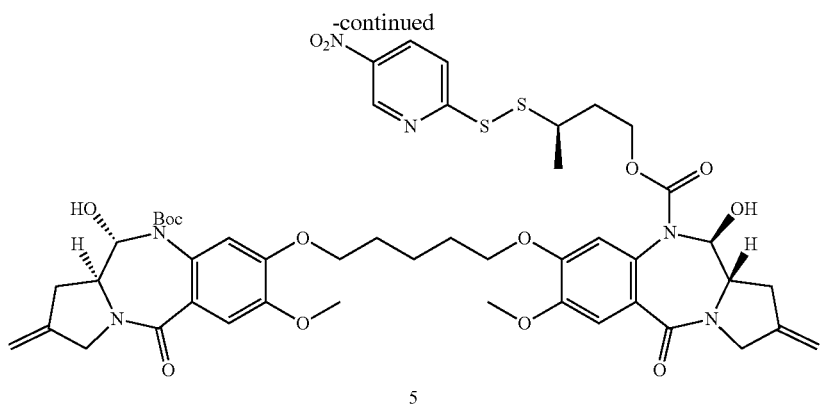

5

To a solution of compound 4 (101 mg, 0.10 mmol) in DCM (5.0 mL) was added DMP (125 mg, 0.29 mmol) at 0° C. The reaction mixture was stirred at 26° C. for 2 h. The reaction was quenched with a sat. solution of $NaHCO_3$/$Na_2SO_3$ (2.0 mL/2.0 mL) and extracted with DCM (3×5 mL). The combined organic layer was washed with $NaHCO_3$/$Na_2SO_3$ (2 mL/2 mL), brine (5 mL), dried and concentrated. The residue was purified by prep-TLC (DCM/MeOH=15:1) to give compound 5 (66 mg, 66.2%) as a yellow foam. LCMS (5-95AB/1.5 min): RT=0.815 min, [(M-100)/2+Na]+476.1 it was extracted with DCM (4×8.0 mL). The combined organic layer was washed with brine (20 mL), dried and concentrated to give the crude product which was purified by prep-TLC (6.25% MeOH in DCM, Rf=0.5) to give CLD-3 (GNT_B343_427-1) (27.4 mg, 47.4%) as a yellow foam. $^1$H NMR (400 MHz, $CDCl_3$) δ 9.21 (s, 1H), 8.38-8.35 (m, 1H), 7.79 (d, J=8.8 Hz, 1H), 7.69 (d, J=4.4 Hz, 1H), 7.47 (s, 1H), 7.17 (s, 1H), 6.80 (s, 1H), 6.50 (s, 1H), 5.57 (d, J=9.2 Hz, 1H), 5.20-5.13 (m, 4H), 4.29-4.25 (m, 5H), 4.14-4.09 (m. 4H), 3.96-3.87 (m, 8H), 3.38 (d, J=8.0 Hz, 1H), 3.58 (d,

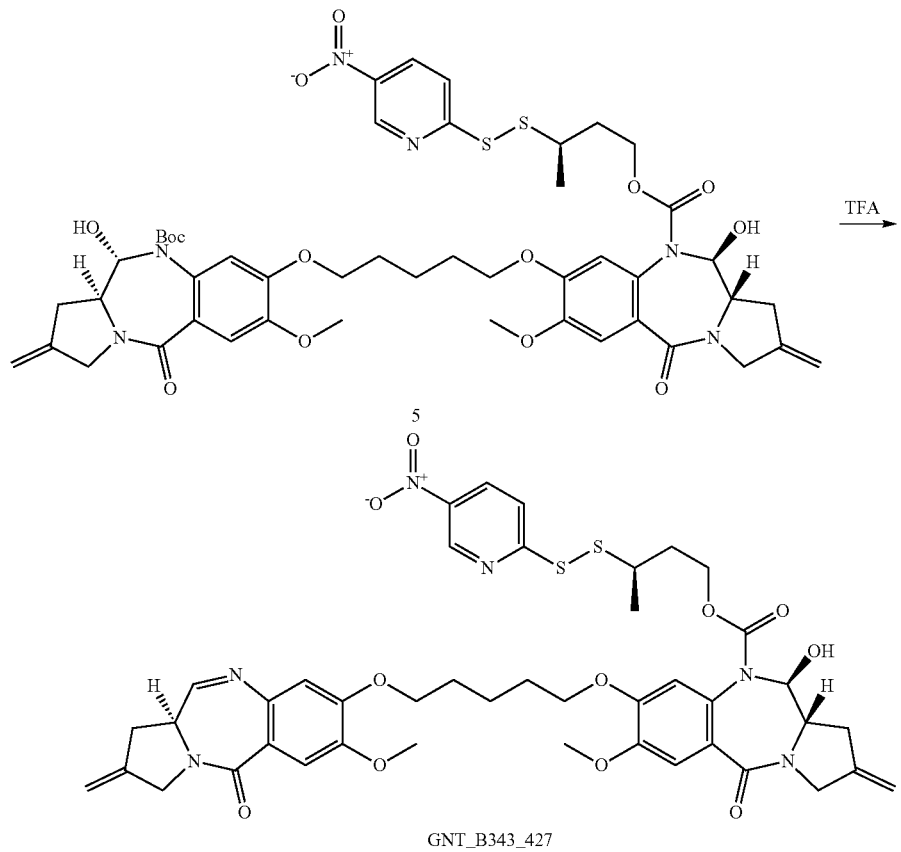

Cold TFA (95% in water, 2.0 mL) was added to compound 5 (66 mg, 0.06 mmol) at 0° C. The reaction mixture was stirred at 0° C. for 30 min. The reaction mixture was added dropwise to a cold sat. aq. $NaHCO_3$ (4.0 mL) at 0° C. and J=8.0 Hz, 2H), 3.44 (s, 1H), 3.16-3.09 (m, 1H), 2.97-2.89 (m, 3H), 2.71-2.67 (m, 1H), 1.95-1.91 (m, 6H), 1.45-1.22 (m, 3H). LCMS (5-95AB/1.5 min): RT=0.750 min, [M+H]+ 889.8.

Synthesis of CLD-5
(R)-2-((4-nitrophenyl)disulfanyl)propyl (11S,11aS)-11-hydroxy-7,8-dimethoxy-5-oxo-2-(quinolin-6-yl)-11,11a-dihydro-1H-benzo[e]pyrrolo[1,2-a][1,4]diazepine-10(5H)-carboxylate
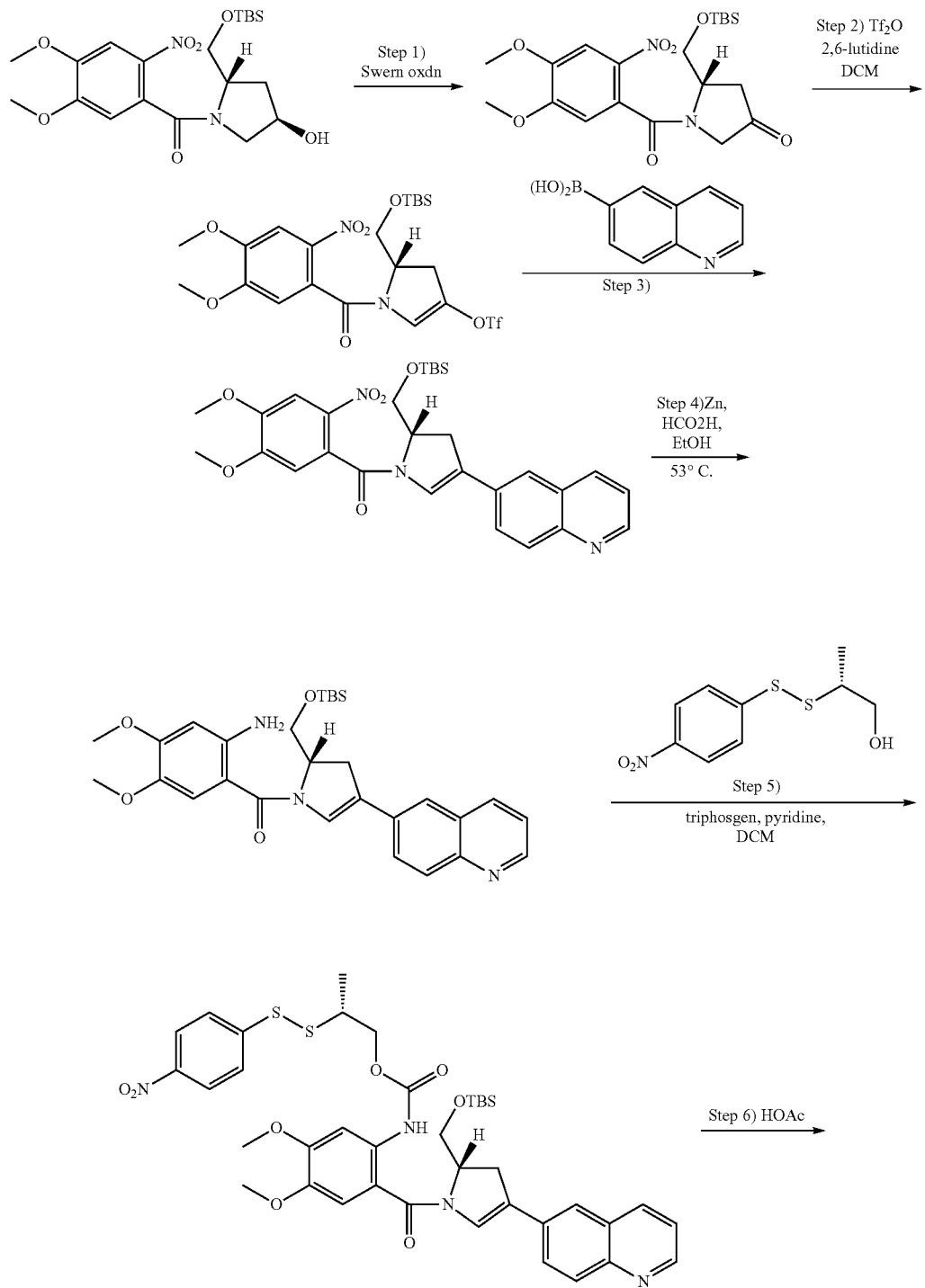

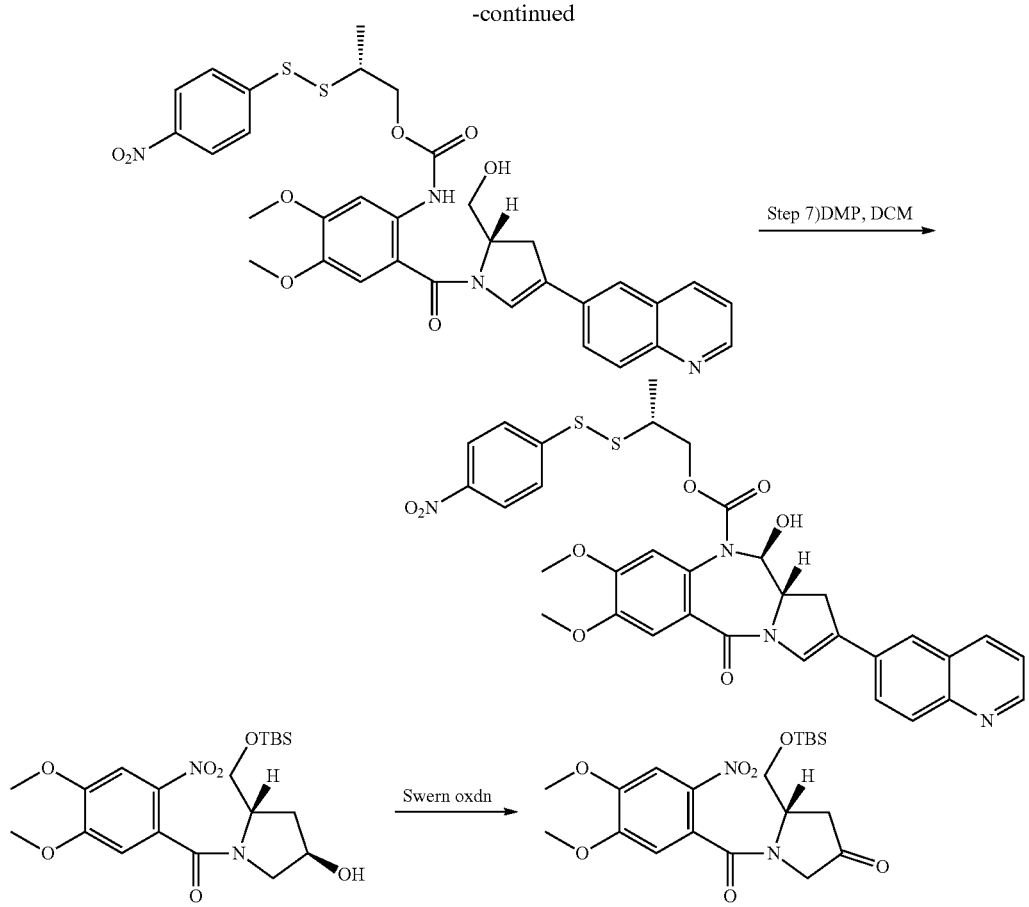

2M oxalyl chloride solution (39 mL, 77.14 mmol) and 60 mL of dichloromethane were mixed in a 500-mL flask, cooled to −78° C. DMSO (5.77 mL, 77.14 mmol) was added via syringe over ~2-3 min. The mixture was stirred for 20 min at −78° C., then (5S)-5-[[tert-butyl(dimethyl)silyl]oxymethyl]-1-(4,5-dimethoxy-2-nitro-benzoyl)pyrrolidin-3-one starting material (11.33 g dissolved in 30 mL of dichloromethane plus 10 mL rinsing, synthesized according to Journal of Medicinal Chemistry, 2010, 53, 2927-2941 and Bioorganic & Medicinal Chemistry Letters, 2000, 10, 1845-1847) via a syringe over. After 30 min at −78° C., Et3N (22.6 mL, 154.3 mmol) was added via syringe over 2 min. After ~4 min, the mixture was warmed to 0° C. and stirred for 1 h. The mixture was poured into 100 mL of water. The dichloromethane was separated. The aqueous layer was extracted with EtOAc (2×75 mL). The combined org extracts were washed with 1N HCl, then sat. sodium bicarbonate, dried over Na2SO4 and concentrated. The residue was purified by silica gel column chromatography (70%-90% EtOAc/Heptane) to give the desired product as a slightly yellow foam (10.12 g).

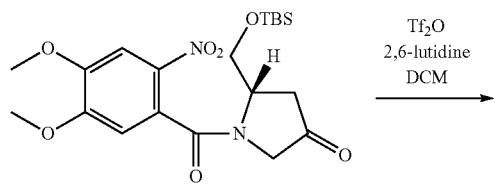

(5S)-5-[[tert-butyl(dimethyl)silyl]oxymethyl]-1-(4,5-dimethoxy-2-nitro-benzoyl)pyrrolidin-3-one (1.20 g, 2.74 mmol), 2,6-lutidine (1.27 mL, 10.9 mmol) were mixed in dichloromethane (45 mL) and then cooled to −35° C. Then triflic anhydride (0.87 mL dissolved in ~5.2 mL of DCM) was added slowly via a syringe—the mixture turned bright yellow and the bath temp increased to −33° C. The reaction temp was kept not to not exceed −20° C. throughout. After total ~1 hr, the reaction mixture was pipetted into a mixture of aq. Saturated NaHCO3 solution, ice and EtOAc, then extracted twice with ethyl acetate (total ~400 mL). The combined organic was washed with 1N aq. HCl, then brine, and then dried over sodium sulfate, concentrated. The residue was purified by silica gel column chromatography (40%-100% EtOAc/Heptane) to give the desired product as a yellow solid (957 mg).

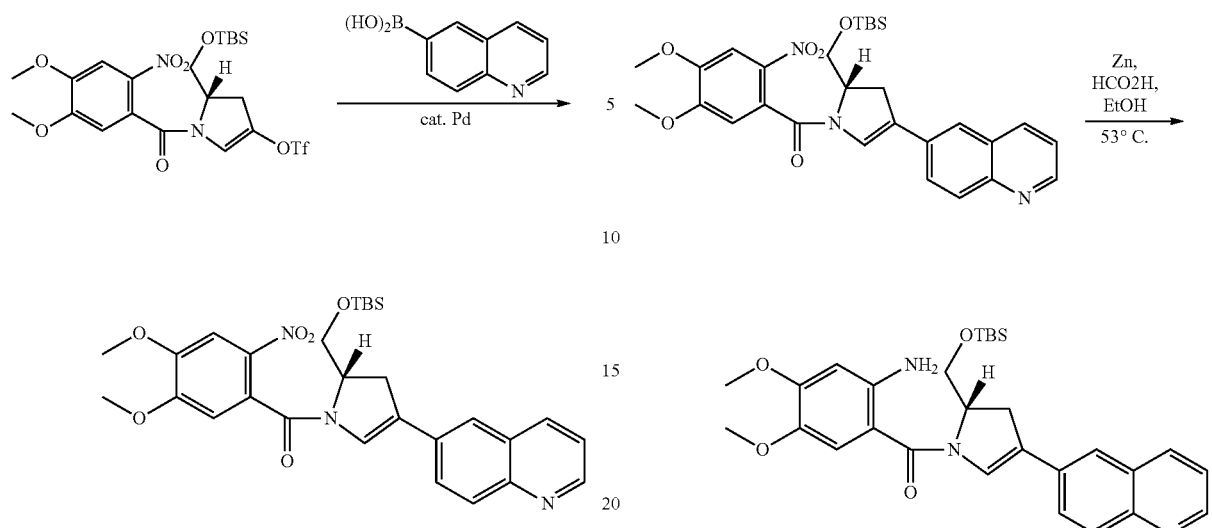

To the vinyl triflate (957 mg, 1.68 mmol) in a 250 mL flask, ethanol (8.75 mL,) and water (2.5 mL,), 6-quinolyl-boronic acid (348 mg 2.01 mmol,), potassium phosphate (1.10 g, 5.03 mmol) and then [1,1'-bis(diphenylphosphino)ferrocene]dichloropalladium(ii) (982 mg, 0.134 mmol) were added. The mixture was flushed with nitrogen and then stirred at room temperature under nitrogen. After the reaction was done (~10 min), EtOAc (50 mL) was added to the reaction mixture. The mixture was filtered to remove any solid. Water (~5 mL) was added to the filtrate. The filtrate was extracted with EtOAc (2×). The combined organics were dried with sodium sulfate and concentrated. The residue was purified by silica gel column chromatography (40%-100% EtOAc/Heptane) to give the desired product as a yellow solid (928 mg).

The nitro starting material (322 mg, 0.586 mmol) was dissolved in 6 mL of ethanol, and then zinc dust (383 mg. 5.86 mmol) was added followed by 1.5 ml of 5% formic acid in water (75 uL of formic acid in 1.5 mL of water). The mixture was then heated to 53° C. and stirred until reaction was complete (~3.5 hrs). The mixture was cooled to room temperature, filtered. The filtrate was diluted with EtOAc (~10 mL) and then 3 M ammonia (~3 mL) was added. The mixture was extracted with EtOAc (3×). The combined organics were dried with sodium sulfate and concentrated to provide the crude aniline, which was used in the next step without purification.

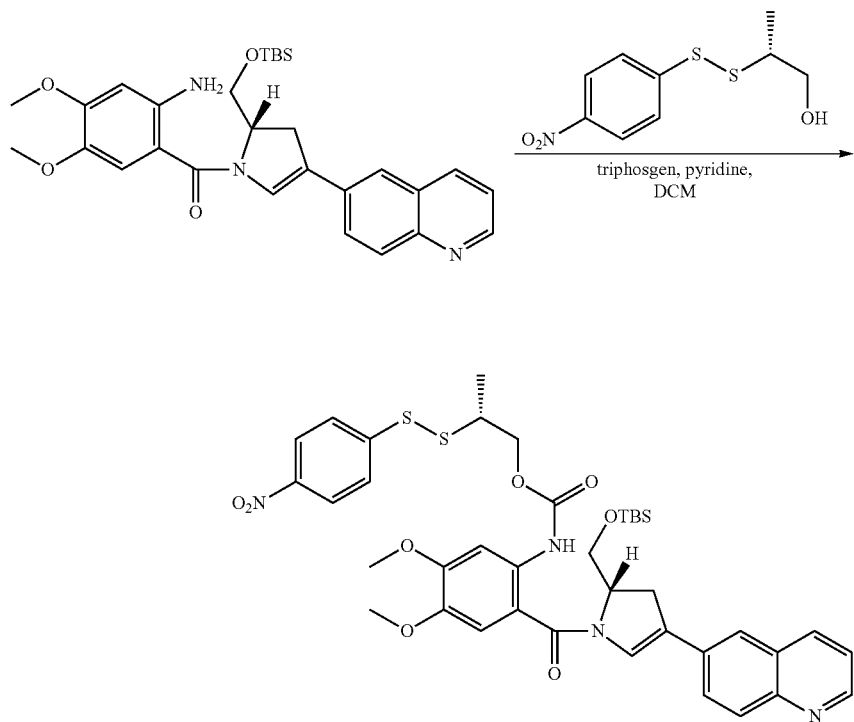

Triphosgen (79.4 mg, 0.268 mmol) was dissolved in 1.5 mL of dichloromethane, then a solution of (2R)-2-[(5-nitro-2-pyridyl)disulfanyl]propan-1-ol (196 mg, 0.797 mmol) and pyridine (0.092 mL) in 2 mL of dicholormethane was added. After 30 min, the above solution was added to a solution of the aniline starting material and pyridine (0.092 mL) in 4.5 mL of dichloromethane. After the reaction was complete (~1 hr), The mixture was diluted with EtOAc, then washed with 1 M HCL solution and then saturated sodium carbonate solution. The organics were dried with sodium sulfate and concentrated. The residue was purified by silica gel column chromatography (30%-70% EtOAc/Heptane) to give the desired carbamate (182 mg).

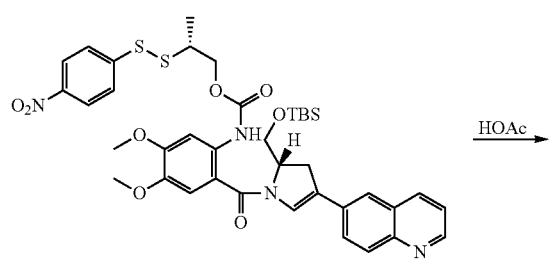

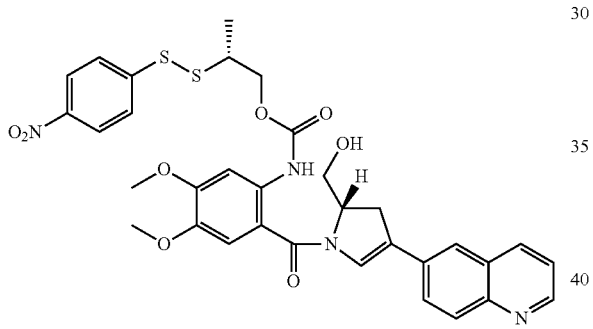

The TBS-protected alcohol (182 mg, 0.230 mmol) was dissolved in 4 mL:1 mL of THF:water, and then 4 mL of acetic acid was added. The mixture was heated to 55° C. After the reaction was done (~two overnights), the mixture was cooled to room temperature and then diluted with 50 mL of ethyl acetate. Potassium carbonate was added to neutralize acetic acid until pH reached ~10. The mixture was extracted with ethyl acetate twice. The combined organics was dried with sodium sulfate and concentrated. The residue was purified by silica gel column chromatography (0%-10% MeOH/EtOAc) to give the desired alcohol (125 mg).

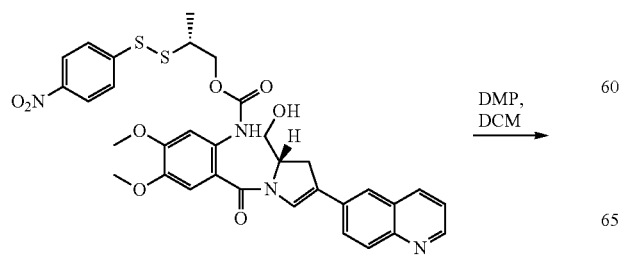

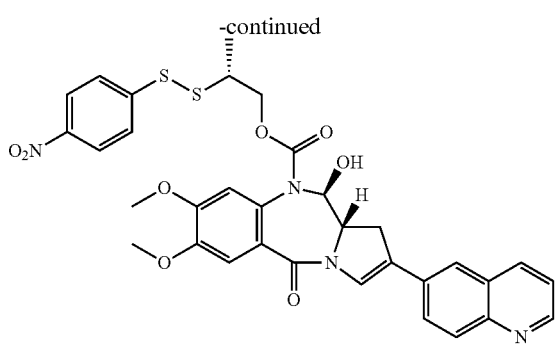

The alcohol starting material (116 mg, 0.171 mmol) was dissolved in 6 mL of dichloromethane and then Dess-Martin periodinane (89.8 mg, 0.205 mmol) was added at room temperature. After ~2.5 hrs, saturated sodium bicarbonate solution (~6 mL) and 1M sodium thiosulfate solution (~4 mL) were added. The mixture was extracted with dichloromethane once and with chloroform twice. The combined organics (~75 mL) was dried over sodium sulfate, concentrated to give ~103 mg of crude product, which was purified by reverse-phase HPLC to give the desired product (29.5 mg).

$^1$H NMR (400 MHz, DMSO-$d_6$) δ 9.24 (s, 1H), 8.83 (dd, J=1.6, 4.2 Hz, 1H), 8.47 (dd, J=2.6, 8.9 Hz, 1H), 8.32 (d, J=8.0 Hz, 1H), 8.12 (dd, J=1.9, 8.9 Hz, 1H), 7.92 (d, J=8.8 Hz, 1H), 7.87 (d, J=1.8 Hz, 1H), 7.80 (s, 1H), 7.75 (d, J=8.5 Hz, 1H), 7.51 (dd, J=4.2, 8.3 Hz, 1H), 7.20 (s, 1H), 7.07 (s, 1H), 6.95 (d, J=6.3 Hz, 1H), 5.78-5.62 (m, 1H), 4.30 (d, J=6.8 Hz, 1H), 4.00 (td, J=3.2, 10.0 Hz, 1H), 3.85 (s, 6H), 3.56-3.44 (m, 1H), 3.08 (d, J=14.6 Hz, 1H), 1.14 (d, J=6.3 Hz, 3H), 0.07 (s, 12H). MS m/z=676 [M+1]$^+$;

Synthesis of CLD-6

2-((4-nitrophenyl)disulfanyl)ethyl (11S,11aS)-11-hydroxy-7,8-dimethoxy-5-oxo-2-(quinolin-6-yl)-11,11a-dihydro-1H-benzo[e]pyrrolo[1,2-a][1,4]diazepine-10(5H)-carboxylate

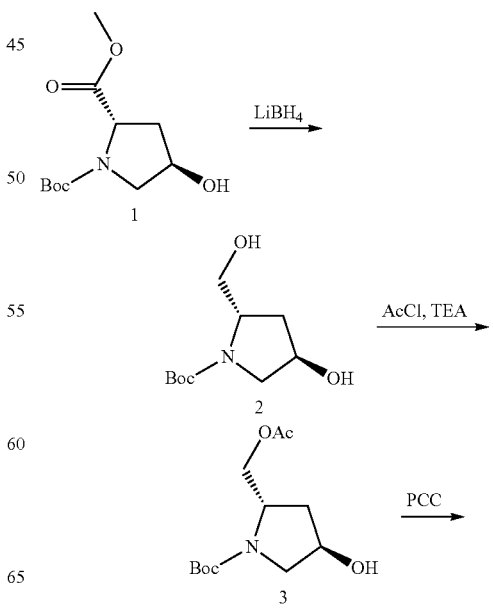

-continued

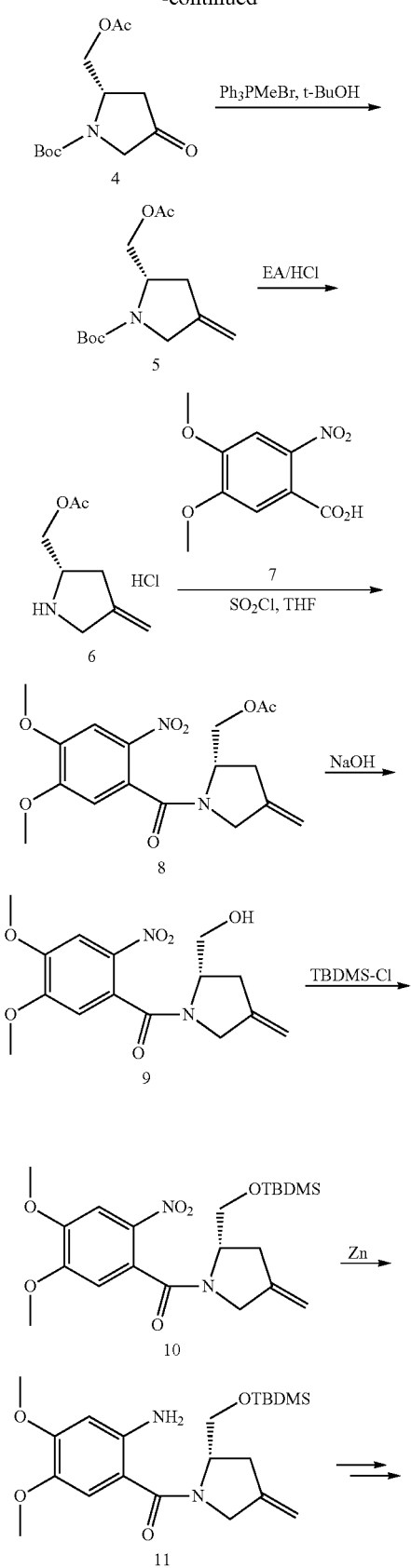

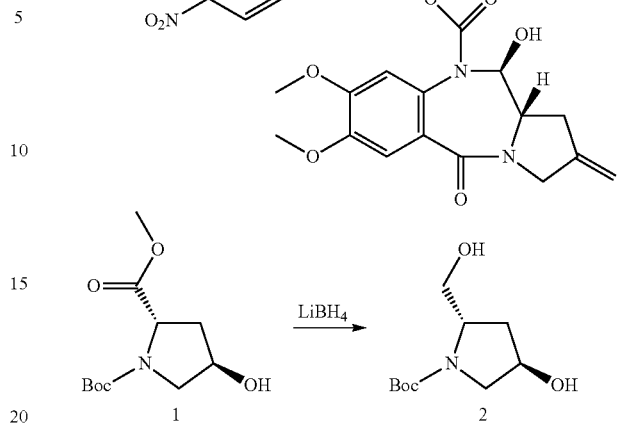

To a solution of compound 1 (1.13 kg, 4.59 mol, 1.00 Eq) in THF (10 L) at 0° C. was added LiBH₄ (99.90 g, 4.59 mol, 1.00 Eq) in two portions (almost no temperature charge during the adding of LiBH₄). The suspension was stirred at 0° C. for 1 h then at 10-20° C. for 18 h. The mixture was cooled to 0° C. and aq NH₄Cl (5 L) were added. The layers were separated and the aqueous layer was extracted with EA (5 L×3). The combined organics were washed with brine. The organic layers were dried over Na₂SO₄, filtered and concentrated to afford compound 2 as a clear oil (1600 g, 7.36 mol, 80.2% yield).

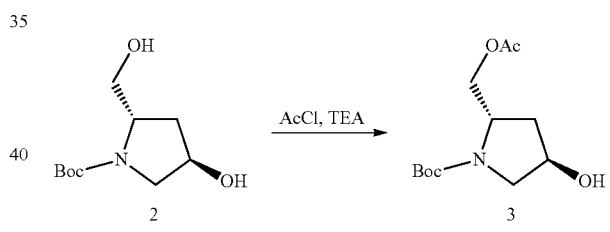

To a 50-L flask was charged compound 2 (1.60 kg, 7.36 mol, 1.00 Eq), DCM (20 L) followed by the addition TEA (1.12 kg, 11.05 mol, 1.50 Eq) and acetyl chloride (635.54 g, 8.10 mol, 1.10 Eq) dropwise in turn with stirring at 0° C. After the addition, the resulting solution was stirred at 15-25° C. for 18 h, quenched by the addition of 5 L of water and extracted with 3×2 L of DCM. The combined organic layers were dried over anhydrous sodium sulfate and concentrated under vacuum to afford compound 3 as a colorless oil (2.46 kg, 9.49 mol, 128.90% yield).

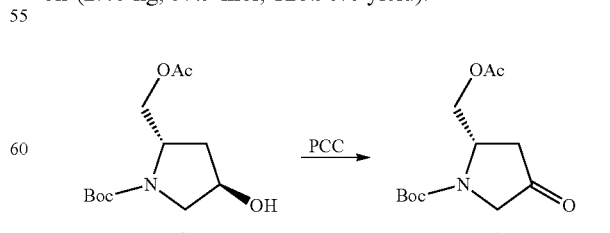

To a 20 L 3-necked round-bottom flask was charged compound 3 (1.23 kg, 4.75 mol, 1.00 Eq) in DCM (12 L)

followed by the addition of PCC (1.54 kg, 7.13 mol) in several batches at 15° C. The resulting solution was stirred at 15-25° C. for 18 h. The solids were filtered off and the filtrate was concentrated under vacuum. The residue was purified on a silica gel column eluting with ethyl acetate: petroleum ether (1:5) to afford compound 4 as a light yellow liquid (1.13 kg, 4.38 mol, 46.15% yield).

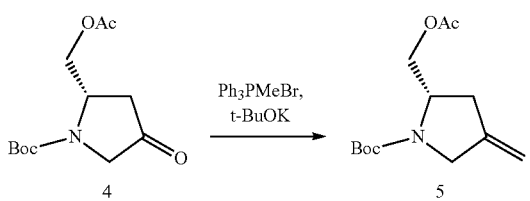 [SMILES: CC(=O)OC[C@@H]1CC(=O)CN1C(=O)OC(C)(C)C ; C=C1C[C@@H](COC(C)=O)N(C(=O)OC(C)(C)C)C1]

To a 10-L 3-necked round-bottom flask was charged methyl(triphenyl)phosphonium bromide (958.03 g, 2.68 mol), THF (2.5 L), followed by the addition of t-BuOK (300.94 g, 2.68 mol) in portions at 0° C. over 2 h. To this was added a solution compound 4 (460.00 g, 1.79 mol) in THF (2.5 L) dropwise with stirring at 0° C. The resulting solution was stirred at −5~−0 OC for 20 min, quenched by the addition of 500 mL of water and extracted with 3×500 mL of ethyl acetate. The combined organic layers were dried over anhydrous sodium sulfate and concentrated under vacuum. The residue was purified on a silica gel column eluting with ethyl acetate: petroleum ether (1:20) to afford compound 5 as a light yellow liquid (275.00 g, 1.08 mol, 30.09%).

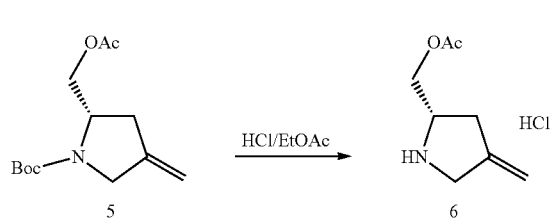 [SMILES: C=C1C[C@@H](COC(C)=O)N(C(=O)OC(C)(C)C)C1 ; C=C1CN[C@H](COC(C)=O)C1 ; Cl]

A mixture of compound 5 (330.00 g, 1.29 mol) in HCl (gas)/EtOAc (3 L, 4M/L) was stirred at 0° C. 20 mins. Then the mixture was stirred at 10-30° C. for 1 h. The mixture was concentrated in vacuum to afford compound 6 as yellow solid (250.00 g, 1.30 mol, 101%), which is used in next step without purification.

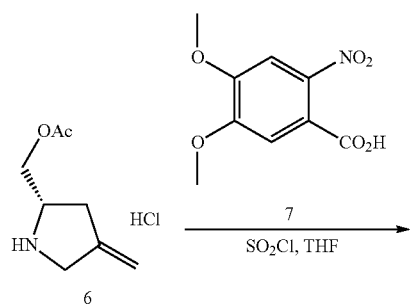

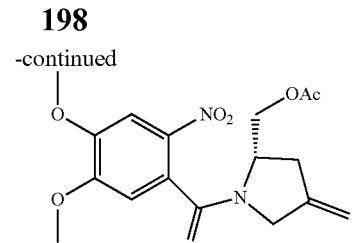

Into a 3000-mL 3-necked round-bottom flask purged and maintained with an inert atmosphere of nitrogen was charged a solution of compound 7 (354.42 g, 1.56 mol, 1.30 Eq) in THF (1.5 L), followed by the addition of SOCl$_2$ (1.71 kg, 14.33 mol, 11.94 Eq) dropwise with stirring. The resulting solution was stirred at 20-30° C. for 4 h and then concentrated under vacuum. Into another 3000-mL 3-necked round-bottom flask purged and maintained with an inert atmosphere of nitrogen was charged a solution of compound 6 (230.00 g, 1.20 mol, 1.00 Eq) in DCM (2.5 L). To this was added Et$_3$N (485.75 g, 4.80 mol, 4.00 Eq) dropwise with stirring at −40° C., followed by the solution in the first flask at −40° C. The temperature was allowed to warm to 0° C. naturally, quenched by the addition of 3000 mL of water/ice and extracted with 3×1000 mL of dichloromethane. The combined organic layers were dried over anhydrous sodium sulfate and concentrated under vacuum. The residue was purified on a silica gel column eluting with EtOAc:PE (1:3) to afford compound 8 as a light brown oil (210.00 g), which is used in next step without purification.

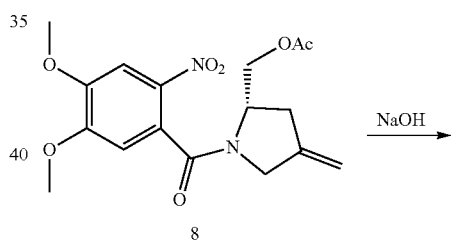

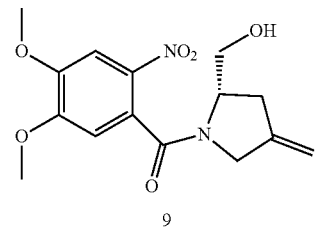

To a mixture of compound 8 (90.00 g, 247.02 mmol, 1.00 Eq) in THF (400 mL), MeOH (100 mL), H$_2$O (400 mL), was added NaOH (29.64 g, 741.05 mmol, 3.00 Eq) in one portion at 0° C. The mixture was stirred at 20-30° C. for 18 h. The aqueous phase was extracted with EtOAc (300 mL×3). The combined organic phase was washed with saturated brine (100 mL), dried with anhydrous Na$_2$SO$_4$, filtered and concentrated in vacuum to afford compound 9 as yellow solid (90.26 g, crude), which was used for the next step without further purification.

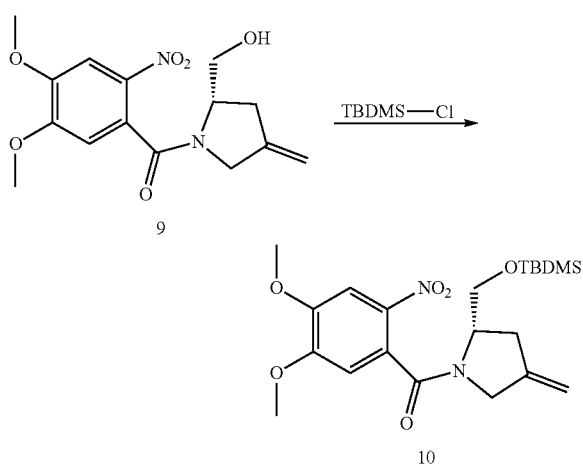

In a 2000 mL three-necked round bottom flask equipped with a temperature probe, magnetic stirrers and a nitrogen inlet, TBDMSCl (126.62 g, 840.12 mmol), imidazole (57.20 g, 840.12 mmol, 3.00 Eq) in DMF (1 L) were added. Then a solution of compound 9 (90.26 g, 280.04 mmol, 1.00 Eq) in DMF (1 L) was added to the mixture at 0° C. The resulting reaction mixture was stirred for 2 h at 25-30° C. The reaction mixture was poured into ice-water (1 L) and then extracted with DCM (200 mL×3). The combined organic phases were washed brine (100 mL), dried over $Na_2SO_4$ and concentrated in vacuum to give the residue, to give compound 10 as a yellow oil (126.00 g), which was used for the next step without further purification.

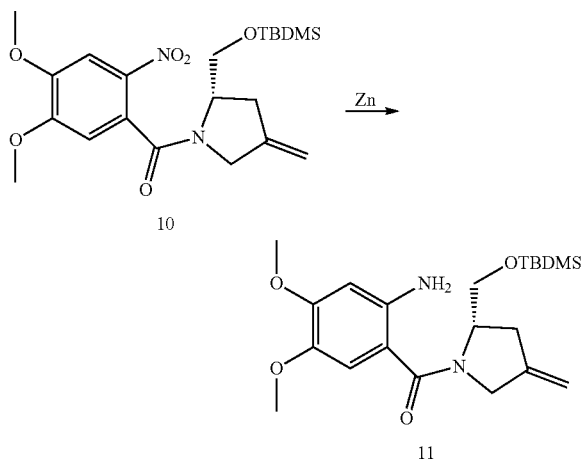

To a mixture of compound 10 (126.00 g, 288.61 mmol, 1.00 Eq) in AcOH (1 L), was added Zn (188.72 g, 2.89 mol) in portions by maintaining the temperature below 30° C. The mixture was stirred at 20-30° C. for 30 min. The residue was poured into EtOAc (500 mL) and filtered. The filtrate was concentrated in vacuum. The residue was purified by silica gel chromatography (PE/EtOAc=10/1, 1/1) to afford 11 as yellow oil (58.00 g, 142.64 mmol, 49% yield).

1H NMR (400 MHz, CHLOROFORM-d) d ppm 6.71 (s, 1 H) 6.22 (s, 1 H) 4.85-4.97 (m, 2 H) 4.52 (br. s., 1 H) 4.14-4.23 (m, 1 H) 3.99-4.13 (m, 1 H) 3.82 (s, 3 H) 3.77 (s, 3 H) 3.59 (d, J=5.73 Hz, 1 H) 2.63-2.72 (m, 2 H) 2.01-2.04 (m, 1 H) 1.23 (t, J=7.06 Hz, 1 H) 0.85 (s, 9 H)–0.06-0.06 (m, 5 H).

2-((4-nitrophenyl)disulfanyl)ethyl (11S,11aS)-11-hydroxy-7,8-dimethoxy-5-oxo-2-(quinolin-6-yl)-11,11a-dihydro-1H-benzo[e]pyrrolo[1,2-a][1,4]diazepine-10(5H)-carboxylate

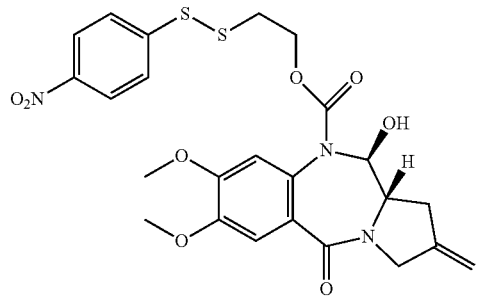 [SMILES: C=C1C[C@H]2[C@H](O)N(C(=O)OCCSSc3ccc([N+](=O)[O-])cc3)c3cc(OC)c(OC)cc3C(=O)N2C1]

The title compound was synthesized following Steps 5-7 as described above. $^1$H NMR (400 MHz, DMSO-$d_6$) δ 9.24 (d, J=2.3 Hz, 1H), 8.66-8.34 (m, 1H), 8.15-7.62 (m, 1H), 7.11 (s, 1H), 6.98 (s, 1H), 6.67 (d, J=5.8 Hz, 1H), 5.37 (dd, J=9.5, 6.3 Hz, 1H), 5.13 (d, J=6.2 Hz, 2H), 4.54-4.31 (m, 1H), 4.12 (d, J=15.6 Hz, 1H), 4.03-3.91 (m, 2H), 3.86-3.78 (m, 6H), 3.76 (d, J=3.4 Hz, 1H), 3.48 (t, J=8.8 Hz, 1H), 3.24-3.00 (m, 2H), 2.96-2.80 (m, 1H). MS m/z=549 [M+1]$^+$ Although the foregoing invention has been described in some detail by way of illustration and example for purposes of clarity of understanding, the descriptions and examples should not be construed as limiting the scope of the invention. All patents, patent applications, and references cited throughout the specification are expressly incorporated by reference.

We claim:
1. An antibody-drug conjugate compound of Formula II:

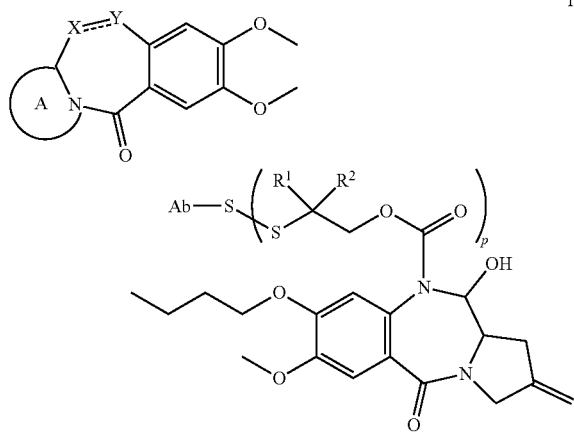

or a pharmaceutically acceptable salt thereof, wherein:
X══Y is selected from the group consisting of $CH_2$—$CH_2$, CH═CH, C(═O)—NH and $CH_2$—NH;
A is a 5-membered or 6-membered heterocyclic ring, optionally substituted with a group selected from F, $C_1$-$C_6$ alkyl, or ═C(R)$_2$ where R is independently selected from H, F, $C_1$-$C_6$ alkyl, or $C_1$-$C_6$ fluoroalkyl;
$R^1$ and $R^2$ are independently selected from H or $C_1$-$C_6$ alkyl, or $R^1$ and $R^2$ form a 3, 4, 5, or 6-membered cycloalkyl or heterocyclyl group;
p is an integer from 1 to 8; and
Ab is an antibody.

2. The antibody-drug conjugate compound of claim 1, or a pharmaceutically acceptable salt thereof, wherein Ab is an antibody which binds to one or more tumor-associated antigens or cell-surface receptors selected from (1)-(53):
(1) BMPR1B (bone morphogenetic protein receptor-type IB);
(2) E16 (LAT1, SLC7A5);
(3) STEAP1 (six transmembrane epithelial antigen of prostate);
(4) MUC16 (0772P, CA125);
(5) MPF (MPF, MSLN, SMR, megakaryocyte potentiating factor, mesothelin);
(6) Napi2b (NAPI-3B, NPTIIb, SLC34A2, solute carrier family 34 (sodium phosphate), member 2, type II sodium-dependent phosphate transporter 3b);
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);
(8) PSCA hlg (2700050C12Rik, C530008O16Rik, RIKEN cDNA 2700050C12, RIKEN cDNA 2700050C12 gene);
(9) ETBR (Endothelin type B receptor);
(10) MSG783 (RNF124, hypothetical protein FLJ20315);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);
(12) TrpM4 (BR22450, FLJ20041, TRPM4, TRPM4B, transient receptor potential cation channel, subfamily M, member 4);
(13) CRIPTO (CR, CR1, CRGF, CRIPTO, TDGF1, teratocarcinoma-derived growth factor);
(14) CD21 (CR2 (Complement receptor 2) or C3DR (C3d/Epstein Barr virus receptor) or Hs 73792);
(15) CD79b (CD79B, CD79β, IGb (immunoglobulin-associated beta), B29);
(16) FcRH2 (IFGP4, IRTA4, SPAP1A (SH2 domain containing phosphatase anchor protein 1a), SPAP1B, SPAP1C);
(17) HER2;
(18) NCA;
(19) MDP;
(20) IL20Rα;
(21) Brevican;
(22) EphB2R;
(23) ASLG659;
(24) PSCA;
(25) GEDA;
(26) BAFF-R (B cell-activating factor receptor, BLyS receptor 3, BR3);
(27) CD22 (B-cell receptor CD22-B isoform);
(28) CD79a (CD79A, CD79α, immunoglobulin-associated alpha);
(29) CXCR5 (Burkitt's lymphoma receptor 1);
(30) HLA-DOB (Beta subunit of MHC class II molecule (Ia antigen));
(31) P2X5 (Purinergic receptor P2X ligand-gated ion channel 5);
(32) CD72 (B-cell differentiation antigen CD72, Lyb-2);
(33) LY64 (Lymphocyte antigen 64 (RP105), type I membrane protein of the leucine rich repeat (LRR) family);
(34) FcRH1 (Fc receptor-like protein 1);
(35) FcRH5 (IRTA2, Immunoglobulin superfamily receptor translocation associated 2);
(36) TENB2 (putative transmembrane proteoglycan);
(37) PMEL17 (silver homolog; SILV; D12S53E; PMEL17; SI; SIL);
(38) TMEFF1 (transmembrane protein with EGF-like and two follistatin-like domains 1; Tomoregulin-1);
(39) GDNF-Ra1 (GDNF family receptor alpha 1; GFRA1; GDNFR; GDNFRA; RETL1; TRNR1; RET1L; GDNFR-alphal; GFR-ALPHA-1);
(40) Ly6E (lymphocyte antigen 6 complex, locus E; Ly67, RIG-E, SCA-2, TSA-1);
(41) TMEM46 (shisa homolog 2 (*Xenopus laevis*); SHISA2);
(42) Ly6G6D (lymphocyte antigen 6 complex, locus G6D; Ly6-D, MEGT1);
(43) LGR5 (leucine-rich repeat-containing G protein-coupled receptor 5; GPR49, GPR67);
(44) RET (ret proto-oncogene; MEN2A; HSCR1; MEN2B; MTC1; PTC; CDHF12; Hs.168114; RET51; RET-ELE1);
(45) LY6K (lymphocyte antigen 6 complex, locus K; LY6K; HSJ001348; FLJ35226);
(46) GPR19 (G protein-coupled receptor 19; Mm.4787);
(47) GPR54 (KISS1 receptor; KISS1R; GPR54; HOT7T175; AXOR12);
(48) ASPHD1 (aspartate beta-hydroxylase domain containing 1; LOC253982);
(49) Tyrosinase (TYR; OCAIA; OCA1A; tyrosinase; SHEP3);
(50) TMEM118 (ring finger protein, transmembrane 2; RNFT2; FLJ14627);
(51) GPR172A (G protein-coupled receptor 172A; GPCR41; FLJ11856; D15Ertd747e);
(52) CD33; or
(53) CLL-1.

3. The antibody-drug conjugate compound of claim 1, or a pharmaceutically acceptable salt thereof, of Formula IIa:

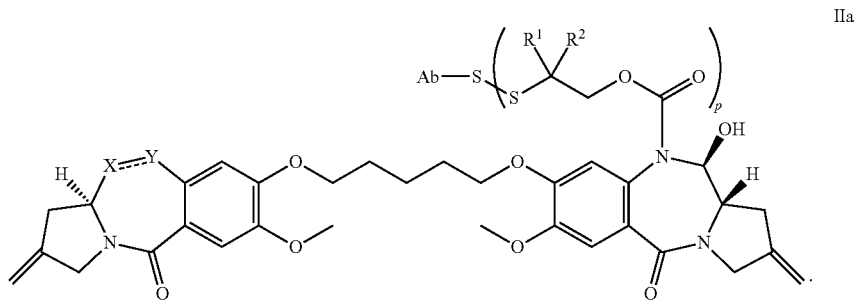

IIa

4. The antibody-drug conjugate compound of claim 1, or a pharmaceutically acceptable salt thereof, of Formula IIb:

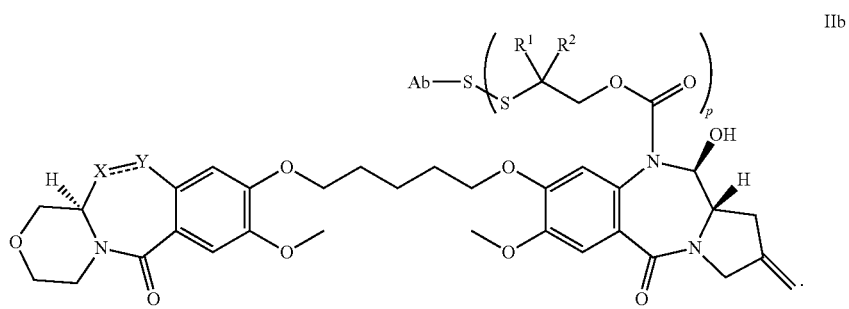

IIb

5. The antibody-drug conjugate compound of claim 1, or a pharmaceutically acceptable salt thereof, of Formula IIc:

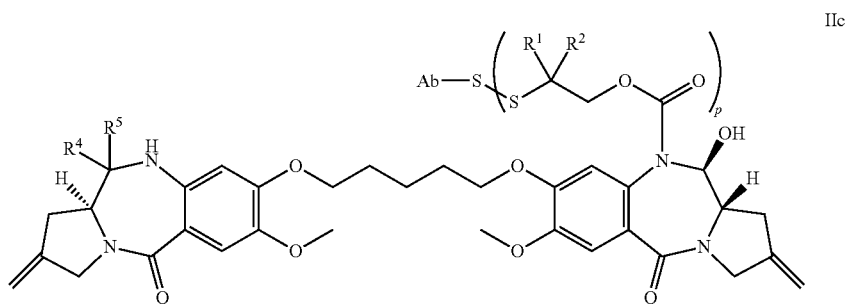

IIc wherein $R^4$ and $R^5$ are each H, or $R^4$ and $R^5$ are =O.

6. The antibody-drug conjugate compound, or a pharmaceutically acceptable salt thereof, of claim 5 wherein $R^4$ and $R^5$ are each H.

7. The antibody-drug conjugate compound, or a pharmaceutically acceptable salt thereof, of claim 5 wherein $R^4$ and $R^5$ are =O.

8. The antibody-drug conjugate compound, or a pharmaceutically acceptable salt thereof, of claim 5 having Formula IId:

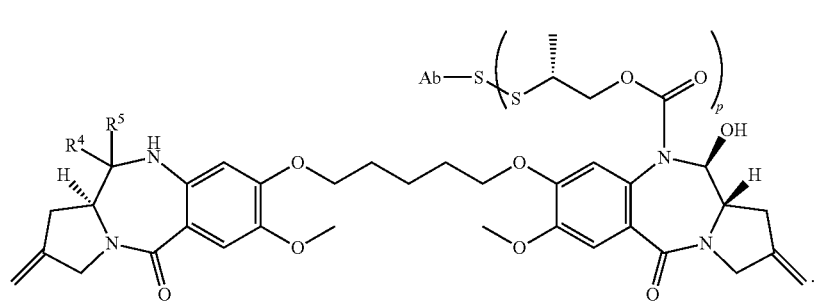

IId

9. The antibody-drug conjugate compound, or a pharmaceutically acceptable salt thereof, of claim 5 having Formula IIe:

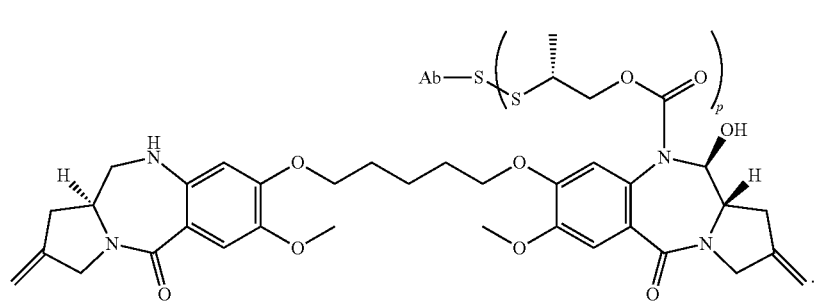

IIe

10. The antibody-drug conjugate compound of claim 5, or a pharmaceutically acceptable salt thereof, having Formula IIf:

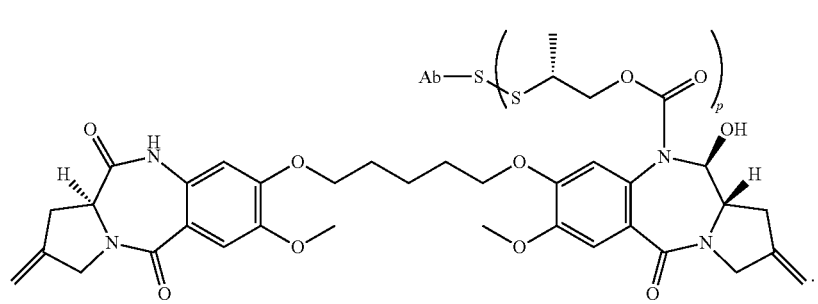

IIf

11. The antibody-drug conjugate compound, or a pharmaceutically acceptable salt thereof, according to claim 1, wherein said Ab is a cysteine-engineered antibody.

12. The antibody-drug conjugate compound, or a pharmaceutically acceptable salt thereof, according to claim 11, wherein the cysteine-engineered antibody comprises K149C substitution in the light chain according to Kabat numbering; or A118C substitution in the heavy chain according to EU numbering as the site of drug conjugation.

13. The antibody-drug conjugate compound, or a pharmaceutically acceptable salt thereof, according to claim 1, wherein Ab is selected from anti-HER2, anti-CD 22, anti-CD33, anti-Napi2b, or anti-CLL-1.

14. The antibody-drug conjugate compound, or a pharmaceutically acceptable salt thereof, according to claim 1, wherein p is 1, 2, 3, or 4.

15. The antibody-drug conjugate compound, or a pharmaceutically acceptable salt thereof, according to claim 1, comprising a mixture of the antibody-drug conjugate compounds, wherein the average drug loading per antibody, p, in the mixture of antibody-drug conjugate compounds is about 2 to about 5.

16. A pharmaceutical composition comprising the antibody-drug conjugate compound, or a pharmaceutically acceptable salt thereof, according to claim 1 and a pharmaceutically acceptable diluent, carrier or excipient.

17. A method of making an antibody-drug conjugate compound, or a pharmaceutically acceptable salt thereof, according to claim 1, the method comprising reacting an antibody with a linker-drug intermediate of Formula I:

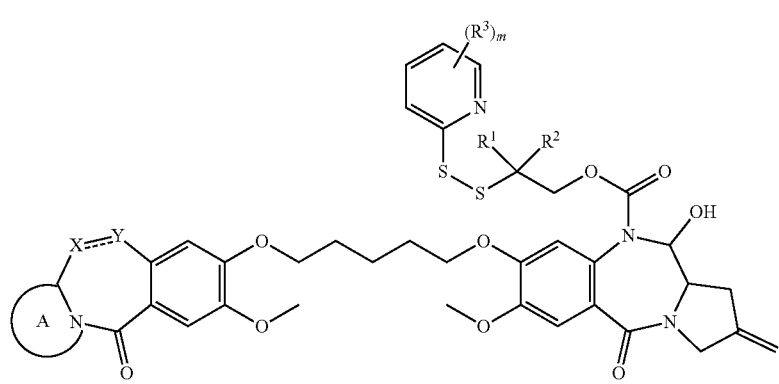

I wherein X═Y is selected from the group consisting of CH$_2$—CH$_2$, CH═CH, C(═O)—NH, and CH$_2$—NH;

A is a 5-membered or 6-membered heterocyclic ring, optionally substituted with F, C$_1$-C$_6$ alkyl, or ═C(R)$_2$ where R is independently H, F, C$_1$-C$_6$ alkyl, or C$_1$-C$_6$ fluoroalkyl;

R$^1$ and R$^2$ are independently selected from the group consisting of H and C$_1$-C$_6$ alkyl, or R$^1$ and R$^2$ form a 3,4,5, or 6-membered cycloalkyl or heterocyclyl group;

each R$^3$ is independently selected from the group consisting of NO$_2$, Cl, F, CN, CO$_2$H and Br; and m is 1 or 2.

18. An antibody-drug conjugate compound of Formula II:

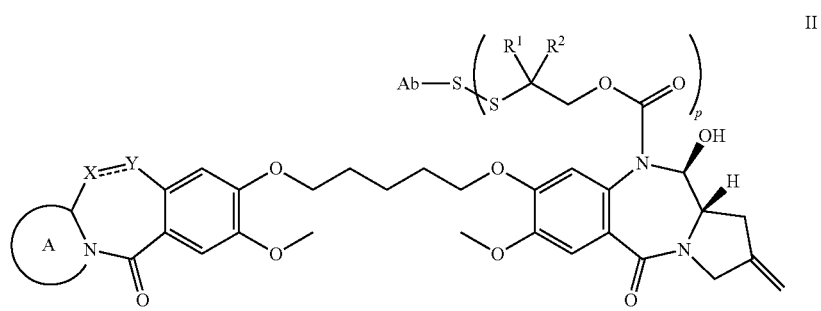

II or a pharmaceutically acceptable salt thereof, wherein:

X═Y is selected from the group consisting of CH$_2$—CH$_2$, CH═CH, C(═O)—NH and CH$_2$—NH;

A is a 5-membered or 6-membered heterocyclic ring, optionally substituted with a group selected from F, C$_1$-C$_6$ alkyl, or ═C(R)$_2$ where R is independently selected from H, F, C$_1$-C$_6$ alkyl, or C$_1$-C$_6$ fluoroalkyl;

R$^1$ and R$^2$ are independently selected from H or C$_1$-C$_6$ alkyl, or R$^1$ and R$^2$ form a 3, 4, 5,or 6-membered cycloalkyl or heterocyclyl group;

p is an integer from 1 to 8; and

Ab is an anti-HER2 antibody comprising (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

19. The antibody-drug conjugate compound, or a pharmaceutically acceptable salt thereof, according to claim 18, wherein the anti-HER2 antibody comprises a light chain variable region comprising the sequence of SEQ ID NO: 17 and a heavy chain variable region comprising the sequence of SEQ ID NO: 18.

20. The antibody-drug conjugate compound, or a pharmaceutically acceptable salt thereof, of claim 18 having Formula IIa:

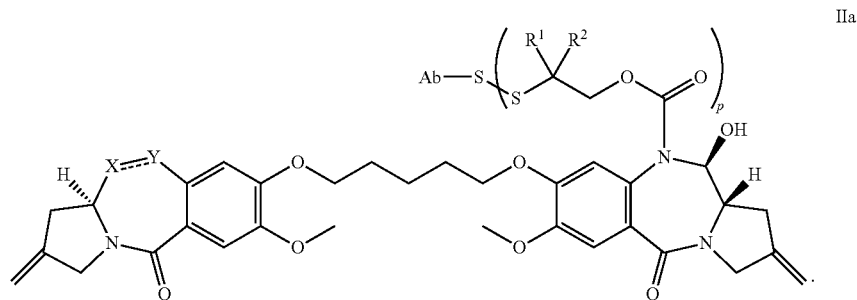

IIa

21. The antibody-drug conjugate compound, or a pharmaceutically acceptable salt thereof, of claim 18 having Formula IIb:

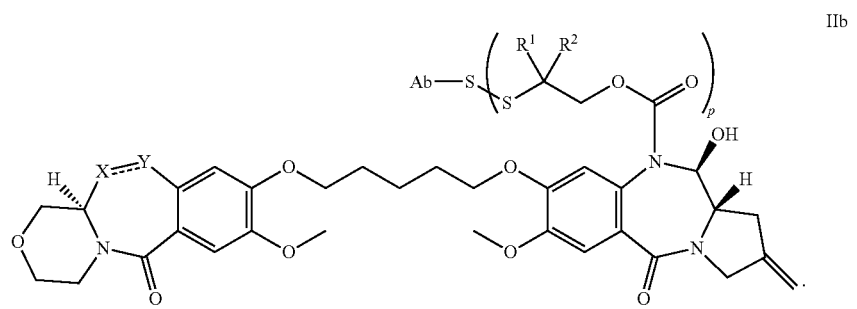

IIb

22. The antibody-drug conjugate compound, or a pharmaceutically acceptable salt thereof, of claim 18 having Formula IIc:

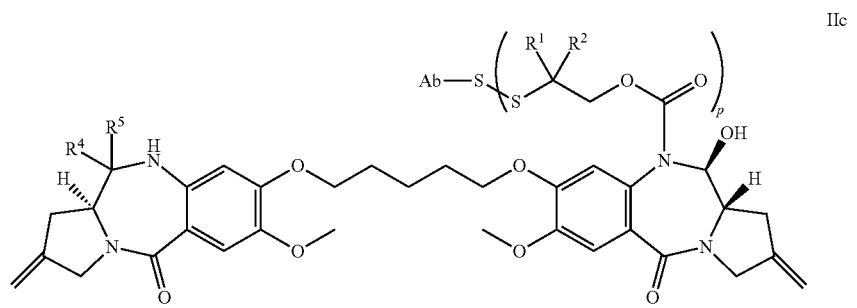

IIc wherein $R^4$ and $R^5$ are each H, or $R^4$ and $R^5$ are =O.

23. The antibody-drug conjugate compound, or a pharmaceutically acceptable salt thereof, of claim 22 wherein $R^4$ and $R^5$ are each H.

24. The antibody-drug conjugate compound, or a pharmaceutically acceptable salt thereof, of claim 22 wherein $R^4$ and $R^5$ are =O.

25. The antibody-drug conjugate compound, or a pharmaceutically acceptable salt thereof, of claim 22 having Formula IId:

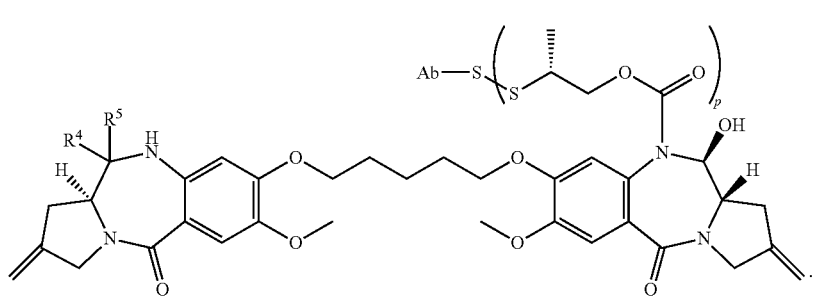

26. The antibody-drug conjugate compound, or a pharmaceutically acceptable salt thereof, of claim 22 having Formula IIe:

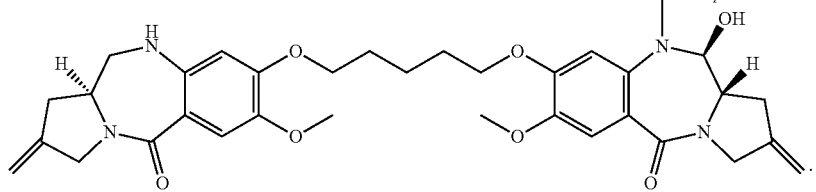

27. The antibody-drug conjugate compound, or a pharmaceutically acceptable salt thereof, of claim 22 having Formula IIf:

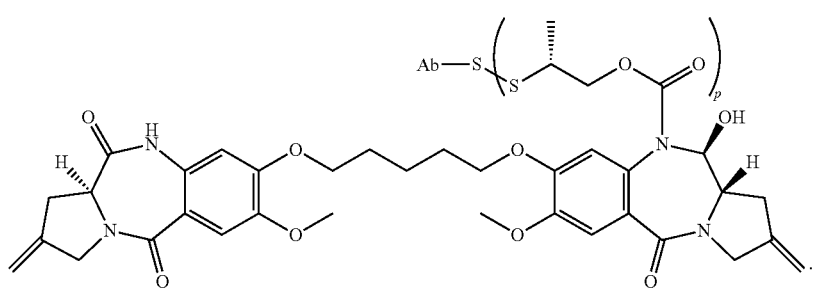

28. The antibody-drug conjugate compound, or a pharmaceutically acceptable salt thereof, according to claim 18, wherein anti-HER2 antibody is a cysteine-engineered antibody.

29. The antibody-drug conjugate compound, or a pharmaceutically acceptable salt thereof, according to claim 28, wherein the cysteine-engineered antibody comprises K149C substitution in the light chain according to Kabat numbering; or A118C substitution in the heavy chain according to EU numbering as the site of drug conjugation.

30. The antibody-drug conjugate compound, or a pharmaceutically acceptable salt thereof, according to claim 18, wherein p is 1, 2, 3, or 4.

31. The antibody-drug conjugate compound, or a pharmaceutically acceptable salt thereof, according to claim 18, comprising a mixture of the antibody-drug conjugate compounds, wherein the average drug loading per antibody, p, in the mixture of antibody-drug conjugate compounds is about 2 to about 5.

32. A pharmaceutical composition comprising the antibody-drug conjugate compound, or a pharmaceutically acceptable salt thereof, according to claim 18 and a pharmaceutically acceptable diluent, carrier or excipient.

33. The pharmaceutical composition of claim 32, further comprising an additional therapeutic agent.

34. The pharmaceutical composition of claim 33, wherein the additional therapeutic agent is a chemotherapeutic agent.

35. The pharmaceutical composition of claim 33, wherein the additional therapeutic agent is an antibody or immunoconjugate that binds HER2.

36. The pharmaceutical composition of claim 35, wherein the additional therapeutic agent is (i) an antibody or immunoconjugate that binds to domain II of HER2, and/or (ii) an antibody or immunoconjugate that binds to domain IV or HER2.

37. The pharmaceutical composition of claim 35, wherein the additional therapeutic agent is (i) an antibody or immunoconjugate that binds to epitope 2C4, and/or (ii) an antibody or immunoconjugate that binds to epitope 4D5.

38. The pharmaceutical composition of claim 33, wherein the additional therapeutic agent is selected from trastuzumab, trastuzumab-MCC-DM1 (T-DM1), or pertuzumab.

39. The pharmaceutical composition of claim 33, further comprising (1) trastuzumab or T-DM1, and (2) pertuzumab.

40. An antibody drug conjugate, or a pharmaceutically acceptable salt thereof, of Formula IIf

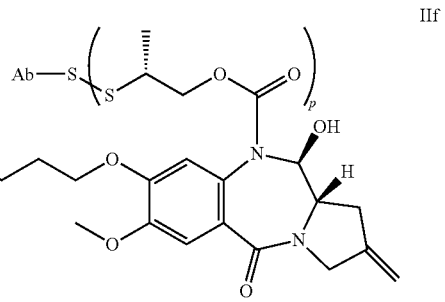

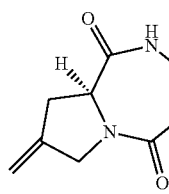

wherein Ab is an anti-HER2 antibody comprising a light chain variable region comprising the sequence of SEQ ID NO: 17 and a heavy chain variable region comprising the sequence of SEQ ID NO: 18; and p is 1,2,3, or 4.

41. The antibody-drug conjugate compound, or a pharmaceutically acceptable salt thereof, of claim 40, wherein the anti-HER2 antibody is a cysteine-engineered antibody.

42. A pharmaceutical composition comprising the antibody-drug conjugate compound, or a pharmaceutically acceptable salt thereof, according to claim 40 and a pharmaceutically acceptable diluent, carrier or excipient.

43. The antibody-drug conjugate compound, or a pharmaceutically acceptable salt thereof, of claim 40, wherein the anti-HER2 antibody comprises: (i) the heavy chain sequence of SEQ ID NO:26 and the light chain sequence of SEQ ID NO:30; or (ii) the heavy chain sequence of SEQ ID NO:31 and the light chain sequence of SEQ ID NO:25.

44. The antibody drug conjugate compound of claim 40 wherein p is about 2.

45. The antibody-drug conjugate compound, or a pharmaceutically acceptable salt thereof, of claim 41 wherein the cysteine-engineered antibody comprises K149C substitution in the light chain according to Kabat numbering; or A118C substitution in the heavy chain according to EU numbering as the site of drug conjugation.

46. An antibody drug conjugate, or a pharmaceutically acceptable salt thereof, of Formula IIe:

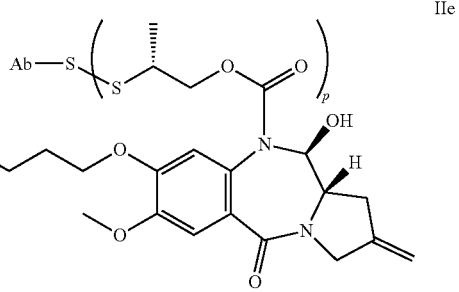

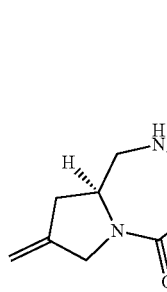

wherein Ab is an anti-HER2 antibody comprising a light chain variable region comprising the sequence of SEQ ID NO: 17 and a heavy chain variable region comprising the sequence of SEQ ID NO: 18; and p is 1, 2, 3, or 4.

47. The antibody-drug conjugate compound, or a pharmaceutically acceptable salt thereof, of claim 46, wherein the anti-HER2 antibody comprises: (i) the heavy chain sequence of SEQ ID NO:26 and the light chain sequence of SEQ ID NO:30; or (ii) the heavy chain sequence of SEQ ID NO:31 and the light chain sequence of SEQ ID NO:25.

48. The antibody-drug conjugate compound, or a pharmaceutically acceptable salt thereof, of claim 46, wherein the anti-HER2 antibody is a cysteine-engineered antibody.

49. The antibody-drug conjugate compound, or a pharmaceutically acceptable salt thereof, of claim 46 wherein the cysteine-engineered antibody comprises K149C substitution in the light chain according to Kabat numbering; or A118C substitution in the heavy chain according to EU numbering as the site of drug conjugation.

50. A pharmaceutical composition comprising the antibody-drug conjugate compound, or a pharmaceutically acceptable salt thereof, according to claim 46 and a pharmaceutically acceptable diluent, carrier or excipient.

51. An antibody drug conjugate compound, or a pharmaceutically acceptable salt thereof, of Formula IIf

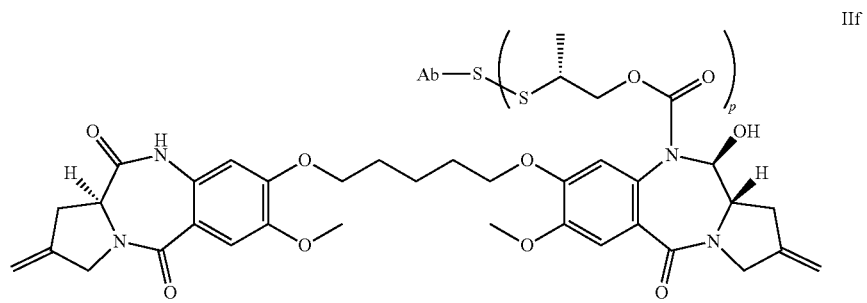

wherein Ab is an anti-HER2 antibody comprising (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21, and p is 1, 2, 3, or 4.

52. The antibody drug conjugate compound of claim 51 wherein p is about 2.

53. A pharmaceutical composition comprising the antibody-drug conjugate compound, or a pharmaceutically acceptable salt thereof, according to claim 51 and a pharmaceutically acceptable diluent, carrier or excipient.

54. An antibody drug conjugate compound, or a pharmaceutically acceptable salt thereof, of Formula IIf

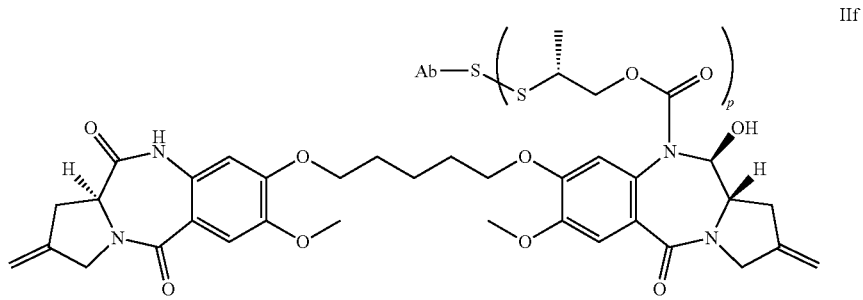

wherein Ab is an anti-HER2 antibody comprising : (i) the heavy chain sequence of SEQ ID NO:26 and the light chain sequence of SEQ ID NO:30; or (ii) the heavy chain sequence of SEQ ID NO:31 and the light chain sequence of SEQ ID NO:25, and p is 1, 2, 3, or 4.

55. The antibody drug conjugate compound of claim 54 wherein p is about 2.

56. A pharmaceutical composition comprising the antibody-drug conjugate compound, or a pharmaceutically acceptable salt thereof, according to claim 54 and a pharmaceutically acceptable diluent, carrier or excipient.

57. The antibody drug conjugate compound of claim 54 wherein the anti-HER2 antibody comprises the heavy chain sequence of SEQ ID NO:26 and the light chain sequence of SEQ ID NO:30.

58. The antibody drug conjugate compound of claim 54 wherein the anti-HER2 antibody comprises the heavy chain sequence of SEQ ID NO:31 and the light chain sequence of SEQ ID NO:25.

* * * * *